United States Patent
Harris et al.

(10) Patent No.: US 10,426,476 B2
(45) Date of Patent: Oct. 1, 2019

(54) CIRCULAR FASTENER CARTRIDGES FOR APPLYING RADIALLY EXPANDABLE FASTENER LINES

(71) Applicant: Ethicon Endo-Surgery, Inc., Cincinnati, OH (US)

(72) Inventors: Jason L. Harris, Lebanon, OH (US); Jerome R. Morgan, Cincinnati, OH (US); Mark S. Zeiner, Mason, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 729 days.

(21) Appl. No.: 14/498,070

(22) Filed: Sep. 26, 2014

(65) Prior Publication Data
US 2016/0089146 A1    Mar. 31, 2016

(51) Int. Cl.
*A61B 17/072* (2006.01)
*A61B 17/10* (2006.01)
(Continued)

(52) U.S. Cl.
CPC .......... *A61B 17/105* (2013.01); *A61B 17/068* (2013.01); *A61B 17/0644* (2013.01); *A61B 17/07207* (2013.01); *A61B 17/07292* (2013.01); *A61B 17/1155* (2013.01); *A61B 2017/00004* (2013.01); *A61B 2017/00526* (2013.01); *A61B 2017/00884* (2013.01); *A61B 2017/00898* (2013.01); *A61B 2017/00942* (2013.01); *A61B 2017/07228* (2013.01); *A61B 2017/07235* (2013.01); *A61B 2017/07242* (2013.01);
(Continued)

(58) Field of Classification Search
CPC ...... A61B 17/1155; A61B 2017/07228; A61B 2017/07235; A61B 17/105; A61B 17/0644; A61B 17/068; A61B 17/07207; A61B 17/07292
See application file for complete search history.

(56) References Cited

U.S. PATENT DOCUMENTS 66,052 A    6/1867    Smith
662,587 A    11/1900    Blake
(Continued)

FOREIGN PATENT DOCUMENTS

AU    2008207624 A1    3/2009
AU    2010214687 A1    9/2010
(Continued)

OTHER PUBLICATIONS

Partial European Search Report for Application No. 15186985.6. dated Feb. 5, 2016 (10 pages).
(Continued)

*Primary Examiner* — Andrew M Tecco

(57) ABSTRACT

A fastener cartridge assembly for use with a circular surgical fastening device. The fastener cartridge assembly includes a cartridge body that has a circular deck. A plurality of fastener cavities is provided in the circular deck. Each fastener cavity includes two cavity ends wherein one cavity end of each of the fastener cavities is positioned on a first circular axis having a first radius and wherein the other cavity end of each fastener cavity is positioned on a second circular axis that has a second radius that differs from the first radius.

9 Claims, 55 Drawing Sheets

(51) Int. Cl.
*A61B 17/064* (2006.01)
*A61B 17/115* (2006.01)
*A61B 17/068* (2006.01)
A61B 17/00 (2006.01)
A61B 17/29 (2006.01)

(52) U.S. Cl.
CPC .............. *A61B 2017/07264* (2013.01); *A61B 2017/07271* (2013.01); *A61B 2017/07278* (2013.01); *A61B 2017/2927* (2013.01)

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,224,882 A | 12/1940 | Peck |
| 2,318,379 A | 5/1943 | Davis et al. |
| 2,329,440 A | 9/1943 | La Place |
| 2,441,096 A | 5/1948 | Happe |
| 2,448,741 A | 9/1948 | Scott et al. |
| 2,450,527 A | 10/1948 | Smith et al. |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,711,461 A | 6/1955 | Happe |
| 2,742,955 A | 4/1956 | Dominguez |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,957,353 A | 10/1960 | Lewis |
| 2,959,974 A | 11/1960 | Emrick |
| 3,032,769 A | 5/1962 | Palmer |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,608,549 A | 9/1971 | Merrill |
| 3,618,842 A | 11/1971 | Bryan |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,666 A | 5/1972 | Foster et al. |
| 3,662,939 A | 5/1972 | Bryan |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,747,603 A | 7/1973 | Adler |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,883,624 A | 5/1975 | McKenzie et al. |
| 3,885,491 A | 5/1975 | Curtis |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,931,051 A | 9/1976 | Brumlik |
| 4,025,216 A | 5/1977 | Hives |
| 4,027,746 A | 6/1977 | Kine |
| 4,034,143 A | 7/1977 | Sweet |
| 4,054,108 A | 10/1977 | Gill |
| 4,060,089 A | 11/1977 | Noiles |
| 4,066,133 A | 1/1978 | Voss |
| 4,100,820 A | 7/1978 | Evett |
| 4,106,446 A | 8/1978 | Yamada et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,135,517 A | 1/1979 | Reale |
| 4,154,122 A | 5/1979 | Severin |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |

(56) References Cited

U.S. PATENT DOCUMENTS

| | | |
|---|---|---|
| 4,278,091 A | 7/1981 | Borzone |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Siegel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,423,456 A | 12/1983 | Zaidenweber |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Krüger |
| 4,461,305 A | 7/1984 | Cibley |
| 4,467,805 A | 8/1984 | Fukuda |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,478,220 A | 10/1984 | Di Giovanni et al. |
| 4,480,641 A | 11/1984 | Failla et al. |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,499,895 A | 2/1985 | Takayama |
| 4,500,024 A | 2/1985 | DiGiovanni et al. |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles et al. |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,914 A | 10/1986 | Ueda |
| 4,619,262 A | 10/1986 | Taylor |
| 4,619,391 A | 10/1986 | Sharkany et al. |
| D287,278 S | 12/1986 | Spreckelmeier |
| 4,628,459 A | 12/1986 | Shinohara et al. |
| 4,629,107 A | 12/1986 | Fedotov et al. |
| 4,632,290 A * | 12/1986 | Green .................. A61B 17/072 227/155 |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |

(56) References Cited

U.S. PATENT DOCUMENTS

| | | |
|---|---|---|
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,763,669 A | 8/1988 | Jaeger |
| 4,767,044 A | 8/1988 | Green |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,833,937 A | 5/1989 | Nagano |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,951,860 A | 8/1990 | Peters et al. |
| 4,951,861 A | 8/1990 | Schulze et al. |
| 4,955,959 A | 9/1990 | Tompkins et al. |
| 4,957,212 A | 9/1990 | Duck et al. |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,973,274 A | 11/1990 | Hirukawa |
| 4,973,302 A | 11/1990 | Armour et al. |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,027,834 A | 7/1991 | Pruitt |
| 5,030,226 A | 7/1991 | Green et al. |
| 5,031,814 A | 7/1991 | Tompkins et al. |
| 5,035,040 A | 7/1991 | Kerrigan et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,104,025 A | 4/1992 | Main et al. |
| 5,104,397 A | 4/1992 | Vasconcelos et al. |

(56) References Cited

U.S. PATENT DOCUMENTS

| | | |
|---|---|---|
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman et al. |
| 5,173,133 A | 12/1992 | Morin et al. |
| 5,176,677 A | 1/1993 | Wuchinich |
| 5,176,688 A | 1/1993 | Narayan et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,292,053 A | 3/1994 | Bilotti et al. |
| 5,297,714 A | 3/1994 | Kramer |
| 5,304,204 A | 4/1994 | Bregen |
| D347,474 S | 5/1994 | Olson |
| 5,307,976 A | 5/1994 | Olson et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,355 A | 9/1994 | Sklar |

(56) References Cited

U.S. PATENT DOCUMENTS

| | | |
|---|---|---|
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,443,197 A | 8/1995 | Malis et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |

(56) References Cited

U.S. PATENT DOCUMENTS

| | | |
|---|---|---|
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |

(56) References Cited

U.S. PATENT DOCUMENTS

| | | |
|---|---|---|
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| D381,077 S | 7/1997 | Hunt |
| 5,643,291 A | 7/1997 | Pier et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,748 A | 6/1998 | Eyerly et al. |
| 5,769,791 A | 6/1998 | Benaron et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |

(56) References Cited

U.S. PATENT DOCUMENTS

| | | |
|---|---|---|
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,737,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |

(56) References Cited

U.S. PATENT DOCUMENTS

| | | |
|---|---|---|
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Törmälä et al. |
| 6,010,520 A | 1/2000 | Pattison |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,667 A | 3/2000 | Manna et al. |
| 6,037,724 A | 3/2000 | Buss et al. |
| 6,037,927 A | 3/2000 | Rosenberg |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,904 B1 | 3/2001 | Ouchi |
| 6,209,414 B1 | 4/2001 | Uneme |
| 6,210,403 B1 | 4/2001 | Klicek |
| 6,213,999 B1 | 4/2001 | Platt, Jr. et al. |
| 6,214,028 B1 | 4/2001 | Yoon et al. |

(56) References Cited

U.S. PATENT DOCUMENTS

| | | |
|---|---|---|
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balázs et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,270,508 B1 | 8/2001 | Klieman et al. |
| 6,270,916 B1 | 8/2001 | Sink et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,315,184 B1 | 11/2001 | Whitman |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,458,077 B1 | 10/2002 | Boebel et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,885 B1 | 12/2002 | Dhindsa |
| 6,494,896 B1 | 12/2002 | D'Alessio et al. |
| 6,498,480 B1 | 12/2002 | Manara |

(56) References Cited

U.S. PATENT DOCUMENTS

| | | |
|---|---|---|
| 6,500,176 B1 | 12/2002 | Truckai et al. |
| 6,500,194 B2 | 12/2002 | Benderev et al. |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,527,782 B2 | 3/2003 | Hogg et al. |
| 6,527,785 B2 | 3/2003 | Sancoff et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,816 B2 | 4/2003 | Kogiso et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,594,552 B1 | 7/2003 | Nowlin et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,109 B2 | 4/2004 | Solingen |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |

(56) References Cited

U.S. PATENT DOCUMENTS

| | | |
|---|---|---|
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,810,359 B2 | 10/2004 | Sakaguchi |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,884,392 B2 | 4/2005 | Malkin et al. |
| 6,884,428 B2 | 4/2005 | Binette et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,899,538 B2 | 5/2005 | Matoba |
| 6,899,593 B1 | 5/2005 | Moeller et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |

(56) References Cited

U.S. PATENT DOCUMENTS

| | | |
|---|---|---|
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,687 B1 | 5/2006 | Reuss et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,412 B2 | 8/2006 | Wang et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |

(56) References Cited

U.S. PATENT DOCUMENTS

| | | |
|---|---|---|
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,161,580 B2 | 1/2007 | Bailey et al. |
| 7,163,563 B2 | 1/2007 | Schwartz et al. |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,636 B2 | 2/2007 | Lowe |
| 7,179,223 B2 | 2/2007 | Motoki et al. |
| 7,179,267 B2 | 2/2007 | Nolan et al. |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,195,627 B2 | 3/2007 | Amoah et al. |
| 7,196,911 B2 | 3/2007 | Takano et al. |
| D541,418 S | 4/2007 | Schechter et al. |
| 7,199,537 B2 | 4/2007 | Okamura et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapius |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,045 B2 | 2/2008 | Clermonts |
| 7,336,048 B2 | 2/2008 | Lohr |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |

(56) References Cited

U.S. PATENT DOCUMENTS

| | | |
|---|---|---|
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |

(56) References Cited

U.S. PATENT DOCUMENTS

| | | |
|---|---|---|
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,578,825 B2 | 8/2009 | Huebner |
| 7,533,063 B2 | 9/2009 | Dooley |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,662,161 B2 | 2/2010 | Briganti et al. |
| 7,665,646 B2 | 2/2010 | Prommersberg |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,712,182 B2 | 5/2010 | Zeiler et al. |
| 7,713,190 B2 | 5/2010 | Brock et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,612 B2 | 7/2010 | Shipp |
| 7,762,462 B2 | 7/2010 | Gelbman |
| 7,762,998 B2 | 7/2010 | Birk et al. |
| 7,730,663 B2 | 8/2010 | Yates et al. |
| 7,730,685 B1 | 8/2010 | Hunt et al. |
| 7,734,662 B2 | 8/2010 | Wales et al. |
| 7,766,207 B2 | 8/2010 | Mather et al. |

(56) References Cited

U.S. PATENT DOCUMENTS

| | | |
|---|---|---|
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,309 B2 | 8/2010 | McMillan et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,085 B2 | 12/2010 | Silverman et al. |
| 7,846,149 B2 | 12/2010 | Jankowski |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |

(56) References Cited

U.S. PATENT DOCUMENTS

| | | |
|---|---|---|
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,563 B2 | 7/2011 | Summerer |
| 7,979,137 B2 | 7/2011 | Tracey et al. |
| 7,980,443 B2 | 7/2011 | Scheib et al. |
| 7,981,132 B2 | 7/2011 | Dubrul et al. |
| 7,987,405 B2 | 7/2011 | Turner et al. |
| 7,938,027 B2 | 8/2011 | Olson et al. |
| 7,938,028 B2 | 8/2011 | Farascioni et al. |
| 7,988,015 B2 | 8/2011 | Mason, II et al. |
| 7,988,026 B2 | 8/2011 | Knodel et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |

(56) References Cited

U.S. PATENT DOCUMENTS

| | | |
|---|---|---|
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,278 B2 | 1/2012 | Deck et al. |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,408 B2 | 2/2012 | Wenchell et al. |
| 8,113,410 B2 | 2/2012 | Hall et al. |
| 8,114,100 B2 | 2/2012 | Smith et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,191,752 B2 | 6/2012 | Scirica |
| 8,192,460 B2 | 6/2012 | Orban, III et al. |
| 8,192,651 B2 | 6/2012 | Young et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,236,010 B2 | 8/2012 | Ortiz et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |

(56) References Cited

U.S. PATENT DOCUMENTS

| | | |
|---|---|---|
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,231,973 B2 | 10/2012 | Wenchell et al. |
| 8,231,974 B2 | 10/2012 | Hessler et al. |
| 8,232,654 B2 | 10/2012 | Ferrari et al. |
| 8,237,561 B2 | 10/2012 | Nunez et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,287,522 B2 | 10/2012 | Moses et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,744 B2 | 11/2012 | Kirschenman |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,343,150 B2 | 1/2013 | Artale |
| 8,347,978 B2 | 1/2013 | Forster et al. |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,161 B2 | 1/2013 | Mueller |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,787 B2 | 2/2013 | Brown et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,382,773 B2 | 2/2013 | Whitfield et al. |
| 8,382,790 B2 | 2/2013 | Uenohara et al. |
| 8,387,848 B2 | 3/2013 | Johnson et al. |
| 8,388,633 B2 | 3/2013 | Rousseau et al. |
| 8,389,588 B2 | 3/2013 | Ringelsen |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,400,851 B2 | 3/2013 | Byun |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,175 B2 | 4/2013 | Lee et al. |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,073 B2 | 4/2013 | Mohr et al. |
| 8,418,906 B2 | 4/2013 | Farascioni et al. |
| 8,418,908 B1 | 4/2013 | Beardsley |

(56) References Cited

U.S. PATENT DOCUMENTS

| | | |
|---|---|---|
| 8,418,909 B2 | 4/2013 | Kostrzewski |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel et al. |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,946 B2 | 6/2013 | Sugita |
| 8,469,973 B2 | 6/2013 | Meade et al. |
| 8,470,355 B2 | 6/2013 | Skalla et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,487,199 B2 | 7/2013 | Palmer et al. |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,528 B2 | 9/2013 | Shelton, IV |
| 8,535,304 B2 | 9/2013 | Sklar et al. |
| 8,535,340 B2 | 9/2013 | Allen |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV et al. |
| 8,574,199 B2 | 11/2013 | von Bülow et al. |
| 8,574,263 B2 | 11/2013 | Mueller |
| 8,575,880 B2 | 11/2013 | Grantz |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,427 B2 | 12/2013 | Viola |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,631,992 B1 | 1/2014 | Hausen et al. |

(56) References Cited

U.S. PATENT DOCUMENTS

| | | |
|---|---|---|
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,634,250 B2 | 4/2014 | Bettuchi et al. |
| 8,684,248 B2 | 4/2014 | Milliman |
| 8,684,249 B2 | 4/2014 | Racenet et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,211 B2 | 4/2014 | Zemlok et al. |
| 8,708,213 B2 | 4/2014 | Shelton, IV et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,795,308 B2 | 8/2014 | Valin |
| 8,795,324 B2 | 8/2014 | Kawai et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |

(56) References Cited

U.S. PATENT DOCUMENTS

| | | |
|---|---|---|
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,219 B2 | 9/2014 | Pierce |
| 8,833,630 B2 | 9/2014 | Milliman |
| 8,833,632 B2 | 9/2014 | Swensgard |
| 8,834,498 B2 | 9/2014 | Byrum et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,844,789 B2 | 9/2014 | Shelton, IV et al. |
| 8,851,215 B2 | 10/2014 | Goto |
| 8,851,354 B2 | 10/2014 | Swensgard et al. |
| 8,852,185 B2 | 10/2014 | Twomey |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,876,858 B2 | 11/2014 | Braun |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,287 B2 | 12/2014 | Racenet et al. |
| 8,905,977 B2 | 12/2014 | Shelton et al. |
| 8,910,846 B2 | 12/2014 | Viola |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,963,714 B2 | 2/2015 | Medhal et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 9,002,518 B2 | 4/2015 | Manzo et al. |
| 9,004,339 B1 | 4/2015 | Park |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,011,439 B2 | 4/2015 | Shalaby et al. |
| 9,011,471 B2 | 4/2015 | Timm et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,021,684 B2 | 5/2015 | Lenker et al. |
| 9,023,014 B2 | 5/2015 | Chowaniec et al. |
| 9,023,071 B2 | 5/2015 | Miller et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |

(56) References Cited

U.S. PATENT DOCUMENTS

| | | |
|---|---|---|
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,050,120 B2 | 6/2015 | Swarup et al. |
| 9,050,123 B2 | 6/2015 | Krause et al. |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Glieman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,091,588 B2 | 7/2015 | Lefler |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,101,475 B2 | 8/2015 | Wei et al. |
| 9,107,663 B2 | 8/2015 | Swensgard |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Sharbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,803 B2 | 10/2015 | Yates et al. |
| 9,168,038 B2 | 10/2015 | Shelton, IV et al. |
| 9,168,039 B1 | 10/2015 | Knodel |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,508 B2 | 12/2015 | Dannaher |
| 9,220,559 B2 | 12/2015 | Worrell et al. |
| 9,220,570 B2 | 12/2015 | Kim et al. |
| 9,226,750 B2 | 1/2016 | Weir et al. |
| 9,226,751 B2 | 1/2016 | Shelton, IV et al. |
| 9,226,767 B2 | 1/2016 | Stulen et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,921 B2 | 1/2016 | Messerly et al. |
| 9,240,740 B2 | 1/2016 | Zeng et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,259,274 B2 | 2/2016 | Prisco |
| 9,261,172 B2 | 2/2016 | Solomon et al. |
| 9,265,500 B2 | 2/2016 | Sorrentino et al. |
| 9,265,516 B2 | 2/2016 | Casey et al. |
| 9,265,585 B2 | 2/2016 | Wingardner et al. |
| 9,239,207 B2 | 3/2016 | Shelton, IV |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,210 B2 | 3/2016 | Baxter, III et al. |

(56) References Cited

U.S. PATENT DOCUMENTS

| | | |
|---|---|---|
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Chellew |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,784 B2 | 3/2016 | Eggert et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,339,226 B2 | 5/2016 | van der Walt et al. |
| 9,345,477 B2 | 5/2016 | Anim et al. |
| 9,345,480 B2 | 5/2016 | Hessler et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,358,003 B2 | 6/2016 | Hall et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,226 B2 | 6/2016 | Zemlok et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,364 B2 | 6/2016 | Smith et al. |
| 9,375,206 B2 | 6/2016 | Vidal et al. |
| 9,375,255 B2 | 6/2016 | Houser et al. |
| 9,381,058 B2 | 7/2016 | Houser et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,398,911 B2 | 7/2016 | Auld |
| 9,402,604 B2 | 8/2016 | Williams et al. |
| 9,402,626 B2 | 8/2016 | Ortiz et al. |
| 9,402,627 B2 | 8/2016 | Stevenson et al. |
| 9,408,604 B2 | 8/2016 | Shelton, IV et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,427,223 B2 | 8/2016 | Park et al. |
| 9,427,231 B2 | 8/2016 | Racenet et al. |
| 9,433,411 B2 | 9/2016 | Racenet et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,445,808 B2 | 9/2016 | Woodard, Jr. et al. |
| 9,445,813 B2 | 9/2016 | Shelton, IV et al. |
| 9,451,958 B2 | 9/2016 | Shelton, IV et al. |
| 9,461,340 B2 | 10/2016 | Li et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,189 B2 | 11/2016 | Williams et al. |
| 9,492,192 B2 | 11/2016 | To et al. |
| 9,498,213 B2 | 11/2016 | Marczyk et al. |
| 9,498,219 B2 | 11/2016 | Moore et al. |
| 9,504,521 B2 | 11/2016 | Deutmeyer et al. |
| D775,336 S | 12/2016 | Shelton, IV et al. |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,521,996 B2 | 12/2016 | Armstrong |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,564 B2 | 12/2016 | Rusin |
| 9,532,783 B2 | 1/2017 | Swayze et al. |
| 9,545,258 B2 | 1/2017 | Smith et al. |
| 9,549,732 B2 | 1/2017 | Yates et al. |

(56) References Cited

U.S. PATENT DOCUMENTS

| | | |
|---|---|---|
| 9,549,735 B2 | 1/2017 | Shelton, IV et al. |
| 9,554,794 B2 | 1/2017 | Baber et al. |
| 9,554,796 B2 | 1/2017 | Kostrzewski |
| 9,554,812 B2 | 1/2017 | Inkpen et al. |
| 9,559,624 B2 | 1/2017 | Philipp |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,566,061 B2 | 2/2017 | Aronhalt et al. |
| 9,566,067 B2 | 2/2017 | Milliman et al. |
| 9,572,574 B2 | 2/2017 | Shelton, IV et al. |
| 9,572,577 B2 | 2/2017 | Lloyd et al. |
| 9,572,592 B2 | 2/2017 | Price et al. |
| 9,574,644 B2 | 2/2017 | Parihar |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,610,080 B2 | 4/2017 | Whitfield et al. |
| 9,614,258 B2 | 4/2017 | Takahashi et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,652 B2 | 4/2017 | Mumaw et al. |
| 9,629,814 B2 | 4/2017 | Widenhouse et al. |
| 9,636,850 B2 | 5/2017 | Stopek et al. |
| 9,642,620 B2 | 5/2017 | Baxter, III et al. |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,624 B2 | 5/2017 | Shelton, IV et al. |
| 9,662,108 B2 | 5/2017 | Williams |
| 9,662,110 B2 | 5/2017 | Huang et al. |
| 9,662,116 B2 | 5/2017 | Smith et al. |
| 9,662,131 B2 | 5/2017 | Omori et al. |
| 9,668,729 B2 | 6/2017 | Williams et al. |
| 9,668,732 B2 | 6/2017 | Patel et al. |
| 9,675,344 B2 | 6/2017 | Combrowski et al. |
| 9,675,351 B2 | 6/2017 | Hodgkinson et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,321 B2 | 7/2017 | Shelton, IV et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,026 B2 | 7/2017 | Malackowski et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,096 B2 | 8/2017 | Thompson et al. |
| 9,724,098 B2 | 8/2017 | Baxter, III et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,770,245 B2 | 9/2017 | Swayze et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,782,169 B2 | 10/2017 | Swayze et al. |
| 9,782,170 B2 | 10/2017 | Zemlok et al. |
| 9,782,214 B2 | 10/2017 | Houser et al. |
| 9,788,834 B2 | 10/2017 | Schmid et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,795,379 B2 | 10/2017 | Leimbach et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |

(56) References Cited

U.S. PATENT DOCUMENTS

| | | |
|---|---|---|
| 9,808,247 B2 | 11/2017 | Shelton, IV et al. |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,873 B2 | 12/2017 | Shelton, IV |
| 9,848,875 B2 | 12/2017 | Aronhalt et al. |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,382 B2 | 1/2018 | Smith et al. |
| 9,867,612 B2 | 1/2018 | Parihar et al. |
| 9,867,618 B2 | 1/2018 | Hall et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,877,721 B2 | 1/2018 | Schellin et al. |
| 9,877,723 B2 | 1/2018 | Hall et al. |
| 9,883,860 B2 | 2/2018 | Leimbach et al. |
| 9,883,861 B2 | 2/2018 | Shelton, IV et al. |
| 9,884,456 B2 | 2/2018 | Schellin et al. |
| 9,888,919 B2 | 2/2018 | Leimbach et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,907,456 B2 | 3/2018 | Miyoshi |
| 9,907,620 B2 | 3/2018 | Shelton, IV et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,918,704 B2 | 3/2018 | Shelton, IV et al. |
| 9,918,715 B2 | 3/2018 | Menn |
| 9,918,716 B2 | 3/2018 | Baxter, III et al. |
| 9,924,942 B2 | 3/2018 | Swayze et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,116 B2 | 4/2018 | Racenet et al. |
| 9,931,118 B2 | 4/2018 | Shelton, IV et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,954 B2 | 4/2018 | Shelton, IV et al. |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,955,965 B2 | 5/2018 | Chen et al. |
| 9,955,966 B2 | 5/2018 | Zergiebel |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,980,713 B2 | 5/2018 | Aronhalt et al. |
| 9,980,729 B2 | 5/2018 | Moore et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 10,004,500 B2 | 6/2018 | Shelton, IV et al. |
| 10,004,506 B2 | 6/2018 | Shelton, IV et al. |
| 10,022,125 B2 | 7/2018 | Stopek et al. |
| 10,024,407 B2 | 7/2018 | Aranyi et al. |
| 10,028,744 B2 | 7/2018 | Shelton, IV et al. |
| 10,029,125 B2 | 7/2018 | Shapiro et al. |
| 10,034,668 B2 | 7/2018 | Ebner |
| 10,039,440 B2 | 8/2018 | Fenech et al. |
| 10,039,545 B2 | 8/2018 | Sadowski et al. |
| 10,041,822 B2 | 8/2018 | Zemlok |
| 10,045,778 B2 | 8/2018 | Yates et al. |
| 10,052,102 B2 | 8/2018 | Baxter, III et al. |
| 10,052,164 B2 | 8/2018 | Overmyer |
| 10,058,317 B2 | 8/2018 | Fan et al. |
| 10,064,620 B2 | 9/2018 | Gettinger et al. |
| 10,064,639 B2 | 9/2018 | Ishida et al. |
| 10,064,649 B2 | 9/2018 | Golebieski et al. |
| 10,076,326 B2 | 9/2018 | Yates et al. |
| 10,085,624 B2 | 10/2018 | Isoda et al. |
| 10,085,751 B2 | 10/2018 | Overmyer et al. |
| 10,085,806 B2 | 10/2018 | Hagn et al. |
| 10,092,292 B2 | 10/2018 | Boudreaux et al. |
| 2001/0000531 A1 | 4/2001 | Casscells et al. |
| 2001/0025183 A1 | 9/2001 | Shahidi |
| 2001/0044637 A1 | 11/2001 | Jacobs et al. |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0026126 A1 | 2/2002 | Burdorff et al. |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0049472 A1 | 4/2002 | Coleman et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0143340 A1 | 10/2002 | Kaneko |
| 2002/0157481 A1 | 10/2002 | Kogiso et al. |
| 2002/0158593 A1 | 10/2002 | Henderson et al. |
| 2002/0165541 A1 | 11/2002 | Whitman |
| 2002/0185514 A1 | 12/2002 | Adams et al. |
| 2002/0188170 A1 | 12/2002 | Santamore et al. |

(56) References Cited

U.S. PATENT DOCUMENTS

| | | |
|---|---|---|
| 2002/0188287 A1 | 12/2002 | Zvuloni et al. |
| 2002/0193808 A1 | 12/2002 | Belef et al. |
| 2003/0009193 A1 | 1/2003 | Corsaro |
| 2003/0011245 A1 | 1/2003 | Fiebig |
| 2003/0023316 A1 | 1/2003 | Brown et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0105478 A1 | 6/2003 | Whitman et al. |
| 2003/0114851 A1 | 6/2003 | Truckai et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0032345 A1 | 2/2004 | Kazuya et al. |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakahibara |
| 2004/0073222 A1 | 4/2004 | Koseki |
| 2004/0078037 A1 | 4/2004 | Batchelor et al. |
| 2004/0085180 A1 | 5/2004 | Juang |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Weisner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0122423 A1 | 6/2004 | Dycus et al. |
| 2004/0133095 A1 | 7/2004 | Dunki-Jacobs et al. |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |
| 2004/0260315 A1 | 12/2004 | Dell et al. |
| 2004/0267297 A1 | 12/2004 | Malackowski |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0116673 A1 | 6/2005 | Carl et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0145675 A1 | 7/2005 | Hartwick et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159184 A1 | 7/2005 | Kerner et al. |
| 2005/0159778 A1 | 7/2005 | Heinrich et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |

(56) References Cited

U.S. PATENT DOCUMENTS

| | | |
|---|---|---|
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251063 A1 | 11/2005 | Basude |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0267530 A1 | 12/2005 | Cummins |
| 2005/0272973 A1 | 12/2005 | Kawano et al. |
| 2005/0274034 A1 | 12/2005 | Hayashida et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0079879 A1 | 4/2006 | Faller et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0100649 A1 | 5/2006 | Hart |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0176031 A1 | 8/2006 | Forman et al. |
| 2006/0178556 A1 | 8/2006 | Hasser et al. |
| 2006/0180633 A1 | 8/2006 | Emmons |
| 2006/0180634 A1 | 8/2006 | Shelton, IV et al. |
| 2006/0185682 A1 | 8/2006 | Marczyk |
| 2006/0199999 A1 | 9/2006 | Ikeda et al. |
| 2006/0200123 A1 | 9/2006 | Ryan |
| 2006/0201989 A1 | 9/2006 | Ojeda |
| 2006/0206100 A1 | 9/2006 | Eskridge et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252990 A1 | 11/2006 | Kubach |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0261763 A1 | 11/2006 | Iott et al. |
| 2006/0264831 A1 | 11/2006 | Skwarek et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton, IV et al. |
| 2007/0016235 A1 | 1/2007 | Tanaka et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0027553 A1 | 2/2007 | Biran et al. |
| 2007/0034668 A1 | 2/2007 | Holsten et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0055228 A1 | 3/2007 | Berg et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0090788 A1 | 4/2007 | Hansford et al. |
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0134251 A1 | 6/2007 | Ashkenazi et al. |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179477 A1 | 8/2007 | Danger |
| 2007/0179528 A1 | 8/2007 | Soltz et al. |
| 2007/0181632 A1 | 8/2007 | Milliman |
| 2007/0185545 A1 | 8/2007 | Duke |
| 2007/0190110 A1 | 8/2007 | Pameijer et al. |
| 2007/0191868 A1 | 8/2007 | Theroux et al. |

(56) References Cited

U.S. PATENT DOCUMENTS

| | | |
|---|---|---|
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0208375 A1 | 9/2007 | Nishizawa et al. |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0250113 A1 | 10/2007 | Hegeman et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0296286 A1 | 12/2007 | Avenell |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0042861 A1 | 2/2008 | Dacquay et al. |
| 2008/0051833 A1 | 2/2008 | Gramuglia et al. |
| 2008/0064921 A1 | 3/2008 | Larkin et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0097563 A1 | 4/2008 | Petrie et al. |
| 2008/0108443 A1 | 5/2008 | Jinno et al. |
| 2008/0114250 A1 | 5/2008 | Urbano et al. |
| 2008/0114315 A1 | 5/2008 | Voegele et al. |
| 2008/0114385 A1 | 5/2008 | Byrum et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0154299 A1 | 6/2008 | Linvneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0200949 A1 | 8/2008 | Hiles et al. |
| 2008/0210738 A1* | 9/2008 | Shelton ............... A61B 17/064 227/176.1 |
| 2008/0228029 A1 | 9/2008 | Mikkaichi et al. |
| 2008/0234709 A1 | 9/2008 | Houser |
| 2008/0241667 A1 | 10/2008 | Kohn et al. |
| 2008/0242939 A1 | 10/2008 | Johnston |
| 2008/0245841 A1 | 10/2008 | Smith et al. |
| 2008/0249536 A1 | 10/2008 | Stahler et al. |
| 2008/0249608 A1 | 10/2008 | Dave |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281254 A1 | 11/2008 | Humayun et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0312687 A1 | 12/2008 | Blier |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048583 A1 | 2/2009 | Williams et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0069842 A1 | 3/2009 | Lee et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1 | 4/2009 | Zemlok et al. |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0179757 A1 | 7/2009 | Cohn et al. |
| 2009/0181290 A1 | 7/2009 | Baldwin et al. |
| 2009/0188964 A1 | 7/2009 | Orlov |

(56) References Cited

U.S. PATENT DOCUMENTS

| | | |
|---|---|---|
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0221993 A1 | 9/2009 | Sohi et al. |
| 2009/0234273 A1 | 9/2009 | Intoccia et al. |
| 2009/0242610 A1 | 10/2009 | Shelton, IV et al. |
| 2009/0247368 A1 | 10/2009 | Chiang |
| 2009/0247901 A1 | 10/2009 | Zimmer |
| 2009/0248007 A1 | 10/2009 | Falkenstein et al. |
| 2009/0248038 A1 | 10/2009 | Blumenkranz et al. |
| 2009/0248041 A1 | 10/2009 | Williams et al. |
| 2009/0253959 A1 | 10/2009 | Yoshie et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0262078 A1 | 10/2009 | Pizzi |
| 2009/0270895 A1 | 10/2009 | Churchill et al. |
| 2009/0277949 A1 | 11/2009 | Viola et al. |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2010/0010511 A1 | 1/2010 | Harris et al. |
| 2010/0012703 A1 | 1/2010 | Calabrese et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0030233 A1 | 2/2010 | Whitman et al. |
| 2010/0036370 A1 | 2/2010 | Mirel et al. |
| 2010/0041945 A1 | 2/2010 | Isbell, Jr. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0065604 A1 | 3/2010 | Weng |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0087840 A1 | 4/2010 | Ebersole et al. |
| 2010/0094289 A1 | 4/2010 | Taylor et al. |
| 2010/0094340 A1 | 4/2010 | Stopek et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0180711 A1 | 7/2010 | Kilibarda et al. |
| 2010/0186219 A1 | 7/2010 | Smith |
| 2010/0191262 A1 | 7/2010 | Harris et al. |
| 2010/0191292 A1 | 7/2010 | DeMeo et al. |
| 2010/0193566 A1 | 8/2010 | Schieb et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249497 A1 | 9/2010 | Peine et al. |
| 2010/0249519 A1 | 9/2010 | Park et al. |
| 2010/0249759 A1 | 9/2010 | Hinman et al. |
| 2010/0256675 A1 | 10/2010 | Romans |
| 2010/0258327 A1 | 10/2010 | Esenwein et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0312261 A1 | 12/2010 | Suzuki et al. |
| 2010/0318085 A1 | 12/2010 | Austin et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0009890 A1 | 1/2011 | Palmer et al. |
| 2011/0011916 A1 | 1/2011 | Levine |
| 2011/0016960 A1 | 1/2011 | Debrailly |
| 2011/0017799 A1 | 1/2011 | Whitman et al. |
| 2011/0021871 A1 | 1/2011 | Berkelaar |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0025311 A1 | 2/2011 | Chauvin et al. |
| 2011/0034910 A1 | 2/2011 | Ross et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060356 A1 | 3/2011 | Reschke et al. |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0084112 A1 | 4/2011 | Kostrzewski |
| 2011/0087276 A1 | 4/2011 | Bedi et al. |
| 2011/0087278 A1 | 4/2011 | Viola et al. |
| 2011/0087279 A1 | 4/2011 | Shah et al. |
| 2011/0088921 A1 | 4/2011 | Forgues et al. |
| 2011/0095064 A1 | 4/2011 | Taylor et al. |
| 2011/0095068 A1 | 4/2011 | Patel |
| 2011/0101065 A1 | 5/2011 | Milliman |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118778 A1 | 5/2011 | Burbank |
| 2011/0121049 A1 | 5/2011 | Malinouskas et al. |
| 2011/0125138 A1 | 5/2011 | Malinouskas et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144640 A1 | 6/2011 | Heinrich et al. |
| 2011/0144764 A1 | 6/2011 | Bagga et al. |
| 2011/0147433 A1 | 6/2011 | Shelton, IV et al. |
| 2011/0155786 A1 | 6/2011 | Shelton, IV |
| 2011/0163146 A1 | 7/2011 | Ortiz et al. |
| 2011/0167619 A1 | 7/2011 | Smith et al. |
| 2011/0172495 A1 | 7/2011 | Armstrong |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0199225 A1 | 8/2011 | Touchberry et al. |
| 2011/0208093 A1 | 8/2011 | Gross et al. |
| 2011/0210156 A1 | 9/2011 | Smith et al. |

(56) References Cited

U.S. PATENT DOCUMENTS

| | | |
|---|---|---|
| 2011/0218400 A1 | 9/2011 | Ma et al. |
| 2011/0218550 A1 | 9/2011 | Ma |
| 2011/0230713 A1 | 9/2011 | Kleemann et al. |
| 2011/0238044 A1 | 9/2011 | Main et al. |
| 2011/0241597 A1 | 10/2011 | Zhu et al. |
| 2011/0253765 A1 | 10/2011 | Nicholas et al. |
| 2011/0257650 A1 | 10/2011 | Deville et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0282446 A1 | 11/2011 | Schulte et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0307023 A1 | 12/2011 | Tweden et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0013326 A1 | 1/2012 | Racenet et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0033360 A1 | 2/2012 | Hsu |
| 2012/0045303 A1 | 2/2012 | Macdonald |
| 2012/0046692 A1 | 2/2012 | Smith et al. |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078071 A1 | 3/2012 | Bohm et al. |
| 2012/0078139 A1 | 3/2012 | Aldridge et al. |
| 2012/0078244 A1 | 3/2012 | Worrell et al. |
| 2012/0078278 A1 | 3/2012 | Bales, Jr. et al. |
| 2012/0080336 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0089131 A1 | 4/2012 | Zemlok et al. |
| 2012/0095458 A1 | 4/2012 | Cybulski et al. |
| 2012/0109186 A1 | 5/2012 | Parrott et al. |
| 2012/0110810 A1 | 5/2012 | Houser et al. |
| 2012/0116261 A1 | 5/2012 | Mumaw et al. |
| 2012/0116265 A1 | 5/2012 | Houser et al. |
| 2012/0116266 A1 | 5/2012 | Houser et al. |
| 2012/0116367 A1 | 5/2012 | Houser et al. |
| 2012/0116388 A1 | 5/2012 | Houser et al. |
| 2012/0116391 A1 | 5/2012 | Houser et al. |
| 2012/0116395 A1 | 5/2012 | Madan et al. |
| 2012/0118595 A1 | 5/2012 | Pellenc |
| 2012/0123203 A1 | 5/2012 | Riva |
| 2012/0125792 A1 | 5/2012 | Cassivi |
| 2012/0132286 A1 | 5/2012 | Lim et al. |
| 2012/0138658 A1 | 6/2012 | Ullrich et al. |
| 2012/0168487 A1* | 7/2012 | Holsten ............ A61B 17/00491 227/176.1 |
| 2012/0171539 A1 | 7/2012 | Rejman et al. |
| 2012/0175398 A1 | 7/2012 | Sandborn et al. |
| 2012/0187179 A1 | 7/2012 | Gleiman |
| 2012/0193398 A1* | 8/2012 | Williams ............ A61B 17/0644 227/179.1 |
| 2012/0197272 A1 | 8/2012 | Oray et al. |
| 2012/0209289 A1 | 8/2012 | Duque et al. |
| 2012/0211542 A1 | 8/2012 | Racenet |
| 2012/0223121 A1 | 9/2012 | Viola et al. |
| 2012/0228355 A1 | 9/2012 | Combrowski et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239068 A1 | 9/2012 | Morris et al. |
| 2012/0241492 A1 | 9/2012 | Shelton, IV et al. |
| 2012/0241493 A1 | 9/2012 | Baxter, III et al. |
| 2012/0241505 A1* | 9/2012 | Alexander, III ............................ A61B 17/00491 227/179.1 |
| 2012/0248167 A1 | 10/2012 | Flanagan et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0277780 A1 | 11/2012 | Smith et al. |
| 2012/0283707 A1 | 11/2012 | Giordano et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0303002 A1 | 11/2012 | Chowaniec et al. |
| 2012/0310255 A1 | 12/2012 | Brisson et al. |
| 2012/0310256 A1 | 12/2012 | Brisson |
| 2012/0325892 A1 | 12/2012 | Kostrzewski |
| 2013/0006227 A1 | 1/2013 | Takashino |
| 2013/0012983 A1 | 1/2013 | Kleyman |
| 2013/0018361 A1 | 1/2013 | Bryant |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0026973 A1 | 1/2013 | Luke et al. |
| 2013/0030462 A1 | 1/2013 | Keating et al. |
| 2013/0030608 A1 | 1/2013 | Taylor et al. |
| 2013/0032626 A1 | 2/2013 | Smith et al. |
| 2013/0037596 A1 | 2/2013 | Bear et al. |
| 2013/0046290 A1 | 2/2013 | Palmer et al. |
| 2013/0060278 A1 | 3/2013 | Bozung et al. |
| 2013/0062391 A1 | 3/2013 | Boudreaux et al. |
| 2013/0068816 A1 | 3/2013 | Mandakolathur Vasudevan et al. |
| 2013/0075446 A1 | 3/2013 | Wang et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0103023 A1 | 4/2013 | Monson et al. |
| 2013/0103024 A1 | 4/2013 | Monson et al. |
| 2013/0105548 A1 | 5/2013 | Hodgkinson et al. |
| 2013/0105552 A1 | 5/2013 | Weir et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123816 A1 | 5/2013 | Hodgkinson et al. |
| 2013/0123822 A1 | 5/2013 | Wellman et al. |
| 2013/0126202 A1 | 5/2013 | Oomori et al. |
| 2013/0126379 A1 | 5/2013 | Medhal et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0146641 A1 | 6/2013 | Shelton, IV et al. |
| 2013/0146642 A1 | 6/2013 | Shelton, IV et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0168431 A1 | 7/2013 | Zemlok et al. |
| 2013/0172929 A1 | 7/2013 | Hess et al. |

(56) References Cited

U.S. PATENT DOCUMENTS

| | | |
|---|---|---|
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233905 A1 | 9/2013 | Sorrentino et al. |
| 2013/0233906 A1 | 9/2013 | Hess et al. |
| 2013/0233908 A1 | 9/2013 | Knodel et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256371 A1 | 10/2013 | Shelton, IV et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0257945 A1 | 10/2013 | Behnke et al. |
| 2013/0261648 A1 | 10/2013 | Laurent et al. |
| 2013/0270322 A1 | 10/2013 | Scheib et al. |
| 2013/0277410 A1 | 10/2013 | Fernandez et al. |
| 2013/0277412 A1 | 10/2013 | Gresham et al. |
| 2013/0282052 A1 | 10/2013 | Aranyi et al. |
| 2013/0310873 A1 | 11/2013 | Stopek et al. |
| 2013/0313304 A1 | 11/2013 | Shelton, IV et al. |
| 2013/0313306 A1 | 11/2013 | Shelton, IV et al. |
| 2013/0317753 A1 | 11/2013 | Kamen et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327552 A1 | 12/2013 | Lovelass et al. |
| 2013/0327809 A1 | 12/2013 | Shelton, IV et al. |
| 2013/0327810 A1 | 12/2013 | Swayze et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0012238 A1 | 1/2014 | Chen et al. |
| 2014/0012289 A1 | 1/2014 | Snow et al. |
| 2014/0012299 A1 | 1/2014 | Stoddard et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0025046 A1 | 1/2014 | Williams et al. |
| 2014/0039549 A1 | 2/2014 | Belsky et al. |
| 2014/0042205 A1 | 2/2014 | Baxter, III et al. |
| 2014/0048580 A1 | 2/2014 | Merchant et al. |
| 2014/0061279 A1 | 3/2014 | Laurent et al. |
| 2014/0061280 A1 | 3/2014 | Ingmanson et al. |
| 2014/0081176 A1 | 3/2014 | Hassan |
| 2014/0100558 A1 | 4/2014 | Schmitz et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0110456 A1 | 4/2014 | Taylor |
| 2014/0114327 A1 | 4/2014 | Boudreaux et al. |
| 2014/0115229 A1 | 4/2014 | Kothamasu et al. |
| 2014/0128850 A1 | 5/2014 | Kerr et al. |
| 2014/0131418 A1 | 5/2014 | Kostrzewski |
| 2014/0138423 A1 | 5/2014 | Whitfield et al. |
| 2014/0151431 A1 | 6/2014 | Hodgkinson et al. |
| 2014/0151433 A1 | 6/2014 | Shelton, IV et al. |
| 2014/0158747 A1* | 6/2014 | Measamer ......... A61B 17/0644 227/179.1 |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0175154 A1 | 6/2014 | Shelton, IV et al. |
| 2014/0188159 A1 | 7/2014 | Steege |
| 2014/0191014 A1 | 7/2014 | Shelton, IV |
| 2014/0191015 A1 | 7/2014 | Shelton, IV |
| 2014/0200561 A1 | 7/2014 | Ingmanson et al. |
| 2014/0203061 A1 | 7/2014 | Hodgkinson |
| 2014/0205637 A1 | 7/2014 | Widenhouse et al. |
| 2014/0207124 A1 | 7/2014 | Aldridge et al. |
| 2014/0207125 A1 | 7/2014 | Applegate et al. |
| 2014/0207166 A1 | 7/2014 | Shelton, IV et al. |
| 2014/0224857 A1 | 8/2014 | Schmid |
| 2014/0228867 A1 | 8/2014 | Thomas et al. |
| 2014/0230595 A1 | 8/2014 | Butt et al. |
| 2014/0232316 A1 | 8/2014 | Philipp |
| 2014/0238184 A1 | 8/2014 | Leimbach et al. |
| 2014/0239036 A1 | 8/2014 | Zerkle et al. |
| 2014/0239038 A1 | 8/2014 | Leimbach et al. |
| 2014/0243865 A1 | 8/2014 | Swayze et al. |
| 2014/0246472 A1 | 9/2014 | Kimsey et al. |
| 2014/0246475 A1 | 9/2014 | Hall et al. |
| 2014/0248167 A1 | 9/2014 | Sugimoto et al. |
| 2014/0249557 A1 | 9/2014 | Koch, Jr. et al. |
| 2014/0249573 A1 | 9/2014 | Arav |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263541 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263572 A1 | 9/2014 | Shelton, IV et al. |
| 2014/0276730 A1 | 9/2014 | Boudreaux et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0288460 A1 | 9/2014 | Ouyang et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |

(56) References Cited

U.S. PATENT DOCUMENTS

| | | |
|---|---|---|
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0303660 A1 | 10/2014 | Boyden et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2014/0367447 A1 | 12/2014 | Woodard, Jr. et al. |
| 2014/0374130 A1 | 12/2014 | Nakamura et al. |
| 2014/0374465 A1 * | 12/2014 | Cole ................ A61B 17/07292 227/177.1 |
| 2014/0378950 A1 | 12/2014 | Chiu |
| 2015/0002089 A1 | 1/2015 | Rejman et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0122870 A1 | 5/2015 | Zemlok et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0148830 A1 | 5/2015 | Stulen et al. |
| 2015/0150554 A1 | 6/2015 | Soltz |
| 2015/0150620 A1 | 6/2015 | Miyamoto et al. |
| 2015/0157354 A1 | 6/2015 | Bales, Jr. et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0209041 A1 | 7/2015 | Milliman et al. |
| 2015/0222212 A1 | 8/2015 | Iwata |
| 2015/0223809 A1 | 8/2015 | Scheib et al. |
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0239180 A1 | 8/2015 | Schellin et al. |
| 2015/0245835 A1 | 9/2015 | Racenet et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272575 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297200 A1 | 10/2015 | Fitzsimmons et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |

(56) References Cited

U.S. PATENT DOCUMENTS

| | | |
|---|---|---|
| 2015/0297236 A1 | 10/2015 | Harris et al. |
| 2015/0303417 A1 | 10/2015 | Koeder et al. |
| 2015/0305729 A1 | 10/2015 | Fitzsimmons et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0324317 A1 | 11/2015 | Collins et al. |
| 2015/0327853 A1 | 11/2015 | Aronhalt et al. |
| 2015/0327864 A1 | 11/2015 | Hodgkinson et al. |
| 2015/0335328 A1 | 11/2015 | Shelton, IV et al. |
| 2015/0335329 A1 | 11/2015 | Shelton, IV et al. |
| 2015/0336249 A1 | 11/2015 | Iwata et al. |
| 2015/0342606 A1 | 12/2015 | Schmid et al. |
| 2015/0342607 A1 | 12/2015 | Shelton, IV et al. |
| 2015/0351758 A1 | 12/2015 | Shelton, IV et al. |
| 2015/0351762 A1 | 12/2015 | Vendely et al. |
| 2015/0352699 A1 | 12/2015 | Sakai et al. |
| 2015/0359536 A1 | 12/2015 | Cropper et al. |
| 2015/0372265 A1 | 12/2015 | Morisaku et al. |
| 2015/0374360 A1 | 12/2015 | Scheib et al. |
| 2015/0374361 A1 | 12/2015 | Gettinger et al. |
| 2015/0374363 A1 | 12/2015 | Laurent, IV et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374371 A1 | 12/2015 | Richard et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2015/0380187 A1 | 12/2015 | Zergiebel et al. |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |
| 2016/0023342 A1 | 1/2016 | Koenig et al. |
| 2016/0030042 A1 | 2/2016 | Heinrich et al. |
| 2016/0030103 A1 | 2/2016 | Manwaring et al. |
| 2016/0051257 A1 | 2/2016 | Shelton, IV et al. |
| 2016/0058443 A1 | 3/2016 | Yates et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066915 A1 | 3/2016 | Baber et al. |
| 2016/0069449 A1 | 3/2016 | Kanai et al. |
| 2016/0073909 A1 | 3/2016 | Zand et al. |
| 2016/0074038 A1 | 3/2016 | Leimbach et al. |
| 2016/0074040 A1 | 3/2016 | Widenhouse et al. |
| 2016/0082161 A1 | 3/2016 | Zilberman et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089147 A1 | 3/2016 | Harris et al. |
| 2016/0089148 A1 | 3/2016 | Harris et al. |
| 2016/0089149 A1 | 3/2016 | Harris et al. |
| 2016/0089198 A1 | 3/2016 | Arya et al. |
| 2016/0095585 A1 | 4/2016 | Zergiebel et al. |
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120547 A1 | 5/2016 | Schmid et al. |
| 2016/0128694 A1 | 5/2016 | Baxter, III et al. |
| 2016/0135812 A1 | 5/2016 | Shelton, IV et al. |
| 2016/0166256 A1 | 6/2016 | Baxter, III et al. |
| 2016/0166308 A1 | 6/2016 | Manwaring et al. |
| 2016/0174969 A1 | 6/2016 | Kerr et al. |
| 2016/0174970 A1 | 6/2016 | Shelton, IV et al. |
| 2016/0174971 A1 | 6/2016 | Baxter, III et al. |
| 2016/0174972 A1 | 6/2016 | Shelton, IV et al. |
| 2016/0174973 A1 | 6/2016 | Shelton, IV et al. |
| 2016/0174974 A1 | 6/2016 | Schmid et al. |
| 2016/0174975 A1 | 6/2016 | Shelton, IV et al. |
| 2016/0174976 A1 | 6/2016 | Morgan et al. |
| 2016/0174983 A1 | 6/2016 | Shelton, IV et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0183947 A1 | 6/2016 | Shelton, IV et al. |
| 2016/0183948 A1 | 6/2016 | Shelton, IV et al. |
| 2016/0183950 A1 | 6/2016 | Shelton, IV et al. |
| 2016/0184039 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192977 A1 | 7/2016 | Manwaring et al. |
| 2016/0192996 A1 | 7/2016 | Spivey et al. |
| 2016/0192997 A1 | 7/2016 | Spivey et al. |
| 2016/0193673 A1 | 7/2016 | Yoshida et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199088 A1 | 7/2016 | Shelton, IV et al. |
| 2016/0199089 A1 | 7/2016 | Hess et al. |
| 2016/0199956 A1 | 7/2016 | Shelton, IV et al. |
| 2016/0206309 A1 | 7/2016 | Hess et al. |
| 2016/0206310 A1 | 7/2016 | Shelton, IV |
| 2016/0206314 A1 | 7/2016 | Scheib et al. |
| 2016/0220246 A1 | 8/2016 | Timm et al. |
| 2016/0220247 A1 | 8/2016 | Timm et al. |
| 2016/0220248 A1 | 8/2016 | Timm et al. |
| 2016/0220249 A1 | 8/2016 | Shelton, IV et al. |
| 2016/0220254 A1 | 8/2016 | Baxter, III et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0238108 A1 | 8/2016 | Kanai et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242780 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249908 A1 | 9/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |

(56) References Cited

U.S. PATENT DOCUMENTS

| | | |
|---|---|---|
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249919 A1 | 9/2016 | Savage et al. |
| 2016/0249922 A1 | 9/2016 | Morgan et al. |
| 2016/0249927 A1 | 9/2016 | Beckman et al. |
| 2016/0249930 A1 | 9/2016 | Hall et al. |
| 2016/0249945 A1 | 9/2016 | Shelton, IV et al. |
| 2016/0256071 A1 | 9/2016 | Shelton, IV et al. |
| 2016/0256153 A1 | 9/2016 | Shelton, IV et al. |
| 2016/0256154 A1 | 9/2016 | Shelton, IV et al. |
| 2016/0256155 A1 | 9/2016 | Shelton, IV et al. |
| 2016/0256156 A1 | 9/2016 | Shelton, IV et al. |
| 2016/0256159 A1 | 9/2016 | Pinjala et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256186 A1 | 9/2016 | Shelton, IV et al. |
| 2016/0256187 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0262760 A1 | 9/2016 | Shelton, IV et al. |
| 2016/0270780 A1 | 9/2016 | Hall et al. |
| 2016/0278765 A1 | 9/2016 | Shelton, IV et al. |
| 2016/0278775 A1 | 9/2016 | Shelton, IV et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0287254 A1 | 10/2016 | Baxter, III et al. |
| 2016/0310143 A1 | 10/2016 | Bettuchi |
| 2016/0331375 A1 | 11/2016 | Shelton, IV et al. |
| 2016/0345976 A1 | 12/2016 | Gonzalez et al. |
| 2016/0346034 A1 | 12/2016 | Arya et al. |
| 2016/0354085 A1 | 12/2016 | Shelton, IV et al. |
| 2016/0367122 A1 | 12/2016 | Ichimura et al. |
| 2016/0367245 A1 | 12/2016 | Wise et al. |
| 2016/0367246 A1 | 12/2016 | Baxter, III et al. |
| 2016/0367247 A1 | 12/2016 | Weaner et al. |
| 2016/0367254 A1 | 12/2016 | Baxter, III et al. |
| 2016/0367255 A1 | 12/2016 | Wise et al. |
| 2016/0367256 A1 | 12/2016 | Hensel et al. |
| 2016/0374675 A1 | 12/2016 | Shelton, IV et al. |
| 2017/0000485 A1 | 1/2017 | Shelton, IV et al. |
| 2017/0007236 A1 | 1/2017 | Shelton, IV et al. |
| 2017/0007237 A1 | 1/2017 | Yates et al. |
| 2017/0007238 A1 | 1/2017 | Yates et al. |
| 2017/0007239 A1 | 1/2017 | Shelton, IV |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007244 A1 | 1/2017 | Shelton, IV et al. |
| 2017/0007245 A1 | 1/2017 | Shelton, IV et al. |
| 2017/0007246 A1 | 1/2017 | Shelton, IV et al. |
| 2017/0007247 A1 | 1/2017 | Shelton, IV et al. |
| 2017/0007248 A1 | 1/2017 | Shelton, IV et al. |
| 2017/0007249 A1 | 1/2017 | Shelton, IV et al. |
| 2017/0007250 A1 | 1/2017 | Shelton, IV et al. |
| 2017/0007251 A1 | 1/2017 | Yates et al. |
| 2017/0007254 A1 | 1/2017 | Jaworek et al. |
| 2017/0007255 A1 | 1/2017 | Jaworek et al. |
| 2017/0007338 A1 | 1/2017 | Swensgard et al. |
| 2017/0007340 A1 | 1/2017 | Swensgard et al. |
| 2017/0007341 A1 | 1/2017 | Swensgard et al. |
| 2017/0007347 A1 | 1/2017 | Jaworek et al. |
| 2017/0014125 A1 | 1/2017 | Shelton, IV et al. |
| 2017/0014129 A1 | 1/2017 | Shelton, IV et al. |
| 2017/0049444 A1 | 2/2017 | Schellin et al. |
| 2017/0049447 A1 | 2/2017 | Barton et al. |
| 2017/0049448 A1 | 2/2017 | Widenhouse et al. |
| 2017/0055986 A1 | 3/2017 | Harris et al. |
| 2017/0055989 A1 | 3/2017 | Shelton, IV et al. |
| 2017/0055996 A1 | 3/2017 | Baxter, III et al. |
| 2017/0055997 A1 | 3/2017 | Swayze et al. |
| 2017/0055998 A1 | 3/2017 | Baxter, III et al. |
| 2017/0055999 A1 | 3/2017 | Baxter, III et al. |
| 2017/0056000 A1 | 3/2017 | Nalagatla et al. |
| 2017/0056001 A1 | 3/2017 | Shelton, IV et al. |
| 2017/0056002 A1 | 3/2017 | Nalagatla et al. |
| 2017/0056004 A1 | 3/2017 | Shelton, IV et al. |
| 2017/0056005 A1 | 3/2017 | Shelton, IV et al. |
| 2017/0056006 A1 | 3/2017 | Shelton, IV et al. |
| 2017/0056007 A1 | 3/2017 | Eckert et al. |
| 2017/0079640 A1 | 3/2017 | Overmyer et al. |
| 2017/0079642 A1 | 3/2017 | Overmyer et al. |
| 2017/0079643 A1 | 3/2017 | Yates et al. |
| 2017/0079644 A1 | 3/2017 | Overmyer et al. |
| 2017/0079647 A1 | 3/2017 | Yates et al. |
| 2017/0086823 A1 | 3/2017 | Leimbach et al. |
| 2017/0086827 A1 | 3/2017 | Vendely et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086832 A1 | 3/2017 | Harris et al. |
| 2017/0086835 A1 | 3/2017 | Harris et al. |
| 2017/0086836 A1 | 3/2017 | Harris et al. |
| 2017/0086837 A1 | 3/2017 | Vendely et al. |
| 2017/0086838 A1 | 3/2017 | Harris et al. |
| 2017/0086839 A1 | 3/2017 | Vendely et al. |
| 2017/0086840 A1 | 3/2017 | Harris et al. |
| 2017/0086841 A1 | 3/2017 | Vendely et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0086845 A1 | 3/2017 | Vendely et al. |
| 2017/0086936 A1 | 3/2017 | Shelton, IV et al. |
| 2017/0119390 A1 | 5/2017 | Schellin et al. |
| 2017/0119397 A1 | 5/2017 | Harris et al. |
| 2017/0128149 A1 | 5/2017 | Heinrich et al. |
| 2017/0135695 A1 | 5/2017 | Shelton, IV et al. |
| 2017/0135697 A1 | 5/2017 | Mozdzierz et al. |
| 2017/0150983 A1 | 6/2017 | Ingmanson et al. |
| 2017/0172672 A1 | 6/2017 | Bailey et al. |
| 2017/0182211 A1 | 6/2017 | Raxworthy et al. |
| 2017/0189018 A1 | 7/2017 | Harris et al. |
| 2017/0189019 A1 | 7/2017 | Harris et al. |
| 2017/0189020 A1 | 7/2017 | Harris et al. |
| 2017/0196558 A1 | 7/2017 | Morgan et al. |
| 2017/0196560 A1 | 7/2017 | Leimbach et al. |
| 2017/0196561 A1 | 7/2017 | Shelton, IV et al. |
| 2017/0196562 A1 | 7/2017 | Shelton, IV et al. |
| 2017/0196637 A1 | 7/2017 | Shelton, IV et al. |
| 2017/0196649 A1 | 7/2017 | Yates et al. |
| 2017/0202596 A1 | 7/2017 | Shelton, IV et al. |
| 2017/0209145 A1 | 7/2017 | Swayze et al. |
| 2017/0209146 A1 | 7/2017 | Yates et al. |
| 2017/0209226 A1 | 7/2017 | Overmyer et al. |
| 2017/0215881 A1 | 8/2017 | Shelton, IV et al. |
| 2017/0224330 A1 | 8/2017 | Worthington et al. |
| 2017/0224331 A1 | 8/2017 | Worthington et al. |
| 2017/0224332 A1 | 8/2017 | Hunter et al. |
| 2017/0224333 A1 | 8/2017 | Hunter et al. |
| 2017/0224334 A1 | 8/2017 | Worthington et al. |
| 2017/0224335 A1 | 8/2017 | Weaner et al. |
| 2017/0224336 A1 | 8/2017 | Hunter et al. |
| 2017/0224339 A1 | 8/2017 | Huang et al. |
| 2017/0224342 A1 | 8/2017 | Worthington et al. |
| 2017/0224343 A1 | 8/2017 | Baxter, III et al. |
| 2017/0231623 A1 | 8/2017 | Shelton, IV et al. |
| 2017/0231626 A1 | 8/2017 | Shelton, IV et al. |
| 2017/0231627 A1 | 8/2017 | Shelton, IV et al. |
| 2017/0231628 A1 | 8/2017 | Shelton, IV et al. |
| 2017/0238928 A1 | 8/2017 | Morgan et al. |
| 2017/0238929 A1 | 8/2017 | Yates et al. |
| 2017/0245952 A1 | 8/2017 | Shelton, IV et al. |
| 2017/0245953 A1 | 8/2017 | Shelton, IV et al. |
| 2017/0249431 A1 | 8/2017 | Shelton, IV et al. |
| 2017/0258469 A1 | 9/2017 | Shelton, IV et al. |
| 2017/0265856 A1 | 9/2017 | Shelton, IV et al. |
| 2017/0281167 A1 | 10/2017 | Shelton, IV et al. |

(56) References Cited

U.S. PATENT DOCUMENTS

| | | |
|---|---|---|
| 2017/0281180 A1 | 10/2017 | Morgan et al. |
| 2017/0290585 A1 | 10/2017 | Shelton, IV et al. |
| 2017/0296169 A1 | 10/2017 | Yates et al. |
| 2017/0296170 A1 | 10/2017 | Shelton, IV et al. |
| 2017/0296171 A1 | 10/2017 | Shelton, IV et al. |
| 2017/0296172 A1 | 10/2017 | Harris et al. |
| 2017/0296173 A1 | 10/2017 | Shelton, IV et al. |
| 2017/0296177 A1 | 10/2017 | Harris et al. |
| 2017/0296178 A1 | 10/2017 | Miller et al. |
| 2017/0296179 A1 | 10/2017 | Shelton, IV et al. |
| 2017/0296180 A1 | 10/2017 | Harris et al. |
| 2017/0296183 A1 | 10/2017 | Shelton, IV et al. |
| 2017/0296184 A1 | 10/2017 | Harris et al. |
| 2017/0296185 A1 | 10/2017 | Swensgard et al. |
| 2017/0296189 A1 | 10/2017 | Vendely et al. |
| 2017/0296190 A1 | 10/2017 | Aronhalt et al. |
| 2017/0296191 A1 | 10/2017 | Shelton, IV et al. |
| 2017/0296213 A1 | 10/2017 | Swensgard et al. |
| 2017/0311944 A1 | 11/2017 | Morgan et al. |
| 2017/0311949 A1 | 11/2017 | Shelton, IV |
| 2017/0311950 A1 | 11/2017 | Shelton, IV et al. |
| 2017/0312040 A1 | 11/2017 | Giordano et al. |
| 2017/0312041 A1 | 11/2017 | Giordano et al. |
| 2017/0312042 A1 | 11/2017 | Giordano et al. |
| 2017/0319201 A1 | 11/2017 | Morgan et al. |
| 2017/0319207 A1 | 11/2017 | Shelton, IV et al. |
| 2017/0319209 A1 | 11/2017 | Morgan et al. |
| 2017/0319777 A1 | 11/2017 | Shelton, IV et al. |
| 2017/0333034 A1 | 11/2017 | Morgan et al. |
| 2017/0333035 A1 | 11/2017 | Morgan et al. |
| 2017/0333070 A1 | 11/2017 | Laurent et al. |
| 2017/0348043 A1 | 12/2017 | Wang et al. |
| 2017/0354415 A1 | 12/2017 | Casasanta, Jr. et al. |
| 2017/0360442 A1 | 12/2017 | Shelton, IV et al. |
| 2017/0367700 A1 | 12/2017 | Leimbach et al. |
| 2017/0367991 A1 | 12/2017 | Widenhouse et al. |
| 2018/0000483 A1 | 1/2018 | Leimbach et al. |
| 2018/0000545 A1 | 1/2018 | Giordano et al. |
| 2018/0008269 A1 | 1/2018 | Moore et al. |
| 2018/0008270 A1 | 1/2018 | Moore et al. |
| 2018/0008271 A1 | 1/2018 | Moore et al. |
| 2018/0008356 A1 | 1/2018 | Giordano et al. |
| 2018/0008357 A1 | 1/2018 | Giordano et al. |
| 2018/0028184 A1 | 2/2018 | Shelton, IV et al. |
| 2018/0028185 A1 | 2/2018 | Shelton, IV et al. |
| 2018/0042611 A1 | 2/2018 | Swayze et al. |
| 2018/0049824 A1 | 2/2018 | Harris et al. |
| 2018/0049883 A1 | 2/2018 | Moskowitz et al. |
| 2018/0055510 A1 | 3/2018 | Schmid et al. |
| 2018/0055513 A1 | 3/2018 | Shelton, IV et al. |
| 2018/0055524 A1 | 3/2018 | Shelton, IV et al. |
| 2018/0055525 A1 | 3/2018 | Shelton, IV et al. |
| 2018/0055526 A1 | 3/2018 | Shelton, IV et al. |
| 2018/0064437 A1 | 3/2018 | Yates et al. |
| 2018/0064440 A1 | 3/2018 | Shelton, IV et al. |
| 2018/0064441 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070939 A1 | 3/2018 | Giordano et al. |
| 2018/0070942 A1 | 3/2018 | Shelton, IV et al. |
| 2018/0070946 A1 | 3/2018 | Shelton, IV et al. |
| 2018/0074535 A1 | 3/2018 | Shelton, IV et al. |
| 2018/0078248 A1 | 3/2018 | Swayze et al. |
| 2018/0085116 A1 | 3/2018 | Yates et al. |
| 2018/0085117 A1 | 3/2018 | Shelton, IV et al. |
| 2018/0085123 A1 | 3/2018 | Shelton, IV et al. |
| 2018/0095487 A1 | 4/2018 | Leimbach et al. |
| 2018/0103952 A1 | 4/2018 | Aronhalt et al. |
| 2018/0103953 A1 | 4/2018 | Shelton, IV et al. |
| 2018/0103955 A1 | 4/2018 | Shelton, IV et al. |
| 2018/0110516 A1 | 4/2018 | Baxter, III et al. |
| 2018/0110518 A1 | 4/2018 | Overmyer et al. |
| 2018/0110519 A1 | 4/2018 | Lytle, IV et al. |
| 2018/0110520 A1 | 4/2018 | Shelton, IV et al. |
| 2018/0110521 A1 | 4/2018 | Shelton, IV et al. |
| 2018/0110522 A1 | 4/2018 | Shelton, IV et al. |
| 2018/0110523 A1 | 4/2018 | Shelton, IV |
| 2018/0110574 A1 | 4/2018 | Shelton, IV et al. |
| 2018/0110575 A1 | 4/2018 | Shelton, IV et al. |
| 2018/0116658 A1 | 5/2018 | Aronhalt, IV et al. |
| 2018/0116662 A1 | 5/2018 | Shelton, IV et al. |
| 2018/0116665 A1 | 5/2018 | Hall et al. |
| 2018/0125481 A1 | 5/2018 | Yates et al. |
| 2018/0125488 A1 | 5/2018 | Morgan et al. |
| 2018/0125489 A1 | 5/2018 | Leimbach et al. |
| 2018/0125590 A1 | 5/2018 | Giordano et al. |
| 2018/0126504 A1 | 5/2018 | Shelton, IV et al. |
| 2018/0132845 A1 | 5/2018 | Schmid et al. |
| 2018/0132850 A1 | 5/2018 | Leimbach et al. |
| 2018/0132851 A1 | 5/2018 | Hall et al. |
| 2018/0132952 A1 | 5/2018 | Spivey et al. |
| 2018/0133856 A1 | 5/2018 | Shelton, IV et al. |
| 2018/0140299 A1 | 5/2018 | Weaner et al. |
| 2018/0140368 A1 | 5/2018 | Shelton, IV et al. |
| 2018/0146960 A1 | 5/2018 | Shelton, IV et al. |
| 2018/0153542 A1 | 6/2018 | Shelton, IV et al. |
| 2018/0161034 A1 | 6/2018 | Scheib et al. |
| 2018/0168575 A1 | 6/2018 | Simms et al. |
| 2018/0168576 A1 | 6/2018 | Hunter et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168580 A1 | 6/2018 | Hunter et al. |
| 2018/0168581 A1 | 6/2018 | Hunter et al. |
| 2018/0168582 A1 | 6/2018 | Swayze et al. |
| 2018/0168583 A1 | 6/2018 | Hunter et al. |
| 2018/0168584 A1 | 6/2018 | Harris et al. |
| 2018/0168589 A1 | 6/2018 | Swayze et al. |
| 2018/0168590 A1 | 6/2018 | Overmyer et al. |
| 2018/0168591 A1 | 6/2018 | Swayze et al. |
| 2018/0168592 A1 | 6/2018 | Overmyer et al. |
| 2018/0168593 A1 | 6/2018 | Overmyer et al. |
| 2018/0168594 A1 | 6/2018 | Shelton, IV et al. |
| 2018/0168595 A1 | 6/2018 | Overmyer et al. |
| 2018/0168596 A1 | 6/2018 | Beckman et al. |
| 2018/0168597 A1 | 6/2018 | Fanelli et al. |
| 2018/0168598 A1 | 6/2018 | Shelton, IV et al. |
| 2018/0168599 A1 | 6/2018 | Bakos et al. |
| 2018/0168600 A1 | 6/2018 | Shelton, IV et al. |
| 2018/0168601 A1 | 6/2018 | Bakos et al. |
| 2018/0168602 A1 | 6/2018 | Bakos et al. |
| 2018/0168603 A1 | 6/2018 | Morgan et al. |
| 2018/0168604 A1 | 6/2018 | Shelton, IV et al. |
| 2018/0168605 A1 | 6/2018 | Baber et al. |
| 2018/0168606 A1 | 6/2018 | Shelton, IV et al. |
| 2018/0168607 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168611 A1 | 6/2018 | Shelton, IV et al. |
| 2018/0168612 A1 | 6/2018 | Shelton, IV et al. |
| 2018/0168613 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168620 A1 | 6/2018 | Huang et al. |
| 2018/0168621 A1 | 6/2018 | Shelton, IV et al. |
| 2018/0168622 A1 | 6/2018 | Shelton, IV et al. |
| 2018/0168623 A1 | 6/2018 | Simms et al. |
| 2018/0168624 A1 | 6/2018 | Shelton, IV et al. |
| 2018/0168625 A1 | 6/2018 | Posada et al. |
| 2018/0168626 A1 | 6/2018 | Shelton, IV et al. |
| 2018/0168627 A1 | 6/2018 | Weaner et al. |
| 2018/0168628 A1 | 6/2018 | Hunter et al. |
| 2018/0168629 A1 | 6/2018 | Shelton, IV et al. |
| 2018/0168630 A1 | 6/2018 | Shelton, IV et al. |
| 2018/0168631 A1 | 6/2018 | Harris et al. |
| 2018/0168632 A1 | 6/2018 | Harris et al. |
| 2018/0168633 A1 | 6/2018 | Shelton, IV et al. |
| 2018/0168634 A1 | 6/2018 | Harris et al. |
| 2018/0168635 A1 | 6/2018 | Shelton, IV et al. |
| 2018/0168636 A1 | 6/2018 | Shelton, IV et al. |
| 2018/0168637 A1 | 6/2018 | Harris et al. |

(56) References Cited

U.S. PATENT DOCUMENTS

| | | |
|---|---|---|
| 2018/0168638 A1 | 6/2018 | Harris et al. |
| 2018/0168639 A1 | 6/2018 | Shelton, IV et al. |
| 2018/0168640 A1 | 6/2018 | Shelton, IV et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168645 A1 | 6/2018 | Shelton, IV et al. |
| 2018/0168646 A1 | 6/2018 | Shelton, IV et al. |
| 2018/0168649 A1 | 6/2018 | Shelton, IV et al. |
| 2018/0168651 A1 | 6/2018 | Shelton, IV et al. |
| 2018/0199940 A1 | 7/2018 | Zergiebel et al. |
| 2018/0206843 A1 | 7/2018 | Yates et al. |
| 2018/0206906 A1 | 7/2018 | Moua et al. |
| 2018/0214147 A1 | 8/2018 | Merchant et al. |
| 2018/0221046 A1 | 8/2018 | Demmy et al. |
| 2018/0221050 A1 | 8/2018 | Kostrzewski et al. |
| 2018/0228490 A1 | 8/2018 | Richard et al. |
| 2018/0250001 A1 | 9/2018 | Aronhalt et al. |
| 2018/0256184 A1 | 9/2018 | Shelton, IV et al. |
| 2018/0256185 A1 | 9/2018 | Shelton, IV et al. |
| 2018/0271520 A1 | 9/2018 | Shelton, IV et al. |
| 2018/0280020 A1 | 10/2018 | Hess et al. |
| 2018/0280021 A1 | 10/2018 | Timm et al. |
| 2018/0280022 A1 | 10/2018 | Timm et al. |
| 2018/0280023 A1 | 10/2018 | Timm et al. |

FOREIGN PATENT DOCUMENTS

| | | | | |
|---|---|---|---|---|
| AU | 2011218702 B2 | 6/2013 | | |
| AU | 2012200178 B2 | 7/2013 | | |
| CA | 1015829 A | 8/1977 | | |
| CA | 1125615 A | 6/1982 | | |
| CA | 2458946 A1 | 3/2003 | | |
| CA | 2477181 A1 | 4/2004 | | |
| CA | 2512960 A1 | 1/2006 | | |
| CA | 2514274 A1 | 1/2006 | | |
| CA | 2639177 A1 | 2/2009 | | |
| CA | 2576347 C | 8/2015 | | |
| CN | 86100996 A | 9/1986 | | |
| CN | 1163558 A | 10/1997 | | |
| CN | 2488482 Y | 5/2002 | | |
| CN | 1424891 A | 6/2003 | | |
| CN | 1523725 A | 8/2004 | | |
| CN | 1545154 A | 11/2004 | | |
| CN | 1634601 A | 7/2005 | | |
| CN | 1636525 A | 7/2005 | | |
| CN | 1636526 A | 7/2005 | | |
| CN | 2716900 Y | 8/2005 | | |
| CN | 2738962 Y | 11/2005 | | |
| CN | 1726874 A | 2/2006 | | |
| CN | 1726878 A | 2/2006 | | |
| CN | 1868411 A | 11/2006 | | |
| CN | 1915180 A | 2/2007 | | |
| CN | 2868212 Y | 2/2007 | | |
| CN | 1960679 A | 5/2007 | | |
| CN | 101011286 A | 8/2007 | | |
| CN | 200942099 Y | 9/2007 | | |
| CN | 101073509 A | 11/2007 | | |
| CN | 200991269 Y | * 12/2007 | ......... | A61B 17/1155 |
| CN | 101095621 A | 1/2008 | | |
| CN | 101111196 A | 1/2008 | | |
| CN | 201001747 Y | 1/2008 | | |
| CN | 101137402 A | 3/2008 | | |
| CN | 101143105 A | 3/2008 | | |
| CN | 201029899 Y | 3/2008 | | |
| CN | 101224122 A | 7/2008 | | |
| CN | 101224124 A | 7/2008 | | |
| CN | 101254126 A | 9/2008 | | |
| CN | 101507620 A | 8/2009 | | |
| CN | 101507622 A | 8/2009 | | |
| CN | 101507623 A | 8/2009 | | |
| CN | 101507625 A | 8/2009 | | |
| CN | 101507628 A | 8/2009 | | |
| CN | 101534724 A | 9/2009 | | |
| CN | 101541251 A | 9/2009 | | |
| CN | 101626731 A | 1/2010 | | |
| CN | 101669833 A | 3/2010 | | |
| CN | 101675898 A | 3/2010 | | |
| CN | 101683280 A | 3/2010 | | |
| CN | 101721236 A | 6/2010 | | |
| CN | 101801284 A | 8/2010 | | |
| CN | 101828940 A | 9/2010 | | |
| CN | 101868203 A | 10/2010 | | |
| CN | 101873834 A | 10/2010 | | |
| CN | 101912285 A | 12/2010 | | |
| CN | 101028205 B | 1/2011 | | |
| CN | 101933824 A | 1/2011 | | |
| CN | 201719298 U | 1/2011 | | |
| CN | 101934098 A | 5/2011 | | |
| CN | 102038531 A | 5/2011 | | |
| CN | 102038532 A | 5/2011 | | |
| CN | 101534722 B | 6/2011 | | |
| CN | 201879759 U | 6/2011 | | |
| CN | 101361666 B | 8/2011 | | |
| CN | 201949071 U | 8/2011 | | |
| CN | 101224119 B | 9/2011 | | |
| CN | 101336835 B | 9/2011 | | |
| CN | 102188270 A | 9/2011 | | |
| CN | 101779977 B | 12/2011 | | |
| CN | 101534723 B | 1/2012 | | |
| CN | 101310680 B | 4/2012 | | |
| CN | 101912284 B | 7/2012 | | |
| CN | 202397539 U | 8/2012 | | |
| CN | 202426586 U | 9/2012 | | |
| CN | 101317782 B | 10/2012 | | |
| CN | 202489990 U | 10/2012 | | |
| CN | 101507639 B | 11/2012 | | |
| CN | 102835977 A | 12/2012 | | |
| CN | 101507633 B | 2/2013 | | |
| CN | 101023879 B | 3/2013 | | |
| CN | 101507624 A | 3/2013 | | |
| CN | 101327137 B | 6/2013 | | |
| CN | 101401736 B | 6/2013 | | |
| CN | 101332110 B | 7/2013 | | |
| CN | 101683281 B | 1/2014 | | |
| CN | 103648408 A | 3/2014 | | |
| CN | 203564285 U | 4/2014 | | |
| CN | 203564287 U | 4/2014 | | |
| CN | 203597997 U | 5/2014 | | |
| CN | 103829983 A | 6/2014 | | |
| CN | 103908313 A | * 7/2014 | ........... | A61B 17/072 |
| CN | 203736251 U | 7/2014 | | |
| CN | 102783741 B | 10/2014 | | |
| CN | 102973300 B | 10/2014 | | |
| CN | 102793571 B | 12/2014 | | |
| CN | 104337556 A | 2/2015 | | |
| CN | 102166129 B | 3/2015 | | |
| CN | 102469995 B | 3/2015 | | |
| CN | 102113902 B | 4/2015 | | |
| CN | 102247177 B | 2/2016 | | |
| CN | 103750872 B | 5/2016 | | |
| DE | 273689 C | 5/1914 | | |
| DE | 1775926 A | 1/1972 | | |
| DE | 3036217 A1 | 4/1982 | | |
| DE | 3212828 A1 | 11/1982 | | |
| DE | 3210466 A1 | 9/1983 | | |
| DE | 3709067 A1 | 9/1988 | | |
| DE | 4228909 A1 | 3/1994 | | |
| DE | 9412228 U1 | 9/1994 | | |
| DE | 19509116 A1 | 9/1996 | | |
| DE | 19534043 A1 | 3/1997 | | |
| DE | 19707373 C1 | 2/1998 | | |
| DE | 19851291 A1 | 1/2000 | | |
| DE | 19924311 A1 | 11/2000 | | |
| DE | 69328576 T2 | 1/2001 | | |
| DE | 20016423 U1 | 2/2001 | | |
| DE | 19941859 A1 | 3/2001 | | |
| DE | 10052679 A1 | 5/2001 | | |
| DE | 20112837 U1 | 10/2001 | | |
| DE | 20121753 U1 | 4/2003 | | |
| DE | 10314827 B3 | 4/2004 | | |
| DE | 10314072 A1 | 10/2004 | | |
| DE | 202004012389 U1 | 11/2004 | | |
| DE | 202007003114 U1 | 6/2007 | | |

(56) References Cited

FOREIGN PATENT DOCUMENTS

| | | |
|---|---|---|
| DE | 102010013150 A1 | 9/2011 |
| EP | 0000756 A1 | 2/1979 |
| EP | 0033633 A2 | 8/1981 |
| EP | 0122046 A1 | 10/1984 |
| EP | 0070230 B1 | 10/1985 |
| EP | 0156774 A2 | 10/1985 |
| EP | 0072754 B1 | 4/1986 |
| EP | 0033548 B1 | 5/1986 |
| EP | 0077262 B1 | 8/1986 |
| EP | 0189807 A2 | 8/1986 |
| EP | 0212278 A2 | 3/1987 |
| EP | 0129442 B1 | 11/1987 |
| EP | 0255631 A1 | 2/1988 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0541950 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0623311 A2 | 11/1994 |
| EP | 0630612 A1 | 12/1994 |
| EP | 0630614 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0387980 B1 | 10/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0686374 A2 | 12/1995 |
| EP | 0364216 B1 | 1/1996 |
| EP | 0699418 A1 | 3/1996 |
| EP | 0702937 A1 | 3/1996 |
| EP | 0488768 B1 | 4/1996 |
| EP | 0705571 A1 | 4/1996 |
| EP | 0528478 B1 | 5/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0623312 B1 | 9/1997 |
| EP | 0621006 B1 | 10/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 B1 | 9/1999 |
| EP | 0843906 B1 | 3/2000 |
| EP | 0552050 B1 | 5/2000 |
| EP | 0833592 B1 | 5/2000 |
| EP | 0832605 B1 | 6/2000 |
| EP | 0830094 B1 | 9/2000 |
| EP | 1034747 A1 | 9/2000 |
| EP | 1034748 A1 | 9/2000 |
| EP | 0726632 B1 | 10/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 0768840 B1 | 12/2001 |
| EP | 0908152 B1 | 1/2002 |
| EP | 0717959 B1 | 2/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 B1 | 2/2003 |
| EP | 1284120 A1 | 2/2003 |
| EP | 1287788 A1 | 3/2003 |
| EP | 0717966 B1 | 4/2003 |
| EP | 0717967 B1 | 5/2003 |
| EP | 0869742 B1 | 5/2003 |
| EP | 0829235 B1 | 6/2003 |
| EP | 0887046 B1 | 7/2003 |
| EP | 1323384 A2 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1411626 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |

(56) References Cited

FOREIGN PATENT DOCUMENTS

| | | | |
|---|---|---|---|
| EP | 1453432 | A2 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1496805 | A2 | 1/2005 |
| EP | 1256318 | B1 | 2/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880333 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |
| EP | 1621141 | A2 | 2/2006 |
| EP | 1621143 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1676539 | A1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1723914 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1791473 | A2 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1806103 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1974678 | A2 | 10/2008 |
| EP | 1980213 | A2 | 10/2008 |
| EP | 1980214 | A2 | 10/2008 |
| EP | 1759645 | B1 | 11/2008 |
| EP | 1987780 | A2 | 11/2008 |
| EP | 1990014 | A2 | 11/2008 |
| EP | 1992296 | A1 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000101 | A2 | 12/2008 |
| EP | 2000102 | A2 | 12/2008 |
| EP | 2005894 | A2 | 12/2008 |
| EP | 2005897 | A2 | 12/2008 |
| EP | 2005901 | A1 | 12/2008 |
| EP | 2008595 | A2 | 12/2008 |
| EP | 2025293 | A1 | 2/2009 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |

(56) References Cited

FOREIGN PATENT DOCUMENTS

| | | | |
|---|---|---|---|
| EP | 2090231 | A1 | 8/2009 |
| EP | 2090237 | A1 | 8/2009 |
| EP | 2090241 | A1 | 8/2009 |
| EP | 2090244 | B1 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2100562 | A2 | 9/2009 |
| EP | 2110082 | A1 | 10/2009 |
| EP | 2110084 | A2 | 10/2009 |
| EP | 2111803 | A2 | 10/2009 |
| EP | 1762190 | B8 | 11/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165654 | A1 | 3/2010 |
| EP | 2165656 | A2 | 3/2010 |
| EP | 2165660 | A2 | 3/2010 |
| EP | 2165663 | A2 | 3/2010 |
| EP | 2165664 | A2 | 3/2010 |
| EP | 1566150 | B1 | 4/2010 |
| EP | 1813206 | B1 | 4/2010 |
| EP | 2184014 | A2 | 5/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 2214610 | A1 | 8/2010 |
| EP | 2218409 | A1 | 8/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |
| EP | 2030578 | B1 | 11/2010 |
| EP | 2036505 | B1 | 11/2010 |
| EP | 2245993 | A2 | 11/2010 |
| EP | 2245994 | A1 | 11/2010 |
| EP | 2253280 | A1 | 11/2010 |
| EP | 1627605 | B1 | 12/2010 |
| EP | 2027811 | B1 | 12/2010 |
| EP | 2130498 | B1 | 12/2010 |
| EP | 2258282 | A2 | 12/2010 |
| EP | 2263568 | A2 | 12/2010 |
| EP | 1994890 | B1 | 1/2011 |
| EP | 2005900 | B1 | 1/2011 |
| EP | 2277667 | A1 | 1/2011 |
| EP | 2283780 | A2 | 2/2011 |
| EP | 2286738 | A2 | 2/2011 |
| EP | 1494595 | B1 | 3/2011 |
| EP | 1690502 | B1 | 3/2011 |
| EP | 1884201 | B1 | 3/2011 |
| EP | 2292153 | A1 | 3/2011 |
| EP | 1769755 | B1 | 4/2011 |
| EP | 2090240 | B1 | 4/2011 |
| EP | 2303388 | A1 | 4/2011 |
| EP | 2305135 | A1 | 4/2011 |
| EP | 2314254 | A2 | 4/2011 |
| EP | 2316345 | A1 | 5/2011 |
| EP | 2316366 | A2 | 5/2011 |
| EP | 2319443 | A1 | 5/2011 |
| EP | 2324776 | A2 | 5/2011 |
| EP | 1813205 | B1 | 6/2011 |
| EP | 2042107 | B1 | 6/2011 |
| EP | 2090243 | B1 | 6/2011 |
| EP | 2329773 | A1 | 6/2011 |
| EP | 2090239 | B1 | 7/2011 |
| EP | 2340771 | A2 | 7/2011 |
| EP | 1728475 | B1 | 8/2011 |
| EP | 2353545 | A1 | 8/2011 |
| EP | 2361562 | A1 | 8/2011 |
| EP | 2377472 | A1 | 10/2011 |
| EP | 1836986 | B1 | 11/2011 |
| EP | 1908414 | B1 | 11/2011 |
| EP | 2153781 | B1 | 11/2011 |
| EP | 2387943 | A2 | 11/2011 |
| EP | 2389928 | A2 | 11/2011 |
| EP | 1847225 | B1 | 12/2011 |
| EP | 2397079 | A1 | 12/2011 |
| EP | 2399538 | A2 | 12/2011 |
| EP | 1785102 | B1 | 1/2012 |
| EP | 1316290 | B1 | 2/2012 |
| EP | 1962711 | B1 | 2/2012 |
| EP | 2415416 | A1 | 2/2012 |
| EP | 2090253 | B1 | 3/2012 |
| EP | 2430986 | A2 | 3/2012 |
| EP | 1347638 | B1 | 5/2012 |
| EP | 1943956 | B1 | 5/2012 |
| EP | 2446834 | A1 | 5/2012 |
| EP | 2455007 | A2 | 5/2012 |
| EP | 2457519 | A1 | 5/2012 |
| EP | 2462878 | A1 | 6/2012 |
| EP | 2462880 | A2 | 6/2012 |
| EP | 1813204 | B1 | 7/2012 |
| EP | 2189121 | B1 | 7/2012 |
| EP | 2248475 | B1 | 7/2012 |
| EP | 2478845 | A2 | 7/2012 |
| EP | 2005895 | B1 | 8/2012 |
| EP | 2090248 | B1 | 8/2012 |
| EP | 2481359 | A1 | 8/2012 |
| EP | 2484304 | A2 | 8/2012 |
| EP | 2486860 | A2 | 8/2012 |
| EP | 2486862 | A2 | 8/2012 |
| EP | 2486868 | A2 | 8/2012 |
| EP | 1908412 | B1 | 9/2012 |
| EP | 1935351 | B1 | 9/2012 |
| EP | 2497431 | A1 | 9/2012 |
| EP | 1550412 | B2 | 10/2012 |
| EP | 1616549 | B1 | 10/2012 |
| EP | 2030579 | B1 | 10/2012 |
| EP | 2090252 | B1 | 10/2012 |
| EP | 2517637 | A1 | 10/2012 |
| EP | 2517638 | A1 | 10/2012 |
| EP | 2517642 | A2 | 10/2012 |
| EP | 2517645 | A2 | 10/2012 |
| EP | 2517649 | A2 | 10/2012 |
| EP | 2517651 | A2 | 10/2012 |
| EP | 2526877 | A1 | 11/2012 |
| EP | 2526883 | A1 | 11/2012 |
| EP | 1884206 | B1 | 3/2013 |
| EP | 2286735 | B1 | 3/2013 |
| EP | 2090238 | B1 | 4/2013 |
| EP | 2586380 | A1 | 5/2013 |
| EP | 2586383 | A2 | 5/2013 |
| EP | 2606812 | A1 | 6/2013 |
| EP | 2606834 | A2 | 6/2013 |
| EP | 1982657 | B1 | 7/2013 |
| EP | 2614782 | A2 | 7/2013 |
| EP | 2617369 | A1 | 7/2013 |
| EP | 2620117 | A1 | 7/2013 |
| EP | 2090234 | B1 | 9/2013 |
| EP | 2633830 | A2 | 9/2013 |
| EP | 2644124 | A1 | 10/2013 |
| EP | 2644209 | A2 | 10/2013 |
| EP | 2649948 | A1 | 10/2013 |
| EP | 2649949 | A1 | 10/2013 |
| EP | 1997438 | B1 | 11/2013 |
| EP | 2684529 | A2 | 1/2014 |
| EP | 2687164 | A2 | 1/2014 |
| EP | 2700367 | A1 | 2/2014 |
| EP | 2713902 | A1 | 4/2014 |
| EP | 1772105 | B1 | 5/2014 |
| EP | 2743042 | A2 | 6/2014 |
| EP | 2759267 | A2 | 7/2014 |

(56) References Cited

FOREIGN PATENT DOCUMENTS

| | | |
|---|---|---|
| EP | 2764826 A1 | 8/2014 |
| EP | 2764827 A2 | 8/2014 |
| EP | 2767243 A2 | 8/2014 |
| EP | 2772206 A2 | 9/2014 |
| EP | 2772209 A1 | 9/2014 |
| EP | 2777520 A1 | 9/2014 |
| EP | 2777524 A2 | 9/2014 |
| EP | 2777528 A2 | 9/2014 |
| EP | 2777537 A1 | 9/2014 |
| EP | 2777538 A2 | 9/2014 |
| EP | 2786714 A2 | 10/2014 |
| EP | 2792313 A2 | 10/2014 |
| EP | 2803324 A2 | 11/2014 |
| EP | 2815704 A1 | 12/2014 |
| EP | 2446835 B1 | 1/2015 |
| EP | 2842500 A1 | 3/2015 |
| EP | 2845545 A1 | 3/2015 |
| EP | 1943960 B1 | 4/2015 |
| EP | 2090255 B1 | 4/2015 |
| EP | 2853220 A1 | 4/2015 |
| EP | 2923647 A2 | 9/2015 |
| EP | 2923653 A2 | 9/2015 |
| EP | 2923660 A2 | 9/2015 |
| EP | 2932913 A1 | 10/2015 |
| EP | 2944270 A1 | 11/2015 |
| EP | 1774914 B1 | 12/2015 |
| EP | 2090235 B1 | 4/2016 |
| EP | 2823773 B1 | 4/2016 |
| EP | 2131750 B1 | 5/2016 |
| EP | 2298220 B1 | 6/2016 |
| EP | 2510891 B1 | 6/2016 |
| EP | 1915957 B1 | 8/2016 |
| EP | 2296559 B1 | 8/2016 |
| EP | 2586379 B1 | 8/2016 |
| EP | 2777533 B1 | 10/2016 |
| EP | 2364651 B1 | 11/2016 |
| EP | 2747235 B1 | 11/2016 |
| EP | 2116192 B1 | 3/2017 |
| EP | 2789299 B1 | 5/2017 |
| EP | 2311386 B1 | 6/2017 |
| EP | 2839787 B1 | 6/2017 |
| EP | 2745782 B1 | 10/2017 |
| ES | 2396594 T3 | 2/2013 |
| FR | 459743 A | 11/1913 |
| FR | 999646 A | 2/1952 |
| FR | 1112936 A | 3/1956 |
| FR | 2452275 B1 | 4/1983 |
| FR | 2598905 A1 | 11/1987 |
| FR | 2689749 B1 | 7/1994 |
| FR | 2765794 A1 | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2426391 A | 11/2006 |
| GB | 2423199 B | 5/2009 |
| GB | 2509523 A | 7/2014 |
| GR | 930100110 A | 11/1993 |
| JP | S 47-11908 Y1 | 5/1972 |
| JP | S 50-33988 U | 4/1975 |
| JP | S 56-112235 A | 9/1981 |
| JP | S 58500053 A | 1/1983 |
| JP | S 58-501360 A | 8/1983 |
| JP | S 59-174920 A | 3/1984 |
| JP | S 60-100955 A | 6/1985 |
| JP | S 60-212152 A | 10/1985 |
| JP | S 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | S 63-203149 A | 8/1988 |
| JP | S63270040 A | 11/1988 |
| JP | H0129503 B2 | 6/1989 |
| JP | H 02-279149 A | 11/1990 |
| JP | H 03-12126 A | 1/1991 |
| JP | H 03-18354 A | 1/1991 |
| JP | H 03-78514 U | 8/1991 |
| JP | H 03-85009 U | 8/1991 |
| JP | H 04-215747 A | 8/1992 |
| JP | H 04-131860 U | 12/1992 |
| JP | H 05-84252 A | 4/1993 |
| JP | H 05-123325 A | 5/1993 |
| JP | H05212039 A | 8/1993 |
| JP | H 05226945 A | 9/1993 |
| JP | H067357 A | 1/1994 |
| JP | H 06-30945 A | 2/1994 |
| JP | H 06-54857 A | 3/1994 |
| JP | H 06-63054 A | 3/1994 |
| JP | H 06-26812 U | 4/1994 |
| JP | H 06-121798 A | 5/1994 |
| JP | H 06-125913 A | 5/1994 |
| JP | H 06-197901 A | 7/1994 |
| JP | H 06-237937 A | 8/1994 |
| JP | H 06-327684 A | 11/1994 |
| JP | H 07-9622 U | 2/1995 |
| JP | H 07-31623 A | 2/1995 |
| JP | H 07-47070 A | 2/1995 |
| JP | H 07-51273 A | 2/1995 |
| JP | H 07-124166 A | 5/1995 |
| JP | H 07-163573 A | 6/1995 |
| JP | H 07-163574 A | 6/1995 |
| JP | H 07-171163 A | 7/1995 |
| JP | H 07-255735 A | 10/1995 |
| JP | H 07-285089 A | 10/1995 |
| JP | H 07-299074 A | 11/1995 |
| JP | H 08-33641 A | 2/1996 |
| JP | H 08-33642 A | 2/1996 |
| JP | H 08-164141 A | 6/1996 |
| JP | H 08-173437 A | 7/1996 |
| JP | H 08-182684 A | 7/1996 |
| JP | H 08-215201 A | 8/1996 |
| JP | H 08-507708 A | 8/1996 |
| JP | H 08-229050 A | 9/1996 |
| JP | H 08-289895 A | 11/1996 |
| JP | H 08-336540 A | 12/1996 |
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H09-323068 A | 12/1997 |
| JP | H 10-113352 A | 5/1998 |
| JP | H 10-118090 A | 5/1998 |
| JP | H10-200699 A | 7/1998 |
| JP | H 10-296660 A | 11/1998 |
| JP | H 10-512465 A | 12/1998 |
| JP | H 10-512469 A | 12/1998 |
| JP | 2000-014632 A | 1/2000 |
| JP | 2000-033071 A | 2/2000 |
| JP | 2000-112002 A | 4/2000 |
| JP | 2000-166932 A | 6/2000 |
| JP | 2000-171730 A | 6/2000 |
| JP | 3056672 B2 | 6/2000 |
| JP | 2000-287987 A | 10/2000 |
| JP | 2000-325303 A | 11/2000 |
| JP | 2001-037763 A | 2/2001 |
| JP | 2001-046384 A | 2/2001 |
| JP | 2001-087272 A | 4/2001 |
| JP | 2001-514541 A | 9/2001 |
| JP | 2001-276091 A | 10/2001 |
| JP | 2001-286477 A | 10/2001 |
| JP | 2001-517473 A | 10/2001 |
| JP | 2002-051974 A | 2/2002 |
| JP | 2002-085415 A | 3/2002 |
| JP | 2002-143078 A | 5/2002 |

(56) References Cited

FOREIGN PATENT DOCUMENTS

| | | |
|---|---|---|
| JP | 2002-204801 A | 7/2002 |
| JP | 2002204801 A | 7/2002 |
| JP | 2002-528161 A | 9/2002 |
| JP | 2002-314298 A | 10/2002 |
| JP | 2002-369820 A | 12/2002 |
| JP | 2002-542186 A | 12/2002 |
| JP | 2003-000603 A | 1/2003 |
| JP | 2003-500153 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-521304 A | 7/2003 |
| JP | 2003-523251 A | 8/2003 |
| JP | 2003-523254 A | 8/2003 |
| JP | 2003-524431 A | 8/2003 |
| JP | 3442423 B2 | 9/2003 |
| JP | 2003-300416 A | 10/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-535217 A | 11/2004 |
| JP | 2004-337617 A | 12/2004 |
| JP | 2004-344662 A | 12/2004 |
| JP | 2004-344663 A | 12/2004 |
| JP | 2005-013573 A | 1/2005 |
| JP | 2005-028147 A | 2/2005 |
| JP | 2005-028148 A | 2/2005 |
| JP | 2005-028149 A | 2/2005 |
| JP | 2005-505309 A | 2/2005 |
| JP | 2005-505322 A | 2/2005 |
| JP | 2005-505334 A | 2/2005 |
| JP | 2005-080702 A | 3/2005 |
| JP | 2005-103280 A | 4/2005 |
| JP | 2005-103281 A | 4/2005 |
| JP | 2005-103293 A | 4/2005 |
| JP | 2005-511131 A | 4/2005 |
| JP | 2005-511137 A | 4/2005 |
| JP | 2005-131163 A | 5/2005 |
| JP | 2005-131164 A | 5/2005 |
| JP | 2005-131173 A | 5/2005 |
| JP | 2005-131211 A | 5/2005 |
| JP | 2005-131212 A | 5/2005 |
| JP | 2005-137423 A | 6/2005 |
| JP | 2005-137919 A | 6/2005 |
| JP | 2005-144183 A | 6/2005 |
| JP | 2005-152416 A | 6/2005 |
| JP | 2005-516714 A | 6/2005 |
| JP | 2005-187954 A | 7/2005 |
| JP | 2005-521109 A | 7/2005 |
| JP | 2005-523105 A | 8/2005 |
| JP | 2005-524474 A | 8/2005 |
| JP | 4461008 B2 | 8/2005 |
| JP | 2005-296412 A | 10/2005 |
| JP | 2005-529675 A | 10/2005 |
| JP | 2005-529677 A | 11/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-034977 A | 2/2006 |
| JP | 2006-034978 A | 2/2006 |
| JP | 2006-034980 A | 2/2006 |
| JP | 2006-043451 A | 2/2006 |
| JP | 2006-506106 A | 2/2006 |
| JP | 2006-510879 A | 3/2006 |
| JP | 3791856 B2 | 6/2006 |
| JP | 2006-187649 A | 7/2006 |
| JP | 2006-218228 A | 8/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-061628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203047 A | 8/2007 |
| JP | 2007-203049 A | 8/2007 |
| JP | 2007-203051 A | 8/2007 |
| JP | 2007-203055 A | 8/2007 |
| JP | 2007-203057 A | 8/2007 |
| JP | 2007-524435 A | 8/2007 |
| JP | 2007-229448 A | 9/2007 |
| JP | 2007-526026 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-068073 A | 3/2008 |
| JP | 2008-510515 A | 4/2008 |
| JP | 2008-516669 A | 5/2008 |
| JP | 2008-528203 A | 7/2008 |
| JP | 2008-206967 A | 9/2008 |
| JP | 2008-212637 A | 9/2008 |
| JP | 2008-212638 A | 9/2008 |
| JP | 2008-212640 A | 9/2008 |
| JP | 2008-220032 A | 9/2008 |
| JP | 2008-220956 A | 9/2008 |
| JP | 2008-237881 A | 10/2008 |
| JP | 2008-259860 A | 10/2008 |
| JP | 2008-264535 A | 11/2008 |
| JP | 2008-283459 A | 11/2008 |
| JP | 2008-307393 A | 12/2008 |
| JP | 2009-000531 A | 1/2009 |
| JP | 2009-006137 A | 1/2009 |
| JP | 2009-502351 A | 1/2009 |
| JP | 2009-502352 A | 1/2009 |
| JP | 2009-022742 A | 2/2009 |
| JP | 2009-506799 A | 2/2009 |
| JP | 2009-507526 A | 2/2009 |
| JP | 2009-072595 A | 4/2009 |
| JP | 2009-072599 A | 4/2009 |
| JP | 2009-090113 A | 4/2009 |
| JP | 2009-106752 A | 5/2009 |
| JP | 2009-189821 A | 8/2009 |
| JP | 2009-189823 A | 8/2009 |
| JP | 2009-189836 A | 8/2009 |
| JP | 2009-189837 A | 8/2009 |
| JP | 2009-189838 A | 8/2009 |
| JP | 2009-189846 A | 8/2009 |
| JP | 2009-189847 A | 8/2009 |
| JP | 2009-201998 A | 9/2009 |
| JP | 2009207260 A | 9/2009 |
| JP | 2009-536082 A | 10/2009 |
| JP | 2009226028 A | 10/2009 |
| JP | 2009-261944 A | 11/2009 |
| JP | 2009-268908 A | 11/2009 |
| JP | 2009-538684 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504813 A | 2/2010 |
| JP | 2010-504846 A | 2/2010 |
| JP | 2010-505524 A | 2/2010 |
| JP | 2010-069307 A | 4/2010 |

(56) References Cited

FOREIGN PATENT DOCUMENTS

| | | |
|---|---|---|
| JP | 2010-069310 A | 4/2010 |
| JP | 2010-075694 A | 4/2010 |
| JP | 2010-075695 A | 4/2010 |
| JP | 2010-088876 A | 4/2010 |
| JP | 2010-094514 A | 4/2010 |
| JP | 2010-098844 A | 4/2010 |
| JP | 2010-520025 A | 6/2010 |
| JP | 2010-142636 A | 7/2010 |
| JP | 2010-148879 A | 7/2010 |
| JP | 2010-214166 A | 9/2010 |
| JP | 4549018 B2 | 9/2010 |
| JP | 2010-240411 A | 10/2010 |
| JP | 2010-240429 | 10/2010 |
| JP | 2010-246948 A | 11/2010 |
| JP | 2010-279690 A | 12/2010 |
| JP | 2010-540041 A | 12/2010 |
| JP | 2010-540192 A | 12/2010 |
| JP | 2011-005260 A | 1/2011 |
| JP | 2011-504391 A | 2/2011 |
| JP | 2011-509786 A | 3/2011 |
| JP | 2011-072797 A | 4/2011 |
| JP | 2011-078763 A | 4/2011 |
| JP | 2011072574 A | 4/2011 |
| JP | 2011-115594 A | 6/2011 |
| JP | 2011-520564 A | 7/2011 |
| JP | 4722849 B2 | 7/2011 |
| JP | 2011-524199 A | 9/2011 |
| JP | 4783373 B2 | 9/2011 |
| JP | 2011-251156 A | 12/2011 |
| JP | 2012-040398 A | 3/2012 |
| JP | 2012-507356 A | 3/2012 |
| JP | 2012-517289 A | 8/2012 |
| JP | 5140421 B2 | 2/2013 |
| JP | 5162595 B2 | 3/2013 |
| JP | 2013-517891 A | 5/2013 |
| JP | 2013-526342 A | 6/2013 |
| JP | 2013-128791 A | 7/2013 |
| JP | 5212039 B2 | 7/2013 |
| JP | 5333899 B2 | 11/2013 |
| JP | 2016-512057 A | 4/2016 |
| JP | 6007357 B2 | 10/2016 |
| KR | 20100110134 A | 10/2010 |
| KR | 20110003229 A | 1/2011 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2007-103563 A | 8/2008 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 886900 A1 | 12/1981 |
| SU | 1009439 A | 4/1983 |
| SU | 1022703 A1 | 6/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO-94/14129 A1 | 6/1994 |
| WO | WO 94/17737 A1 | 8/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/30659 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 97/41767 A2 | 11/1997 |
| WO | WO 98/01080 A1 | 1/1998 |
| WO | WO 98/17180 A1 | 4/1998 |

(56) References Cited

FOREIGN PATENT DOCUMENTS

| | | |
|---|---|---|
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/33755 A1 | 6/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 2003/079909 A3 | 3/2003 |
| WO | WO 03/030743 A2 | 4/2003 |
| WO | WO 03/037193 A1 | 5/2003 |
| WO | WO 2003/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 2003/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 2003/094746 A1 | 11/2003 |
| WO | WO 2003/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/004578 A1 | 1/2004 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034375 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A1 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/048809 A1 | 6/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/110243 A2 | 11/2005 |
| WO | WO 2005/112806 A2 | 12/2005 |
| WO | WO 2005/112808 A2 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/026520 A2 | 3/2006 |

(56) References Cited

FOREIGN PATENT DOCUMENTS

| | | |
|---|---|---|
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/050360 A1 | 5/2006 |
| WO | WO 2006/051252 A1 | 5/2006 |
| WO | WO 2006/057702 A2 | 6/2006 |
| WO | WO 2006/059067 A1 | 6/2006 |
| WO | WO 2006/073581 A2 | 7/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/034161 A2 | 3/2007 |
| WO | WO 2007/051000 A2 | 5/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A2 | 12/2007 |
| WO | WO 2008/020964 A2 | 2/2008 |
| WO | WO 2008/021687 A1 | 2/2008 |
| WO | WO 2008/021969 A2 | 2/2008 |
| WO | WO 2008/027972 A1 | 3/2008 |
| WO | WO 2008/039237 A1 | 4/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO-2008/061566 A1 | 5/2008 |
| WO | WO 2008/070763 A1 | 6/2008 |
| WO | WO 2008/080148 A2 | 7/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109123 A2 | 9/2008 |
| WO | WO 2008/109125 A1 | 9/2008 |
| WO | WO 2008/112912 A2 | 9/2008 |
| WO | WO 2008/118728 A1 | 10/2008 |
| WO | WO 2008/118928 A2 | 10/2008 |
| WO | WO 2008/124748 A1 | 10/2008 |
| WO | WO 2008/131357 A1 | 10/2008 |
| WO | WO 2009/005969 A2 | 1/2009 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/066105 A1 | 5/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2009/152307 A1 | 12/2009 |
| WO | WO 2010/028332 A2 | 3/2010 |
| WO | WO 2010/030434 A1 | 3/2010 |
| WO | WO 2010/045425 A1 | 4/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO-2010134913 A1 | 11/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO-2011056458 A1 | 5/2011 |
| WO | WO 2011/084969 A1 | 7/2011 |
| WO | WO 2011/127137 A1 | 10/2011 |
| WO | WO 2012/006306 A2 | 1/2012 |
| WO | WO 2012/009431 A2 | 1/2012 |
| WO | WO-2012/013577 A1 | 2/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/044854 A1 | 4/2012 |
| WO | WO 2012/058213 A2 | 5/2012 |
| WO | WO 2012/068156 A2 | 5/2012 |
| WO | WO 2012/109760 A1 | 8/2012 |
| WO | WO 2012/127462 A1 | 9/2012 |
| WO | WO 2012/135705 A1 | 10/2012 |
| WO | WO 2012/143913 A2 | 10/2012 |
| WO | WO 2012/148667 A2 | 11/2012 |
| WO | WO 2012/148668 A2 | 11/2012 |
| WO | WO 2012/148703 A2 | 11/2012 |
| WO | WO 2012/160163 A1 | 11/2012 |
| WO | WO 2012/166503 A1 | 12/2012 |
| WO | WO 2013/009252 A2 | 1/2013 |
| WO | WO 2013/009699 A2 | 1/2013 |
| WO | WO 2013/023114 A1 | 2/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/062978 A2 | 5/2013 |
| WO | WO 2013/116869 A1 | 8/2013 |
| WO | WO 2013/148762 A2 | 10/2013 |
| WO | WO-2013151888 A1 | 10/2013 |
| WO | WO 2013/167427 A1 | 11/2013 |
| WO | WO 2013/188130 A1 | 12/2013 |
| WO | WO 2014/004199 A1 | 1/2014 |
| WO | WO 2014/004294 A2 | 1/2014 |
| WO | WO 2014/008289 A2 | 1/2014 |
| WO | WO-2014/113438 A1 | 7/2014 |
| WO | WO 2014/134034 A2 | 9/2014 |
| WO | WO 2014/172213 A2 | 10/2014 |
| WO | WO-2014158882 A2 | 10/2014 |
| WO | WO 2015/032797 A1 | 3/2015 |
| WO | WO 2015/148136 A1 | 10/2015 |
| WO | WO 2015/148141 A1 | 10/2015 |
| WO | WO 2015/153642 A1 | 10/2015 |
| WO | WO 2007/014355 A2 | 2/2017 |

OTHER PUBLICATIONS

Extended European Search Report, Application No. 15186936.9, dated Feb. 5, 2016 (8 pages).
International Search Report for Application No. PCT/US2015/048862, dated Dec. 14, 2015 (6 pages).
Extended European Search Report for Application No. 15186985.6, dated May 30, 2016 (15 pages).
International Preliminary Report on Patentability for Application No. PCT/US2015/048862, dated Mar. 28, 2017 (8 pages).
International Search Report for Application No. PCT/US2015/052301, dated May 3, 2016 (14 pages).

(56) References Cited

OTHER PUBLICATIONS

International Preliminary Report on Patentability for Application No. PCT/US2015/052301, dated Mar. 28, 2017 (18 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 a Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).
"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~ /media/Files/Datasheets/A3941-Datasheet.ashx?la=en.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Data Sheet of LM4F230H5QR. 2007.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
U.S. Appl. No. 12/031,573, filed Feb. 14, 2008.
Anonymous, Analog Devices Wiki, Chapter 11: The Current Mirror, Aug. 20, 2017, 22 pages. https://wiki.analog.com/university/courses/electronics/text/chapter-11?rev=1503222341.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.

(56) References Cited

OTHER PUBLICATIONS

Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.

Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.

Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.

Yan et al, Comparison of the effects of Mg—6Zn and Ti—3Al—2.5V alloys on TGF-$\beta$/TNF-$\alpha$/VEGF/b-FGF in the healing of the intestinal track in vivo, Biomed. Mater. 9 (2014), 11 pages.

Yan et al., "Comparison of the effects of Mg—6Zn and titanium on intestinal tract in vivo," J Mater Sci: Mater Med (2013), 11 pages.

\* cited by examiner

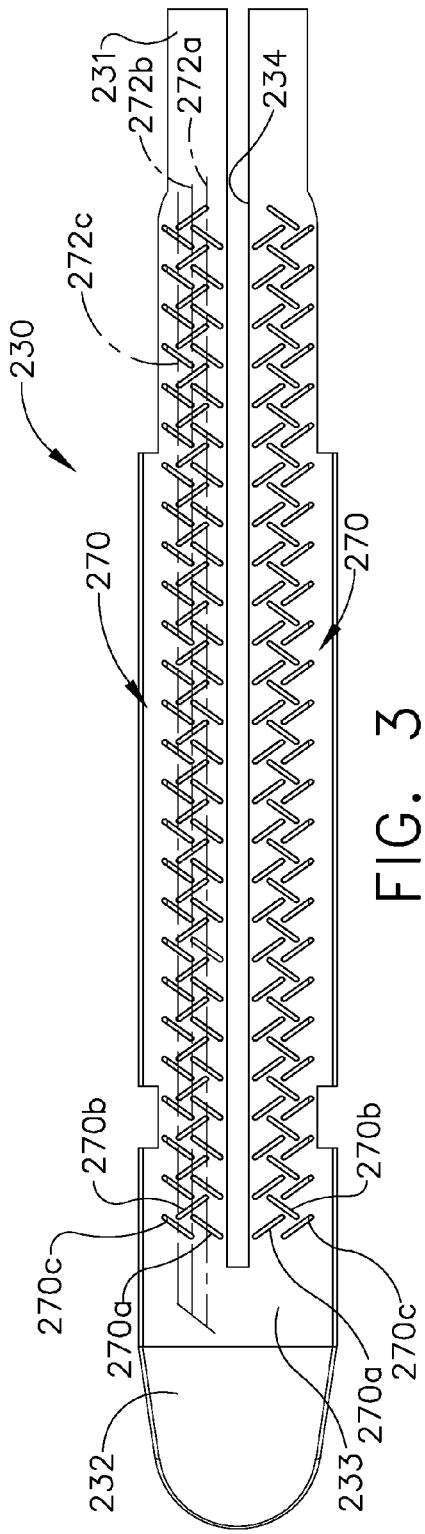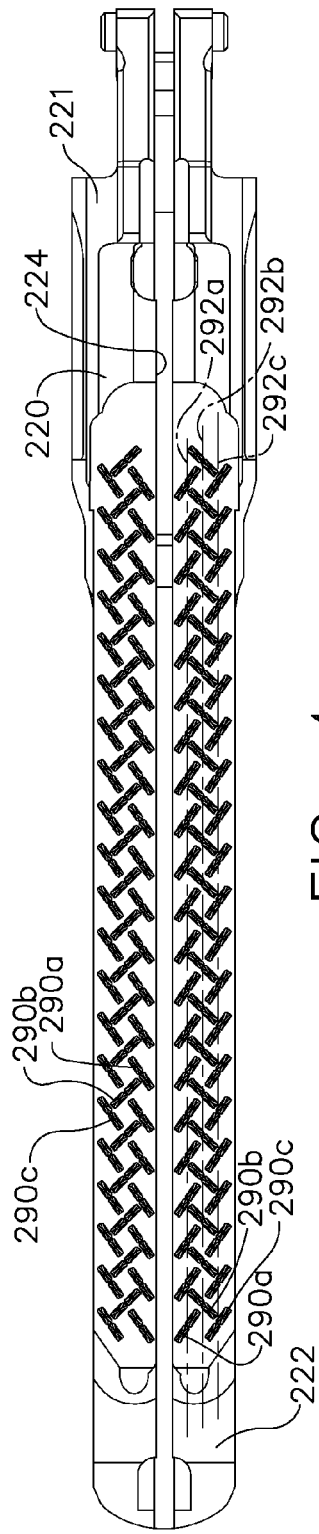

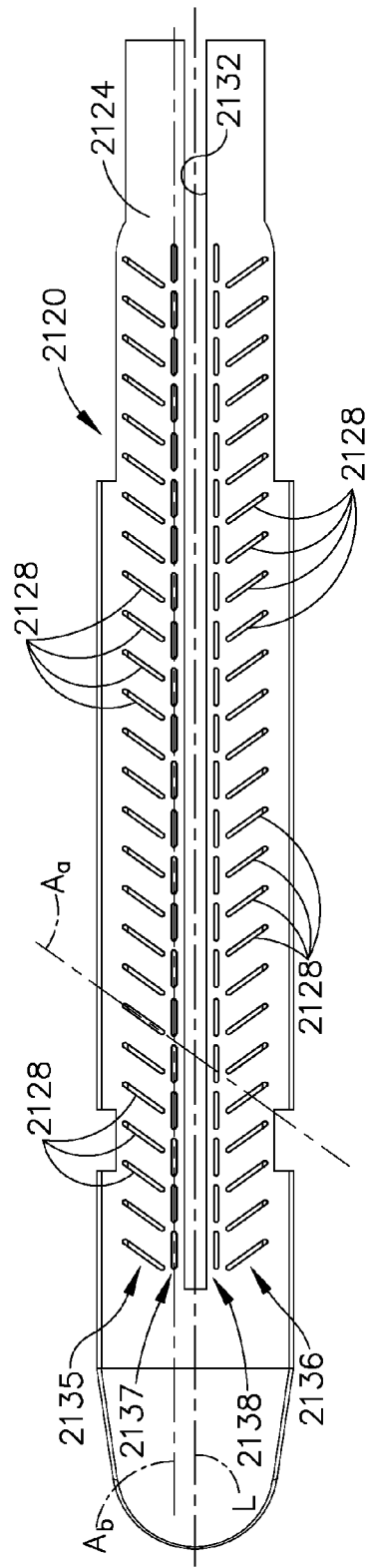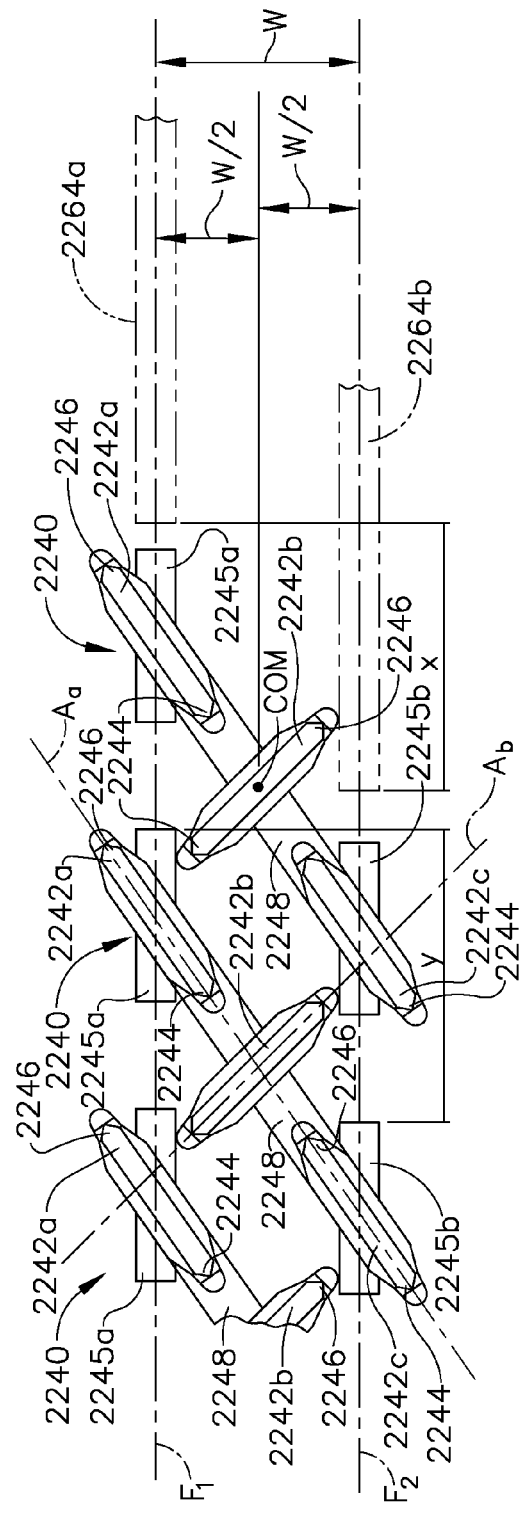

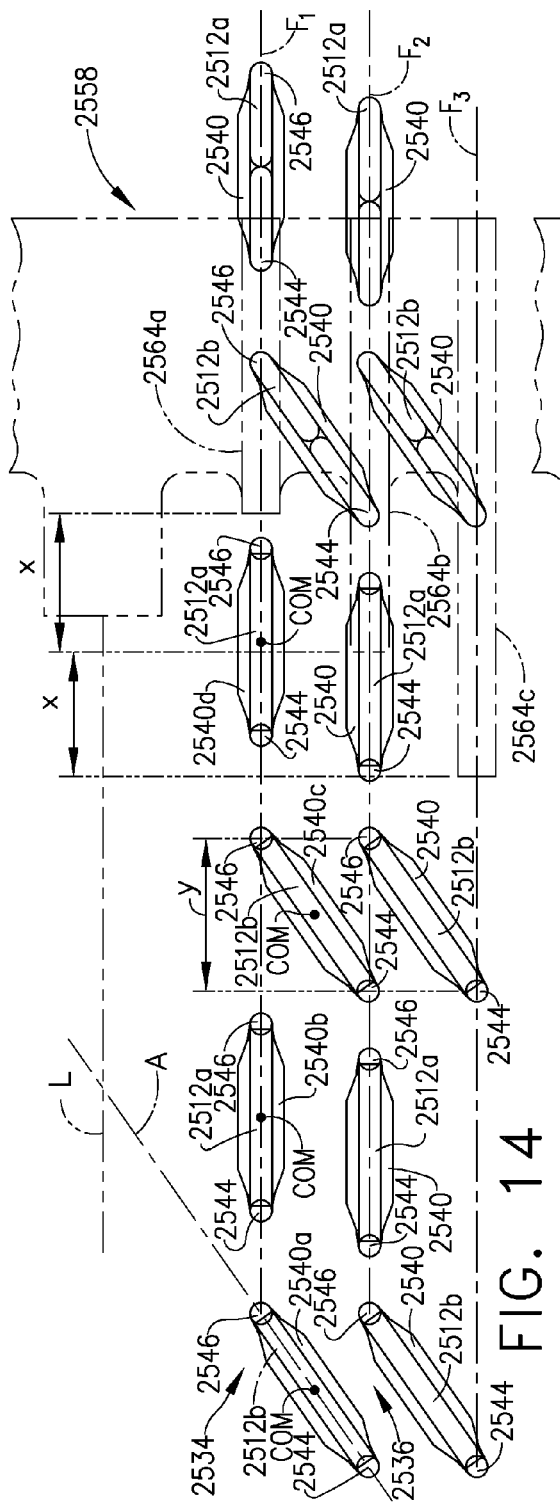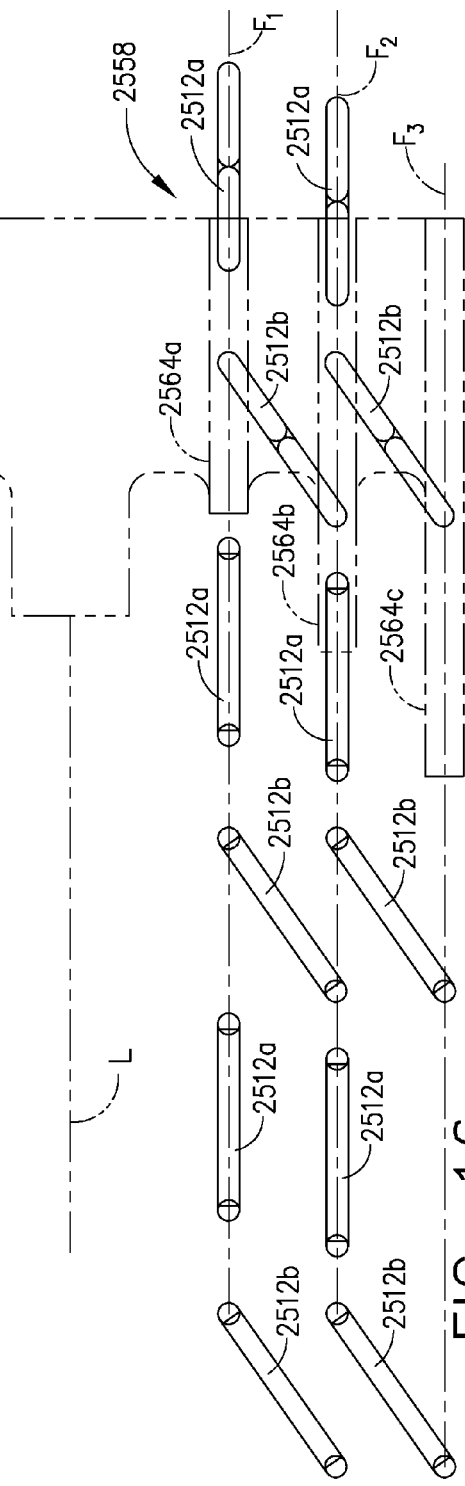

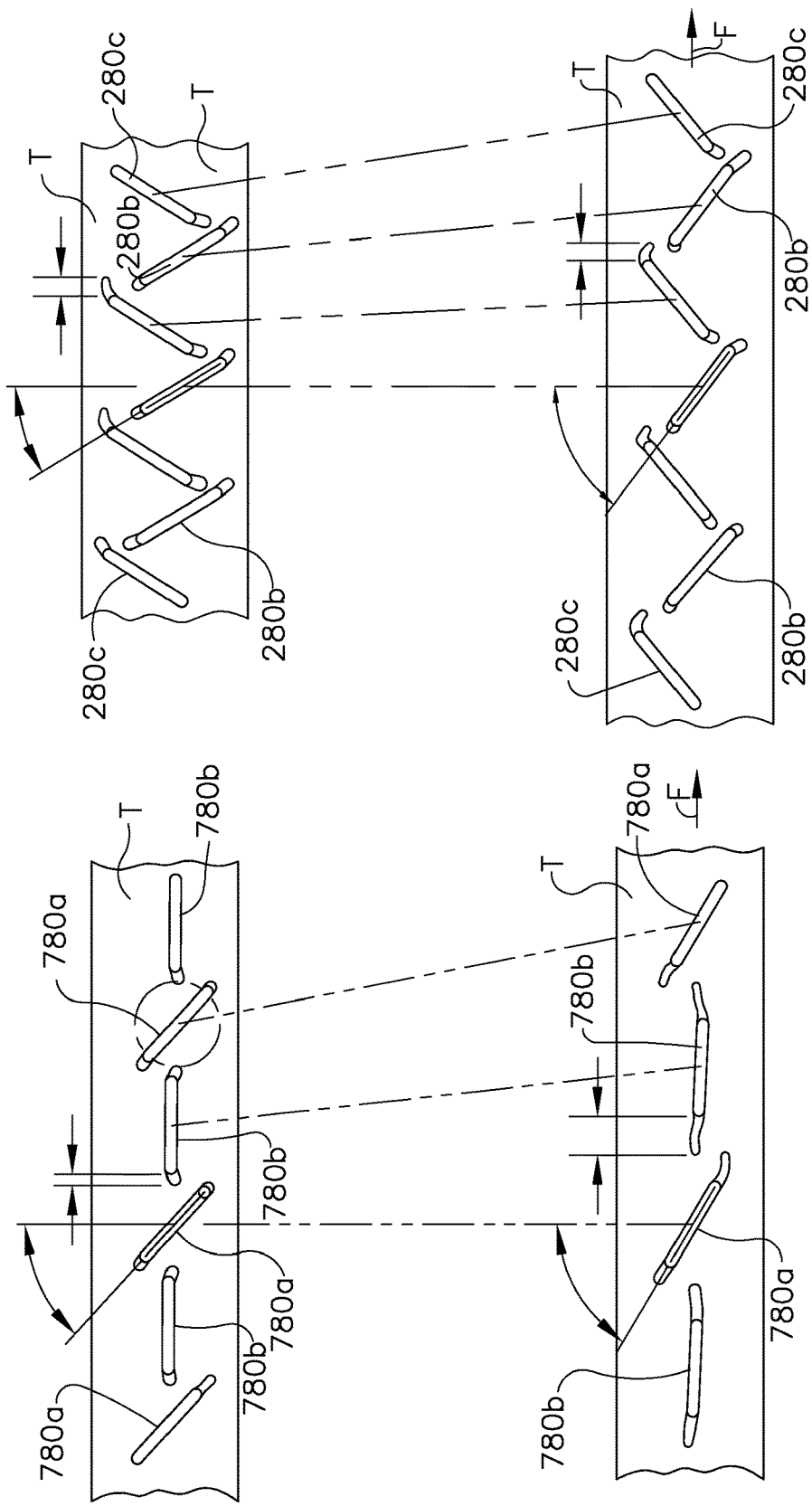

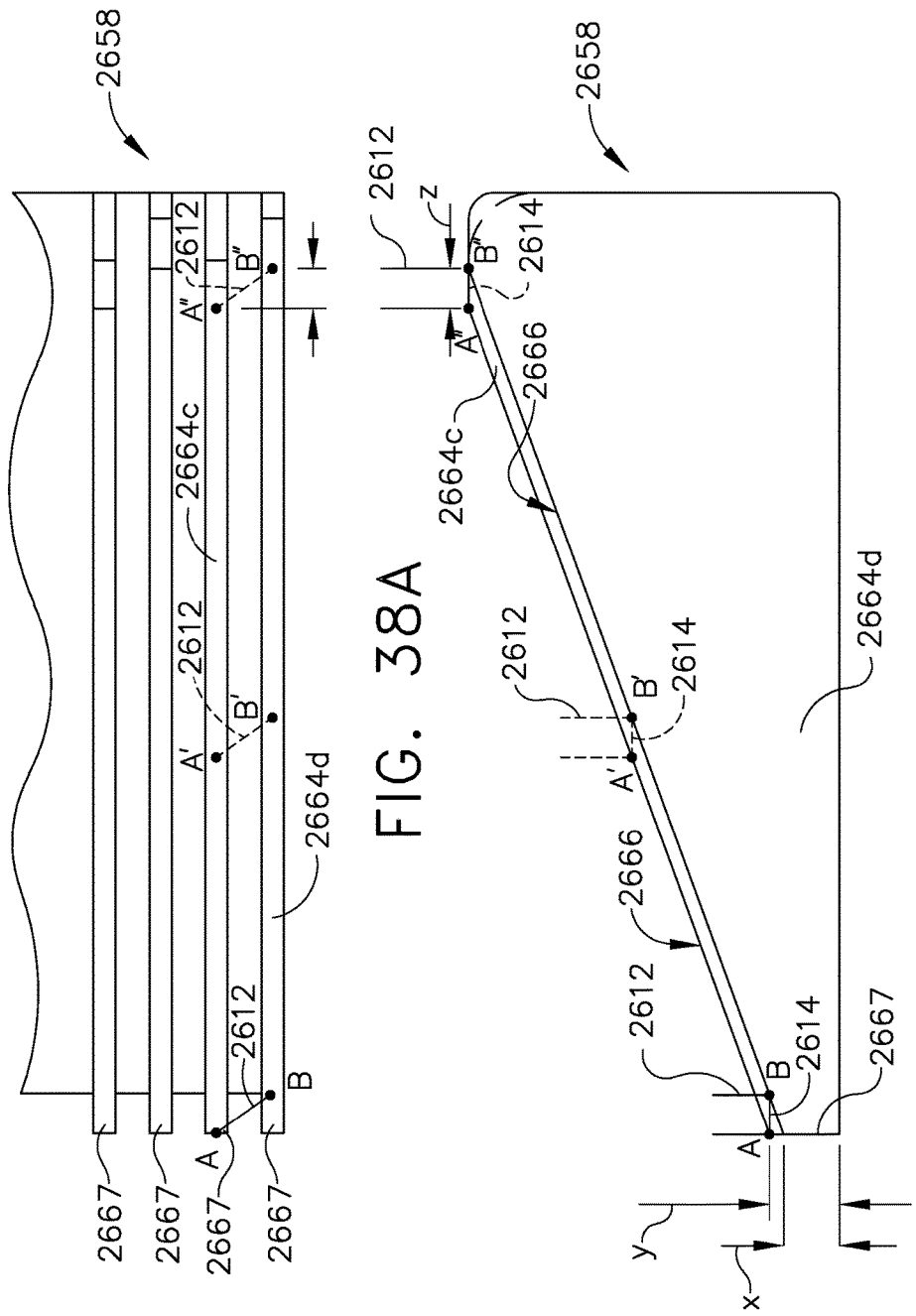

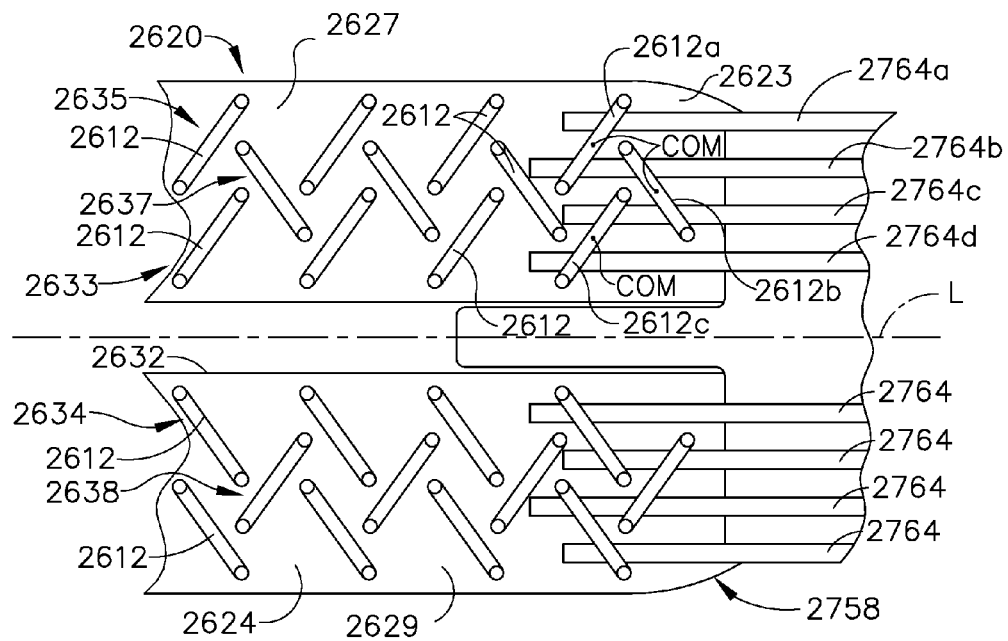
FIG. 39A
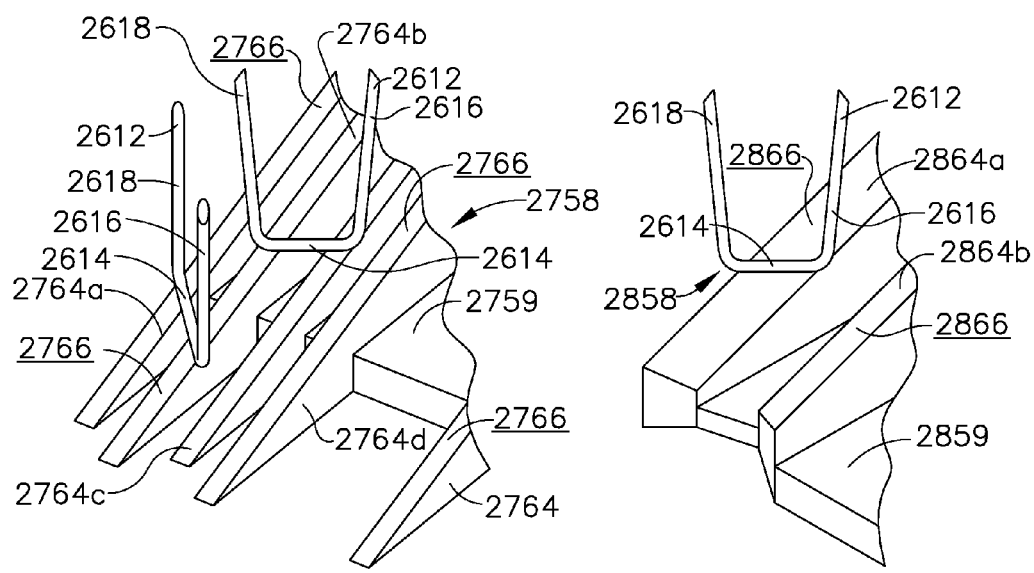
FIG. 39B
FIG. 40

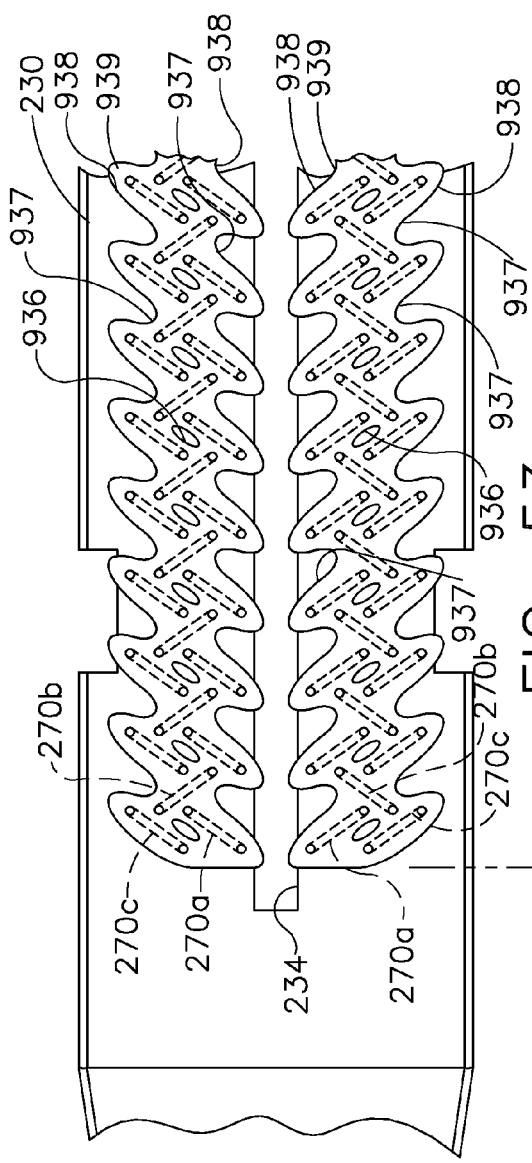
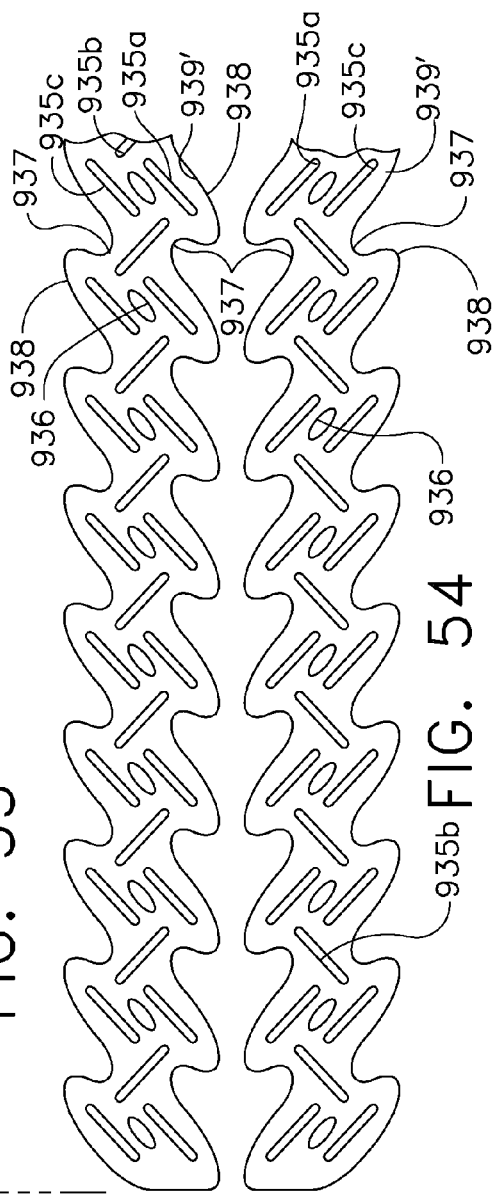
FIG. 53
FIG. 54

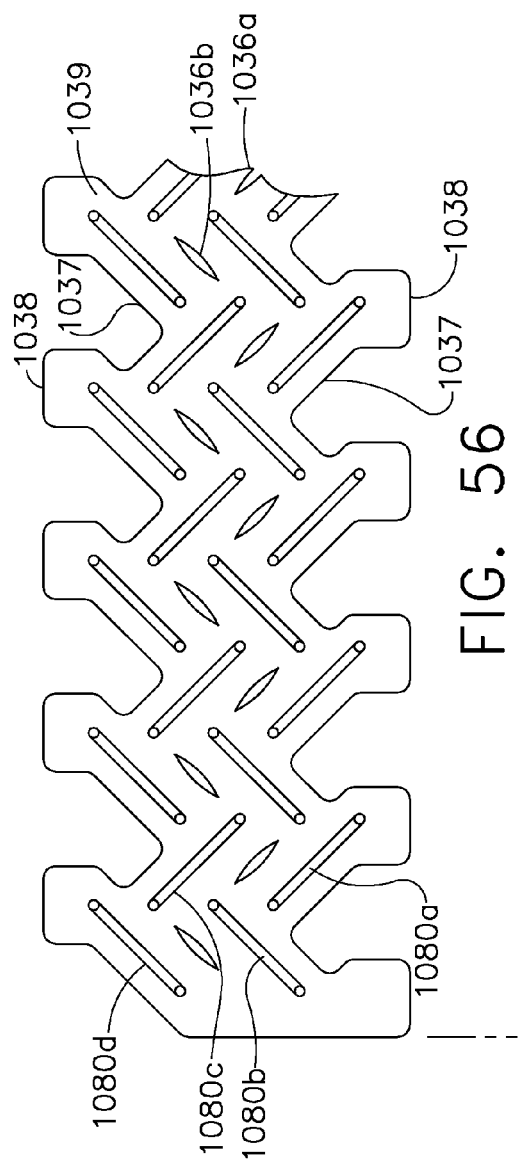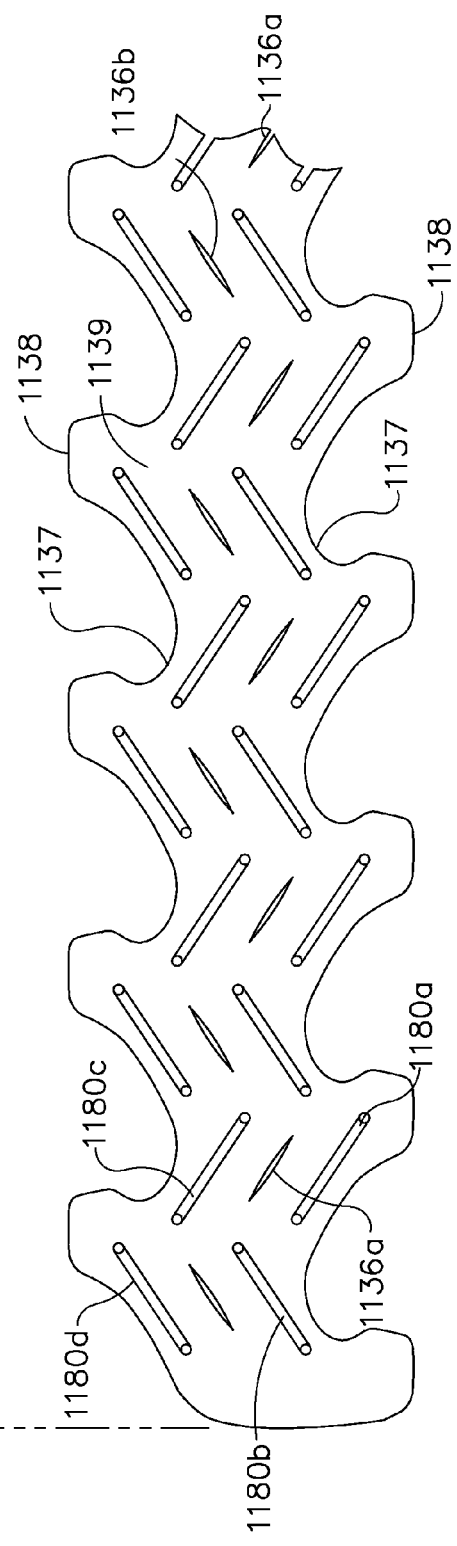
FIG. 56
FIG. 57

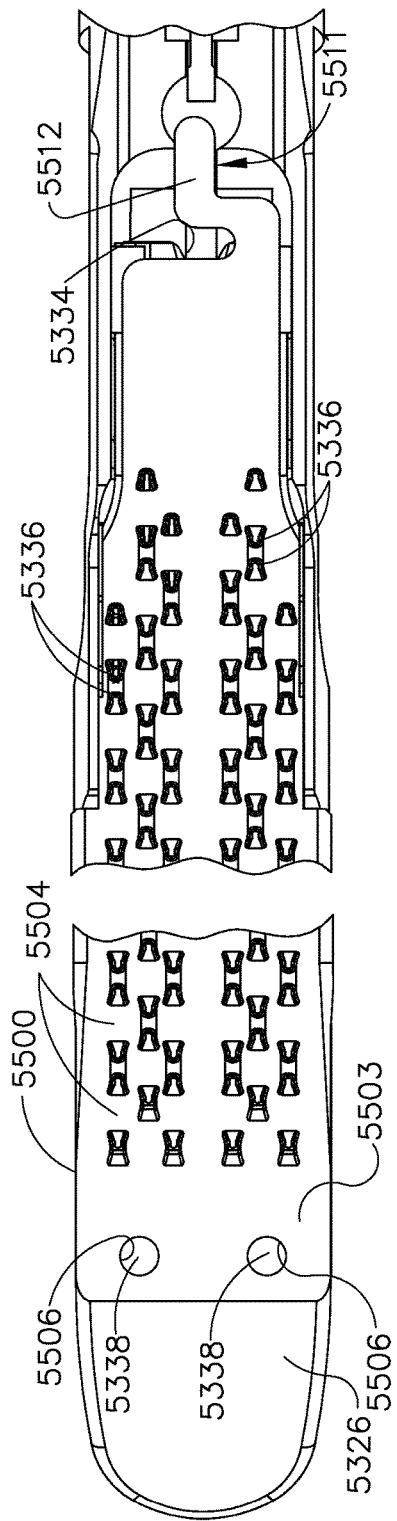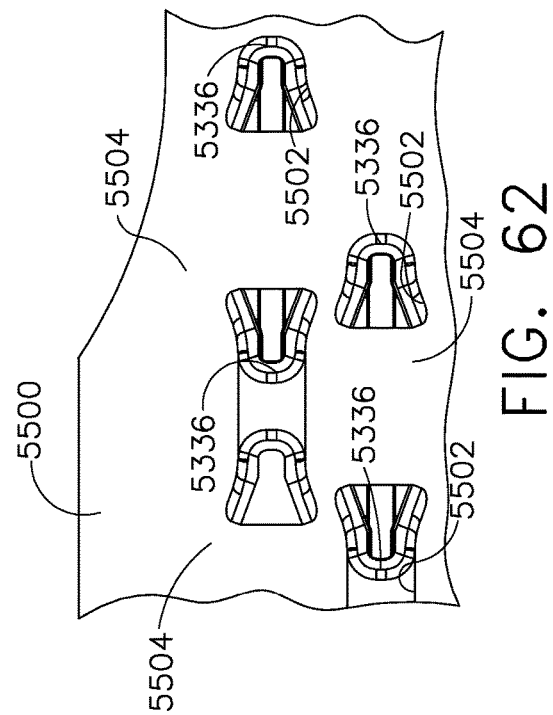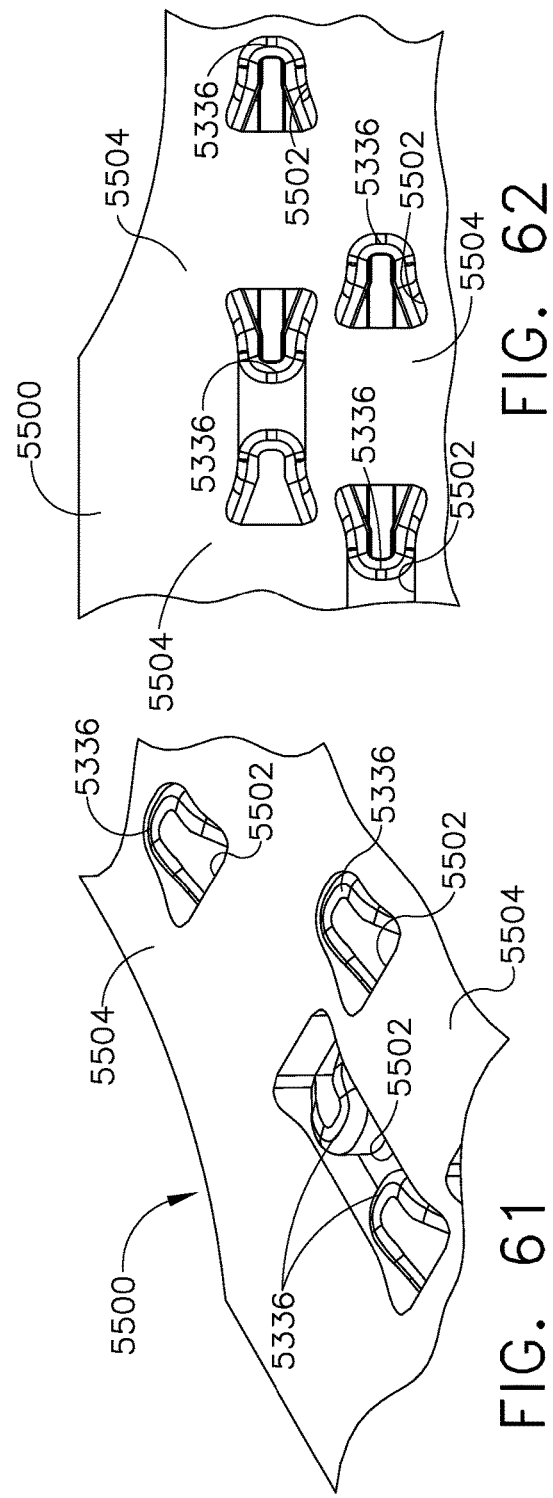
FIG. 60
FIG. 62
FIG. 61

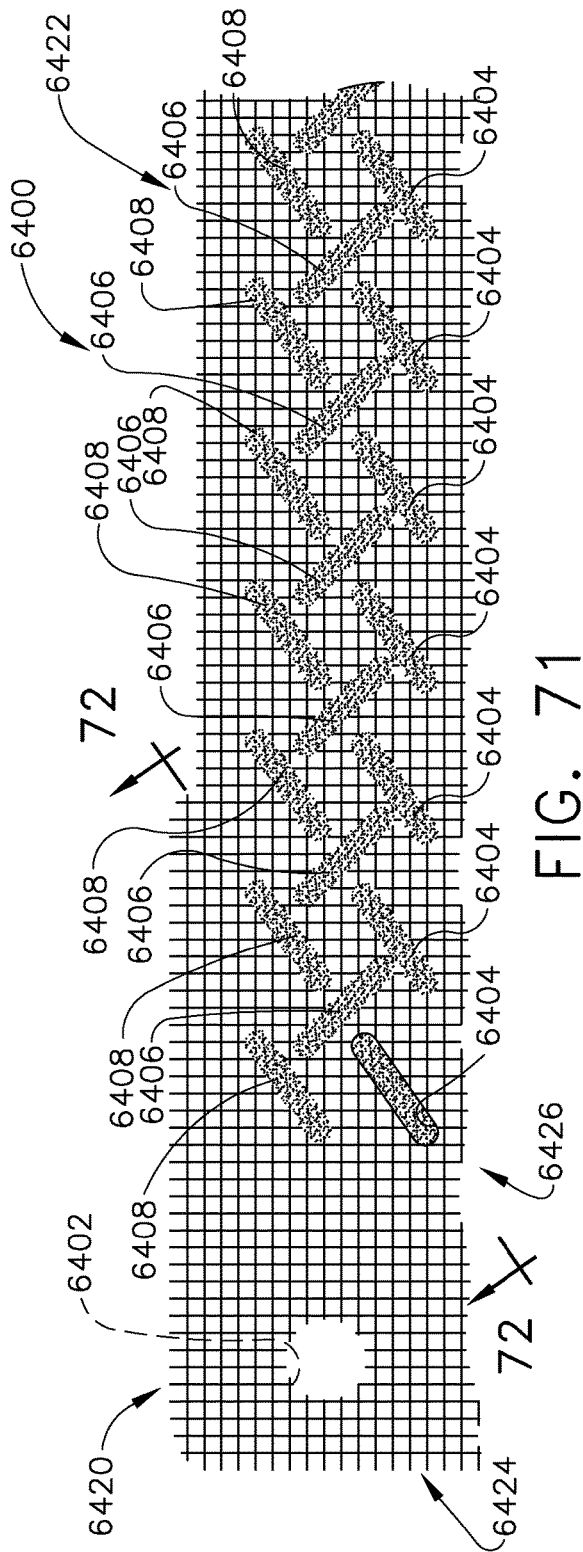
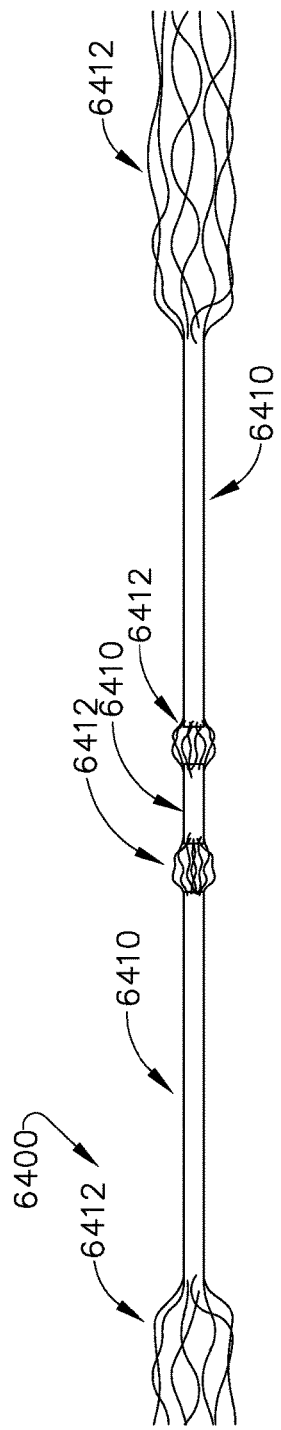
FIG. 71
FIG. 72

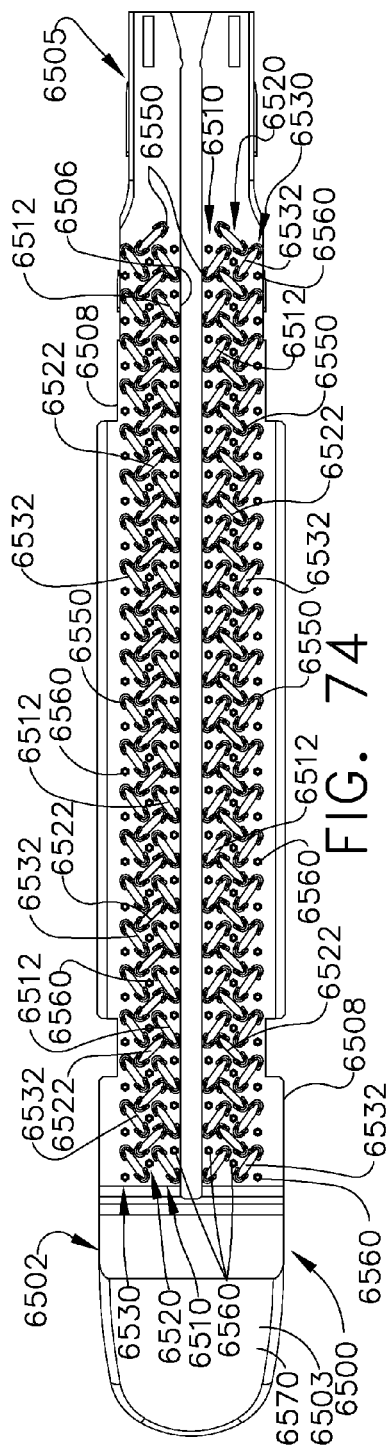
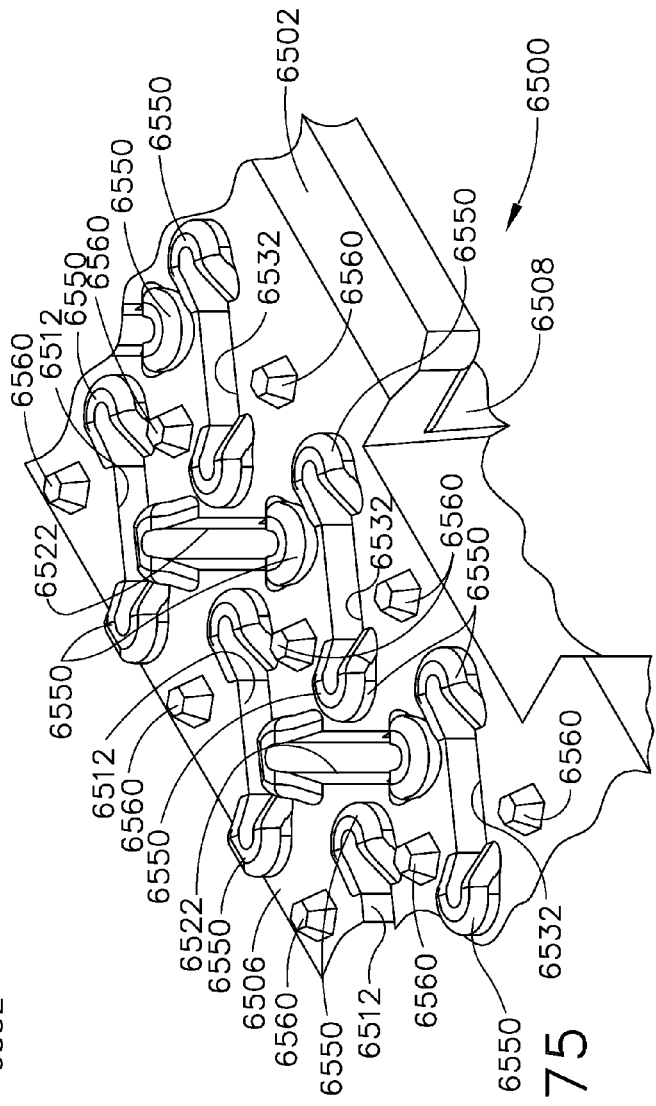
FIG. 74
FIG. 75

US 10,426,476 B2

CIRCULAR FASTENER CARTRIDGES FOR APPLYING RADIALLY EXPANDABLE FASTENER LINES

BACKGROUND

The present invention relates to stapling instruments and, in various embodiments, to a surgical stapling instrument for producing one or more rows of staples.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows. Examples of such stapling instruments are disclosed in U.S. Pat. No. 7,794,475, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, the entire disclosure of which is hereby incorporated by reference herein.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows:

FIG. 3 is a top plan view of a fastener cartridge of the end effector of FIG. 2;

FIG. 4 is a bottom plan view of an anvil of the end effector of FIG. 2;

FIG. 10 is a plan view of a staple cartridge according to various embodiments of the present disclosure;

FIG. 11 is a plan view of an arrangement of multi-staple drivers and driving wedges, according to various embodiments of the present disclosure;

FIG. 14 is a plan view of an arrangement of single-staple drivers and driving wedges, according to various embodiments of the present disclosure;

FIG. 16 is a plan view of an arrangement of staples and driving wedges, according to various embodiments of the present disclosure;

FIG. 23 depicts tissue stapled by a staple line in accordance with at least one embodiment;

FIG. 24 depicts tissue stapled by a staple line in accordance with at least one embodiment;

FIG. 38A is a partial plan view of the sled of FIG. 37 and a staple, depicting the deployment progression of the staple;

FIG. 38B is an elevation view of the sled of FIG. 37 and a staple, depicting the deployment progression of the staple;

FIG. 39A is a partial plan view of a driverless staple cartridge having angled staples and the sled of FIG. 39, according to various embodiments of the present disclosure;

FIG. 39B is a partial perspective view of the sled of FIG. 39 and the staples of FIG. 20, according to various embodiments of the present disclosure;

FIG. 40 is a partial, perspective view of a sled and a staple, according to various embodiments of the present disclosure;

FIG. 53 is a partial plan view of a staple cartridge comprising a cartridge body and an implantable adjunct material positioned on the cartridge body in accordance with at least one embodiment;

FIG. 54 is a partial plan view of an implantable adjunct material in accordance with at least one embodiment;

FIG. 56 is a partial plan view of an implantable adjunct material in accordance with at least one embodiment;

FIG. 57 is a partial plan view of an implantable adjunct material in accordance with at least one embodiment;

FIG. 60 is a top view of the surgical staple cartridge and buttress member of FIG. 59;

FIG. 61 is a perspective view of a portion of the surgical staple cartridge and buttress member of FIGS. 59 and 60;

FIG. 62 is a top view of another portion of the surgical staple cartridge and buttress member of FIGS. 59-61;

FIG. 71 is a top view of a portion of another buttress member;

FIG. 72 is a cross-sectional view of the buttress member of FIG. 71 taken along line 72-72 in FIG. 71;

FIG. 74 is a top view of the surgical staple cartridge of FIG. 73;

FIG. 75 is an enlarged perspective view of a portion of the surgical staple cartridge of FIGS. 73 and 74;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
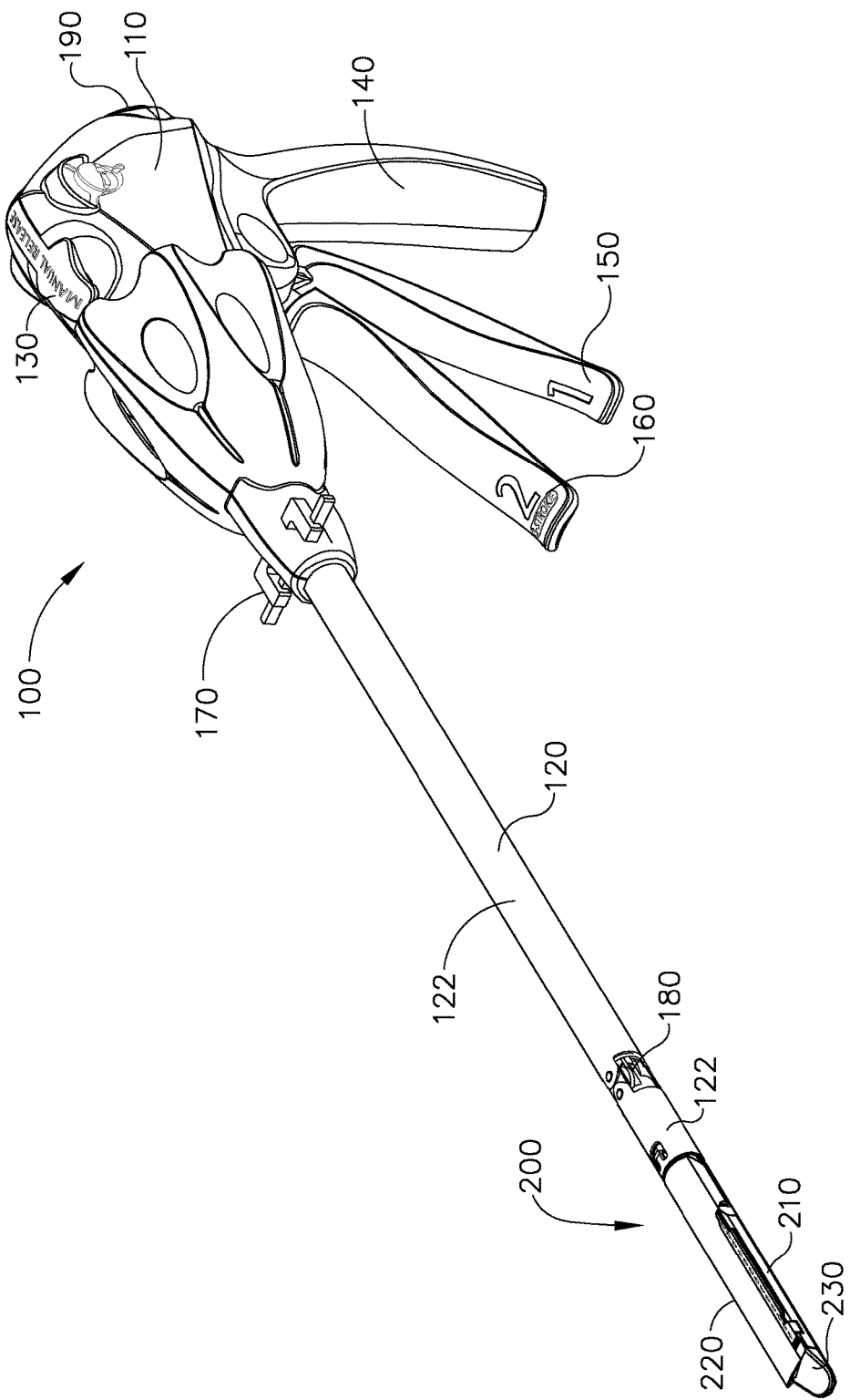
FIG. 1 is a perspective view of a surgical fastening instrument in accordance with at least one embodiment.

Applicant of the present application owns the following patent applications which were filed on Sep. 26, 2014 and which are each herein incorporated by reference in their respective entireties:

U.S. patent application Ser. No. 14/498,087, entitled SURGICAL STAPLE AND DRIVER ARRANGEMENTS FOR STAPLE CARTRIDGES, now U.S. Patent Application Publication No. 2016/00891407;

U.S. patent application Ser. No. 14/498,105, entitled SURGICAL STAPLE AND DRIVER ARRANGEMENTS FOR STAPLE CARTRIDGES, now U.S. Pat. No. 9,801,628;

U.S. patent application Ser. No. 14/498,107, entitled SURGICAL STAPLING BUTTRESSES AND ADJUNCT MATERIALS, now U.S. Patent Application Publication No. 2016/0089143;

U.S. patent application Ser. No. 14/498,121, entitled FASTENER CARTRIDGE FOR CREATING A FLEXIBLE STAPLE LINE, now U.S. Patent Application Publication No. 2016/0089141; and U.S. patent application Ser. No. 14/498,145, entitled METHOD FOR CREATING A FLEXIBLE STAPLE LINE, now U.S. Patent Application Publication No. 2016/0089142.

Applicant of the present application owns the following patent applications which were filed on Jun. 30, 2014 and which are each herein incorporated by reference in their respective entireties:

U.S. patent application Ser. No. 14/318,996, entitled FASTENER CARTRIDGES INCLUDING EXTENSIONS HAVING DIFFERENT CONFIGURATIONS;

U.S. patent application Ser. No. 14/319,006, entitled FASTENER CARTRIDGE COMPRISING FASTENER CAVITIES INCLUDING FASTENER CONTROL FEATURES;

U.S. patent application Ser. No. 14/319,014, entitled END EFFECTOR COMPRISING AN ANVIL INCLUDING PROJECTIONS EXTENDING THEREFROM;

U.S. patent application Ser. No. 14/318,991, entitled SURGICAL FASTENER CARTRIDGES WITH DRIVER STABILIZING ARRANGEMENTS;

U.S. patent application Ser. No. 14/319,004, entitled SURGICAL END EFFECTORS WITH FIRING ELEMENT MONITORING ARRANGEMENTS;

U.S. patent application Ser. No. 14/319,008, entitled FASTENER CARTRIDGE COMPRISING NON-UNIFORM FASTENERS;

U.S. patent application Ser. No. 14/318,997, entitled FASTENER CARTRIDGE COMPRISING DEPLOYABLE TISSUE ENGAGING MEMBERS;

U.S. patent application Ser. No. 14/319,002, entitled FASTENER CARTRIDGE COMPRISING TISSUE CONTROL FEATURES;

U.S. patent application Ser. No. 14/319,013, entitled FASTENER CARTRIDGE ASSEMBLIES AND STAPLE RETAINER COVER ARRANGEMENTS; and U.S. patent application Ser. No. 14/319,016, entitled FASTENER CARTRIDGE INCLUDING A LAYER ATTACHED THERETO.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

A surgical fastening instrument 100 is depicted in FIG. 1. The surgical fastening instrument 100 is configured to deploy an expandable staple line. Various expandable staple lines are disclosed herein and the surgical fastening instrument 100 is capable of deploying any one of these expandable staple lines. Moreover, surgical instruments other than the surgical fastening instrument 100 are capable of deploying any one of the expandable staple lines disclosed herein.

The surgical fastening instrument 100 comprises a handle 110, a shaft 120, and an end effector 200. The handle 110 comprises a pistol grip 140, a closure trigger 150 configured to operate a closure system, a firing trigger 160 configured to operate a firing system, and an articulation actuator 170 configured to operate an articulation system for articulating the end effector 200 relative to the shaft 120. The disclosure of U.S. Pat. No. 7,845,537, entitled SURGICAL INSTRUMENT HAVING RECORDING CAPABILITIES, which issued on Dec. 7, 2010, is incorporated by reference in its entirety. Other embodiments are envisioned which comprise a single trigger configured to operate a closure system and a firing system. Various embodiments are envisioned in which the end effector of the surgical instrument is not articulatable. The disclosure of U.S. patent application Ser. No. 13/974,166, entitled FIRING MEMBER RETRACTION DEVICES FOR POWERED SURGICAL INSTRUMENTS, which was filed on Aug. 23, 2013, is incorporated by reference in its entirety.

Figure 2:
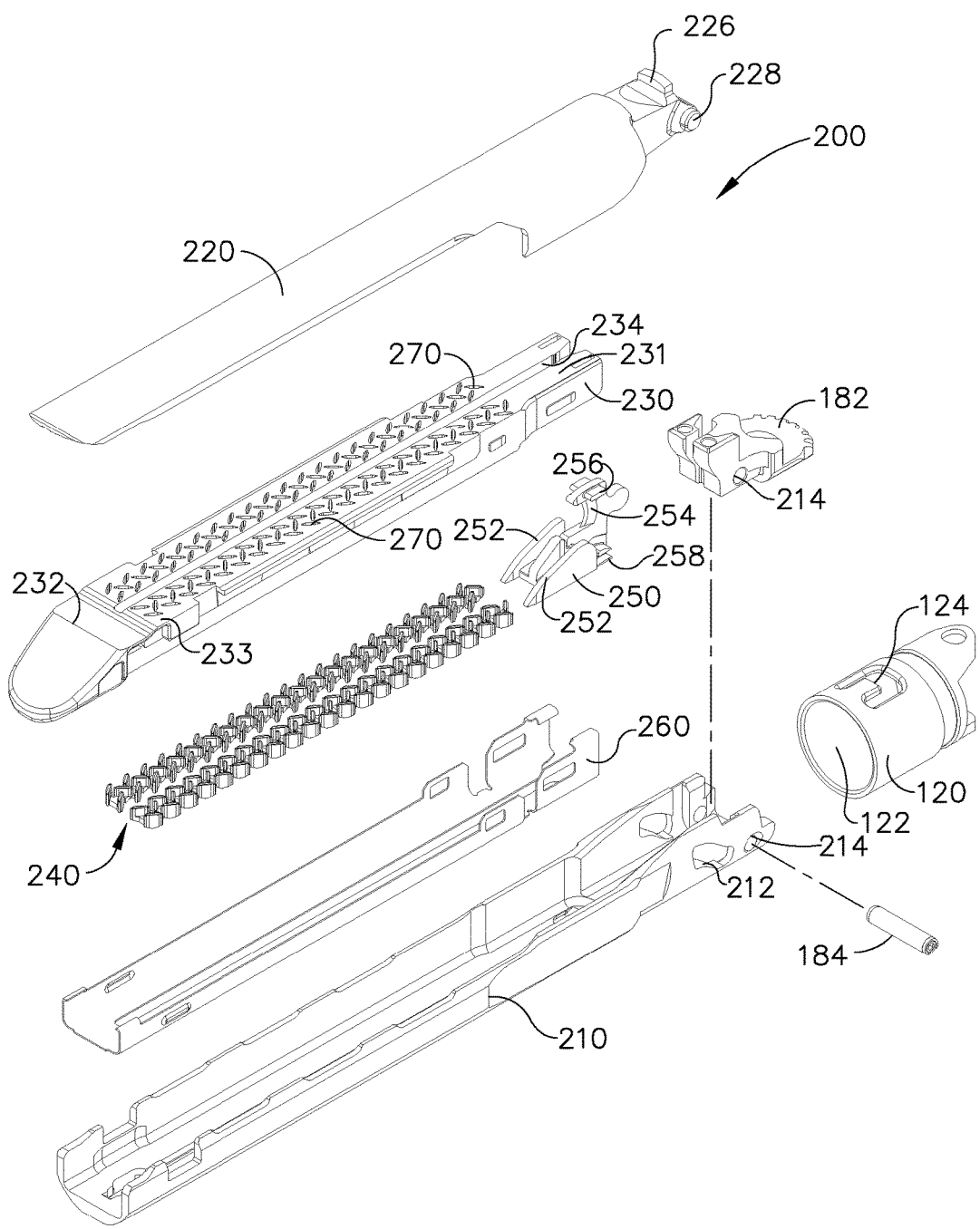
FIG. 2 is an exploded view of an end effector of the surgical fastening instrument of FIG. 1.

The closure trigger 150 is rotatable toward the pistol grip 140 to actuate the closure system. Referring primarily to FIG. 2, the closure system comprises a closure tube 122 which is advanced distally when the closure trigger 150 is moved toward the pistol grip 140. The closure tube 122 is engaged with a first jaw including an anvil 220 of the end effector 200. In at least one instance, the anvil 220 comprises one or more projections 228 extending therefrom which are positioned in one or more elongated slots 212 defined in a second jaw. The projections 228 and the elongated slots 212 are structured and arranged to permit the anvil 220 to be rotated between an open position and a closed position relative to a stationary, or fixed, cartridge channel 210 of the second jaw. In various alternative embodiments, a cartridge channel can be rotatable relative to a stationary, or fixed, anvil 220. Regardless of whether the cartridge channel or the anvil of an end effector is fixed, the end effector may be articulatable or non-articulatable relative to the shaft.

Referring again to FIG. 2, the anvil 220 includes a tab 226 which is engaged with a slot 124 defined in the closure tube 122. When the closure tube 122 is moved distally by the closure trigger 150, a sidewall of the slot 124 can engage the tab 226 and rotate the anvil 220 toward the cartridge channel 210. When the closure tube 122 is moved proximally, another sidewall of the slot 124 can engage the tab 226 and rotate the anvil 220 away from the cartridge channel 210. In some instances, a biasing spring can be positioned intermediate the anvil 220 and the cartridge channel 210 which can be configured to bias the anvil 220 away from the cartridge channel 210.

Referring again to FIG. 2, the firing trigger 160 is rotatable toward the pistol grip 140 to actuate the firing system. The firing system comprises a firing member extending within the shaft 120. The firing system further comprises a sled 250 which is operably engaged with the firing member. When the firing trigger 160 is rotated toward the pistol grip 140, the firing trigger 160 drives the firing member and the sled 250 distally within the end effector 200. The end effector 200 further comprises a staple cartridge 230 positioned within the cartridge channel 210. The staple cartridge 230 is replaceable and, thus, removable from the cartridge channel 210; however, other embodiments are envisioned in which the staple cartridge 230 is not readily replaceable and/or removable from the cartridge channel 210.

The staple cartridge 230 comprises a plurality of staple cavities 270. Each staple cavity 270 is configured to removably store a staple therein, although it is possible that some staple cavities 270 may not contain a staple stored therein. The staple cartridge 230 further comprises a plurality of staple drivers 240 movably positioned therein. Each driver 240 is configured to support three staples and/or lift the three staples out of their respective staple cavities 270 at the same time, or concurrently. Although each driver 240 of the embodiment depicted in FIGS. 1-4 deploys three staples concurrently, other embodiments are envisioned in which a driver may deploy less than three staples or more than three staples concurrently. The sled 250 comprises one or more ramp surfaces 252 which are configured to slide under the drivers 240 and lift the drivers 240 upwardly toward a deck surface 233 of the staple cartridge 230. The sled 250 is movable from a proximal end 231 of the staple cartridge 230 toward a distal end 232 to sequentially lift the drivers 240. When the drivers 240 are lifted toward the deck by the sled 250, the drivers 240 lift the staples toward the anvil 220. As the sled 250 is progressed distally, the staples are driven against the anvil 220 and are ejected from the staple cavities 270 by the drivers 240. The staple cartridge 230 can further comprise a support pan 260 attached thereto which extends around the bottom of the staple cartridge 230 and retains the drivers 240, the staples, and/or the sled 250 within the cartridge 230.

The sled 250 and/or the pusher member which advances the sled 250 distally can be configured to engage the first jaw including the anvil 220 and/or the second jaw including the staple cartridge 230 and position the anvil 220 and the staple cartridge 230 relative to one another. In at least one instance, the sled 250 comprises at least one first projection 256 extending therefrom which is configured to engage the anvil 220 and at least one second projection 258 configured to engage the cartridge channel 210. The projections 256 and 258 can position the anvil 220 and the staple cartridge 230 relative to one another. As the sled 250 is advanced distally, the projections 256 and 258 can position the anvil 220 and set the tissue gap between the anvil 220 and the deck 233.

The end effector 200 can further comprise a cutting member configured to incise tissue captured between the staple cartridge 230 and the anvil 220. Referring again to FIG. 2, the sled 250 includes a knife 254; however, any suitable cutting member could be utilized. As the sled 250 is being advanced distally to deploy the staples from the staple cavities 270, the knife 254 is moved distally to transect the tissue. In certain alternative embodiments, the firing member which pushes the sled 250 distally can include a cutting member. The cartridge 230 includes a longitudinal slot 234 configured to at least partially receive the knife 254. The anvil 220 also includes a longitudinal slot configured to at least partially receive the knife 254; however, embodiments are envisioned in which only one of the cartridge 230 and the anvil 220 includes a slot configured to receive a cutting member.

Further to the above, referring primarily to FIG. 1, the handle 110 of the surgical instrument 100 comprises an articulation actuator 170 which, when actuated, can articulate the end effector 200 about an articulation joint 180. When the actuator 170 is pushed in a first direction, the end effector 200 can be rotated in a first direction and, when the actuator 170 is pushed in a second direction, the end effector 200 can be rotated in a second, or opposite, direction. Referring now to FIG. 2, the end effector 200 includes an articulation lock plate 182 mounted to the proximal end thereof. In the illustrated embodiment, the lock plate 182 is mounted to the cartridge channel 210 via a pin 184 which extends through apertures 214 defined in the cartridge channel 210 and the lock plate 182. The shaft 120 can further include a lock movable between a first, engaged, position in which the lock is engaged with the lock plate 182 and a second, or disengaged, position in which the lock is disengaged from the lock plate. When the lock is in its engaged position, the lock can hold the end effector 200 in position. When the lock is in its disengaged position, the end effector 200 can be rotated about the articulation joint 180. The disclosure of U.S. patent application Ser. No. 14/314,788, entitled ROBOTICALLY-CONTROLLED SHAFT BASED ROTARY DRIVE SYSTEMS FOR SURGICAL INSTRUMENTS, which was filed on Jun. 25, 2014, is incorporated by reference in its entirety. The disclosure of U.S. Patent Application Publication No. 2013/0168435, entitled SURGICAL STAPLING INSTRUMENT WITH AN ARTICULATABLE END EFFECTOR, which was filed on Feb. 26, 2013, is incorporated by reference in its entirety.

Turning now to FIGS. 3 and 4, the staple cavities 270 of the staple cartridge 200 can be positioned and arranged such that the staples stored in the staple cavities are deployed as part of an extensible staple line. The staple cavities 270 are arranged in a staple cavity array. The staple cavity array comprises a first row of staple cavities 270a which removably stores a first row of staples. The first row of staple cavities 270a extends along a first longitudinal axis 272a adjacent the longitudinal slot 234. The staple cavity array comprises a second row of staple cavities 270b which removably stores a second row of staples. The second row of staple cavities 270b extends along a second longitudinal axis 272b adjacent the first row of staple cavities 270a. The staple cavity array comprises a third row of staple cavities 270c which removably stores a third row of staples. The third row of staple cavities 270c extends along the second row of staple cavities 270b.

Referring again to FIGS. 3 and 4, the first longitudinal axis 272a is parallel, or at least substantially parallel, to the second longitudinal axis 272b; however, other arrangements are possible in which the first longitudinal axis 272a is not parallel to the second longitudinal axis 272b. The second longitudinal axis 272b is parallel, or at least substantially parallel, to the third longitudinal axis 272c; however, other arrangements are possible in which the second longitudinal axis 272b is not parallel to the third longitudinal axis 272c. The first longitudinal axis 272a is parallel, or at least substantially parallel, to the third longitudinal axis 272c; however, other arrangements are possible in which the first longitudinal axis 272a is not parallel to the third longitudinal axis 272c.

Referring again to FIGS. 3 and 4, the staple cartridge 230 comprises a first portion of the staple cavity array including a first row 270a, a second row 270b, and a third row 270c on a first side of the longitudinal slot 234 and a second portion of the cavity array including a first row 270a, a second row 270b, and a third row 270c on a second side of the longitudinal slot 234. The first cavity array portion is a mirror image of the second cavity array portion with respect to the longitudinal slot; however, other arrangements may be utilized.

Figure 52:
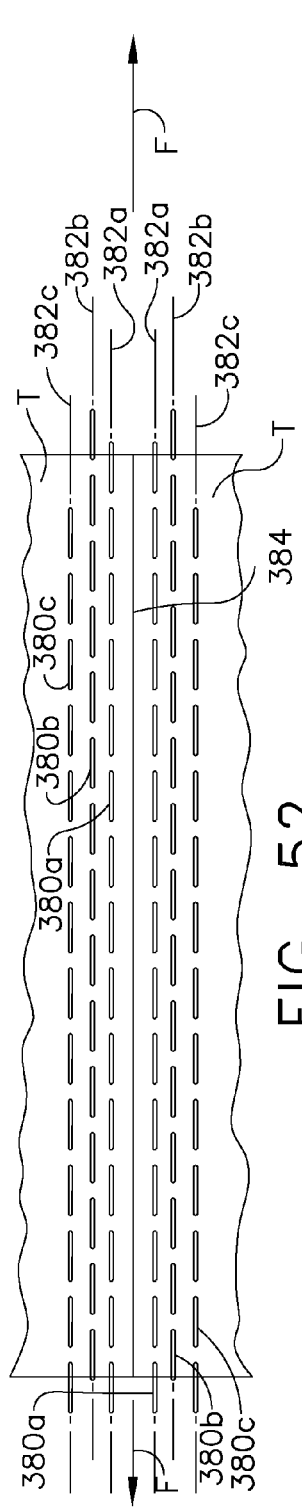
FIG. 52 depicts a previous staple pattern implanted in tissue.
Figure 52A:
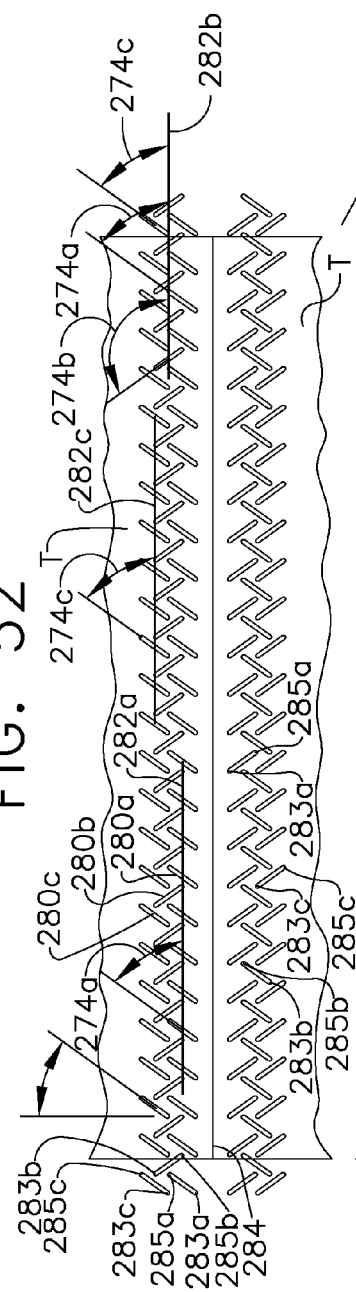
FIG. 52A depicts the staple pattern deployed by the staple cartridge of FIG. 3.

The staple cartridge 230 is configured to deploy the staple array depicted in FIG. 52A. The staple cartridge 230 is configured to deploy a first row of staples 280a along a first longitudinal axis 282a, a second row of staples 280b along a second longitudinal axis 282b, and a third row of staples 280c along a third longitudinal axis 282c. In various instances, the staple cartridge 230 is configured to deploy a first row of staples 280a, a second row of staples 280b, and a third row of staples 280c on a first side of a longitudinal incision 284 and a first row of staples 280a, a second row of staples 280b, and a third row of staples 280c on a second side of the longitudinal incision 284. The first rows of staples 280a can be positioned adjacent the longitudinal incision 284 and the third row of staples 280c can be positioned furthest away from the longitudinal incision 284. Each second row of staples 280b can be positioned intermediate a first row of staples 280a and a third row of staples 280c.

Further to the above, the first staples 280a are removably stored in the first staple cavities 270a, the second staples 280b are removably stored in the second staple cavities 270b, and the third staples 280c are removably stored in the third staple cavities 270c. The staple cavities 270a-270c are configured and arranged to deploy the staples 280a-280c in the arrangement depicted in FIG. 52A. The first staples 280a are oriented at a first angle 274a with respect to the longitudinal axis 282a. The second staples 280b are oriented at a second angle 274b with respect to a longitudinal axis 282b. The third staples 280c are oriented at a third angle 274c with respect to the longitudinal axis 282c. The first angle 274a is different than the second angle 274b; however, in other embodiments, the first angle 274a and the second angle 274b can be the same. The third angle 274c is different than the second angle 274b; however, in other embodiments, the third angle 274c and the second angle 274b can be the same. The first angle 274a is the same as the third angle 274c; however, in other embodiments, the first angle 274a and the third angle 274c can be different.

Further to the above, the first angle 274a can be measured with respect to the first longitudinal axis 282a, the second angle 274b can be measured with respect to the second longitudinal axis 282b, and the third angle 274c can be measured with respect to the third longitudinal axis 282c. When the first longitudinal axis 282a, the second longitudinal axis 282b, and/or the third longitudinal axis 282c are parallel to one another, the first angle 274a, the second angle 274b, and/or the third angle 274c can be measured with respect to any one of the first longitudinal axis 282a, the second longitudinal axis 282b, and the third longitudinal axis 282c. When the first longitudinal axis 282a, the second longitudinal axis 282b, and/or the third longitudinal axis 282c are parallel to the longitudinal slot 234, the first angle 274a, the second angle 274b, and/or the third angle 274c can be measured with respect to the longitudinal slot 234. Correspondingly, when the first longitudinal axis 282a, the second longitudinal axis 282b, and/or the third longitudinal axis 282c are parallel to the tissue transection 284, the first angle 274a, the second angle 274b, and/or the third angle 274c can be measured with respect to the tissue transection 284.

The first staples 280a, the second staples 280b, and the third staples 280c can be positioned and arranged such that they provide laterally-overlapping staple lines. More particularly, referring again to FIG. 52A, the longitudinal row of second staples 280b is positioned laterally with respect to the longitudinal row of first staples 280a such that the second staples 280b are aligned with the gaps between the first staples 280a and, similarly, the longitudinal row of third staples 280c is positioned laterally with respect to the longitudinal row of second staples 280b such that the third staples 280c are aligned with the gaps between the second staples 280b. Such an arrangement can limit the flow of blood from the tissue T to the transection 284.

In the illustrated embodiment, each first staple 280a comprises a distal leg 283a which is distal with respect to a distal leg 283b of an adjacent second staple 280b and, in addition, a proximal leg 285a which is proximal with respect to the distal leg 283b. Similarly, each third staple 280c comprises a distal leg 283c which is distal with respect to the distal leg 283b of the adjacent second staple 280b and, in addition, a proximal leg 285c which is proximal with respect to the distal leg 283b. The second staple 280b adjacent the first staple 280a and the third staple 280c mentioned above comprises a proximal leg 285b which is proximal with respect to the proximal leg 285a of the first staple 280a and the proximal leg 285c of the third staple 280c. This is but one exemplary embodiment and any suitable arrangement could be utilized.

Further to the above, the first staples 280a straddle the first longitudinal axis 282a. The distal legs 283a of the first staples 280a are positioned on one side of the first longitudinal axis 282a and the proximal legs 285a are positioned on the other side of the first longitudinal axis 282a. Stated another way, the legs of the first staples 280a are offset with respect to the first longitudinal axis 282a. Alternative embodiments are envisioned in which the first staples 280a are aligned with or collinear with the first longitudinal axis 282a.

The second staples 280b straddle the second longitudinal axis 282b. The distal legs 283b of the second staples 280b are positioned on one side of the second longitudinal axis 282b and the proximal legs 285b are positioned on the other side of the second longitudinal axis 282b. Stated another way, the legs of the second staples 280b are offset with respect to the second longitudinal axis 282b. Alternative embodiments are envisioned in which the second staples 280b are aligned with or collinear with the second longitudinal axis 282b.

The third staples 280c straddle the third longitudinal axis 282c. The distal legs 283c of the third staples 280c are positioned on one side of the third longitudinal axis 282c and the proximal legs 285c are positioned on the other side of the third longitudinal axis 282c. Stated another way, the legs of the third staples 280c are offset with respect to the third longitudinal axis 282c. Alternative embodiments are envisioned in which the third staples 280c are aligned with or collinear with the third longitudinal axis 282c.

In certain embodiments, a first staple 280a can comprise a proximal leg 285a which is aligned with the distal leg 283b of an adjacent second staple 280b. Similarly, a third staple 280c can comprise a proximal leg 285c which is aligned with the distal leg 283b of an adjacent second staple 280b. In various embodiments, a first staple 280a can comprise a proximal leg 285a which is positioned distally with respect to the distal leg 283b of an adjacent second staple 280b. Similarly, a third staple 280c can comprise a proximal leg 285c which is positioned distally with respect to the distal leg 283b of an adjacent second staple 280b.

The row of second staples 280b is bounded by the row of first staples 280a and the row of third staples 280c. A second staple 280b is bounded on one side by a first staple 280a and on the other side by a third staple 280c. More particularly, a first staple 280a is positioned laterally inwardly with respect to the proximal leg 285b of a second staple 280b and, similarly, a third staple 280c is positioned laterally outwardly with respect to the distal leg 283b of the second staple 280b. As a result, the first staples 280a can provide a boundary on one side of the second staples 280b and the third staples 280b can provide a boundary on the other side of the second staples 280b.

A traditional staple array is illustrated in FIG. 52. This staple array comprises a first row of staples 380a positioned along a first longitudinal axis 382a, a second row of staples 380b positioned along a second longitudinal axis 382b, and a third row of staples 380c positioned along a third longitudinal axis 382c positioned on a first side of an incision 384 in the tissue T. The staples 380a are aligned, or at least substantially aligned, with the first longitudinal axis 382a; the staples 380b are aligned, or at least substantially aligned, with the second longitudinal axis 382b; and the staples 380c are aligned, or at least substantially aligned, with the third longitudinal axis 382c. Stated another way, the first staples 380a are not oriented at an angle with respect to the first longitudinal axis 382a, the second staples 380b are not oriented at an angle with respect to the second longitudinal axis 382b, and the third staples 380c are not oriented at an angle with respect to the third longitudinal axis 382c. This staple array also comprises a first row of staples 380a positioned along a first longitudinal axis 382a, a second row of staples 380b positioned along a second longitudinal axis 382b, and a third row of staples 380c positioned along a third longitudinal axis 382c positioned on a second, or opposite, side of the incision 384.

When a longitudinal tensile force is applied to the tissue T stapled by the staple array illustrated in FIG. 52, the tissue will stretch longitudinally. Moreover, in various instances, the staples 380a, 380b, and 380c can translate longitudinally as the tissue is stretched longitudinally. Such an arrangement can be suitable in many circumstances; however, the staples 380a, 380b, and 380c can restrict the stretching and/or movement of the tissue. In some instances, the tissue that has been stapled by the staples 380a, 380b, and 380c may be far less flexible than the adjacent tissue that has not been stapled. Stated another way, the staple array comprising the staples 380a, 380b, and 380c can create a sudden change in the material properties of the tissue. In at least one instance, a large strain gradient can be created within the tissue as a result of the staple array which, in turn, can create a large stress gradient within the tissue.

When the staples 380a-380c are ejected from the staple cartridge, the legs of the staples can puncture the tissue T. As a result, the staple legs create holes in the tissue. Various types of tissue are resilient and can stretch around the staple legs as the staple legs pass through the tissue. In various instances, the resiliency of the tissue can permit the tissue to stretch and resiliently return toward the staple legs to reduce or eliminate gaps present between the tissue and the staple legs. Such resiliency can also permit the tissue to stretch when a stretching force is applied to the tissue; however, such resiliency can be inhibited by certain staple patterns. In at least one instance, the staple pattern depicted in FIG. 52 can inhibit the longitudinal stretching of the tissue. When a longitudinal stretching force is applied to the tissue stapled by the staple pattern of FIG. 52, the tissue may begin to pull away from the staple legs and create gaps therebetween. In some instances, especially in bariatric resection applications, such gaps can result in increased bleeding from the stomach tissue. In certain instances, especially in lung resection applications, air leaks can result in the lung tissue.

The staple array depicted in FIG. 52A is more flexible than the staple array depicted in FIG. 52. When a longitudinal tensile force is applied to the tissue T, referring now to FIG. 52B, the staples 280a, 280b, and 280c can, one, translate longitudinally as the tissue is stretched longitudinally and/or, two, rotate as the tissue is stretched longitudinally. The compliant staple array depicted in FIG. 52 can create significant extensibility along the staple lines, such as in the longitudinal direction defined by the staple lines, for example. Such longitudinal extensibility can reduce the stress and/or strain gradient within the stapled tissue T and/or the tissue T surrounding the stapled tissue T. Moreover, the compliant staple array depicted in FIG. 52A can reduce or eliminate the gaps between the staple legs and the tissue T when a longitudinal stretching force is applied to the tissue and, as a result, reduce the bleeding and/or air leaks between the staple legs and the tissue.

With regard to the longitudinal translation of the staples 280a, 280b, and 280c, the first staples 280a can move along the first longitudinal axis 282a, the second staples 280b can move along the second longitudinal axis 282b, and the third staples 280c can move along the third longitudinal axis 282c. When the first staples 280a move along the first longitudinal axis 282a, the first staples 280a can spread out across the first longitudinal axis 282a. Stated another way, the distance between the first staples 280a, or gap distance, can increase when a longitudinal force is applied to the tissue along, and/or parallel to, the first longitudinal axis 282a. Similarly, the second staples 280b can spread out across the second longitudinal axis 282b when the second staples 280b move along the second longitudinal axis 282b. The distance between the second staples 280b, or gap distance, can increase when a longitudinal force is applied to the tissue along, and/or parallel to, the second longitudinal axis 282b. Also, similarly, the third staples 280c can spread out across the third longitudinal axis 282c when the third staples 280c move along the third longitudinal axis 282c. The distance between the third staples 280c, or gap distance, can increase when a longitudinal force is applied to the tissue along, and/or parallel to, the third longitudinal axis 282c.

As discussed above, the staples 280a, 280b, and/or 280c can move with the tissue T when the tissue T is stretched. When the tissue T is pulled longitudinally, further to the above, the first longitudinal axis 282a, the second longitudinal axis 282b, and/or the third longitudinal axis 282c can remain parallel to one another. In some instances, the orientation of the first longitudinal axis 282a, the second longitudinal axis 282b, and/or the third longitudinal axis 282c can become non-parallel, such as when a transverse force, i.e., a force which is transverse to the longitudinal force, is applied to the tissue T, for example. In certain instances, the first longitudinal axis 282a, the second longitudinal axis 282b, and/or the third longitudinal axis 282c can move closer to each other when the tissue T is pulled longitudinally. Such movement can be the result of transverse contraction that occurs within the tissue T when a longitudinal stretching force is applied to the tissue T. In some instances, the first longitudinal axis 282a, the second longitudinal axis 282b, and/or the third longitudinal axis 282c can move away from each other, such as when a transverse force is applied to the tissue T, for example.

With regard to the rotational movement of the staples 280a, 280b, and 280c, the first staples 280a can rotate with respect to the first longitudinal axis 282a when a longitudinal tensile force is applied to the tissue T. Each first staple 280a can rotate between an initial first angle 274a and another first angle 274a when a longitudinal tensile force is applied to the tissue T. In at least one instance, each first staple 280a can rotate between an initial orientation in which the first staple 280a extends in a transverse direction to the first longitudinal axis 282a and another orientation which is closer to being aligned with the first longitudinal axis 282a. In some instances, the application of a longitudinal tensile force to the tissue T can cause the first staples 280a to rotate into an orientation which is collinear with the first longitudinal axis 282a. In various instances, each first staple 280a can rotate about an axis extending through the first longitudinal axis 282a.

As discussed above, a first staple 280a can rotate between an initial first angle 274a and another first angle 274a when a longitudinal tensile force is applied to the tissue T. In various embodiments, the initial, or unstretched, first angle 274a can be between approximately 5 degrees and approximately 85 degrees, for example. In certain embodiments, the initial, or unstretched, first angle 274a can be between approximately 30 degrees and approximately 60 degrees, for example. In at least one embodiment, the initial, or unstretched, first angle 274a can be approximately 45 degrees, for example. In at least one embodiment, the initial, or unstretched, first angle 274a can be approximately 10 degrees, approximately 20 degrees, approximately 30 degrees, approximately 40 degrees, approximately 50 degrees, approximately 60 degrees, approximately 70 degrees, and/or approximately 80 degrees, for example.

In various instances, the stretched first angle 274a can be between approximately 5 degrees and approximately 85 degrees, for example. In certain instances, the stretched first angle 274a can be between approximately 30 degrees and approximately 60 degrees, for example. In at least one instance, the stretched first angle 274a can be approximately 45 degrees, for example. In at least one instance, the stretched first angle 274a can be approximately 10 degrees, approximately 20 degrees, approximately 30 degrees, approximately 40 degrees, approximately 50 degrees, approximately 60 degrees, approximately 70 degrees, and/or approximately 80 degrees, for example.

In various instances, the difference between the unstretched first angle 274a and the stretched first angle 274a can be between approximately 1 degree and approximately 45 degrees, for example. In certain instances, the difference between the unstretched first angle 274a and the stretched first angle 274a can be approximately 1 degree, approximately 2 degrees, approximately 3 degrees, approximately 4 degrees, and/or approximately 5 degrees, for example. In certain instances, the difference between the unstretched first angle 274a and the stretched first angle 274a can be approximately 5 degrees, approximately 10 degrees, approximately 15 degrees, approximately 20 degrees, and/or approximately 25 degrees, for example.

Further to the above, the second staples 280b can rotate with respect to the second longitudinal axis 282b when a longitudinal tensile force is applied to the tissue T. Each second staple 280b can rotate between an initial second angle 274b and another second angle 274b when a longitudinal tensile force is applied to the tissue T. In at least one instance, each second staple 280b can rotate between an initial orientation in which the second staple 280b extends in a transverse direction to the second longitudinal axis 282b and another orientation which is closer to being aligned with the second longitudinal axis 282b. In some instances, the application of a longitudinal tensile force to the tissue T can cause the second staples 280b to rotate into an orientation which is collinear with the second longitudinal axis 282b. In various instances, each second staple 280b can rotate about an axis aligned with and/or extending through the second longitudinal axis 282b.

As discussed above, a second staple 280b can rotate between an initial second angle 274b and another second angle 274b when a longitudinal tensile force is applied to the tissue T. In various embodiments, the initial, or unstretched, second angle 274b can be between approximately 5 degrees and approximately 85 degrees, for example. In certain embodiments, the initial, or unstretched, second angle 274b can be between approximately 30 degrees and approximately 60 degrees, for example. In at least one embodiment, the initial, or unstretched, second angle 274b can be approximately 45 degrees, for example. In at least one embodiment, the initial, or unstretched, second angle 274b can be approximately 10 degrees, approximately 20 degrees, approximately 30 degrees, approximately 40 degrees, approximately 50 degrees, approximately 60 degrees, approximately 70 degrees, and/or approximately 80 degrees, for example.

In various instances, the stretched second angle 274b can be between approximately 5 degrees and approximately 85 degrees, for example. In certain instances, the stretched second angle 274b can be between approximately 30 degrees and approximately 60 degrees, for example. In at least one instance, the stretched second angle 274b can be approximately 45 degrees, for example. In at least one instance, the stretched second angle 274b can be approximately 10 degrees, approximately 20 degrees, approximately 30 degrees, approximately 40 degrees, approximately 50 degrees, approximately 60 degrees, approximately 70 degrees, and/or approximately 80 degrees, for example.

In various instances, the difference between the unstretched second angle 274b and the stretched second angle 274b can be between approximately 1 degree and approximately 45 degrees, for example. In certain instances, the difference between the unstretched second angle 274b and the stretched second angle 274b can be approximately 1 degree, approximately 2 degrees, approximately 3 degrees, approximately 4 degrees, and/or approximately 5 degrees, for example. In certain instances, the difference between the unstretched second angle 274b and the stretched second angle 274b can be approximately 5 degrees, approximately 10 degrees, approximately 15 degrees, approximately 20 degrees, and/or approximately 25 degrees, for example.

Further to the above, the third staples 280c can rotate with respect to the third longitudinal axis 282c when a longitudinal tensile force is applied to the tissue T. Each third staple 280c can rotate between an initial third angle 274c and another third angle 274c when a longitudinal tensile force is applied to the tissue T. In at least one instance, each third staple 280c can rotate between an initial orientation in which the third staple 280c extends in a transverse direction to the third longitudinal axis 282c and another orientation which is closer to being aligned with the third longitudinal axis 282c. In some instances, the application of a longitudinal tensile force to the tissue T can cause the third staples 280c to rotate into an orientation which is collinear with the third longitudinal axis 282c. In various instances, each third staple 280c can rotate about an axis aligned with and/or extending through the third longitudinal axis 282c.

As discussed above, a third staple 280c can rotate between an initial third angle 274c and another third angle 274c when a longitudinal tensile force is applied to the tissue T. In various embodiments, the initial, or unstretched, third angle 274c can be between approximately 5 degrees and approximately 85 degrees, for example. In certain embodiments, the initial, or unstretched, third angle 274c can be between approximately 30 degrees and approximately 60 degrees, for example. In at least one embodiment, the initial, or unstretched, third angle 274c can be approximately 45 degrees, for example. In at least one embodiment, the initial, or unstretched, third angle 274c can be approximately 10 degrees, approximately 20 degrees, approximately 30 degrees, approximately 40 degrees, approximately 50 degrees, approximately 60 degrees, approximately 70 degrees, and/or approximately 80 degrees, for example.

In various instances, the stretched third angle 274c can be between approximately 5 degrees and approximately 85 degrees, for example. In certain instances, the stretched third angle 274c can be between approximately 30 degrees and approximately 60 degrees, for example. In at least one instance, the stretched third angle 274c can be approximately 45 degrees, for example. In at least one instance, the stretched third angle 274c can be approximately 10 degrees, approximately 20 degrees, approximately 30 degrees, approximately 40 degrees, approximately 50 degrees, approximately 60 degrees, approximately 70 degrees, and/or approximately 80 degrees, for example.

In various instances, the difference between the unstretched third angle 274c and the stretched third angle 274c can be between approximately 1 degree and approximately 45 degrees, for example. In certain instances, the difference between the unstretched third angle 274c and the stretched third angle 274c can be approximately 1 degree, approximately 2 degrees, approximately 3 degrees, approximately 4 degrees, and/or approximately 5 degrees, for example. In certain instances, the difference between the unstretched third angle 274c and the stretched third angle 274c can be approximately 5 degrees, approximately 10 degrees, approximately 15 degrees, approximately 20 degrees, and/or approximately 25 degrees, for example.

In various instances, the first staples 280a in the first row of staples can rotate a first amount and the second staples 280b in the second row of staples can rotate a second amount which is different than the first amount. The first amount can be less than or more than the second amount. In various instances, the first staples 280a in the first row of staples can rotate a first amount and the third staples 280c in the third row of staples can rotate a third amount which is different than the first amount. The first amount can be less than or more than the third amount. In various instances, the third staples 280c in the third row of staples can rotate a third amount and the second staples 280b in the second row of staples can rotate a second amount which is different than the third amount. The third amount can be less than or more than the second amount.

In at least one application, it may be desirable for the innermost rows of staples, i.e., the row of staples closest to the incision, to be more inflexible, or inextensible, than the other rows of staples. It may also be desirable for the outermost rows of staples, i.e., the row of staples furthest away from the incision, to be more flexible, or extensible, than the other rows of staples. When the angle between the first staple axes and the first longitudinal axis is smaller than the angle between the second staple axes and the second longitudinal axis, the first staples may have less room to rotate toward the first longitudinal axis than the second staples have to rotate toward the second longitudinal axis and, thus, may stiffen the tissue more than the second staples. Similarly, when the angle between the second staple axes and the second longitudinal axis is smaller than the angle between the third staple axes and the third longitudinal axis, the second staples may have less room to rotate toward the second longitudinal axis than the third staples have to rotate toward the third longitudinal axis and, thus, may stiffen the tissue more than the third staples Further to the above, the staple pattern disclosed in FIG. 52A comprises six longitudinal rows of staples. Other embodiments are envisioned which comprise less than six rows of staples, such as four rows of staples, for example, or more than six rows of staples, such as eight rows of staples, for example.

The first staples 280a, the second staples 280b, and the third staples 280c can comprise any suitable configuration such as, for example, a V-shaped configuration or a U-shaped configuration. A staple comprising a V-shaped configuration can include a base, a first leg extending from a first end of the base, and a second leg extending from a second end of the base, wherein the first leg and the second leg extend in directions which are non-parallel to one another. A staple comprising a U-shaped configuration can include a base, a first leg extending from a first end of the base, and a second leg extending from a second end of the base, wherein the first leg and the second leg extend in directions which are parallel to one another.

With regard to the staple pattern disclosed in FIG. 52A, for example, each first staple 280a comprises a proximal staple leg 285a and a distal staple leg 283a. A staple cartridge configured to deploy the staple pattern disclosed in FIG. 52A can include a proximal end and a distal end. The proximal staple leg 285a can be closer to the proximal end of the staple cartridge than the distal staple leg 283a and, similarly, the distal staple leg 283a can be closer to the distal end of the staple cartridge than the proximal staple leg 285a. The base of each first staple 280a can define a first base axis. The proximal staple leg 285a and the distal staple leg 283a can extend from the first base axis. The first staples 280a can be positioned and arranged such that the first base axes extend toward the longitudinal cut line 284 and toward the distal end of the staple cartridge.

With regard to the staple pattern disclosed in FIG. 52A, for example, each second staple 280b comprises a proximal staple leg 285b and a distal staple leg 283b. As discussed above, a staple cartridge configured to deploy the staple pattern disclosed in FIG. 52A can include a proximal end and a distal end. The proximal staple leg 285b can be closer to the proximal end of the staple cartridge than the distal staple leg 283b and, similarly, the distal staple leg 283b can be closer to the distal end of the staple cartridge than the proximal staple leg 285b. The base of each second staple 280b can define a second base axis. The proximal staple leg 285b and the distal staple leg 283b can extend from the second base axis. The second staples 280b can be positioned and arranged such that the second base axes extend toward the longitudinal cut line 284 and toward the proximal end of the staple cartridge.

With regard to the staple pattern disclosed in FIG. 52A, for example, each third staple 280c comprises a proximal staple leg 285c and a distal staple leg 283c. As discussed above, a staple cartridge configured to deploy the staple pattern disclosed in FIG. 52A can include a proximal end and a distal end. The proximal staple leg 285c can be closer to the proximal end of the staple cartridge than the distal staple leg 283c and, similarly, the distal staple leg 283c can be closer to the distal end of the staple cartridge than the proximal staple leg 285c. The base of each third staple 280c can define a third base axis. The proximal staple leg 285c and the distal staple leg 283c can extend from the third base axis. The third staples 280c can be positioned and arranged such that the third base axes extend toward the longitudinal cut line 284 and toward the distal end of the staple cartridge.

With regard to the staple pattern disclosed in FIG. 52A, for example, the first staples 280a can be aligned with the third staples 280c. The proximal staple leg 285a of a first staple 280a can be aligned with the proximal staple leg 285c of a third staple 280c. When the proximal staple leg 285a is aligned with the proximal staple leg 285c, the proximal staple leg 285a and the proximal leg 285c can be positioned along an axis which is perpendicular to the cut line 284. The distal staple leg 283a of the first staple 280a can be aligned with the distal staple leg 283c of the third staple 280c. When the distal staple leg 283a is aligned with the distal staple leg 283c, the distal staple leg 283a and the distal staple leg 283c can be positioned along an axis which is perpendicular to the cut line 284. In such circumstances, the third staple 280c can seal the tissue in the event that the first staple 280a is malformed. Similarly, the first staple 280a can hold the tissue together in the event that the third staple 280c is malformed. In other embodiments, the first staples 280a may not be aligned with the third staples 280c.

Further to the above, the first staples 280a can be aligned with the third staples 280c when the staple pattern is in an unstretched condition. When the staple pattern is stretched longitudinally, the first staples 280a and/or the third staples 280c can translate and/or rotate. In various circumstances, the first staples 280a can remain aligned with the third staples 280c when the tissue is stretched longitudinally. In other circumstances, the first staples 280a may not remain aligned with the third staples 280c.

With regard to the staple pattern disclosed in FIG. 52A once again, the distal staple leg 283b of a second staple 280b can be aligned with the proximal staple leg 285a of a first staple 280a and/or the proximal leg 285c of a third staple 280c. The distal staple leg 283b of the second staple 280b, the proximal staple leg 285a of the first staple 280a, and/or the proximal staple leg 285c of the third staple 280c can be positioned along an axis which is perpendicular to the cut line 284. The proximal staple leg 285b of a second staple 280b can be aligned with the distal staple leg 283a of a first staple 280a and/or the distal staple leg 283c of a third staple 280c. The proximal staple leg 285b of the second staple 280b, the distal staple leg 283a of the first staple 280a, and/or the distal staple leg 283c of the third staple 280c can be positioned along an axis which is perpendicular to the cut line 284.

Further to the above, the staple legs of the second staples 280b can be aligned with the staple legs of the first staples 280a and/or the third staples 280c when the staple pattern is in an unstretched condition. When the staple pattern is stretched longitudinally, the first staples 280a, the second staples 280b, and/or the third staples 280c can translate and/or rotate. In various circumstances, the legs of the second staples 280b may not remain aligned with the legs of the first staples 280a and/or the third staples 280c when the tissue is stretched longitudinally. In other circumstances, the legs of the second staples 280b can remain aligned with the legs of the first staples 280a and/or the third staples 280c when the tissue is stretched longitudinally.

In various embodiments, a staple pattern can be arranged such that the staples in one longitudinal staple row overlap with the staples in another longitudinal staple row. For instance, the distal staple leg 283b of a second staple 280b can be positioned distally with respect to the proximal staple leg 285a of a first staple 280a and/or the proximal leg 285c of a third staple 280c. For instance, the proximal staple leg 285b of a second staple 280b can be positioned proximally with the distal staple leg 283a of a first staple 280a and/or the distal staple leg 283c of a third staple 280c. The proximal staple leg 285b of the second staple 280b, the distal staple leg 283a of the first staple 280a, and/or the distal staple leg 283c of the third staple 280c can be positioned along an axis which is perpendicular to the cut line 284.

As discussed above, the second staples 280b can overlap with the first staples 280a and/or the third staples 280c when the staple pattern is in an unstretched condition. When the staple pattern is stretched longitudinally, the first staples 280a, the second staples 280b, and/or the third staples 280c can translate and/or rotate. In various circumstances, the second staples 280b can remain overlapped with the first staples 280a and/or the third staples 280c when the tissue is stretched longitudinally. In some circumstances, the second staples 280b may no longer be overlapped with the first staples 280a and/or the third staples 280c when the tissue is stretched longitudinally.

Figure 52B:
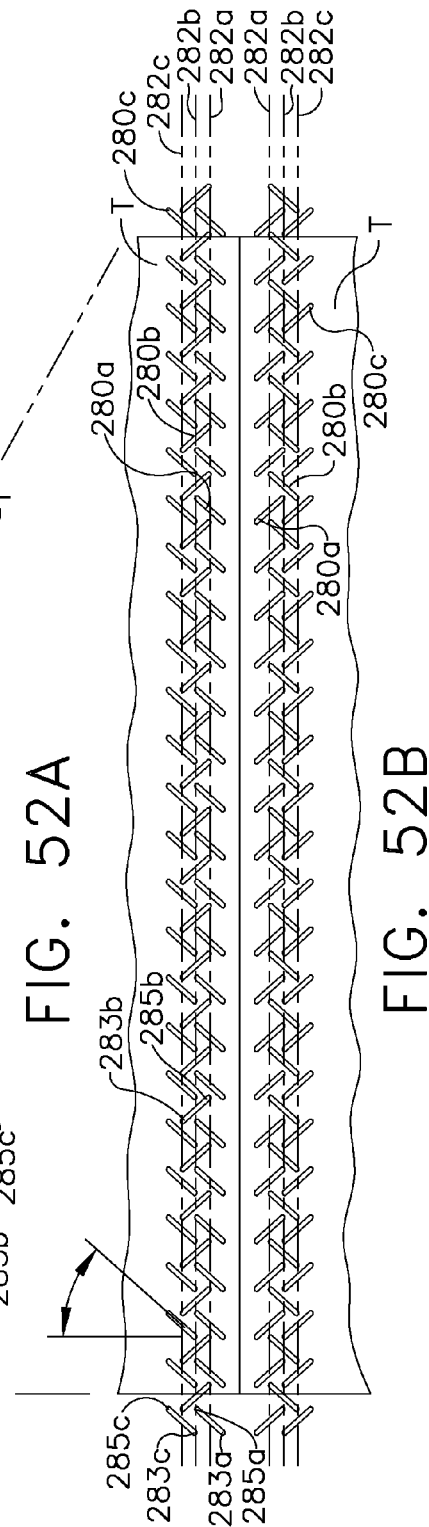
FIG. 52B depicts the staple pattern of FIG. 52A in a stretched condition.

The staple pattern depicted in FIG. 52A is depicted in an unstretched condition. When the tissue stapled by the staple pattern depicted in FIG. 52A is stretched longitudinally, the staples can move longitudinally with the tissue and/or rotate within the tissue, as illustrated in FIG. 52B. Such movement is also illustrated in FIG. 24.

The surgical instrument 100 is configured to be used during a laparoscopic surgical procedure. The end effector 200 and the shaft 120 are sized and dimensioned to be inserted through a trocar, or cannula, into a patient. The trocar can comprise an inner passage comprising an inner diameter. In some instances, the inner diameter can be approximately 5 mm or approximately 12 mm, for example. The end effector 200 is a linear end effector that applies staples along straight lines. Other surgical instruments are envisioned which apply staples along at least partially curved lines, such as those disclosed in U.S. Pat. No. 8,827,133, entitled SURGICAL STAPLING DEVICE HAVING SUPPORTS FOR A FLEXIBLE DRIVE MECHANISM, which issued on Sep. 9, 2014, for example. The entire disclosure of U.S. Pat. No. 8,827,133, entitled SURGICAL STAPLING DEVICE HAVING SUPPORTS FOR A FLEXIBLE DRIVE MECHANISM, which issued on Sep. 9, 2014, is incorporated by reference in its entirety. Such surgical instruments could be adapted to apply curved expandable staple lines utilizing the principles disclosed herein. While the surgical instrument 100 is adapted to be used during laparoscopic surgical procedures, the surgical instrument 100 could be utilized during an open surgical procedure where the surgical instrument 100 is inserted through a large incision in the patient. Moreover, the expandable staple lines disclosed herein could be applied by an open surgical stapler, such as those disclosed in U.S. Patent Application Publication No. 2014/0042205, entitled SURGICAL STAPLING INSTRUMENT, which was filed on Oct. 21, 2013, for example. The disclosure of U.S. Patent Application Publication No. 2014/0042205, entitled SURGICAL STAPLING INSTRUMENT, which was filed on Oct. 21, 2013, is incorporated by reference herein in its entirety.

Turning now to FIG. 4, the anvil 220 includes an array of forming pockets 290a, 290b, and 290c defined therein configured to deform the staples 280a, 280b, and 280c, respectively. The first forming pockets 290a are positioned along a first longitudinal axis 292a, the second longitudinal pockets 290b are positioned along a second longitudinal axis 292b, and the third forming pockets 290c are positioned along a third longitudinal axis 292c. The longitudinal axes 292a, 292b, and 292c are parallel and extend between a proximal end 221 and a distal end 222 of the anvil 220. The anvil 220 further comprises a longitudinal slot 224 defined therein configured to receive at least a portion of a firing member. In at least one instance, the firing member includes a cutting portion that extends between the anvil 220 and the staple cartridge 230. The anvil 220 comprises a row of first forming pockets 290a, a row of second forming pockets 290b, and a row of third forming pockets 290c on one side of the longitudinal slot 224 and another row of first forming pockets 290a, row of second forming pockets 290b, and row of third forming pockets 290c on the other side of the longitudinal slot 224. As the reader will appreciate, the forming pockets 290a, 290b, and 290c are aligned with and correspond to the staple cavities 270a, 270b, and 270c, respectively, defined in the staple cartridge 230.

The forming pockets 290a, 290b, and 290c are configured to deform the staples 280a, 280b, and 280c into a B-shaped configuration, for example. In various instances, the forming pockets 290a, 290b, and 290c are configured to deform U-shaped staples and/or V-shaped staples, for example, into such a B-shaped configuration. Each forming pocket 290a, 290b, and 290c comprises a proximal end configured to receive a proximal leg of a staple and a distal end configured to receive the distal leg of the staple. That said, any suitable anvil can be utilized to form the staples ejected from a staple cartridge into any suitable shape. Each forming pocket 290a, 290b, and 290c can comprise a groove extending between the proximal end and the distal end thereof. The groove can include sidewalls configured to deform a staple within a plane and prevent, or at least limit, the movement of the staple legs out of that plane as the staple legs are deformed.

Figure 5:
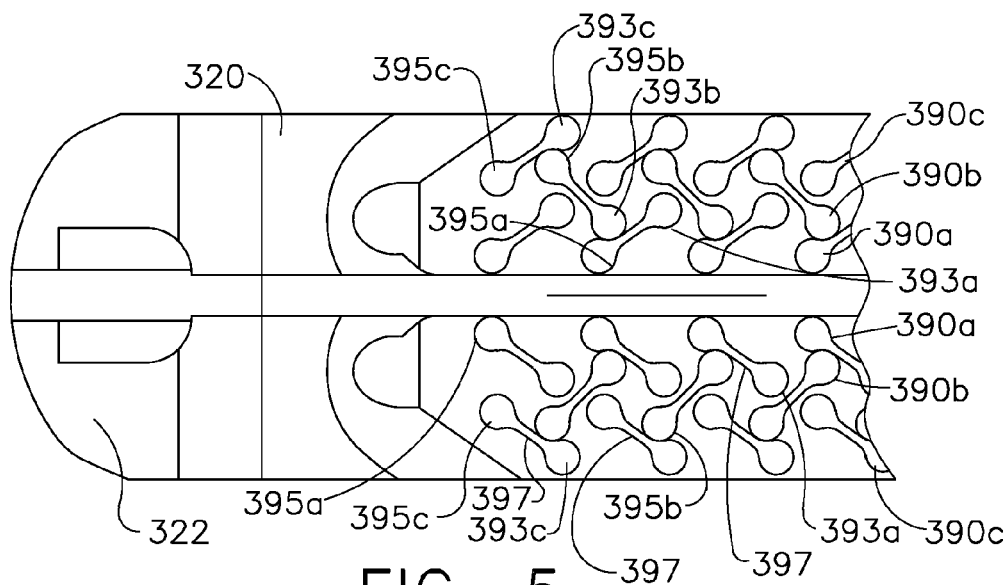
FIG. 5 is a partial bottom plan view of an anvil in accordance with at least one embodiment.

Turning now to FIG. 5, an anvil 320 comprises an array of forming pockets 390a, 390b, and 390c defined therein. Similar to the above, a plurality of first forming pockets 390a are arranged along a first longitudinal axis, a plurality of second forming pockets 390b are arranged along a second longitudinal axis, and a plurality of third forming pockets 390c are arranged along a third longitudinal axis. Each forming pocket 390a, 390b, and 390c includes a proximal forming pocket end and a distal forming pocket end. For example, each first forming pocket 390a includes a proximal end 393a configured to receive a proximal leg of a first staple and a distal end 395a configured to receive a distal leg of the first staple, each second forming pocket 390b includes a proximal end 393b configured to receive a proximal leg of a second staple and a distal end 395b configured to receive a distal leg of the second staple, and each forming pocket 390c includes a proximal end 393c configured to receive a proximal leg of a third staple and a distal end 395c configured to receive a distal leg of the third staple.

The proximal ends 393a, 393b, and 393c and the distal ends 395a, 395b, and 395c can comprise any suitable configuration. Referring again to FIG. 5, the proximal ends 393a, 393b, and 393c and the distal ends 395a, 395b, and 395c each comprise an enlarged cup. The enlarged cups are wider than a groove 397 defined therebetween. In certain instances, the enlarged cups and the groove extending therebetween can comprise an hourglass shape, for example. When the legs of a staple enter such a forming pocket, the legs can enter the enlarged cups and, as the staple legs are deformed, the enlarged cups can guide the staple legs into the groove 397. Each enlarged cup can include curved and/or angled sidewalls which can be configured to guide a staple leg toward the groove 397. The enlarged cups can, in certain instances, adjust the orientation of a misaligned staple leg.

The staple forming pockets 390a, 390b, and 390c are nested. For instance, the distal enlarged cup 395b of a second forming pocket 390b is positioned intermediate the enlarged cups 393c, 395c of an adjacent third staple forming pocket 390c and, additionally, the proximal enlarged cup 393b of a second forming pocket 390b is positioned intermediate the enlarged cups 393a, 395a of an adjacent first forming pocket 390a. Also, for instance, the proximal enlarged cup 393a of a first forming pocket 390a is positioned intermediate the enlarged cups 393b, 395b of an adjacent second forming pocket 390b. Additional, for instance, the distal enlarged cup 395c of a third forming pocket 390c is positioned intermediate the enlarged cups 393b, 395b of an adjacent second forming pocket 390b. The enlarged forming cups of each staple cavity can define a rectangular perimeter within which the entire forming pocket can be positioned. As a result of the nesting arrangement described above, the rectangular perimeter of one staple forming cavity can overlap the rectangular perimeter of another forming cavity. For instance, the rectangular perimeter of a second forming cavity 390b can overlap the rectangular perimeter of a first forming cavity 390a and/or the rectangular perimeter of a third forming cavity 390c.

Figure 6:
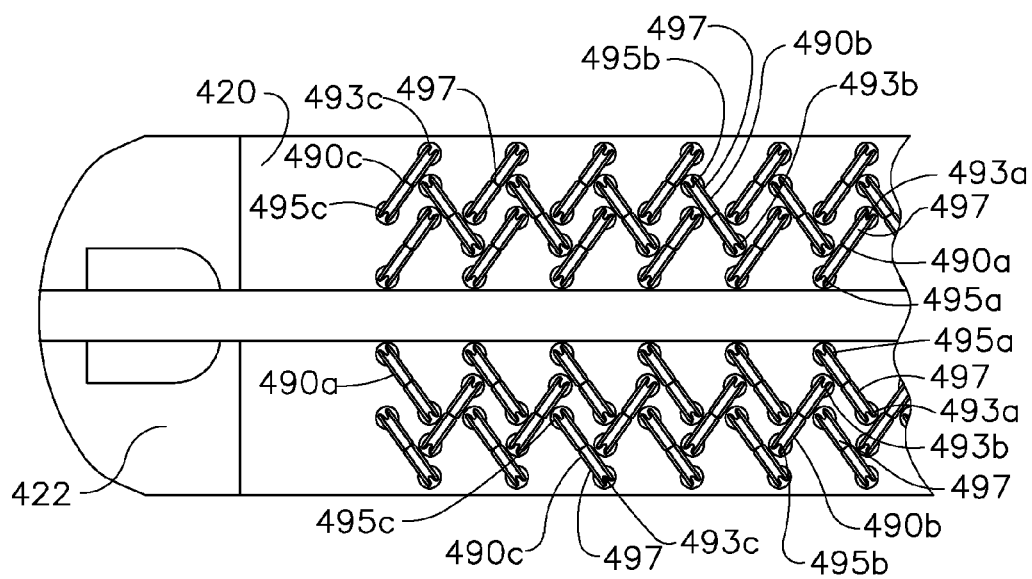
FIG. 6 is a partial bottom plan view of an anvil in accordance with at least one embodiment.

Turning now to FIG. 6, an anvil 420 comprises an array of forming pockets 490a, 490b, and 490c defined therein. Similar to the above, a plurality of first forming pockets 490a are arranged along a first longitudinal axis, a plurality of second forming pockets 490b are arranged along a second longitudinal axis, and a plurality of third forming pockets 490c are arranged along a third longitudinal axis. Each forming pocket 490a, 490b, and 490c includes a proximal forming pocket end and a distal forming pocket end. For example, each first forming pocket 490a includes a proximal end 493a configured to receive a proximal leg of a first staple and a distal end 495a configured to receive a distal leg of the first staple, each second forming pocket 490b includes a proximal end 493b configured to receive a proximal leg of a second staple and a distal end 495b configured to receive a distal leg of the second staple, and each forming pocket 490c includes a proximal end 493c configured to receive a proximal leg of a third staple and a distal end 495c configured to receive a distal leg of the third staple.

The proximal ends 493a, 493b, and 493c and the distal ends 495a, 495b, and 495c can comprise any suitable configuration. Referring again to FIG. 6, the proximal ends 493a, 493b, and 493c and the distal ends 495a, 495b, and 495c each comprise an enlarged cup. The enlarged cups are wider than a groove 497 defined therebetween. In certain instances, the enlarged cups and the groove extending therebetween can comprise an hourglass shape, for example. When the legs of a staple enter such a forming pocket, the legs can enter the enlarged cups and, as the staple legs are deformed, the enlarged cups can guide the staple legs into the groove 497. Each enlarged cup can include curved and/or angled sidewalls which can be configured to guide a staple leg toward the groove 497. The enlarged cups can, in certain instances, adjust the orientation of a misaligned staple leg.

The staple forming pockets 490a, 490b, and 490c are nested. For instance, the distal enlarged cup 495b of a second forming pocket 490b is positioned intermediate the enlarged cups 493c, 495c of an adjacent third staple forming pocket 490c and, additionally, the proximal enlarged cup 493b of a second forming pocket 490b is positioned intermediate the enlarged cups 493a, 495a of an adjacent first forming pocket 490a. Also, for instance, the proximal enlarged cup 493a of a first forming pocket 490a is positioned intermediate the enlarged cups 493b, 495b of an adjacent second forming pocket 490b. Additional, for instance, the distal enlarged cup 495c of a third forming pocket 490c is positioned intermediate the enlarged cups 493b, 495b of an adjacent second forming pocket 490b. The enlarged forming cups of each staple cavity can define a rectangular perimeter within which the entire forming pocket can be positioned. As a result of the nesting arrangement described above, the rectangular perimeter of one staple forming cavity can overlap the rectangular perimeter of another forming cavity. For instance, the rectangular perimeter of a second forming cavity 490b can overlap the rectangular perimeter of a first forming cavity 490a and/or the rectangular perimeter of a third forming cavity 490c.

Figure 32:
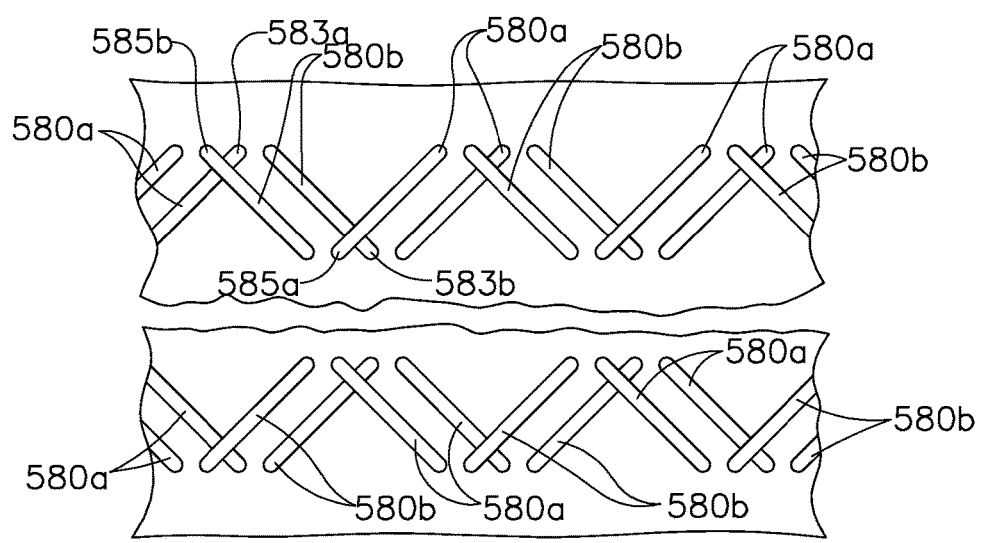
FIG. 32 depicts tissue stapled by a staple line in accordance with at least one embodiment wherein at least some of the staples in the staple line overlap.

Referring again to FIG. 52A, the staples 280a, 280b, and 280c do not overlap. Other embodiments are envisioned in which at least some of the staples in a staple pattern overlap. Turning now to FIG. 32, a staple pattern disclosed therein comprises a first row of longitudinal staples 580a and a second row of longitudinal staples 580b. As the reader will appreciate, some of the staples 580a in the first row and the staples 580b in the second row are overlapped. In at least one instance, the base of a second staple 580b extends under the base of a first staple 580a. In such an instance, the distal leg 585b of the second staple 580b is positioned on one side of the base of the first staple 580a and the proximal leg 583b of the second staple 580b is positioned on the other side of the base of the first staple 580a. Similarly, in at least one instance, the base of a first staple 580a extends under the base of a second staple 580b. In such an instance, the distal leg 585a of the first staple 580a is positioned on one side of the base of the second staple 580b and the proximal leg 583a of the first staple 580a is positioned on the other side of the base of the second staple 580b. As a result of the above, the first staples 580a are interweaved with the second staples 580b.

Referring again to FIG. 32, the staple pattern comprises a first row of staples 580a and a second row of staples 580b positioned on one side of a longitudinal tissue incision and a first row of staples 580a and a second row of staples 580b positioned on the other side of the longitudinal tissue incision. The first staples 580a are oriented distally and toward the longitudinal tissue incision and the second staples 580b are oriented proximally and toward the longitudinal tissue incision.

Referring again to FIG. 32, the first row of staples 580a is positioned along a first longitudinal axis and the second row of staples 580b is positioned along the second longitudinal axis. As a result of the overlap between the first staples 580a and the second staples 580b, the first longitudinal axis can be adjacent the second longitudinal axis, in certain instances. In some instances, the overlap between a first row of staples and a second row of staples can permit angled staples in these rows of staples to have the same centerline spacing that can be achieved with traditional, longitudinally-arranged staple patterns, such as the staple pattern illustrated in FIG. 52, for example. In some instances, the overlap between a first row of staples and a second row of staples can permit angled staples in these rows of staples to have a closer centerline spacing than can be achieved with traditional, longitudinally-arranged staple patterns. In at least one embodiment, the first longitudinal axis can be collinear with the second longitudinal axis.

The staple pattern depicted in FIG. 32 comprises a repeating pattern. The repeating pattern comprises two first staples 580a followed by two second staples 580b followed by two first staples 580a followed by two second staples 580b, and so forth. This repeating pattern extends longitudinally in the proximal-distal direction. The first row of staples 580a has breaks therein which are filled by staples 580b and, similarly, the second row of staples 580b has breaks therein which are filled by staples 580a. A repeating pattern is present on one side of the longitudinal incision and a repeating pattern is present on the other side of the longitudinal incision. These repeating patterns are mirror-images of one another. Other repeating patterns are contemplated.

Figure 33:
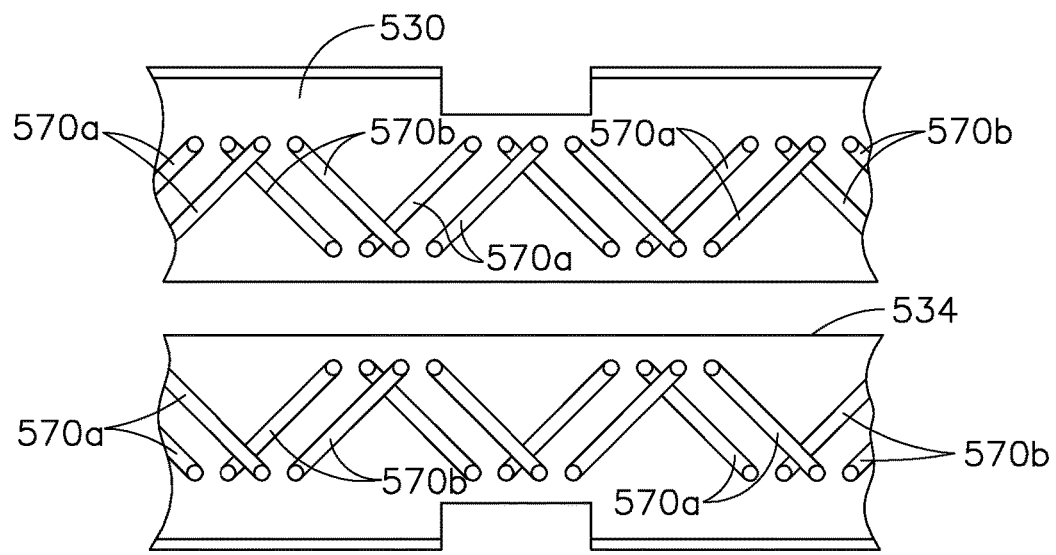
FIG. 33 is a partial plan view of a staple cartridge configured to deploy the staple line of FIG. 32.

A staple cartridge 530 configured to removably store and deploy the staple pattern disclosed in FIG. 32 is illustrated in FIG. 33. The staple cartridge 530 includes a first row of staple cavities 570a for removably storing the first staples 580a and a second row of staple cavities 570b for removably storing the second staples 580b. At least some of the first staple cavities 570a and the second staple cavities 570b are interconnected to removably store the overlapping first staples 580a and second staples 580b. A first row of staple cavities 570a can be arranged along a first longitudinal axis and a row of second staple cavities 570b can be arranged along a second longitudinal axis. The first longitudinal axis and the second longitudinal axis can be adjacent or collinear, as appropriate, in order to deploy the staple patterns disclosed herein. A first row of staple cavities 570a and a second row of staple cavities 570b are positioned on a first side of a longitudinal slot 534 and a first row of staple cavities 570a and a second row of staple cavities 570b are positioned on a second side of the longitudinal slot 534. The longitudinal slot 534 is configured to receive a firing member. The firing member can include a cutting element, such as a knife, for example.

Figure 34:
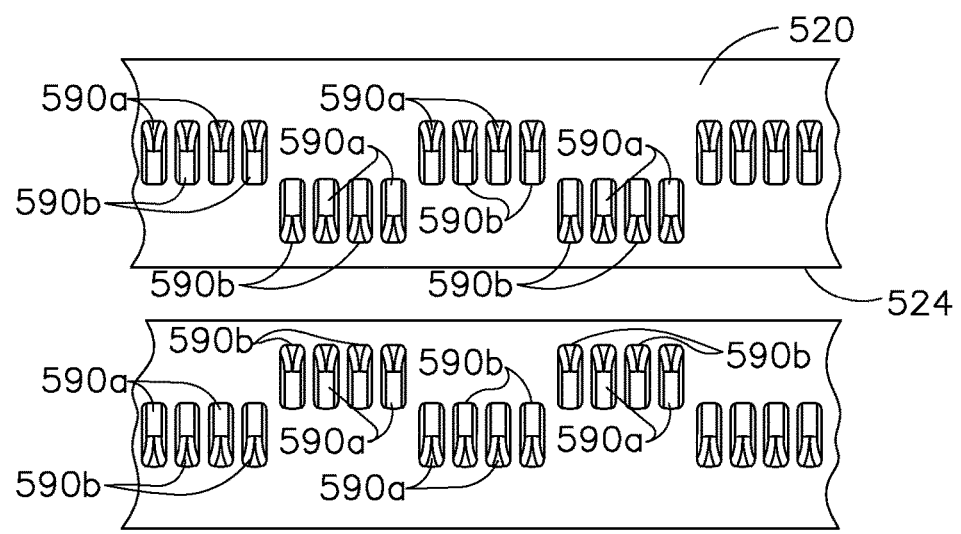
FIG. 34 is a partial plan view of an anvil configured to deform the staples ejected from the staple cartridge of FIG. 33.

An anvil 520 configured to deform the staples of the staple pattern disclosed in FIG. 32 is illustrated in FIG. 34. The anvil 520 includes a repeating pattern of forming cavities including first forming cavities 590a configured to deform the legs of the first staples 580a and second forming cavities 590b configured to deform the legs of the second staples 580b. The first forming cavities 590a and the second forming cavities 590b are arranged in an alternating pattern. The alternating pattern comprises arrays of first forming cavities 590a and second forming cavities 590b positioned along a first longitudinal axis and arrays of first forming cavities 590a and second forming cavities 590b positioned along a second longitudinal axis which are positioned on one side of a longitudinal slot 524. The alternating pattern further comprises arrays of first forming cavities 590a and second forming cavities 590b positioned along a first longitudinal axis and arrays of first forming cavities 590a and second forming cavities 590b positioned along a second longitudinal axis which are positioned on the other side of the longitudinal slot 524. The arrays of forming cavities 590a, 590b can define a mirror image with respect to the longitudinal slot 524. The longitudinal slot 524 is configured to receive a firing member. The firing member can include a cutting element, such as a knife, for example.

The staple pattern depicted n FIG. 32 comprises two rows of staples on each side of the longitudinal tissue incision; however, such a staple pattern could include more than two rows of staples, such as three rows of staples, for example. Such a third row of staples could be interweaved with the first row of staples 580a and/or the second row of staples 580b. Alternatively, such a third row of staples may not be interweaved with either the first row of staples 580a or the second row of staples 580b. In such an embodiment, the first row of staples 580a and the second row of staples 580b can be interweaved and the third row of staples could be adjacent the first row of staples 580a and/or the second row of staples 580b, for example.

Figure 35:
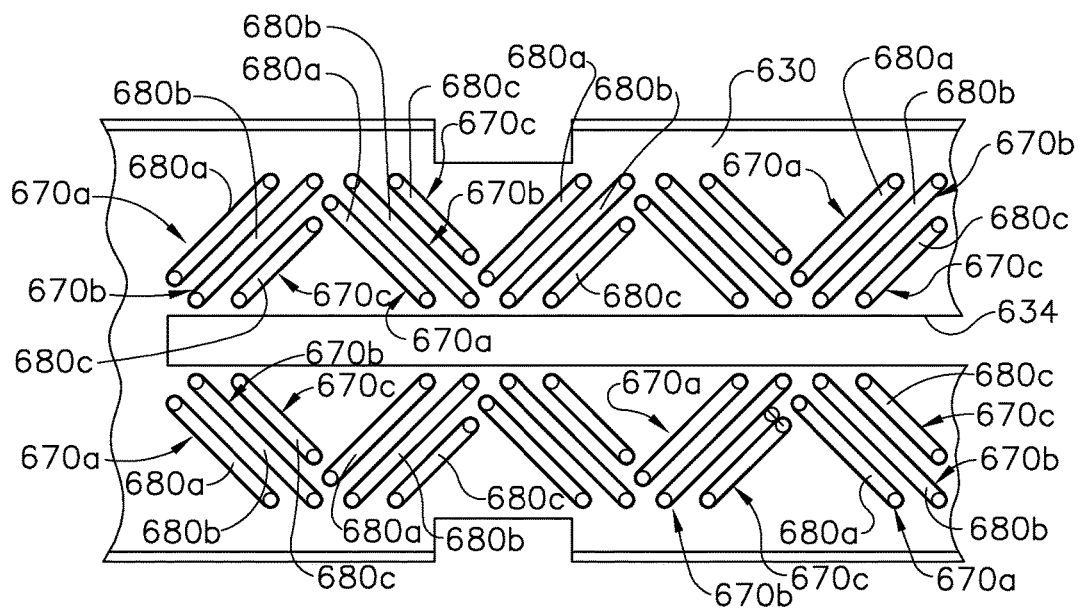
FIG. 35 is a partial plan view of a staple cartridge configured to deploy a staple line in accordance with at least one embodiment.

The staple pattern depicted in FIG. 35 includes a longitudinal row of first staples 680a, a longitudinal row of second staples 680b, and a longitudinal row of third staples 6870c. The first staples 680a have a first base width. The second staples 680b have a second base width. The third staples 680c have a third base width. The width of a staple base can be defined as the distance between a first staple leg extending from the base and a second staple leg extending from the base measured along the base extending between the first staple leg and the second staple leg. In at least one instance, the base width is measured between the cross-sectional center of the first staple leg and the cross-sectional center of the second staple leg. In any event, the first base width is shorter than the second base width; however, other embodiments are envisioned in which the second base width is shorter than the first base width. The third base width is shorter than the first base width and the second base width; however, other embodiments are envisioned in which the third base width is longer than the first base width and/or the second base width.

In the embodiment depicted in FIG. 35, the second staples 680b have the longest base width. As a result, when the staples in the staple pattern rotate within tissue as the tissue is being stretched longitudinally, the second staples 680b will sweep through a larger arc length than the first staples 680a. Similarly, the first staples 680a will sweep through a larger arc length than the third staples 680c. In various instances, as a result, the first staples 680a will sweep through a first arc length, the second staples 680b will sweep through a second arc length, and the third staples 680c will sweep through a third arc length, wherein the first arc length, the second arc length, and the third arc length are different. Such arc lengths can be different even though the degree in which the staples 680a, 680b, and/or 680c are the same. In certain instances, the first arc length, the second arc length, and/or the third arc length can be the same.

In the embodiment depicted in FIG. 35, the first staples 680a are positioned and arranged in an alternating arrangement in a staple cartridge 630. The distal most first staple 680a is oriented toward the distal end of the staple cartridge 630 and toward a longitudinal slot 634 defined in the staple cartridge 630. The next first staple 680a in the second longitudinal row is oriented toward the proximal end of the staple cartridge 630 and toward the longitudinal slot 634. This pattern then repeats within the longitudinal row of first staples 680a.

The second staples 680b are positioned and arranged in an alternating arrangement in a staple cartridge 630. The distal most second staple 680b is oriented toward the distal end of the staple cartridge 630 and toward a longitudinal slot 634 defined in the staple cartridge 630. The next second staple 680b in the second longitudinal row is oriented toward the proximal end of the staple cartridge 630 and toward the longitudinal slot 634. This pattern then repeats within the longitudinal row of second staples 680b.

The third staples 680c are positioned and arranged in an alternating arrangement in a staple cartridge 630. The distal most third staple 680c is oriented toward the distal end of the staple cartridge 630 and toward a longitudinal slot 634 defined in the staple cartridge 630. The next third staple 680c in the third longitudinal row is oriented toward the proximal end of the staple cartridge 630 and toward the longitudinal slot 634. This pattern then repeats within the longitudinal row of third staples 680c.

With further reference to the staple pattern depicted in FIG. 35, the longitudinal row of first staples 380a is nested within the longitudinal row of second staples 380b. Similarly, the longitudinal row of third staples 380c is nested within the longitudinal row of second staples 380b.

Figure 36:
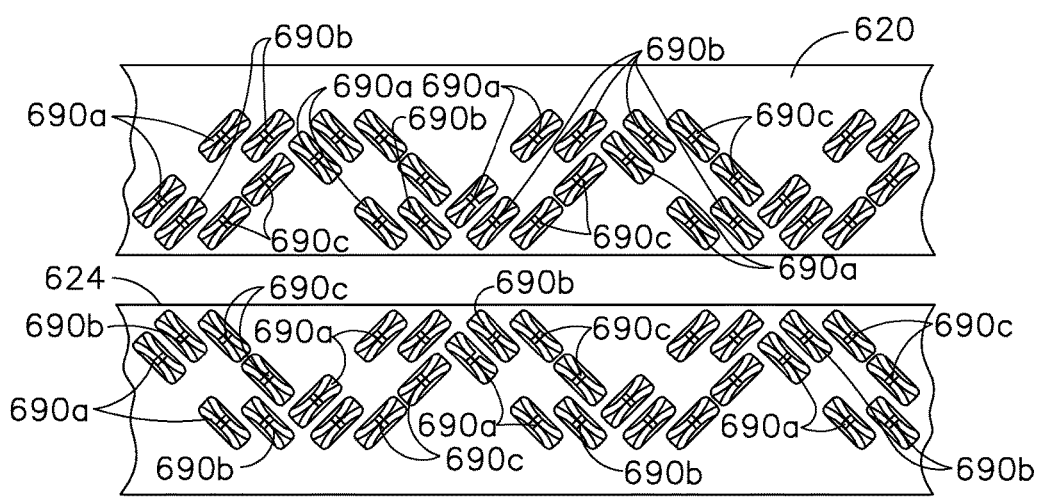
FIG. 36 is a partial plan view of an anvil configured to deform the staples ejected from the staple cartridge of FIG. 35.

The staple cartridge 630, further to the above, comprises a plurality of first staple cavities 670a configured to removably store the first staples 680a therein. The staple cartridge 630 further comprises a plurality of second staple cavities 670b configured to removably store the second staples 680b and a plurality of third staple cavities 670c configured to removably store the third staples 680c. Referring to FIG. 36, an anvil 620 can be configured to deform the staples 680a, 680b, and 680c as they are ejected from the staple cartridge 630. The anvil 620 comprises a staple forming pocket pattern that is aligned with the staple cavities 670a, 670b, and 670c. For instance, the anvil 620 comprises a plurality of first forming pockets 690a aligned with the first staple cavities 670a, a plurality of second forming pockets 690b aligned with the second staple cavities 670b, and a plurality of third forming pockets 690c aligned with the third staple cavities 670c.

As discussed above, a staple pattern can comprise several rows. The staples in each row can have the same orientation or different orientations. FIG. 23 illustrates an embodiment comprising a row of staples having a first group of staples 780a oriented in a first direction and a second group of staples 780b oriented in a second direction. The first staples 780a and the second staples 780b are positioned along a longitudinal axis. The first staples 780a are angled with respect to the longitudinal axis and the second staples 780b are aligned with the longitudinal axis. Other arrangements are possible. The staples 780a are arranged in an alternating pattern with the staples 780b.

With continued reference to FIG. 23 and referring again to FIG. 24, the staples within a staple row can translate and rotate within tissue when the tissue is stretched longitudinally. In some instances, the translation and/or rotation of the staples within the tissue can create holes, or gaps, between the staples and the tissue. Such holes, or gaps, can create leaks. Even though various staple patterns disclosed herein can minimize such leaks, certain improvements to the staples themselves can be made to reduce and/or eliminate these leaks.

Figure 17:
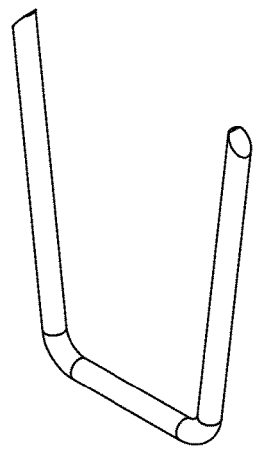
FIG. 17 is a perspective view of a staple in accordance with at least one embodiment illustrated in an unformed, or unfired, configuration.
Figure 18:
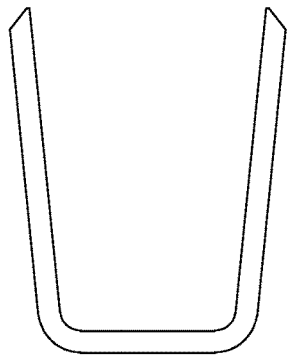
FIG. 18 is an elevational view of the staple of FIG. 17.
Figure 19:
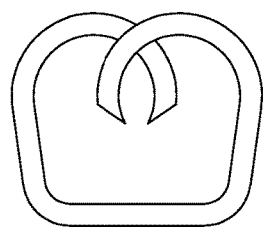
FIG. 19 is an elevational view of the staple of FIG. 17 in a formed, or fired, configuration.
Figure 20:
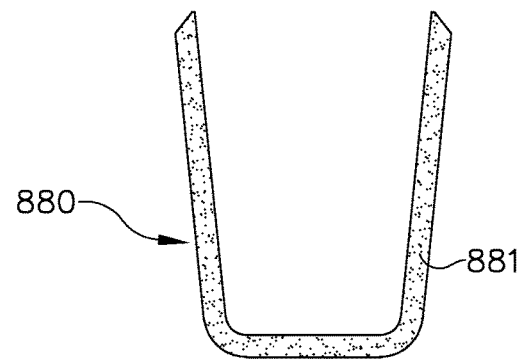
FIG. 20 is an elevational view of a staple comprising an expandable coating in accordance with at least one embodiment illustrated in an unformed, or unfired, configuration.
Figure 21:
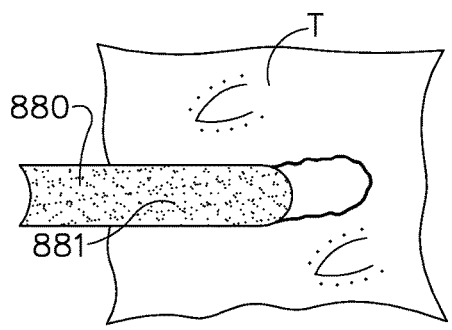
FIG. 21 is a partial bottom plan view of the staple of FIG. 20 deployed into the tissue of a patient.
Figure 22:
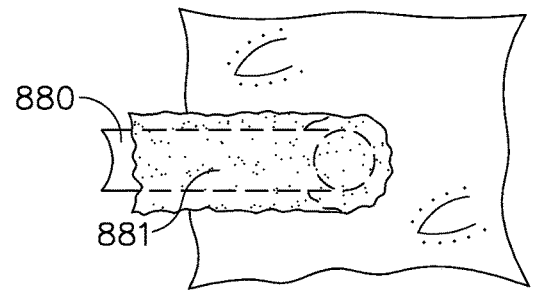
FIG. 22 is a partial bottom plan view of the staple of FIG. 20 deployed into the tissue of a patient illustrating the coating in an expanded condition.
Figure 25:
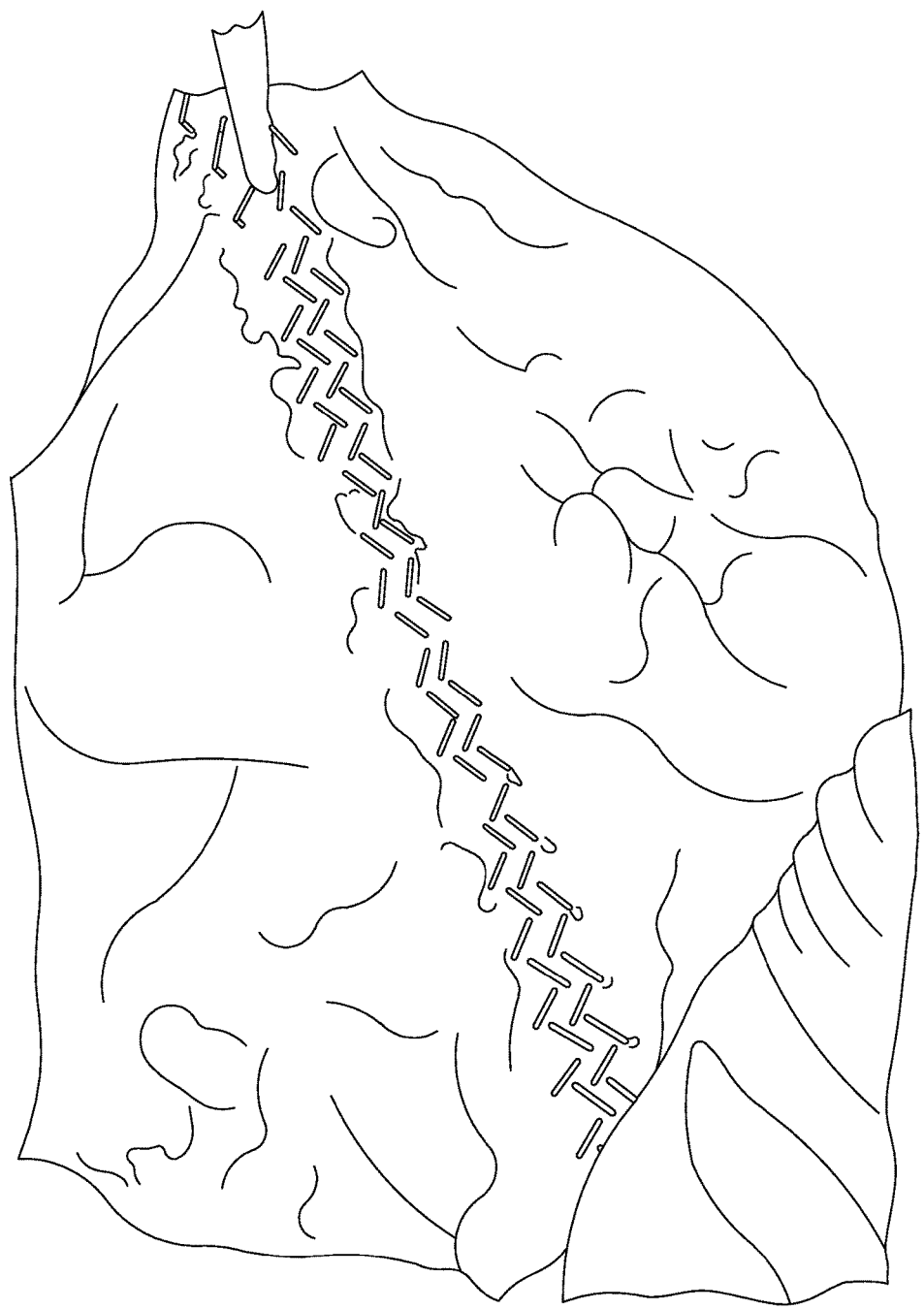
FIG. 25 depicts tissue stapled by a staple line in accordance with at least one embodiment.

Turning now to FIGS. 17 and 18, a staple, such as staples 280a, 280b, 280c, 380a, 380b, 380c, 580a, 580b, 680a, 680b, 680c, 780a, and/or 780b, for example, is depicted in an unfired configuration. The unfired configuration of this staple is V-shaped; however, the principles discussed herein can be applied to any suitably-shaped staple. FIG. 19 illustrates the staple of FIGS. 17 and 18 in a fired configuration. The fired configuration of this staple is B-shaped; however, the principles discussed herein can be applied to any suitably-shaped staple. FIG. 20 depicts the staple of FIGS. 17-19 including a coating 881 thereon; this staple will hereinafter be referred to as staple 880. FIG. 21 illustrates the staple 880 deployed into tissue and a hole, or gap, 882 present between the staple 880 and the tissue. FIG. 22 illustrates the coating 881 on the staple 880 in an expanded state. The expanded coating 881 can fill the entirety of the gap 882. In some circumstances, the expanded coating 881 can stretch the tissue. In various other circumstances, the coating 881 may not fill the entirety of the gap 882.

The staple 880 can be comprised of any suitable material, such as metal, for example. In certain instances, the staple 880 can be comprised of titanium and/or stainless steel, for example.

The expandable staple coating 881 can be comprised of any suitable material. The staple coating 881 can be comprised of Poly-L-lactic acid and/or Poly-95L/5D-lactic acid, for example. Other copolymer compositions of PLA could be utilized. In various instances, the staple coating 881 can begin to form a gel as soon as the staple 880 is implanted into the tissue wherein the gel can expand to fill, or at least partially fill, the gap 882. In various instances, the coating 881 can be applied to the staple 880 by immersing the staple wire in one or more solutions that coat the wire. In at least one instance, the staple wire can be immersed in a first solution to apply a base coating and then a second solution to apply the PLA, for example. In some instances, the coating 881 can be applied to staples 880 when the staples 880 are positioned in a staple cartridge. The entire disclosure of ELASTOMERIC BIOMATERIALS FOR TISSUE ENGINEERING, Progress In Polymer Science 38 (2013) 584-671 by Q. Chen et al. is hereby incorporated by reference herein.

The staple coating 881 can be comprised of a hydrophilic material, for example. A hydrophilic material can comprise a hydrogel derivitized with a peptide containing RGD peptide sequence microspheres, for example. The metal wire of the staple 880 can be coated with a natural biopolymer, such as hyaluronan or hyaluronic acid, for example. Other hydrogels could be utilized. In various instances, the staple coating 881 can begin to expand as soon as the staple 880 is implanted into the tissue wherein the coating 881 can expand to fill, or at least partially fill, the gap 882. In various instances, the coating 881 can be applied to the staple 880 by immersing the staple wire in one or more solutions that coat the wire. In at least one instance, the staple wire can be immersed in a first solution to apply a base coating and then a second solution to apply the hyaluronan loaded with peptides, for example. In some instances, the coating 881 can be applied to staples 880 when the staples 880 are positioned in a staple cartridge. The entire disclosure of ATTACHMENT OF HYALURONAN TO METALLIC SURFACES, J. Biomed. Mater. Res. 68A: 95-106 (2004) by William G. Pitt et al. is incorporated by reference herein.

The staple coating 881 can be comprised of xerogel, for example. The staple coating 881 can be comprised of gelatin microspheres and/or nanospheres, for example. Gelatin comprises an at least partially denatured, or completely denatured, form of collagen that cells can bind to and degrade through enzymatic action. In various instances, the gelatin can be loaded with fibroblast and/or platelet-derived growth factor, for example. As the coating 881 degrades, the coating 881 can at least partially fill and at least partially seal the gap 882. In various instances, the coating 881 can be applied to the staple 880 by immersing the staple wire in a water-in-oil emulsion and then lyophilizing the gelatin microspheres and/or nanospheres onto the staple wire. The entire disclosure of GELATIN MICROSPHERES CROSS-LINKED WITH GENIPIN FOR LOCAL DELIVERY OF GROWTH FACTORS, J. Tissue Eng. Regen. Med. 4: 514-523 (2010) by Luis Solorio et al. is incorporated by reference herein.

Figure 55:
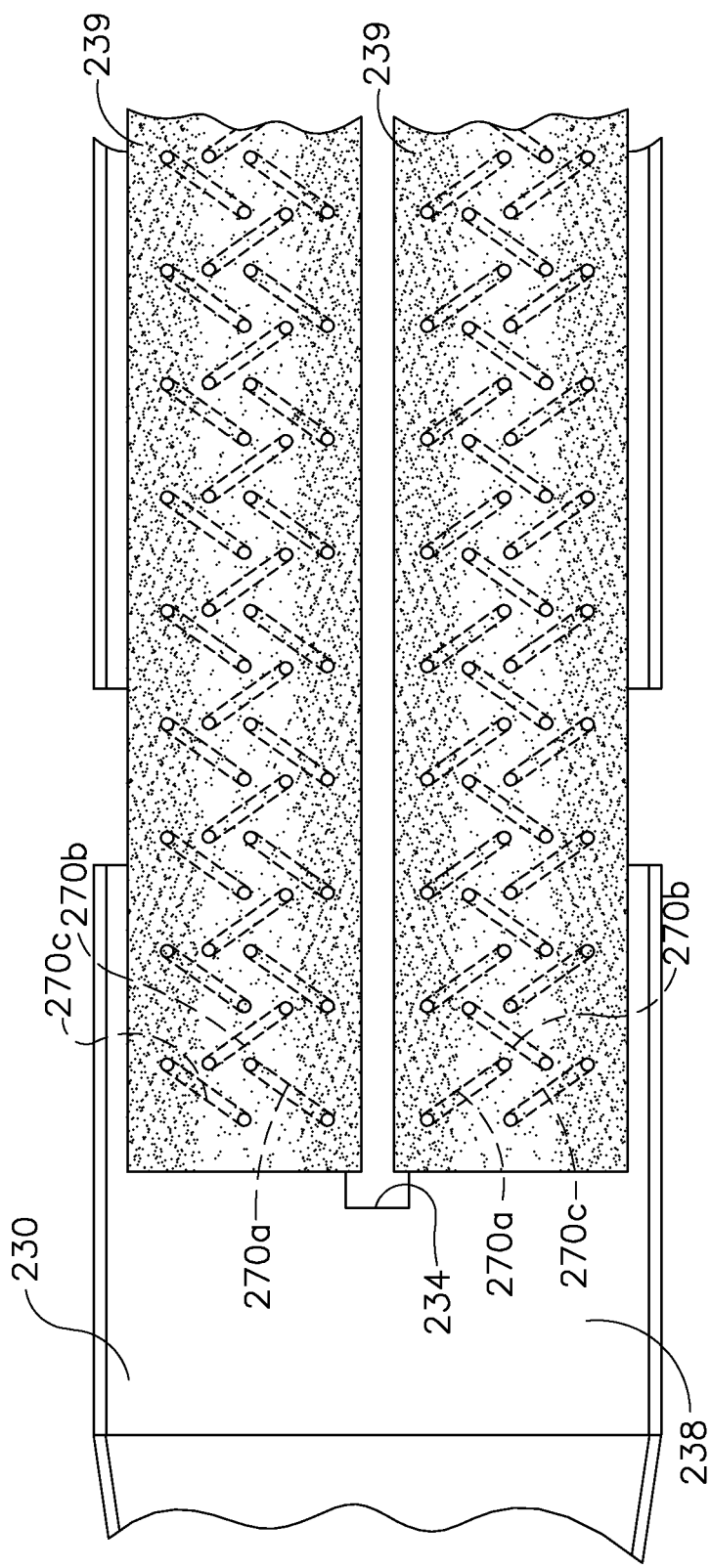
FIG. 55 is a partial plan view of a staple cartridge comprising a cartridge body and an implantable adjunct material positioned on the cartridge body in accordance with at least one embodiment.

The staple 880 is comprised of a wire having a circular cross-section; however, the staple 880 can be comprised of a wire having any suitable cross-section, such as a polygonal cross-section, for example. Non-circular cross-sections can have larger perimeters than circular cross-sections for a certain overall width. Such non-circular cross-sections can support a larger quantity of coating material than circular cross-sections which can allow the coating to expand and fill larger holes than staples having circular cross-sections. In certain instances, a non-circular cross section can be formed be creating one or more grooves in a circular cross-section. In at least one such instance, such grooves can extend longitudinally along the staple legs. In some instances, a longitudinal groove can extend along an axis. In certain instances, a longitudinal groove can wrap around a staple leg. In at least one instance, such a longitudinal groove can extend around a leg in a helical manner The staples of a staple cartridge can be deployed with or without the use of an adjunct material, such as buttress material, for example. Often, an adjunct material can be placed on the top surface, or deck, of a staple cartridge such that, when the staples are ejected from the staple cartridge, the staples can capture the adjunct material against the tissue. FIG. 55 illustrates two pieces of adjunct material 239 positioned on a deck surface 238 of the staple cartridge 230.

A first piece of adjunct material 239 is positioned on a first side of the longitudinal slot 234 and a second piece of adjunct material 239 is positioned on a second side of the longitudinal slot 234. Alternative embodiments are envisioned in which a single piece of adjunct material is supported by the deck surface 238 which extends over the longitudinal slot 234 and both sides of the staple cartridge 230. Referring again to FIG. 55, each piece of adjunct material 239 is substantially rectangular and extends over a staple pattern including a row of first staple cavities 270a, a row of second staple cavities 270b, and a row of third staple cavities 270c. The staples 280a, 280b, and 280c stored in the staple cavities 270a, 270b, and 270c, respectively, penetrate the adjunct material 239 when they are ejected from the staple cartridge 230 and capture a portion of the adjunct material 239 therein as the staples 280a, 280b, and 280c are formed by the anvil 220.

In addition to or in lieu of the adjunct material positioned on the staple cartridge, adjunct material may be positioned on an anvil. The staples penetrating the tissue could penetrate the anvil adjunct before contacting the anvil and then re-penetrate the anvil adjunct before re-entering into the tissue.

After the staples 280a, 280b, and 280c have been deformed by the anvil 220, further to the above, the adjunct material 239 is captured against the tissue by the staples 280a, 280b, and 280c. Stated another way, the adjunct material 239 is implanted against the tissue by the staples 280a, 280b, and 280c. When the tissue is stretched longitudinally, as discussed above, the adjunct material 239 can stretch with the tissue.

Adjunct materials can provide many benefits. Adjunct materials can assist in sealing the puncture holes created by the staple legs. In various instances, the staple legs can push the adjunct material into the puncture holes as the staple legs pass through the tissue. Adjunct materials can also assist in sealing gaps created between the staple legs and the tissue when the tissue is stretched longitudinally. Adjunct materials can bolster the tissue. In various instances, the adjunct material can strengthen the tissue and inhibit the staples from tearing through the tissue.

Referring again to FIG. 55, the reader will appreciate that portions of the adjunct material 239 are not captured by the staples 280a, 280b, and 280c. For instance, the portions of the adjunct material extending around the perimeter thereof may not be captured by the staples. Similarly, portions of the adjunct material positioned intermediate the staples may not be captured by the staples. Such uncaptured portions of the adjunct material 239 may not provide the sealing benefits discussed above and, at the same time, inhibit the extensibility provided by the staple patterns discussed herein. Such uncaptured portions may also inhibit the rotation of the staples within the tissue, as discussed above. Improvements to the embodiment of FIG. 55 are depicted in FIGS. 53, 54, 56, and 57. Such embodiments comprise recesses, notches, cuts, slits, apertures, and/or any other suitable interruptions configured to increase the extensibility of an adjunct material. Moreover, such interruptions may facilitate the rotation of the staples within the tissue.

Referring to FIG. 53, an adjunct material 939 comprises scalloped edges, or sides, 938. The scalloped sides 938 include recesses, or notches, 937 defined therein. Notches 937 comprise a curved configuration; however, an suitable configuration can be utilized. The notches 937 reduce the perimeter of uncaptured material extending around the perimeter of the adjunct material 939 and increase the flexibility and extensibility of the adjunct material 939.

Referring again to FIG. 53, the adjunct material 939 further comprises apertures 936 defined therein. The apertures 936 are oblong and comprise through holes; however, alternative embodiments are envisioned. The apertures 936 are located intermediate adjacent second staple cavities 270b and intermediate a first staple cavity 270a and a third staple cavity 270c; however, alternate locations are envisioned. The apertures 936 reduce the uncaptured material within the staples lines and increase the flexibility and extensibility of the adjunct material 939.

Referring again to FIG. 53, the body of the adjunct material 939 extends over the staple cavities 270a, 270b, and 270c. Alternative embodiments are envisioned in which the adjunct material 939 does not extend over the staple cavities 270a, 270b, and/or 270c. Turning now to FIG. 54, the adjunct material 939' includes slots, or openings, 935a, 935b, and 935c which partially extend over the staple cavities 270a, 270b, and 270c, respectively. The openings 935a, 935b, and 935c are larger than the apertures 936; however, the openings 935a, 935b, and/or 935c can be the same size as and/or larger than the apertures 936.

Referring to FIG. 56, an adjunct material 1039 comprises notched edges, or sides, 1038. The notched sides 1038 include recesses, or notches, 1037 defined therein. Notches 1037 comprise an angular configuration; however, an suitable configuration can be utilized. The notches 1037 reduce the perimeter of uncaptured material extending around the adjunct material 1039 and increase the flexibility and extensibility of the adjunct material 1039.

Referring again to FIG. 56, the adjunct material 1039 further comprises slits 1036 defined therein. The slits 1036 are oblong and comprise through holes; however, alternative embodiments are envisioned. The adjunct material 1039 comprises a first row of slits 1036a and a second row of slits 1036b. The slits 1036a are located intermediate adjacent second staples 1080b and intermediate a first staple 1080a and a third staple 1080c; however, alternate locations are envisioned. The slits 1036b are located intermediate adjacent third staples 1080c and intermediate a second staple 1080b and a fourth staple 1080d; however, alternate locations are envisioned. The slits 1036a are parallel to the first staples 1080a and the third staples 1080c and, similarly, the slits 1036b are parallel to the second staples 1080b and the fourth staples 1080d; however, the slits may have any suitable direction. The slits 1036a and 1036b reduce the uncaptured material within the staple lines and increase the flexibility and extensibility of the adjunct material 1039. The slits 1036a and 1036b are shorter than the bases of the staples 1080a, 1080b, 1080c, and 1080d; however, embodiments are envisioned in which the slits 1036a and/or 1036b are the same length as and/or longer than the bases of staples 1080a, 1080b, 1080c, and 1080d.

Referring to FIG. 57, an adjunct material 1139 comprises notched edges, or sides, 1138. The notched sides 1138 include recesses, or notches, 1137 defined therein. Notches 1137 comprise a curved configuration; however, an suitable configuration can be utilized. The notches 1137 reduce the perimeter of uncaptured material extending around the adjunct material 1139 and increase the flexibility and extensibility of the adjunct material 1139.

Referring again to FIG. 57, the adjunct material 1139 further comprises slits 1136 defined therein. The slits 1136 are oblong and comprise through holes; however, alternative embodiments are envisioned. The adjunct material 1139 comprises a first row of slits 1136a and a second row of slits 1136b. The slits 1136a are located intermediate adjacent second staples 1180b and intermediate a first staple 1180a and a third staple 1180c; however, alternate locations are envisioned. The slits 1136b are located intermediate adjacent third staples 1180c and intermediate a second staple 1180b and a fourth staple 1180d; however, alternate locations are envisioned. The slits 1136a are parallel to the first staples 1180a and the third staples 1180c and, similarly, the slits 1136b are parallel to the second staples 1180b and the fourth staples 1180d; however, the slits may have any suitable direction. The slits 1136a and 1136b reduce the uncaptured material within the staple lines and increase the flexibility and extensibility of the adjunct material 1139. The slits 1136a and 1136b are shorter than the bases of the staples 1180a, 1180b, 1180c, and 1180d; however, embodiments are envisioned in which the slits 1136a and/or 1136b are the same length as and/or longer than the bases of the staples 1180a, 1180b, 1180c, and 1180d.

As described herein, a firing member and/or wedge sled can traverse a staple cartridge to fire and/or eject staples from the staple cavities that are defined into the staple cartridge. For example, a firing member and/or a wedge sled can translate along a firing path within a staple cartridge, and the firing member and/or the wedge sled can engage a staple driver and/or the staple itself along the firing path to drive the staple from the staple cavity. As also described herein, staple arrangements that include angularly-oriented staples can provide various benefits and advantages. For example, an array of angularly-oriented staples can provide increased flexibility and/or longitudinal stretchability within stapled tissue.

When a staple is angularly-oriented relative to the firing path, at least a portion of the staple driver and/or the staple may not overlap and/or overlie the firing path. For example, the base of an angularly-oriented staple can cross the firing path such that the staple legs are positioned on opposite sides of the firing path. Additionally, an angularly-oriented staple driver can traverse the firing path, and the ends of the staple driver can be positioned on opposite sides of the firing path. In other instances, only an end of the staple and/or the staple driver may overlie the firing path and, in still other instances, the staple and/or the staple driver may be entirely offset from the firing path, for example.

In instances where at least a portion of the staple and/or the staple driver is offset from the firing path, a moment arm between the firing path and the portion(s) of the staple and/or the staple driver positioned on either side of the firing path may generate a torque within the staple and/or within the staple driver. Torque could affect tilting and/or tipping of the staples during deployment. As a result, the staple legs of a torqued staple may not engage tissue with equivalent force and/or speed, and/or the staple legs may not pierce and/or capture the tissue simultaneously. Because torqueing and/or rotation of a staple during deployment may adversely impact tissue penetration and/or staple formation, in various instances, it can be desirable to prevent and/or minimize torque generation during deployment of an array of angularly-oriented staples.

When a staple driver is angled relative to the firing path of a wedge sled, only a portion of the angled driver may receive the driving or lifting force from the wedge sled. For example, the driving force can be applied to the angled driver along a diagonal path. To stabilize the angled driver and prevent torqueing and/or rotation of the driver, and thus, of the staple supported thereon, the wedge sled can include multiple driving wedges, and at least two driving wedges can contact the driver to apply the driving force at multiple locations on the driver. For example, a pair of laterally-spaced driving wedges can engage and lift an angled driver such that the driving force is distributed at laterally-spaced intervals along the length of the driver. Moreover, in at least one instance, the laterally-spaced driving wedges can be equidistant from the center of mass of the angled driver, such that the driver is mass balanced relative to the multiple driving wedges.

Additionally or alternatively, to stabilize the angled drivers and prevent torqueing and/or rotation of the drivers, and thus, torqueing and/or rotation of the angled staples supported thereon, multiple drivers can be connected and/or linked together. In some instances, an angled multi-staple driver can be integrally formed. Connected drivers and/or a multi-staple driver can support multiple staples, which can reduce the number of moving parts within a staple cartridge and can prevent relative movement between the staple supporting surfaces of each interconnected and/or integrally formed staple cradle. Moreover, an angled multi-staple driver can be larger, i.e., wider and/or longer, than a single-staple driver. As a result, a multi-staple driver can be have an increased aspect ratio. For example, a multi-staple driver can have an aspect ratio of 1:1. In certain instances, the aspect ratio may be 3:2 or 2:1. In still other instances, the aspect ratio can be less than 1:1 or more than 2:1, for example. The greater aspect ratio of a multi-staple driver can provide greater stability to the staples supported thereon.

In various instances, a single driving wedge can engage an angled multi-staple driver, and, in certain instances, the driving force exerted on the driver by the driving wedge can be balanced relative to the center of mass of the driver. In other instances, multiple driving wedges can engage an angled multi-staple driver, which can distribute the driving force laterally across the driver. In various instances, the cumulative driving force exerted on an angled multi-staple driver by laterally-spaced driving wedges can be balanced relative to the center of mass of the driver.

In other circumstances, to stabilize angled staples within a staple cartridge and prevent torqueing and/or rotation thereof during deployment, the staples can be fired without drivers. For example, the wedge sled can include a staple-engagement surface that directly engages sled-engagement surfaces of staples in a driverless staple cartridge. The wedge sled can contact each staple at multiple laterally-spaced positions along the base of the staple. For example, the wedge sled can include multiple driving wedges, and at least two driving wedges can contact the angled staple to apply the driving force at multiple locations. In various instances, a pair of laterally-spaced driving wedges can engage and lift the angled staple such that the driving force is equally distributed at laterally-spaced intervals along the length of the base of the staple. Moreover, in at least one instance, the laterally-spaced driving wedges can be equidistant from the center of mass of the angled staple, such that the staple is mass balanced relative to the driving wedges.

Figure 7:
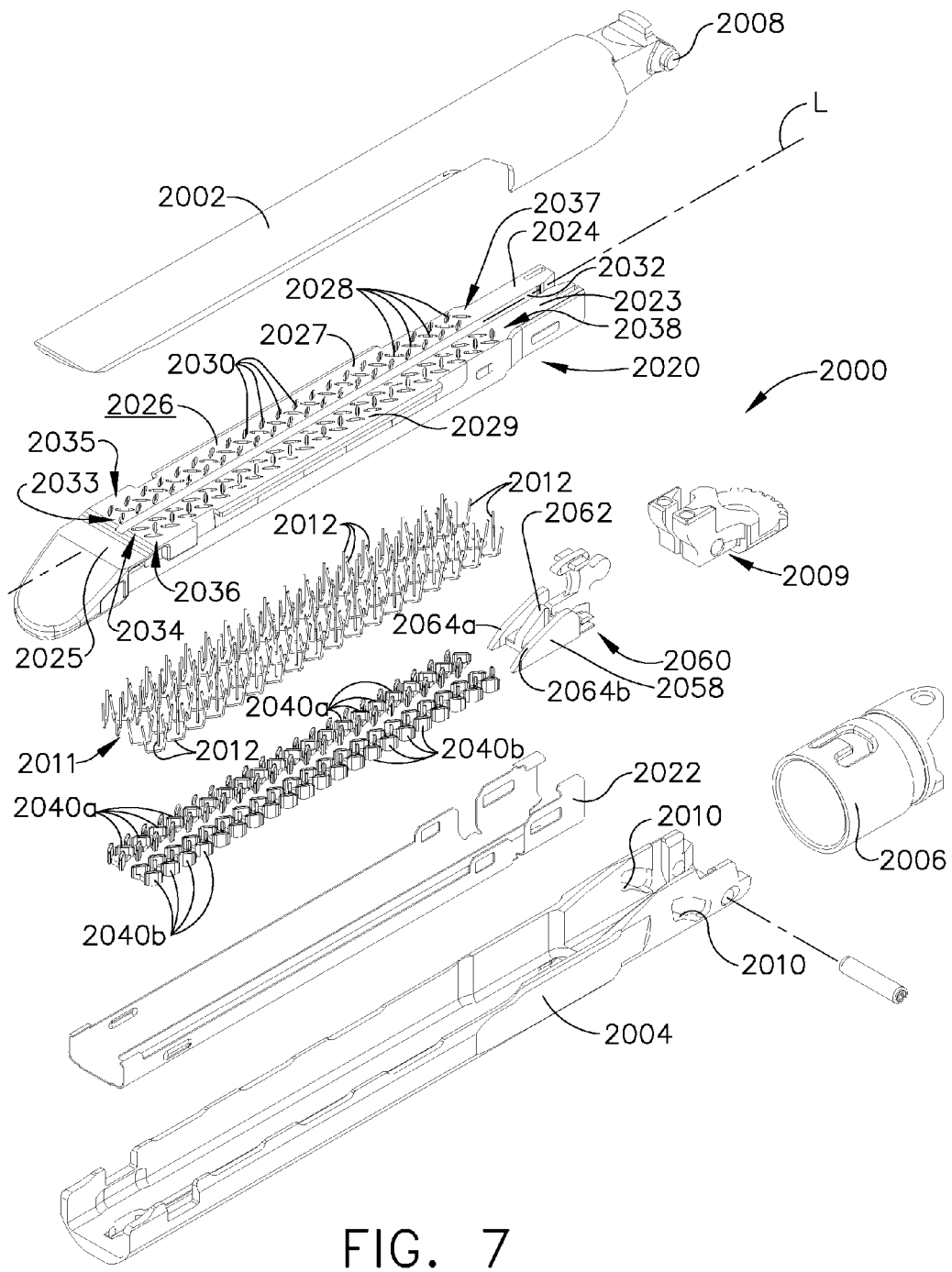
FIG. 7 is an exploded perspective view of an end effector including a staple cartridge that includes angularly-oriented staples, a group of first multi-staple drivers, and a group of second multi-staple drivers, according to various embodiments of the present disclosure.

An end effector assembly 2000 is disclosed in FIG. 7. As depicted, the end effector assembly 2000 includes a first jaw 2002, a second jaw 2004, a closure tube or frame 2006, and an end effector articulation joint 2009. The end effector assembly 2000 is movable between a first or open position and a second or closed position. As depicted, the first jaw 2002 includes pivot pins 2008, which are movably positioned within closure slots 2010 of the second jaw 2004. For example, the pivot pins 2008 are configured to pivot and translate in the closure slots 2010 of the second jaw 2004 as the first jaw 2002 pivots relative to the second jaw 2004 and relative to the frame 2006 of the depicted end effector assembly 2000.

In other instances, the first jaw 2002 can be fixed relative to the frame 2006, and the second jaw 2004 can pivot relative to the first jaw 2002 to open and close the jaws 2002, 2004 of the end effector assembly 2000. In still other instances, both jaws 2002, 2004 can pivot and/or otherwise move to open and/or close the jaws 2002, 2004 of the end effector assembly 2000. For example, at least one of the jaws 2002, 2004 can rotate, spin, slide and/or translate relative to the other jaw 2002, 2004 and/or relative to the frame 2006 to open and/or close the jaws 2002, 2004 of the end effector assembly 2000.

Referring still to FIG. 7, the end effector assembly 2000 is dimensioned and structured to receive a staple cartridge 2020, which is configured for removable positioning within the end effector assembly 2000. For example, the depicted staple cartridge 2020 can be a single-use and/or disposable cartridge, which can be replaced with another staple cartridge after firing the staples 2012 therefrom. The staple cartridge 2020 disclosed in FIG. 7 includes a deck 2026, a cartridge body 2024, and a casing 2022 which partially surrounds or encloses the cartridge body 2024. The depicted staple cartridge 2020 also includes staples 2012 which can be ejectably positioned in the cartridge body 2024. The staples 2012 disclosed in FIG. 7 are generally "V-shaped" staples, which have non-parallelly extending legs.

In various instances, a staple cartridge, such as the staple cartridge 2020, for example, can be integrally formed with the end effector assembly 2000 and/or can be permanently fixed within one of the jaws 2002, 2004, for example. In such instances, the end effector assembly 2000 can be a single-use and/or disposable end effector. In other instances, a staple cartridge that is fixed to the end effector assembly 2000 can be reloaded with additional staples for subsequent firings, for example.

Referring again to the staple cartridge 2020 disclosed in FIG. 7, a longitudinal slot 2032 is defined at least partially though the cartridge body 2024. The depicted longitudinal slot 2032 extends along a longitudinal axis L, which extends between a proximal end 2023 and a distal end 2025 of the cartridge body 2024. The longitudinal slot 2032 shown in FIG. 7 extends from the proximal end 2023 toward the distal end 2025 and traverses a portion of the length of the cartridge body 2024.

In some instances, the longitudinal slot 2032 can traverse the entire length of the cartridge body 2024. In other instances, the longitudinal slot 2032 can extend from the distal end 2023 toward the proximal end 2025, for example. In still other instances, the cartridge body 2024 may not include a predefined and/or preformed longitudinal slot. For example, a firing member and/or a cutting element can transect and/or cut the cartridge body 2024 during the firing stroke to form a slot therein.

The staple cartridge 2020 disclosed in FIG. 7 is configured to fire an array 2011 of staples 2012 into tissue. The staple array 2011 shown in FIG. 7 includes angled staples 2012, which are angled relative to the longitudinal axis L and relative to the firing paths of the driving wedges 2064a, 2064b, which are further described herein. The staple cartridge 2020 disclosed in FIG. 7 also includes multi-staple drivers 2040a, 2040b, which are further described herein, to drivingly support the angled staples 2012 in the array 2011.

The angled staples 2012 are removably positioned in angled staple cavities 2028 which are defined into the cartridge body 2024 disclosed in FIG. 7. For example, the depicted staple cavities 2028 are angularly-oriented relative to the longitudinal axis L. The depicted arrangement of staple cavities 2028 corresponds to the depicted staple array 2011 positioned in the staple cartridge 2020. Each staple cavity 2028 shown in FIG. 7 includes an opening 2030 in the deck 2026, and each opening 2030 includes a proximal end, a distal end, and a staple axis extending between the proximal end and the distal end. The staple axis of the openings 2030 are skewed and/or angled relative to the longitudinal axis L of the cartridge body 2024. For example, in the staple cartridge 2020 of FIG. 7, all the staple cavities 2028 defined into the cartridge body 2024 are angularly-oriented relative to the longitudinal axis L and various staple cavities 2028 are angularly-oriented relative to other staple cavities 2028.

The staple cavities 2028 disclosed in FIG. 7 are arranged in multiple rows on each side of the longitudinal slot 2032. For example, a portion of the staple cavities 2028 are arranged in a first inside row 2033, a first outside row 2035, and a first intermediate row 2037 on a first side 2027 of the longitudinal slot 2032, and another portion of the staple cavities 2028 are arranged in a second inside row 2034, a second outside row 2038, and a second intermediate row 2036 on a second side 2029 of the longitudinal slot 2032. In the staple cartridge 2020 depicted in FIG. 7, the staple cavities 2028 and rows 2033, 2034, 2035, 2036, 2037, 2038 thereof are symmetrical relative to the longitudinal slot 2032.

Though the depicted staple cavities 2028 do not cross or otherwise contact each other, the longitudinal rows 2033, 2034, 2035, 2036, 2037, 2038 of staple cavities 2028 overlap. For example, various staple cavities 2028 shown in FIG. 7 extend laterally outboard and/or laterally inboard past the staple cavities 2028 in adjacent rows of staple cavities 2028. Additionally, various depicted staple cavities 2028 extend proximally and/or distally past the staple cavities 2028 in adjacent rows of staple cavities 2028. Because the staples 2012 are arranged in an overlapping array 2011, bleeding and/or fluid flow in the stapled tissue can be controlled. An overlapping array of staples, like the staple array 2011, for example, could be incorporated into other staple cartridges and/or end effector assemblies disclosed herein.

In other instances, greater than or fewer than three rows of staple cavities 2028 can be positioned on either side 2027, 2029 of the longitudinal slot 2032. In some instances, one of the sides 2027, 2029 of the staple cartridge 2020 can include a different number of rows of staple cavities 2028 than the other side 2027, 2029. In some instances, the staple cavities 2028 may not longitudinally and/or laterally overlap the staple cavities 2028 in adjacent rows. Additionally or alternatively, in certain instances, the staple cavities 2028 and/or rows thereof can be asymmetrical relative to the longitudinal slot 2032 and/or the longitudinal axis L.

Referring still to FIG. 7, the depicted staple cavities 2028 in each longitudinal row are parallel or substantially parallel. For example, as disclosed in FIG. 7, the staple cavities 2028 in the first inside row 2033 are parallel to each other, the staple cavities 2028 in the first outside row 2035 are parallel to each other, the staple cavities 2028 in the first intermediate row 2037 are parallel to each other, the staple cavities 2028 in the second inside row 2034 are parallel to each other, the staple cavities 2028 in the second outside row 2036 are parallel to each other, and the staple cavities 2028 in the second intermediate row 2038 are parallel to each other.

As also disclosed in FIG. 7, the staple cavities 2028 in each longitudinal row are angularly-oriented relative to the staple cavities 2028 in the adjacent longitudinal row(s). For example, on the first side 2027 of the depicted cartridge body 2024, the staple cavities 2028 in the first intermediate row 2037 are angularly-oriented relative to the staple cavities 2028 in the first inner row 2033 and in the first outer row 2035. Additionally, on the second side 2029 of the depicted cartridge body 2024, the staple cavities 2028 in the second intermediate row 2038 are angularly-oriented relative to the staple cavities 2028 in the second inner row 2034 and the second outer row 2036.

In other instances, only a portion of the staples cavities 2028 in each longitudinal row 2033, 2034, 2035, 2036, 2037, 2038 may be parallel to each other and/or less than all of the longitudinal rows 2033, 2034, 2035, 2036, 2037, 2038 can include staple cavities 2028 that are parallel to each other. Additionally or alternatively, in certain instances, at least a portion of the staple cavities 2028 can be randomly oriented. In some instances, at least one of the staple cavities 2028 in a longitudinal row 2033, 2034, 2035, 2036, 2037, 2038 can be parallel to at least one of the staple cavities 2028 in an adjacent longitudinal row 2033, 2034, 2035, 2036, 2037, 2038. In certain instances, the staple cartridge 2020 can include at least one staple cavity 2028 and/or at least one row of staple cavities that are parallel to the longitudinal axis L of the cartridge body 2024. See, for example, FIG. 10.

Figure 8:
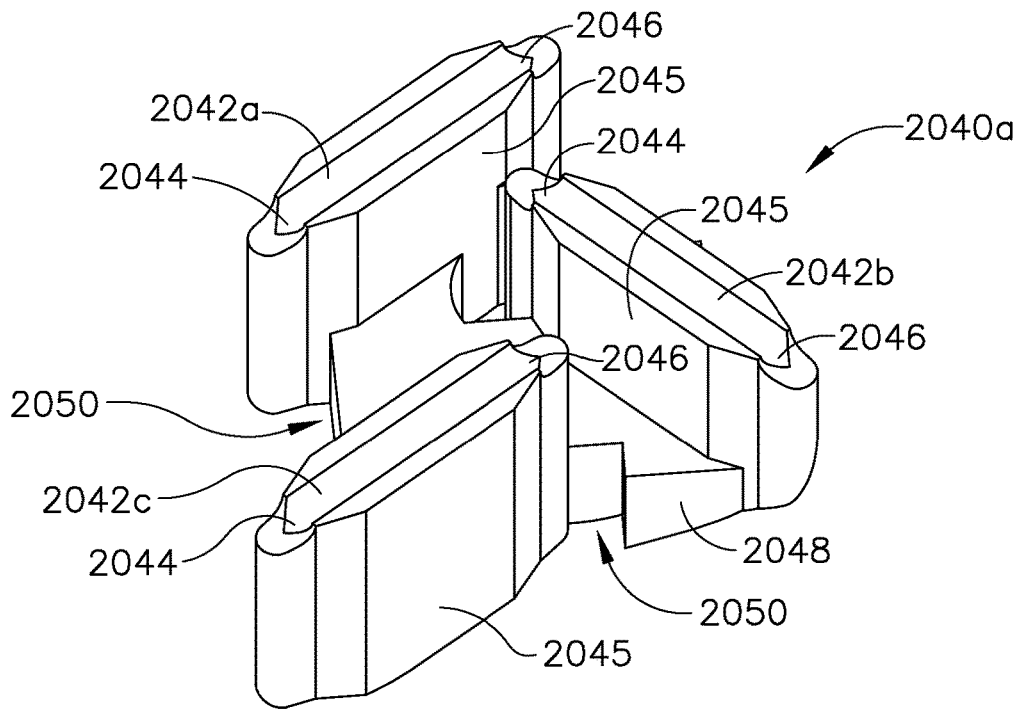
FIG. 8 is a perspective view of one of the first multi-staple drivers of FIG. 7.
Figure 8B:
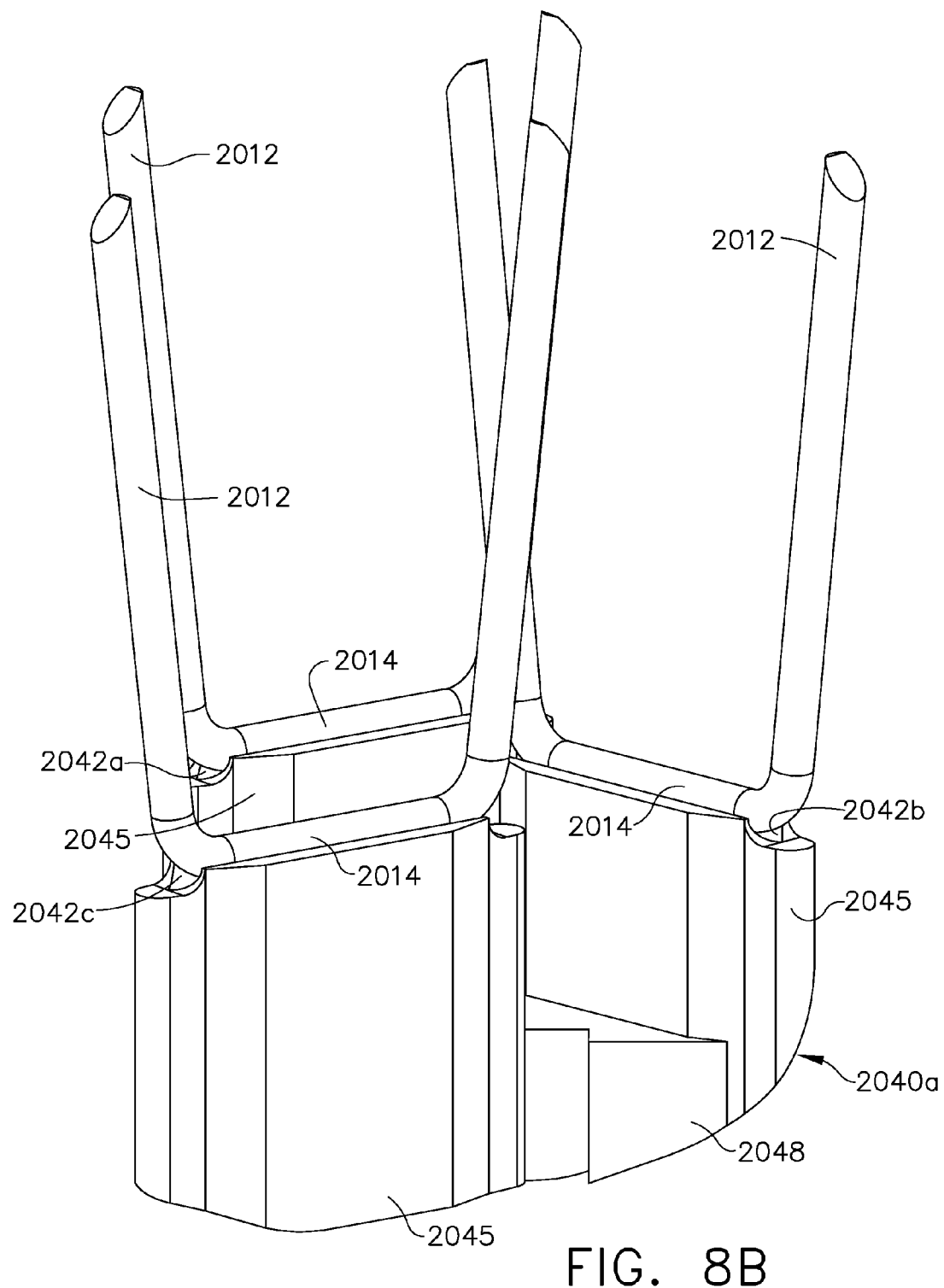
FIG. 8B is a perspective view of the first multi-staple driver of FIG. 8 and further showing staples of FIG. 7 supported by the multi-staple driver.
Figure 8C:
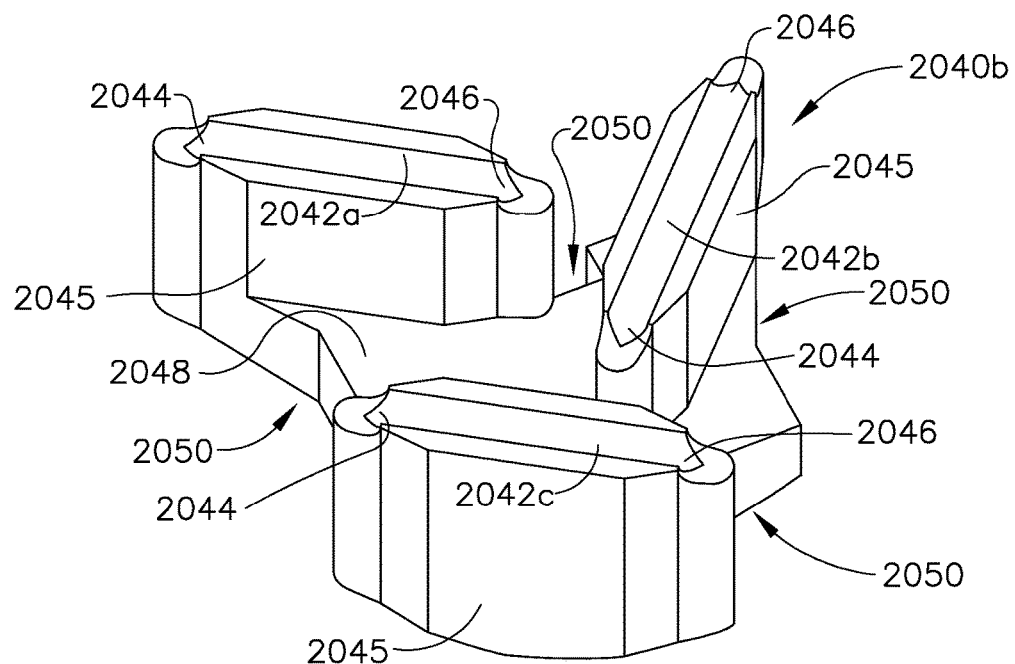
FIG. 8C is perspective view of one of the second multi-staple drivers of FIG. 7.
Figure 9:
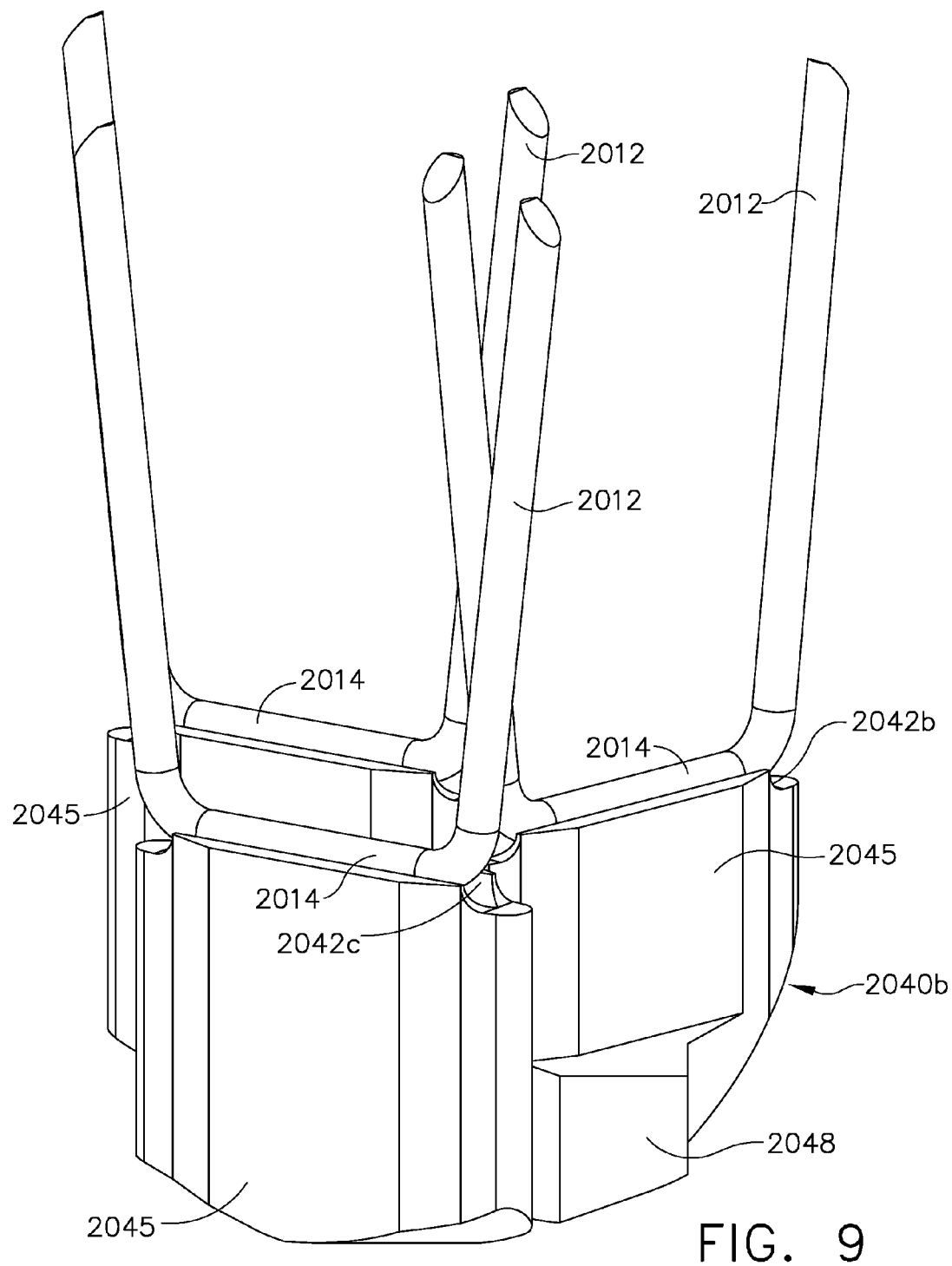
FIG. 9 is a perspective view of the second multi-staple driver of FIG. 8C and further showing staples of FIG. 7 supported by the multi-staple driver.

The staple cartridge 2020 disclosed in FIG. 7 includes drivers 2040a, 2040b, which are structured and dimensioned to movably fit within the cartridge body 2024 (FIG. 7). Referring to FIGS. 7-9, the drivers 2040a, 2040b include first drivers 2040a (FIGS. 8-8B) and second drivers 2040b (FIGS. 8C-9). The first and second drivers 2040a, 2040b are each configured to support multiple staples 2012. As shown in FIGS. 7-9, the multi-staple first drivers 2040a have a first geometry and the multi-staple second drivers 2040b have a second geometry. The geometry of the multi-staple drivers 2040a, 2040b corresponds to the array 2011 of staples 2012 and to the arrangement of staple cavities 2028 shown in FIG. 7.

As described herein, the arrangement of staples 2012 and staple cavities 2028 on the first side 2027 of the longitudinal slot 2032 is a mirror image of the arrangement of staples 2012 and staple cavities 2028 on the second side 2029 of the longitudinal slot 2032. Additionally, the geometry of the first drivers 2040a is a mirror image of the geometry of the second drivers 2040b. As depicted in FIG. 7, the first drivers 2040a are positioned on a first side 2027 of the longitudinal slot 2032, and the second drivers 2040b are positioned on a second side 2029 of the longitudinal slot 2032.

In some instances, the drivers on one side of a cartridge body may not be a mirror image of the drivers on the other side of the cartridge body. Additionally, the first multi-staple drivers 2040a and/or the second multi-staple drivers 2040b can be positioned on different and/or both sides 2027, 2029 of the longitudinal slot 2032. For example, multi-staple drivers having different geometries can be positioned on the same side of the longitudinal slot 2032. In still other instances, the staple cartridge 2020 can include multi-staple drivers of three or more different geometries. For example, a specialized and/or different staple driver can correspond to a particular staple and/or group of staples. Alternatively, in some instances, all multi-staple drivers in the staple cartridge 2020 can have the same geometry.

The first and second multi-staple drivers 2040a, 2040b disclosed in FIGS. 7-9 include multiple troughs or staple supporting cradles 2042. Moreover, each depicted driver 2040a, 2040b is configured to drive multiple staples 2012. For example, the first drivers 2040a (FIGS. 8-8B) include a first cradle 2042a, a second cradle 2042b, and a third cradle 2042c, which are each dimensioned and structured to support one staple 2012. For example, the base 2014 (FIG. 8B) of a staple 2012 is positioned in each cradle 2042a, 2042b, 2042c of the first driver 2040a. Additionally, referring primarily to FIGS. 8C-9, the second drivers 2040b also include a first cradle 2042a, a second cradle 2042b, and a third cradle 2042c, which are each dimensioned and structured to support one staple 2012. For example, the base 2014 (FIG. 9) of a staple 2012 is positioned in each cradle 2042a, 2042b, 2042c of the second driver 2040a.

As disclosed in FIG. 7, the first drivers 2040a are right-side drivers, which are positioned in the right side, or the first side 2027, of the staple cartridge 2020. The first cradle 2042a (FIGS. 8-8B) of each first driver 2040a is configured to be aligned with a staple 2012 in the first outer row 2035 of staple cavities 2028, the second cradle 2042b (FIGS. 8-8B) of each first driver 2040a is configured to be aligned with a staple 2012 in the first intermediate row 2037 of staple cavities 2028, and the third cradle 2042c (FIGS. 8-8B) of each first driver 2040a is configured to be aligned with a staple 2012 in the first inner row 2033 of staple cavities 2028.

As further disclosed in the FIG. 7, the second drivers 2040b are left-side drivers, which are positioned in the left side, or second side 2029, of the staple cartridge 2020. For example, the first cradle 2042a (FIGS. 8C-9) of each second driver 2040b is configured to be aligned with a staple 2012 in the second outer row 2036 of staple cavities 2028, the second cradle 2042b (FIGS. 8C-9) of each second driver 2040b is configured to be aligned with a staple 2012 in the second intermediate row 2038 of staple cavities 2028, and the third cradle 2042c (FIGS. 8C-9) of each second driver 2040b is configured to be aligned with a staple 2012 in the second inner row 2034 of staple cavities 2028.

Each cradle 2042a, 2042b, 2042c disclosed in FIGS. 8-9 is defined into a step or platform 2045 of the first driver 2040a or the second driver 2040b. For example, the depicted first drivers 2040a and depicted second drivers 2040b include platforms 2045, and a cradle 2042a, 2042b, 2042c is defined into each of the platforms 2045. The platforms 2045 disclosed in FIGS. 8-9 of the driver 2040a, 2040b are the same height or elevation, and are configured to hold each staple 2012 in the array 2011 at the same height or elevation relative to the other staples 2012 in the array 2011. Referring still to FIGS. 8-9, a connecting flange 2048 is also disclosed, which extends between the steps 2045 of each driver 2040a, 2040b. The connecting flange 2048 can limit and/or restrain relative movement between the steps 2045.

In other instances, the steps or platforms 2045 can have different heights and/or elevations. For example, the height of each step 2045 can be varied to control the formed height of staples 2012, and thus, the compression of tissue captured within the formed staples 2012. Additionally or alternatively, the depth of each cradle 2042a, 2042b, 2042c can be varied to control the height of the formed staples 2012, and thus, the compression of tissue captured within the formed staples 2012.

Figure 8A:
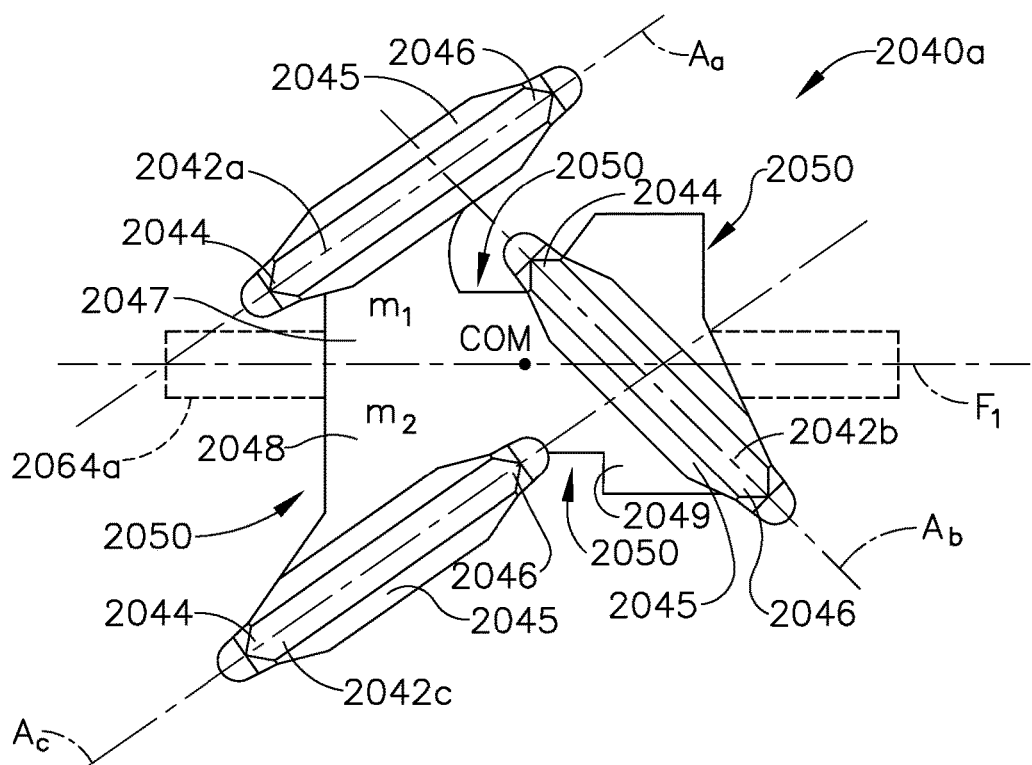
FIG. 8A is a plan view of the first multi-staple driver of FIG. 8.
Figure 8D:
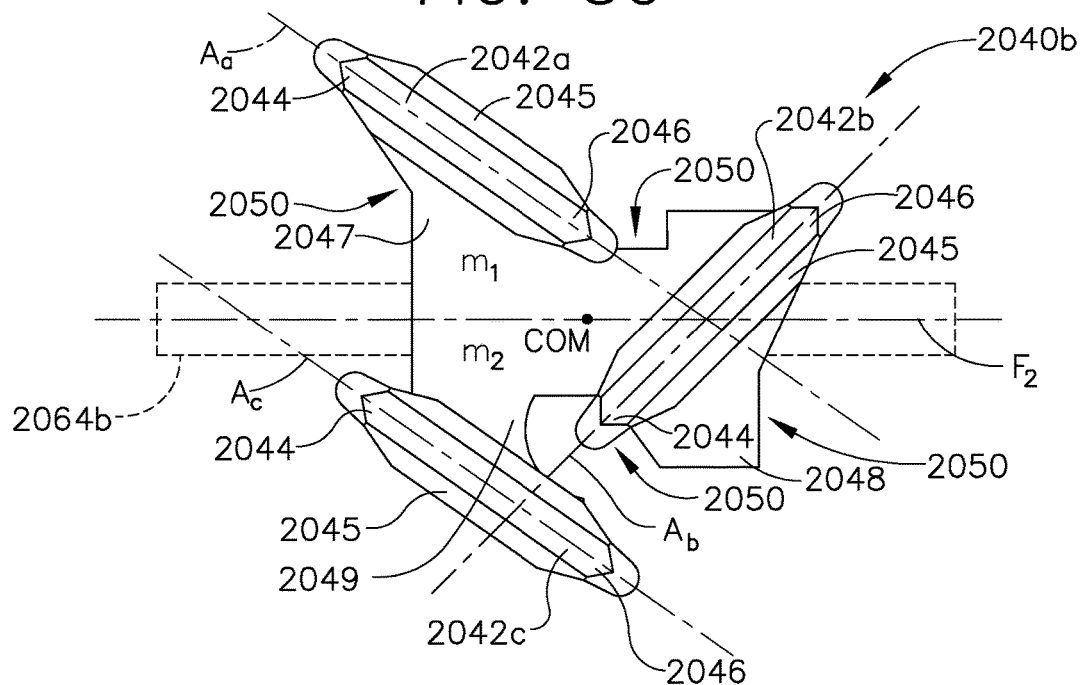
FIG. 8D is a plan view of the second multi-staple driver of FIG. 8C.

The first and second drivers 2040a, 2040b and the cradles 2042a, 2042b, 2042c thereof are oriented in an arrangement that complements the arrangement of staple cavities 2028 and staple array 2011 in the staple cartridge 2020 As disclosed in FIGS. 8A and 8D, each cradle 2042a, 2042b, 2042c includes a first end 2044 and a second end 2046, and the first end 2044 of each cradle 2042a, 2042b, 2042c is distal to the second end 2046 of the same cradle 2042a, 2042b, 2042c. Additionally, an axis is defined between the first end 2044 and the second end 2046 of each cradle 2042a, 2042b, 2042c. For example, a first axis $A_a$ is defined by the first cradle 2042*a*, a second axis A*_b_* is defined by the second cradle 2042*b*, and a third axis A*_c_* is defined by the third cradle 2042*c*.

In the depicted arrangement, the orientation of the first axis A*_a_* is configured to match or correspond to the orientation of the angled staple 2012 supported by the first cradle 2042*a*, the orientation of the second axis A*_b_* is configured to match or correspond to the orientation of the angled staple 2012 supported by the second cradle 2042*b*, and the orientation of the third axis A*_c_* is configured to match or correspond to the orientation of the angled staple 2012 supported by the third cradle 2042*c*.

As disclosed in FIGS. 8A and 8D, the first axis A*_a_* is parallel, or generally parallel, to the third axis A*_c_*. Additionally, the second axis A*_b_* depicted in FIGS. 8A and 8D traverses both the first axis A*_a_* and the third axis A*_c_*. For example, as disclosed in FIGS. 8A and 8D, the second axis A*_b_* is perpendicular, or generally perpendicular, to the first axis A*_a_* and the third axis A*_c_*.

In instances where the drivers 2040*a*, 2040*b* are used in a staple cartridge having a different arrangement of staples 2012 and staple cavities 2028, the relative orientations of the cradles 2042*a*, 2042*b*, 2042*c* can be different. In some arrangements, for example, all of the axes A*_a_*, A*_b_*, A*_c_* may be parallel. In still other arrangements, for example, all of the axes A*_a_*, A*_b_*, A*_c_* may cross. In certain instances, one axis A*_a_*, A*_b_*, A*_c_* may be perpendicular to at least one other axis A*_a_*, A*_b_*, A*_c_*. Additionally or alternatively, in some instances, one axis A*_a_*, A*_b_*, A*_c_* may be parallel to at least one other axis A*_a_*, A*_b_*, A*_c_*.

Referring primarily to FIGS. 8-8C, the first and second drivers 2040*a*, 2040*b* are integrally formed pieces. For example, each driver 2040*a*, 2040*b* consists of an integrally molded part. In other instances, at least one step 2045 and/or connecting flange 2048 can be independently formed. In such instances, the multiple pieces can be glued, welded, and/or otherwise adhered together, for example, to form a unitary piece.

The multi-staple drivers 2040*a*, 2040*b* disclosed in FIGS. 7-9 are configured to drive staples 2012 from staple cavities 2028 across multiple longitudinal rows 2033, 2034, 2035, 2036, 2037, 2039. In the staple cartridge 2020 depicted in FIG. 7, the staples 2012 are arranged in three longitudinal rows on each side of the slot 2032, and the drivers 2040*a*, 2040*b* are configured to support and drive staples 2012 in each of the three longitudinal rows. For example, each depicted first driver 2040*a* is configured to drive a staple 2012 positioned in the first inner row 2033, a staple 2012 positioned in the first intermediate row 2037, and a staple 2012 positioned in the first outer row 2035 of staple cavities 2028. Additionally, each depicted second driver 2040*b* is configured to drive a staple 2012 positioned in the second inner row 2034, a staple 2012 positioned in the second intermediate row 2038, and a staple 2012 positioned in the second outer row 2036 of staple cavities 2028.

In other instances, the staples 2012 can be arranged in more than three longitudinal rows or less than three longitudinal rows on each side of the slot 2032, and the drivers 2040*a*, 2040*b* can be configured to engage staples 2012 in each of the longitudinal rows on each side of the slot 2032. For example, the staple cartridge 2020 can have two rows of staple cavities 2028 on either side of the longitudinal axis L, and a multi-staple driver positioned therein can include two cradles, which can be configured to support a staple in each of the two rows. In some instances, a multi-staple driver can fire multiple staples 2012 from the same row of staple cavities 2028. For example, a multi-staple driver can fire adjacent staples 2012 in the same row, such as a more proximal staple 2012 and a more distal staple 2012, for example. In certain instances, a multi-staple driver may not engage staples 2012 in every row on a side of the longitudinal slot 2032. For example, a separate and distinct driver may engage staples in one of the rows, such as an outermost row and/or an innermost row, for example. Additionally or alternatively, in certain instances, the staple cartridge 2020 can include at least one multi-staple driver and at least one single-staple driver. See, for example, FIG. 12.

The end effector assembly 2000 disclosed in FIG. 7 further includes a firing member 2060, which is configured to move relative to the cartridge body 2024. During a firing stroke, the firing member 2060 is configured to traverse the cartridge body 2024, and drivingly engage a sled 2058 to move the sled 2058 through the cartridge body 2024. For example, a portion of the depicted firing member 2060 is dimensioned and positioned to fit within the longitudinal slot 2032. As disclosed in FIG. 7, the portion of the firing member 2060 that is configured to fit within the longitudinal slot 2032 includes a cutting edge 2061, which is configured to incise tissue clamped between the first jaw 2002 and the second jaw 2004 of the end effector assembly 2000.

The wedge sled 2058 disclosed in FIG. 7 is configured to engage the drivers 2040*a*, 2040*b* to lift the drivers 2040*a*, 2040*b*, and thus, fire the staples 2012 supported thereon, into tissue. In the depicted end effector assembly 2000, an intermediate wedge 2062 of the sled 2058 can slide and/or translate within the longitudinal slot 2032, and laterally positioned driving wedges or driving rails 2064*a*, 2064*b* defined on the sled 2058 can engage the staple drivers 2040*a*, 2040*b*. For example, the sled 2058 shown in FIG. 7 includes driving wedges or rails 2064*a*, 2064*b*, which are configured to move along firing paths $F_1$ (FIG. 8A) and $F_2$ (FIG. 8D) during a firing stroke to contact the multi-staple first and second drivers 2040*a*, 2040*b* that are longitudinally aligned with the firing paths $F_1$, $F_2$.

As disclosed in FIG. 7, the sled 2058 includes a driving wedge 2064*a*, 2064*b* on either side of the central portion 2062. The driving wedge 2064*a* on the first side 2027 of the staple cartridge 2020 is configured to move along the first firing path $F_1$ (FIG. 8A), and the driving wedge 2064*b* on the second side 2029 of the staple cartridge 2020 is configured to move along the second firing path $F_2$ (FIG. 8D).

Each driving wedge 2064*a*, 2064*b* disclosed in FIG. 7 is configured to engage one of the multi-staple drivers 2040*a*, 2040*b* to lift the drivers 2040*a*, 2040*b* within the staple cavities 2028 and eject the staples 2012 from the cartridge body 2024. In the depicted arrangement, the three steps 2045 of each first driver 2040*a* remain fixed relative to each other, and the three steps 2045 of each second driver 2040*b* remain fixed relative to each other. In other words, the steps 2045 of a single driver 2040*a*, 2040*b* do not move and/or rotate relative to each other. Because the steps 2045 of a single driver 2040*a*, 2040*b* do not move and/or rotate relative to each other, relative movement of the staples 2012 supported by each driver 2040*a*, 2040*b* is also restrained. Additionally, each driver 2040*a*, 2040*b* has a larger base or footprint within the cartridge body 2042, which can further reduce rotation and/or torqueing of the drivers 2040*a*, 2040*b*. As a result, shifting and/or tilting of the staples 2012 during deployment may be prevented, minimized and/or controlled by the multi-staple drivers 2040*a*, 2040*b*. Multi-staple drivers, like the drivers 2040*a*, 2040*b*, for example, could be incorporated into other staple cartridge and/or end effector assemblies disclosed herein.

In various instances, the driving wedges 2064a, 2064b of the sled 2058 can be dimensioned, structured and positioned to engage a driving surface of the drivers 2040a, 2040b, respectively. For example, the drivers 2040a, 2040b can include a ramped surface and/or track, which is configured to guide and/or receive a portion of a driving wedge 2064a, 2064b, respectively, as the firing member 2060 and the sled 2058 move through the staple cartridge 2020.

The relative placement of the driving wedges 2064a, 2064b, and their corresponding firing paths $F_1$, $F_2$, respectively, to the drivers 2040a, 2040b and the staples 2012 supported by the drivers 2040a, 2040b may be selected to prevent, reduce, and/or control torqueing of the drivers 2040a, 2040b and/or the staples 2012 during firing. For example, the geometry and/or material of the drivers 2040a, 2040b can be selected to place the center of mass (COM) of each driver 2040a, 2040b into alignment with the corresponding firing path $F_1$, $F_2$, respectively. Additionally or alternatively, the driving wedges 2064a, 2064b, and thus the firing paths $F_1$, $F_2$, respectively, can be positioned within the cartridge 2020 to extend through the center of mass (COM) of the drivers 2040a, 2040b, respectively.

In other instances, as further described herein, the sled 2058 can include more than one driving wedge 2064a, 2064b on each side of the intermediate portion 2062. For example, multiple driving wedges 2064a, 2064b can move through either side 2027, 2029 of the cartridge body 2024. Additionally or alternatively, the driving wedges 2064a, 2064b of the wedge sled 2058 can be configured to directly engage and drive the staples 2012, as further described herein.

Referring primarily to FIGS. 8A and 8D, the first and second drivers 2040a, 2040b overlie the firing paths $F_1$, $F_2$, respectively, of the driving wedges 2064a, 2064b, respectively. For example, the first driver 2040a overlies the first firing path $F_1$ and the second driver 2040b overlies the second firing path $F_2$. Moreover, various portions of each driver 2040a, 2040b are positioned on either side of the respective driving wedge 2064a, 2064b, and thus, on either side of the firing paths $F_1$, $F_2$. Referring still to FIGS. 8A and 8D, the depicted drivers 2040a, 2040b are dimensioned and structured such that the center of mass (COM) of each driver 2040a, 2040b overlaps the corresponding firing path $F_1$, $F_2$ of the driving wedge 2064a, 2064b, respectively, for example. In other words, each depicted driver 2040a, 2040b is mass balanced relative to the corresponding firing path $F_1$, $F_2$.

For example, as disclosed in FIG. 8A, a first portion 2047 of the first driver 2040a is positioned on a first side of the firing path $F_1$, and a second portion 2049 of the first driver 2040a is positioned on a second side of the firing path $F_1$. The first portion 2047 of the first driver 2040a has a first mass $m_1$ and the second portion 2049 of the first driver 2040a has a mass $m_2$, which equals, or substantially equals, the first mass $m_1$. Additionally, as disclosed in FIG. 8D, a first portion 2047 of the second driver 2040b is positioned on a first side of the firing path $F_2$, and a second portion 2049 of the second driver 2040b is positioned on a second side of the firing path $F_2$. The first portion 2047 of the second driver 2040b has a first mass $m_1$ and the second portion 2049 of the second driver 2040b has a mass $m_2$, which equals or substantially equals the first mass $m_1$. Because the drivers 2040a, 2040b are mass balanced relative to the respective firing paths $F_1$, $F_2$, torquing of the drivers 2040a, 2040b and the staples 2012 supported thereon during firing can be minimized and/or otherwise controlled. Additionally, the group of staples 2012 deployed by each driver 2040a, 2040b can be synchronously lifted relative to the cartridge body 2024 and simultaneously driven or fired into tissue. Mass balanced drivers, like the drivers 2040a, 2040b, for example, could be incorporated into other embodiments disclosed herein.

Additionally, as disclosed in FIGS. 8-9, at least one cutout 2050 is defined into the first and second multi-staple drivers 2040a, 2040b. For example, various cutouts 2050 are defined into the connecting flange 2048 of the drivers 2040a, 2040b. The cutouts 2050 are dimensioned and positioned to adjust the mass of the drivers 2040a, 2040b, and balance the center of mass (COM) of each driver 2040a, 2040b relative to the corresponding firing path $F_1$, $F_2$. Additionally, the cutouts 2050 are dimensioned and positioned to accommodate for the geometry of the staple cavities 2028, in which the drivers 2040a, 2040b are movably positioned.

In certain instances, multiple staple cavities can be defined into a staple cartridge, at least one staple cavity can be parallel to the longitudinal axis of the staple cartridge, and at least one staple cavity can be angularly-oriented relative to the longitudinal axis of the staple cartridge. Referring to the staple cartridge 2120 depicted in FIG. 10, for example, multiple staple cavities 2128 are defined into the staple cartridge 2120, and multiple staple cavities 2128 are parallel to the longitudinal axis L of the staple cartridge 2120.

In the depicted staple cartridge 2120, a longitudinal slot 2032 is defined partially through the cartridge body 2124. Also defined in the cartridge body 2124 is a row of staple cavities 2128 on either side of the longitudinal slot 2032 which includes staple cavities 2128 that are oriented parallel to the longitudinal axis L. In the depicted staple cartridge 2120, a first row 2137 of staple cavities 2128 and a second row 2138 of staple cavities 2128 are adjacent to the longitudinal slot 2032, and the staple cavities 2128 in the first row 2137 and in the second row 2138 are oriented parallel to the longitudinal axis L. For example, as disclosed in FIG. 10, the staple cavities 2128 in the first row 2137 are aligned with an axis $A_b$, which is parallel to the longitudinal axis L.

The staple cartridge 2120 disclosed in FIG. 10 includes additional rows of staple cavities 2128. For example, the depicted staple cartridge 2120 includes a third row 2135 of staple cavities 2128 and a fourth row 2136 of staple cavities 2128, which include staple cavities 2128 that are angularly-oriented relative to the longitudinal axis L. In such instances, the staple cavities 2128 in the third and fourth rows 2135, 2136 are also angularly-oriented relative to the staple cavities 2128 in the first and second rows 2137, 2138 and are also angularly-oriented relative to each other. For example, a staple cavity 2128 in the third row 2135 is aligned with an axis $A_a$, which traverses the longitudinal axis L and traverses the axis $A_b$ of the first row 2137 of staple cavities 2128. As further disclosed in FIG. 10, the staple cavities 2128 in the fourth row 2136 extend along an axis that traverses the axis $A_a$ of a staple cavity 2128 in the third row 2135. The first and third rows 2137, 2135 of staple cavities 2128 are positioned on a first side 2127 of the depicted cartridge body 2124, and the second and fourth rows 2136, 2138 are positioned on a second side 2129 of the depicted cartridge body 2124.

In various instances, the staple cartridge 2120 disclosed in FIG. 10 can be used with the end effector assembly 2000 depicted in FIG. 7. For example, the staple cartridge 2120 can be loaded into the elongate channel of the second jaw 2004 of the end effector assembly 2000. The staple cartridge 2120 can be fired with single-staple drivers, multi-staple drivers, and/or a combination thereof. For example, a multi-staple driver may be configured to fire staples from the staple cavities 2128 in the first and third rows 2137, 2135 on the first side 2127 of the cartridge body 2124, and another multi-staple driver can be configured to fire staples from the staple cavities 2128 in the second and fourth rows 2136, 2138 on the second side 2129 of the cartridge body 2124. In various instances, the drivers can be positioned within the cartridge body 2124 such that the cradles of the drivers are aligned with the staples positioned in the staple cavities 2128. In such instances, the drivers and/or the staples supported thereon can be mass balanced relative to the firing path(s) of a sled, such as the sled 2058 (FIG. 7), for example, which can be configured to traverse the cartridge body 2124 and engage the drivers therein.

In other instances, the staple cartridge 2120 may not include drivers. For example, a firing member and/or sled, such as the firing member 2060 and/or the sled 2058 (FIG. 7), for example, can be configured to directly contact, engage, and/or drive the staples movably positioned in the staple cavities 2128. In such instances, the staples can be mass balanced relative to the firing path(s) of the sled 2058. In still other instances, the staples can be held in position within the cartridge body 2124, and can be crushed and/or otherwise deformed within the cartridge body 2124, for example.

In various instances, a multi-staple driver can be balanced relative to multiple driving wedges that concurrently engage and cooperatively lift the driver during deployment. For example, multi-staple drivers 2240 and a pair of driving wedges 2264a, 2264b are depicted in FIG. 11. The multi-staple drivers 2240 are configured for use with the staple cartridge 2020, for example. Additionally or alternatively, the drivers 2240 can be used with various other staple cartridges having a staple array that matches the array 2011 (FIG. 7) and corresponds to the arrangement of drivers 2240 shown in FIG. 11.

In various instances, a staple that is fired from the staple cartridge 2120 can be formed to a variable formed height. For example, the staple can have a greater height between one of the staple legs and the base than between the other staple leg and the base. In such instances, the staple can exert a greater compressive force on tissue at the shorter end of the staple. As described in greater detail herein, the height of a staple can be varied when the staple driver comprises a step or height differential (see, for example, FIG. 79), and/or when the staple forming pockets in the anvil comprise a step or height differential (see, for example, FIG. 80).

When an angled staple is deformed to a variable height, the compressive force exerted on the tissue by the angled staple can vary longitudinally and laterally. In certain instances, for example, it can be desirable to compress tissue closer to the cutline, i.e., laterally inboard, more than tissue farther from the cutline, i.e., laterally outboard. In such instances, the lateral tissue variation afforded by an angled staple that has been deformed to different compressed heights can exert a greater compressive force on a laterally inboard portion of tissue and a reduced compressive force on a laterally outboard portion of tissue.

Referring again to FIG. 10, in certain instances, the staples ejected from the third row 2135 of staple cavities 2128 and from the fourth row 2136 of staple cavities 2128 can be deformed to variable heights. For example, the staples can have a reduced height closer to the longitudinal axis L, and a greater height farther from the longitudinal axis L. Additionally or alternatively, the staples ejected from the first row 2137 of staple cavities 2128 and from the second row of staple cavities 2138 can be deformed to a uniform height, which can be less than the reduced, or smaller height, of the staples ejected from the third row 2135 and the fourth row 2136 of staple cavities 2128. In such instances, the compressive force exerted on the tissue can be greatest closer to the cutline, and can gradually decrease farther outboard toward the lateral sides of the staple line.

Each driver 2240 disclosed in FIG. 11 includes multiple troughs or staple supporting cradles 2242a, 2242b, 2242c. For example, each driver 2240 includes a first cradle 2242a, a second cradle 2242b, and a third cradle 2242c, which are each dimensioned and structured to support one staple, such as one of the staples 2012 (FIG. 7). For example, the base of a staple can be positioned in each cradle 2242a, 2242b, 2242c. Referring again to the staple cartridge 2020 depicted in FIG. 7, the first cradle 2242a can be aligned with a staple 2012 in the first outer row 2035 of staple cavities 2028, the second cradle 2242b can be aligned with a staple 2012 in the first intermediate row 2037 of staple cavities 2028, and the third cradle 2242c can be aligned with a staple 2012 in the first inner row 2033 of staple cavities 2028. In such instances, the first cradle 2242a corresponds to an outer cradle, the second cradle 2242b corresponds to an intermediate cradle, and the third cradle 2242c corresponds to an inner cradle. In various instances, another driver arrangement can be positioned on the opposite side of the staple cartridge, and the other driver arrangement can be the mirror image reflection of the driver arrangement depicted in FIG. 11.

The cradles 2242a, 2242b, 2242c depicted in FIG. 11 are defined into a support member 2248. The support member 2248 can support staples across multiple rows of staple cavities. Additionally, the support member 2248 can support staples 2012 oriented at varying angles relative to the longitudinal axis L of the staple cartridge, and/or relative to the longitudinal firing paths of the driving wedges 2264a, 2264b, for example. Referring to the depicted support member 2248, the support member 2248 is angularly-oriented relative to the firing paths of the driving wedges 2264a, 2264b. Additionally, the support member 2248 is angularly-oriented relative to at least one of the cradles 2242a, 2242b, 2242c defined therein. For example, the intermediate cradle 2242b disclosed in FIG. 11 is angularly-oriented relative to the support member 2248. Moreover, as disclosed in FIG. 11, the outer cradle 2242c and the inner cradle 2242a are aligned with the support member 2248.

In certain instances, the height of the support member 2248 can be uniform, or generally uniform, such that each staple supported by the support member 2248 is positioned at the same height or elevation. In other instances, the support member 2248 can include steps having different heights and/or elevations. For example, the height of a step can be varied to control the height of the formed staples, and thus, the compression of tissue captured within the formed staples. Additionally or alternatively, the depth of each cradle 2242a, 2242b, 2242b can be varied to control the height of the formed staples, and thus, the compression of tissue captured within the formed staples.

Each cradle 2242a, 2242b, 2242c disclosed in FIG. 11 includes a first end 2244 and a second end 2246. The first end 2244 of each cradle 2242a, 2242b, 2242c is distal to the second end 2246 of the same cradle 2242a, 2242b, 2242c. Additionally, an axis is defined between the first end 2244 and the second end 2246 of each cradle 2242a, 2242b, 2242c. For example, a first axis $A_a$ is defined by the first cradle 2242a and the third cradle 2242c, and a second axis $A_b$ is defined by the second cradle 2242b. As depicted in FIG. 11, the second axis $A_b$ traverses the first axes $A_a$. In certain instances, the second axis $A_b$ can be perpendicular, or generally perpendicular, to the first axis $A_a$.

Referring still to FIG. 11, the multi-staple drivers 2240 include rails 2245a, 2045b, which are connected to the support member 2248. The rails 2245a, 2245b are positioned to engage the driving wedges 2264a, 2264b of a wedge sled. For example, the depicted rails 2245a, 2245b are aligned with the firing paths $F_1$, $F_2$ of the driving wedges 2264a, 2264b. In such instances, the rails 2245a, 2245b can provide an elongated surface area for receiving the driving force from the driving wedges and for stabilizing the multi-staple drivers 2240 when the driving wedges 2264a, 2264b drivingly engage the rails 2245a, 2245b.

The drivers 2240 can include multiple independently formed parts, which can be glued, welded, and/or otherwise adhered together. For example, the support member 2248 can be joined together with the rails 2245a, 2245b to form the driver 2240. In other instances, each driver 2240 can be an integrally molded part, which includes the support member 2248 and the rails 2245a, 2245b.

The drivers 2240 that are disclosed in FIG. 11 overlie the firing paths $F_1$, $F_2$ of the driving wedges 2264a, 2264b. Moreover, various portions of each depicted driver 2240 are positioned on either side of the wedges 2264a, 2264b. As shown in FIG. 11, the drivers 2240 are dimensioned and structured such that the center of mass (COM) of each driver 2240 is equidistant from the drive axes, e.g., equidistant from the firing paths $F_1$, $F_2$ of the driving wedges 2264a, 2264b. For example, the firing paths $F_1$, $F_2$, depicted in FIG. 11, are separated by a width w, and the center of mass of each driver 2240 is positioned between the firing paths $F_1$, $F_2$. As shown in FIG. 11, the center of mass of each driver 2240 is laterally offset from the first firing path $F_1$ by a width w/2 and laterally offset from the second firing path $F_2$ by a width w/2. As a result, each depicted driver 2240 is mass balanced relative to the firing paths $F_1$, $F_2$. Because the drivers 2240 are mass balanced relative to the firing paths $F_1$, $F_2$, torqueing of the drivers 2240 and staples during deployment may be prevented, minimized and/or otherwise controlled. Mass balanced drivers, like the drivers 2240, for example, could be incorporated into other staple cartridges and end effector assemblies disclosed herein.

In other instances, the firing member can include a single driving wedge aligned with the drivers 2240, and the drivers 2240 can be mass balanced relative to the driving wedge. For example, the driving wedge can define a firing path that extends through the center of mass (COM) of each driver 2240. In such instances, the driving wedge may have a greater width to increase the stability of the drivers 2240. In other instances, the firing member can include three or more driving wedges, and the cumulative drive force exerted by the driving wedges can be balanced relative to the geometry of the driver 2240.

Each rail 2245a, 2245b disclosed in FIG. 11 is aligned with one of the firing paths $F_1$, $F_2$. Specifically, the first rail 2245a is aligned with the first firing path $F_1$, and the second rail 2245b is aligned with the second firing path $F_2$. The driving wedges 2264a, 2264b are configured to contact the rails 2245a, 2245b to lift the drivers 2240 and the staples supported thereon. Referring still to FIG. 11, the depicted driving wedges 2264a, 2264b are longitudinally staggered by a distance x. For example, the first wedge 2264a trails the second wedge 2264b by the distance x indicated in FIG. 11. Additionally, the first rail 2245a is longitudinally staggered relative to the second rail 2245b. For example, the second rail 2245b is distally offset from the first rail 2245a by the distance y indicated in FIG. 11. In the arrangement disclosed in FIG. 11, the distance x equal, or substantially equals, the distance y, such that driving wedges 2264a, 2264b simultaneously contact and drive the rails 2245a, 2245b, respectively, during a firing stroke.

Because the driving wedges 2264a, 2264b disclosed in FIG. 11 simultaneously engage and drivingly lift the rails 2245a, 2245b, respectively, on either side of the center of mass (COM) of the driver 2240 and equidistant therefrom, the cumulative driving force is balanced throughout the entire deployment of the driver 2240. As a result, torqueing and/or rotation of the driver 2240, and thus of the staples supported thereon, may be prevented, minimized, and/or controlled. Longitudinally offset driving wedges, like the driving wedges 2264a, 2264b, for example, could be incorporated into other embodiments disclosed herein.

Figure 12:
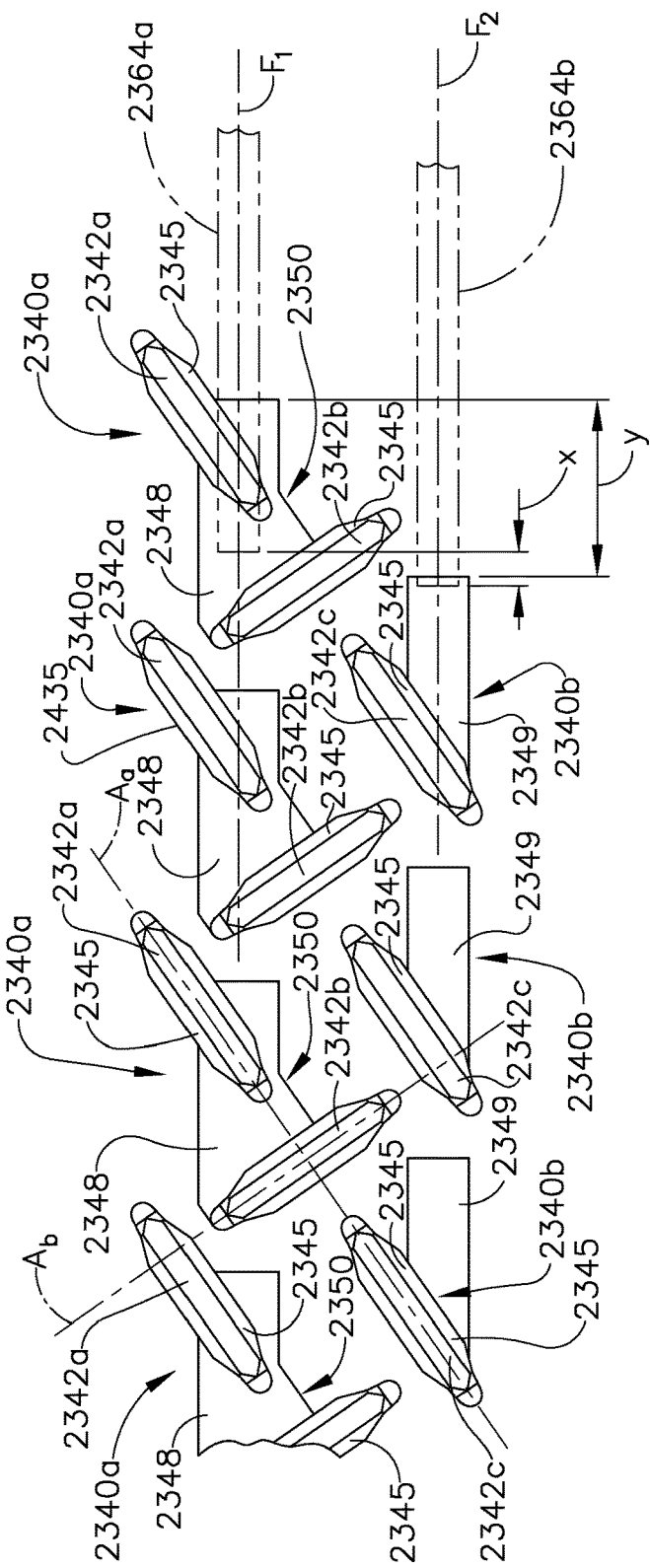
FIG. 12 is a plan view of an arrangement of multi-staple drivers and driving wedges, according to various embodiments of the present disclosure.

An arrangement of multi-staple drivers 2340a and single-staple drivers 2340b is disclosed in FIG. 12. Because the arrangement of drivers 2340a, 2340b corresponds to the array 2011 of staples 2012 depicted in FIG. 7, the drivers 2340a, 2340b can be used with the staple cartridge 2020 (FIG. 7). Additionally or alternatively, the drivers 2340a, 2340b can be used with various other staple cartridges having a staple array that corresponds to the arrangement of drivers 2340a, 2340b depicted in FIG. 12.

The drivers 2340a, 2340b include multiple troughs or staple supporting cradles 2342a, 2342b, 2342c. For example, the multi-staple drivers 2340a include a first cradle 2342a and a second cradle 2342b, which are each dimensioned and structured to support a staple, such as two of the staples 2012 shown in FIG. 7. Additionally, the single-staple drivers 2340b include a third cradle 2342c, which is dimensioned and structured to support another staple, such as another of the staples 2012 shown in FIG. 7. For example, the base of a staple 2012 can reside in each cradle 2342a, 2342b, 2342c.

Referring again to the staple cartridge 2020 depicted in FIG. 7, the first cradle 2342a can be aligned with a staple 2012 in the first outer row 2035 of staple cavities 2028, the second cradle 2342b can be aligned with a staple 2012 in the intermediate row 2037 of staple cavities 2028, and the third cradle 2342c can be aligned with a staple 2012 in the inner row 2033 of staple cavities 2028. In such instances, the first cradle 2342a corresponds to an outer cradle, the second cradle 2342b corresponds to an intermediate cradle, and the third cradle 2342c corresponds to an inner cradle. Additionally, another driver arrangement can be positioned on the opposite side of the staple cartridge 2020, which can be the mirror image of the driver arrangement disclosed in FIG. 12.

Referring still to FIG. 12, each cradle 2342a, 2342b, 2342c is defined into a step and/or support portion 2345. Additionally, each of the drivers 2340a, 2340b includes a base 2348, 2349, respectively. The base 2348 of each multi-staple driver 2340a extends between the steps 2345 of the driver 2340a. Additionally, the base 2349 of each single-staple driver 2340b extends from the step 2345 thereof.

As disclosed in FIG. 12, each driver 2340a, 2340b is aligned with a firing path $F_1$, $F_2$ within a staple cartridge. Specifically, each first driver 2340a is aligned with the first firing path $F_1$, and each second driver 2340b is aligned with the second firing path $F_2$. The depicted driving wedges 2364a, 2364b are configured to move along the firing paths $F_1$, $F_2$ during a firing stroke. Additionally, the driving wedges 2364a, 2364b contact the drivers 2340a, 2340b, respectively, to lift the drivers 2240a, 2340b and the staples supported thereon.

The bases 2348, 2349 can act as counterweights to adjust and/or control the center of mass of the drivers 2340a,

2340b. For example, the geometry and material of each base 2348, 2349 can be selected to maintain and/or shift the center of mass of each driver 2340a, 2340b into alignment with the corresponding firing path $F_1$, $F_2$. As depicted in FIG. 12, the first bases 2348 include at least one cutout 2350. The dimensions, placement, and geometry of the cutouts 2350 are selected to mass balance the first drivers 2340a relative to the first firing path $F_1$. For example, each first base 2348 can be configured to shift or maintain the center of mass of the multi-staple driver 2340a into alignment with the first firing path $F_1$, and each second base 2349 can be configured to shift the center of mass of the single-staple driver 2340b into alignment with the second firing path $F_2$.

Additionally, the bases 2348, 2349 provide an elongated surface area for stabilizing the drivers 2340 when the driving wedges 2364a, 2364b drivingly engage the drivers 2340a, 2340b. For example, the larger footprint of the drivers 2340a, 2340b may promote stability and prevent torqueing and/or rotation of the drivers 2340a, 2340b during deployment. Moreover, because the bases 2348, 2349 provide a larger surface area, the driving force can be distributed to promote a balanced driver and staple deployment. Drivers having elongated surface areas, such as the bases 2348, 2349, for example, could be incorporated into other embodiments disclosed herein.

Referring still to FIG. 12, the depicted driving wedges 2364a, 2364b are longitudinally staggered by a distance x. For example, the first wedge 2364a trails the second wedge 2364b by the distance x. As further depicted in FIG. 12, the depicted drivers 2340a, 2340b are longitudinally staggered by a distance y. In the depicted arrangement, the distance x is different than the distance y, such that the driving wedges 2364a, 2364b do not contact the drivers 2340a, 2340 simultaneously. For example, in the depicted arrangement, the first wedge 2364a contacts the first driver 2340a before the second wedge 2364b contacts the second driver 2340b. In such instances, deployment of the first driver 2340a, and thus movement of the first cradle 2342a and the second cradle 2342c, is initiated before deployment of the second staple 2340b, and thus movement of the third cradle 2342c. As a result, the staples aligned with the first driver 2340a are fired before the staples aligned with the second driver 2340b.

In certain instances, it is desirable to fire a staple or a group of staples before firing another staple or group of staples. For example, to control bleeding and/or fluid flow within the stapled tissue, staples positioned further inboard, such as the staples adjacent to the longitudinal slot, and thus, adjacent to the cut line, may be fired before staples further outboard.

In other instances, the staples aligned with the second driver 2340b can be fired before the staples aligned with the first driver 2340a. Alternatively, the first driver 2340a and the second driver 2340b can be fired simultaneously, such that the three staples supported by adjacent multi-staple and single staple drivers 2340a, 2340b pierce and capture tissue simultaneously.

Figure 13:
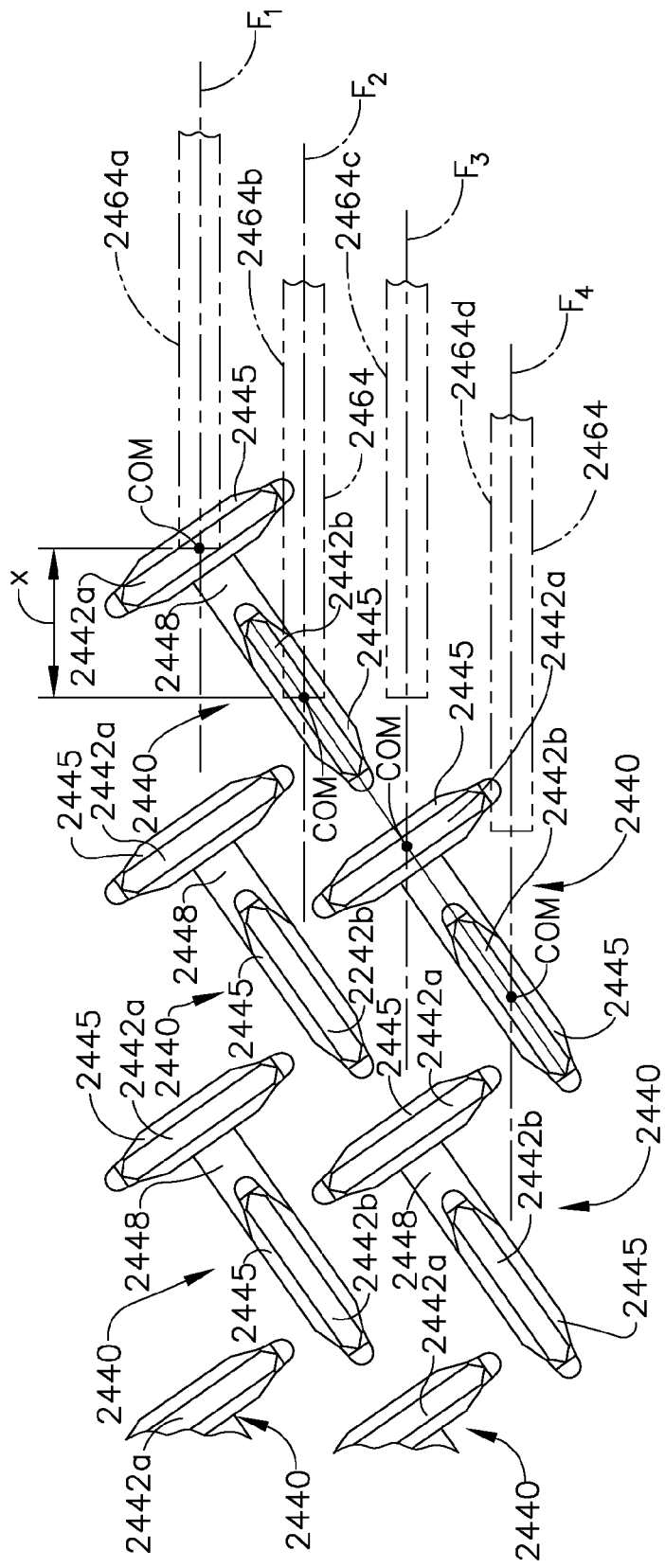
FIG. 13 is a plan view of an arrangement of multi-staple drivers and driving wedges, according to various embodiments of the present disclosure.

An arrangement of dual-staple drivers 2440 is depicted in FIG. 13. As arranged in FIG. 13, the dual-staple drivers 2440 are configured to fire staples from a staple cartridge that has four adjacent rows of staple cavities. For example, the driver arrangement depicted in FIG. 13 can be configured to fire staples from four rows of staple cavities on one side of a longitudinal slot in a cartridge body, and a corresponding mirror image driver arrangement can be configured to fire staples from four rows of staple cavities on the other side of the longitudinal slot.

In other instances, a single row of dual-staple drivers 2440 can be positioned on a first side of the a staple cartridge, and a single row of dual-staple drivers 2440 can be positioned on a second, opposite side of the staple cartridge. In such instances, the dual-staple drivers 2440 can be arranged to fire staples from two adjacent rows of staple cavities on either side of a cut line. In other instances, rows of dual-staple drivers 2440 can be added to the arrangement shown in FIG. 13. For example, the dual-staple drivers can be arranged to fire staples from six or more adjacent rows of staple cavities.

The dual-staple drivers 2440 depicted in FIG. 13 include a pair of troughs or staple supporting cradles 2442a, 2442b. For example, each dual-staple drivers 2440 includes a first cradle 2442a and a second cradle 2442b, which are dimensioned and structured to support a staple, such as one of the staples 2012 (FIG. 7). For example, the base of a staple can be positioned in each cradle 2442a, 2442b.

The first cradle 2442a of one of the dual-staple drivers 2440 can be aligned with a staple in a row of staple cavities, and the second cradle 2442b of the same dual-staple driver 2440 can be aligned with a staple in another row of staple cavities. Additionally, the first cradle 2442a of another dual-staple driver 2440 can be aligned with a staple in another row of staple cavities, and the second cradle 2442b of that dual-staple driver 2440 can be aligned with a staple in yet another row of staple cavities.

Referring still to FIG. 13, each dual-staple driver 2440 includes steps and/or support portions 2445, and each cradle 2442a, 2442b is defined into one of the steps 2445. Additionally, each of the drivers 2440 includes a base or connecting flange 2448 that extends between the steps 2445 of the dual-staple driver 2440. Because the steps 2445 are connected by the connecting flange 2448, the cradles 2442a, 2442b are linked such that coordinated and/or synchronized staple deployment can be initiated by the dual-staple driver 2440.

The steps 2445 of the drivers 2440 can be the same height. Alternatively, in some instances, a driver 2440 can include steps of different heights. In still other instances, different drivers 2440 can have steps of different heights, for example.

As disclosed in FIG. 13, each dual-staple driver 2440 overlies a pair of firing paths. Specifically, one of the drivers 2440 overlies the first and second firing paths $F_1$, $F_2$, and another of the drivers 2440 overlies the third and fourth firing paths $F_3$, $F_4$. Multiple driving wedges 2464a, 2464b, 2464b, 2464d are also depicted in FIG. 13. As shown in FIG. 13, the driving wedges 2464a, 2464b, 2464c, 2464d are configured to contact the dual-staple drivers 2440 to lift the dual-staple drivers 2240 and the staples positioned thereon.

Referring still to FIG. 13, each step 2445 includes a center of mass (COM). Additionally, each of the firing paths $F_1$, $F_2$, $F_3$, $F_4$ is aligned with a center of mass of a step 2045. As a result, each step 2445 is mass balanced relative to the corresponding firing paths $F_1$, $F_2$, $F_3$, $F_4$.

In various instances, the base 2448 extending between the steps 2445 can also be mass balanced relative to the respective firing paths $F_1$, $F_2$, $F_3$, $F_4$, such that the base 2448 maintains the mass balance of the dual-staple driver 2440. In some instances, the base 2448 can contribute an insignificant and/or negligible shift and/or variation to the mass balance of the dual-staple driver 2440. In such instances, the mass balance of the drivers 2240 can be approximated by the mass balance of the steps 2445 thereof, for example.

Referring still to FIG. 13, the depicted driving wedges 2464a, 2464b are longitudinally staggered by a distance x. For example, the first wedge 2464a trails the second wedge 2464b by the distance x. Additionally, the center of mass (COM) of the steps 2445 of each dual-staple driver 2440 are longitudinally staggered by the distance x. In such instances, the driving wedges 2464a, 2464b can move into engagement with the driver 2440 simultaneously. Because the wedges 2464a, 2464c contact each driver 2444 simultaneously, deployment of the pair of staples supported by each driver 2440 can be synchronized, and the staples can be simultaneously driven or fired into tissue. Longitudinally staggered wedges, like the wedges 2464a, 2464b, for example, could be incorporated into other embodiments disclosed herein.

In various instances, the geometry of a driving wedge can be selected, in combination with an arrangement of staples and drivers within a staple cartridge, to balance the forces exerted upon the staples and drivers during deployment. Additionally, in certain instances, the geometry of the driving wedge can be selected to coordinate the deployment of staples.

For example, a driver can include staggered and/or longitudinally offset driving wedges, which can be configured to simultaneously engage an angularly-oriented staple and/or an angularly-oriented driver within the staple cartridge. For example, staggered driving wedges can move into engagement with a first or proximal end of a driver and a second or distal end of the same driver at the same time. Because both ends of the angled driver are engaged by the staggered wedges simultaneously, the staggered driving wedges concurrently lift the driver. As a result, torqueing and/or rotation of the driver during deployment, and thus the staple supported thereon, may be prevented, limited, and/or controlled.

In other driverless embodiments, further described herein, staggered driving wedges can move into engagement with a first or proximal end of an angled staple and a second or distal end of the same angled staple at the same time. Because both ends of the angled staple are engaged by the staggered wedges simultaneously, the staggered driving wedges concurrently lift the staple. As a result, torqueing and/or rotation of the staple during deployment may be prevented, limited, and/or controlled.

Additionally or alternatively, the geometry of a driver can define at least one firing path that is aligned with non-angularly-oriented staples and/or drivers within the staple cartridge. For example, the firing path can be collinear with the axes of various drivers and staples that are oriented parallel to the longitudinal axis of the staple cartridge. Because the firing path is collinear with the staple and/or driver axis, the staple and/or driver can be balanced relative to the driving wedge, and torqueing and/or rotation of the driver and/or the staple can be prevented, limited, and/or controlled.

Figure 15:
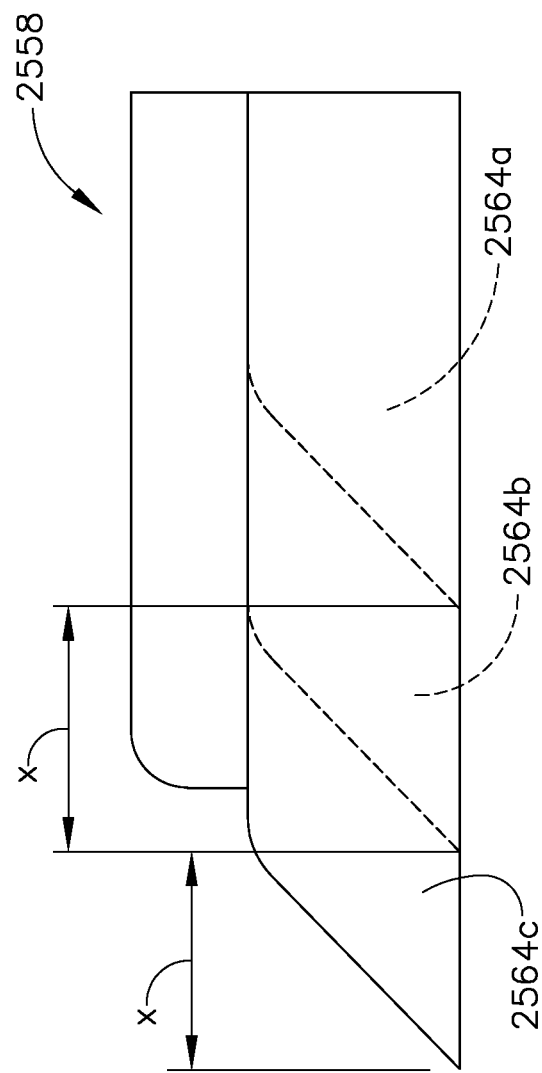
FIG. 15 is an elevation view of the driving wedges of FIG. 14.

An arrangement of drivers 2540, staples 2512a, 2512b, and driving wedges 2564a, 2564b, 2564c of a wedge sled 2558 is depicted in FIGS. 14 and 15. The driving wedges 2564a, 2564b, 2564c disclosed in FIGS. 14 and 15 are configured to move along the firing paths $F_1$, $F_2$, and $F_3$ (FIG. 14), respectively, which extend through a staple cartridge. In various instances, the arrangement of drivers 2540 can be utilized in a staple cartridge having an arrangement of staples 2512a, 2512b and staple cavities that corresponds to the depicted driver arrangement.

As disclosed in FIG. 14, the drivers 2540 and the staples 2512a, 2512b are arranged in multiple rows 2534, 2536. Additionally, various drivers 2540 and staples 2512a in each row are oriented parallel to a longitudinal axis L, and various drivers 2540 and staples 2512b in each row are oriented at an angle relative to the longitudinal axis L. For example, the depicted arrangement includes a pair of longitudinal rows 2534, 2536, and the drivers 2540 and staples 2512a, 2512b in each row 2534, 2536 alternate between a parallel orientation and an angled orientation relative to the longitudinal axis L. For example, the drivers 2540 shown in the first row 2534 include a first driver 2540a angularly-oriented relative to the longitudinal axis L, a second driver 2540b oriented parallel to the longitudinal axis L, a third driver 2540c angularly-oriented relative to the longitudinal axis L, and a fourth driver 2540d oriented parallel to the longitudinal axis L.

As disclosed in FIG. 14, the second driver 2540b and the fourth driver 2540d of the first row 2534 are aligned with the first firing path $F_1$. More particularly, both the proximal ends 2546 and the distal ends 2544 of the second and fourth drivers 2540b, 2540d are aligned with the first firing path $F_1$. In such instances, the first firing path $F_1$ extends through the center of masses (COM) of the second driver 2540b and the fourth driver 2540d. Because the first firing path $F_1$ is aligned with the second and fourth drivers 2540b, 2540d, the second and fourth drivers 2540b, 2540d are mass balanced relative to the first firing path $F_1$ and torqueing and/or rotation of the second and fourth drivers 2540b, 2540d shown in FIG. 14, and thus the staples supported thereon, may be prevented, limited, and/or controlled.

As disclosed in FIG. 14, the first driver 2540a is aligned with an axis A, which traverses the longitudinal axis L and the firing paths $F_1$, $F_2$, and $F_3$. Additionally, the third driver 2540c is oriented parallel to the axis A. As depicted in FIG. 14, the first and third drivers 2540a, 2540c are oriented at an angle relative to the longitudinal axis L and overlie multiple firing paths. For example, the depicted first and third drivers 2540a, 2540c overlie the first and second firing paths $F_1$, $F_2$. As depicted in FIG. 14, the first firing path $F_1$ extends through the proximal ends 2546 of the first and third drivers 2540a, 2540c, and the second firing path $F_2$ extends through the distal ends 2544 of the first and third drivers 2540a, 2540c.

The center of masses (COM) of the first and second drivers 2540a, 2540c are intermediate the first firing path $F_1$ and the second firing path $F_2$. For example, the center of masses of the first and second drivers 2540a, 2540c are equidistant from the first firing path $F_1$ and the second firing path $F_2$, and thus, the drivers 2540a, 2540c are mass balanced relative to the first and second firing paths $F_1$, $F_2$. As a result, torqueing and/or rotation of the second and fourth drivers 2540b, 2540d shown in FIG. 14, and thus the staples supported thereon, may be prevented, limited, and/or controlled.

Additionally, the driving wedges 2564a, 2564c, 2564c shown in FIGS. 14 and 15 are longitudinally staggered. For example, the first driving wedge 2564a distally trails the second driving wedge 2564b by a distance x and the second driving wedge 2564b distally trails the third driving wedge 2564c by the distance x. As depicted in FIG. 14, the proximal end 2546 and the distal end 2544 of the angularly-oriented third driver 2540c are offset by a longitudinal distance y. In the arrangement depicted in FIGS. 14 and 15, the longitudinal distance y between the proximal end 2546 and the distal end 2544 of third driver 2540c equals the longitudinal distance x between the first driving wedge 2564a, which is aligned with the proximal end 2546 of the third driver 2540c, and the second driving wedge 2564b, which is aligned with the distal end 2544 of the third driver 2540c.

In the arrangement disclosed in FIGS. 14 and 15, the first driving wedge 2564a and the second driving wedge 2564b moves into engagement with the third driver 2540c simultaneously. For example, the first driving wedge 2564a contacts the proximal end 2546 of the third staple driver 2540c as the second driving wedge 2564b contacts the distal end 2544 of the third staple driver 2540c. Because the driving wedges 2564a, 2564b, 2564c depicted in FIG. 14 are configured to engage the ends of the angled drivers, the lifting force is applied directly below the legs of the staple that is supported on the angled third driver 2540c. As a result, the staple legs are further stabilized, and tilting and/or tipping of the staples legs during deployment can be prevented, minimized, and/or controlled.

The first and second driving wedges 2564a, 2564b shown in FIGS. 14 and 15 are configured to similarly engage additional drivers 2540 in the first row 2534, and can sequentially deploy the staples 2512a, 2512b supported thereon. For example, the first driving wedge 2564a is configured to subsequently contact the proximal end 2546 of the first driver 2540a as the second driving wedge 2564b contacts the distal end 2544 of the first driver 2440a. Additionally, the first driving wedge 2564a is configured to sequentially engage and fire the parallel drivers 2540b, 2540d and staples 2512a in the first row 2534.

In various instances, the proximal end 2546 and the distal end 2544 of the third driver 2540c can be equidistant from the center of mass of the third driver 2540c. Because the driving wedges 2464a and 2464b disclosed in FIGS. 14 and 15 are configured to simultaneously contact the opposing ends of the angularly-oriented third staple driver 2540c and to exert a driving and/or lifting force on the opposing ends of the staple driver 2540c equidistant from the center of mass, the staple driver 2540c is balanced throughout its deployment. As a result, rotation and/or torqueing of the third staple driver 2540c may be prevented, avoided, and/or controlled.

In other instances, the driving wedges 2564a, 2564b may not contact the ends 2546, 2544 of the angled staple drivers 2540. In such instances, however, the driving wedges 2564a, 2564b may be configured to engage the angled staple drivers 2540 at a location that is equidistant from the center of mass of the driver 2540. Moreover, the driving wedges 2564a, 2564b can be sufficiently offset to simultaneously contact and lift the spaced locations of the driver 2540c.

Additionally, the second and third driving wedges 2564b, 2564c shown in FIGS. 14 and 15 are configured to similarly engage the drivers 2540 in the second row 2536 and sequentially deploy the staples 2512a, 2512b supported thereon. Referring still to the arrangement depicted in FIG. 14, for example, the drivers 2540 in the second row 2536 are oriented at an angle such that the distance between the proximal end 2546 and the distal end 2544 of each driver is also separated by the longitudinal distance y, which equals the longitudinal distance x between the second driving wedge 2564b and the third driving wedge 2564c.

In other instances, the longitudinal distance between the second driving wedge 2564b and the third driving wedge 2564c can be greater than and/or less than the longitudinal distance between the first driving wedge 2564a and the second driving wedge 2564b. Additionally or alternatively, the angled staples 2512b in the second row 2536 can be oriented at a different angle than the angled staples 2512b in the first row 2534. Moreover, in various instances, additional rows of drivers 2540 and staples 2512a, 2512b can be added to the arrangement depicted in FIG. 14, and additional driving wedges can be configured to engage the additional drivers 2540 to fire the additional staples 2512a, 2512b. In still other instances, the arrangement can further include a single row of drivers 2540 and staples 2512a, 2512b, for example.

The arrangement of staples 2512a, 2512b depicted in FIG. 14 can also be fired from a driverless staple cartridge. For example, referring to FIG. 16, the staples 2512a, 2512b can be arranged within a driverless cartridge, such as the staple cartridge 2620 (FIG. 37), for example, which is further described herein. The staples 2512a, 2512b in a driverless staple cartridge can be directly engaged and/or driven by a sled and/or a firing member. For example, the staples 2512a, 2512b can include a sled-engagement surface, which is configured to be directly engaged by a staple-engagement surface of one or more of the driving wedges 2564a, 2564b, and/or 2564c of the wedge sled 2558.

As described herein, each staple 2512a, 2512b can be mass balanced relative to the firing path(s) $F_1$, $F_2$, $F_3$ that is/are aligned with the staple 2512a, 2512b. For example, referring to FIG. 16, the staples 2512a, which are arranged parallel to the longitudinal axis L, are aligned with one of the firing paths $F_1$, $F_2$, $F_3$. In the depicted arrangement, one of the driving wedges 2564a, 2564b, 2564c drivingly engages the parallel staples 2512a along the length of the base of the staple 2512a. Additionally, the center of mass of each parallel staple 2512a is aligned with one of the firing paths $F_1$, $F_2$, $F_3$. Stated differently, one of the firing paths $F_1$, $F_2$, $F_3$ extends through the center of mass of each parallel staple 2512a, and thus, the staples 2512a are mass balanced relative to the respective firing path $F_1$, $F_2$, $F_3$ during deployment. In such an arrangement, torqueing and/or rotation of the staples 2512a during firing can be prevented, minimized, and/or controlled.

Additionally, where the staple arrangement depicted in FIG. 14 is utilized in a driverless cartridge, a pair of offset driving wedges 2564a, 2564b, 2564c is configured to simultaneously move into engagement with each angularly-oriented staple 2512b. For example, the first and second driving wedges 2564a, 2564b are configured to simultaneously contact an angled staple 2512b in the first row 2534, and the second and third driving wedges 2564b, 2564c are configured to simultaneously contact an angled staple 2512b in the second row 2536. Thereafter, the wedge sled 2558 is configured to continue to translate relative to the staples 2512a, 2512b, to sequentially contact and directly drive the staples 2512a, 2512b from the driverless staple cartridge.

Figure 37:
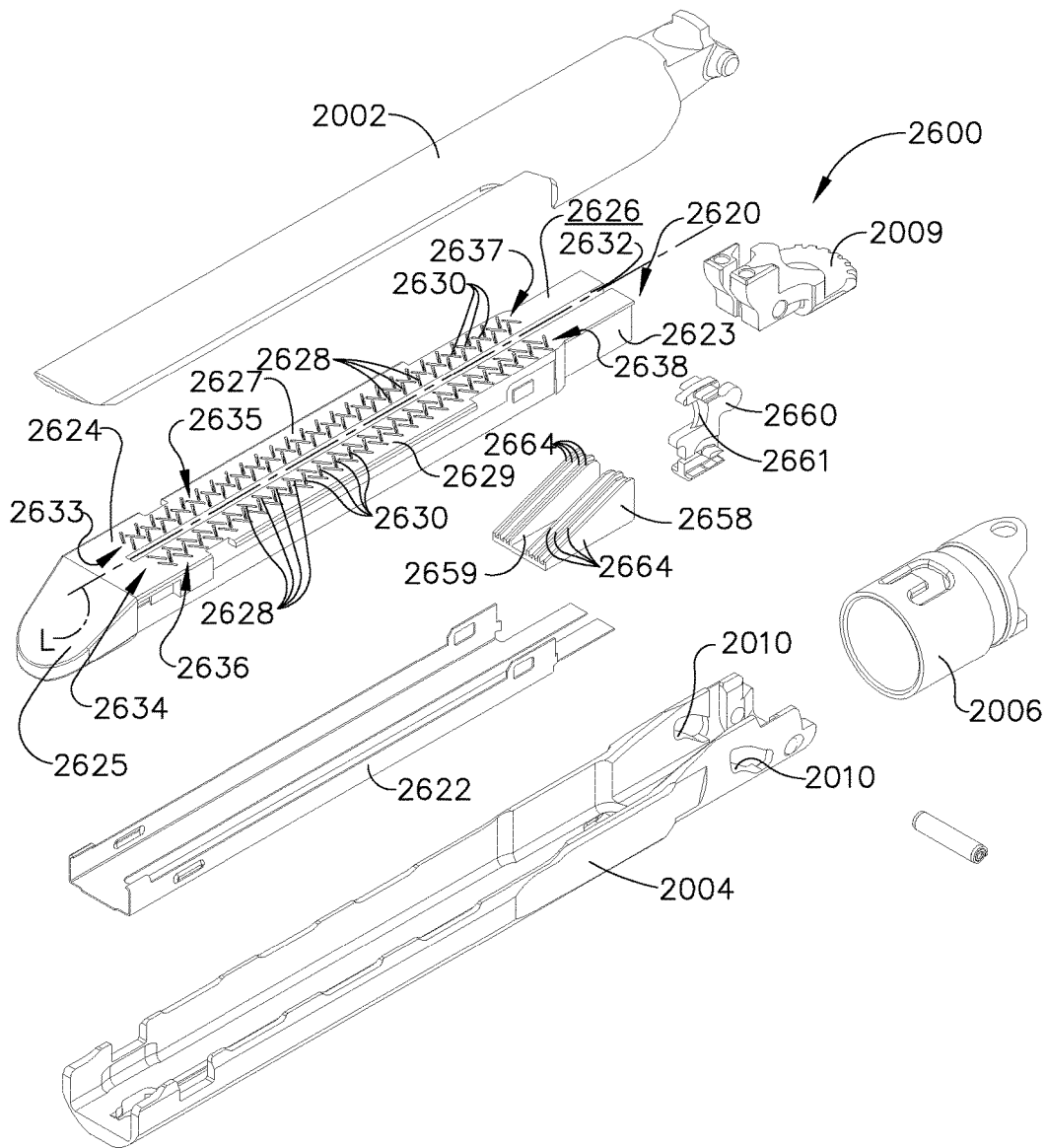
FIG. 37 is an exploded perspective view of an end effector including a driverless staple cartridge having a sled, according to various embodiments of the present disclosure.

As described herein, a driverless staple cartridge can be employed to hold and fire a staple array that includes angularly-oriented staples. An end effector assembly 2600 including the first jaw 2002, the second jaw 2004, the frame 2006, the articulation joint 2009, and a driverless staple cartridge 2620 is disclosed in FIG. 37. The staple cartridge 2620 can be a single-use and/or disposable cartridge, which can be replaced with another staple cartridge after firing. FIG. 37 discloses a staple cartridge 2620 that includes a deck 2626, a cartridge body 2624, and a casing 2622, which partially surrounds or encloses the cartridge body 2624. Additionally, an array of staples, such as the staples 2612 (FIGS. 39A and 39B), for example, can be removably positioned in the cartridge body 2624.

In certain instances, the staple cartridge 2620 can be integrally formed with the end effector assembly 2600 and/or can be permanently fixed within one of the jaws 2002, 2004, for example. In such instances, the end effector assembly 2600 can be a single-use and/or disposable end effector. In other instances, the staple cartridge 2620 can be fixed to the end effector assembly 2600, and may be reloaded with additional staples for subsequent firings, for example.

Referring to the staple cartridge 2620 depicted in FIG. 37, a longitudinal slot 2632 is defined at least partially though the cartridge body 2624. The longitudinal slot 2632 extends along a longitudinal axis L, which extends between a proximal end 2623 and a distal end 2625 of the cartridge body 2624. The longitudinal slot 2632 shown in FIG. 37 extends from the proximal end 2623 toward the distal end 2625 and traverses a portion of the length of the cartridge body 2624.

In some instances, the longitudinal slot 2632 can traverse the entire length of the cartridge body 2624. In other instances, the longitudinal slot 2632 can extend from the distal end 2623 toward the proximal end 2625, for example. In still other instances, the cartridge body 2624 may not include a predefined and/or preformed longitudinal slot. For example, a firing member and/or a cutting element can transect and/or cut the cartridge body 2624 during the firing stroke, for example.

The staple cartridge 2620 disclosed in FIG. 37 is configured to fire an array of angled staples 2612 (FIGS. 38A and 38B), which can be oriented like the staple array 2011 shown in FIG. 7, for example. The angled staples 2612 can be removably positioned in angled staple cavities 2628, shown in FIG. 37, which are defined into the cartridge body 2624. For example, the depicted staple cavities 2628 are angularly-oriented relative to the longitudinal axis L. Additionally, the depicted arrangement of staple cavities 2628 corresponds to the arrangement of staples 2612 positioned in the cartridge 2620. Each staple cavity 2628 shown in FIG. 37 includes an opening 2630 in the deck 2626, and each opening 2630 includes a proximal end and a distal end. A staple axis can extend between the proximal end and the distal end, and the staple axis of the openings 2630 shown in FIG. 37 are skewed and/or angled relative to the longitudinal axis L of the cartridge body 2624. In the staple cartridge 2620 of FIG. 37, all the staple cavities 2628 are angularly-oriented relative to the longitudinal axis L and various staple cavities 2628 are angularly-oriented relative to other staple cavities 2628.

The staple cavities 2628 depicted in FIG. 37 are arranged in multiple rows on each side of the longitudinal slot 2632. For example, the staple cavities 2628 are arranged in a first inside row 2633, a first outside row 2635, and a first intermediate row 2637 on a first side 2627 of the longitudinal slot 2632, and staple cavities 2628 are arranged in a second inside row 2634, a second outside row 2638, and a second intermediate row 2636 on a second side 2629 of the longitudinal slot 2632. Though the staple cavities 2628 do not cross or otherwise contact each other, the longitudinal rows 2633, 2634, 2635, 2636, 2637, 2638 of staple cavities 2628 overlap. For example, a staple cavity 2628 extends laterally outboard and/or inboard past the staple cavity 2628 in an adjacent row of staple cavities 2628, and a staple cavity 2628 extends proximally and/or distally past the staple cavity 2628 in an adjacent row of staple cavities 2628. Because the staple cavities 2628 and the staples positioned therein are arranged in an overlapping array, bleeding and/or fluid flow in the stapled tissue can be controlled. In the staple cartridge 2620 depicted in FIG. 37, the staple cavities 2628 and rows thereof are symmetrical relative to the longitudinal slot 2632.

In other instances, greater than or fewer than three rows of staple cavities 2628 can be positioned on each side of the longitudinal slot 2632 and, in some instances, one of the sides 2627, 2629 of the staple cartridge 2620 can include a different number of rows of staple cavities 2628 than the other side 2627, 2629 of the staple cartridge 2620. In some instances, the staple cavities 2628 may not longitudinally and/or laterally overlap the staple cavities 2628 in adjacent rows. Additionally or alternatively, in certain instances, the staple cavities 2628 and/or the rows thereof can be asymmetrical relative to the longitudinal slot 2632 and/or the longitudinal axis L.

Referring still to FIG. 37, the depicted staple cavities 2628 in each longitudinal row are parallel or substantially parallel. In other words, the staple cavities 2628 in the first inside row 2633 are parallel to each other, the staple cavities 2628 in the first outside row 2635 are parallel to each other, the staple cavities 2628 in the first intermediate row 2637 are parallel to each other, the staple cavities 2628 in the second inside row 2634 are parallel to each other, the staple cavities 2628 in the second outside row 2636 are parallel to each other, and the staple cavities 2628 in the second intermediate row 2638 are parallel to each other.

As also depicted in FIG. 37, the staple cavities 2628 in each longitudinal row are angularly-oriented relative to the staple cavities 2628 in the adjacent longitudinal row(s) on the same side of the longitudinal slot 2632. For example, on the first side 2627 of the cartridge body 2624, the staple cavities 2628 in the first intermediate row 2637 are angularly-oriented relative to the staple cavities 2628 in the first inner row 2633 and in the first outer row 2635. Additionally, on the second side 2629 of the cartridge body 2624, the staple cavities 2628 in the second intermediate row 2638 are angularly-oriented relative to the staple cavities 2628 in the second inner row 2634 and the second outer row 2636.

In other instances, only a portion of the staples cavities 2628 in each longitudinal row 2633, 2634, 2635, 2636, 2637, 2638 may be parallel to each other and/or less than all of the longitudinal rows 2633, 2634, 2635, 2636, 2637, 2638 can include staple cavities 2628 that are parallel to each other. Additionally or alternatively, in certain instances, at least a portion of the staple cavities 2628 can be randomly oriented. In some instances, at least one of the staple cavities 2628 in a longitudinal row 2633, 2634, 2635, 2636, 2637, 2638 can be parallel to at least one of the staple cavities 2628 in an adjacent longitudinal row 2633, 2634, 2635, 2636, 2637, 2638. In certain instances, a staple cartridge 2620 can include at least one staple cavity 2628 that is parallel to the longitudinal axis L of the cartridge body 2624. See, for example, FIG. 11.

Referring still to FIG. 37, the depicted end effector assembly 2600 includes a firing bar 2660 movably positioned relative to the cartridge body 2624. The firing bar 2660 is configured to traverse the cartridge body 2624 to fire the staples 2612 (FIGS. 38A and 38B) from the staple cavities 2628. The depicted firing bar 2660 further includes a cutting edge 2661, which is configured to incise tissue as the firing bar 2660 translates between the first jaw 2002 and the second jaw 2004.

The depicted firing member 2660 is dimensioned and positioned to fit within the longitudinal slot 2632, and to drivingly engage a sled, such as a sled 2658 (FIGS. 37-38B), a sled 2758 (FIGS. 39-39B) or a sled 2858 (FIG. 40) movably positioned within the driverless cartridge 2620. As the firing bar 2660 translates through the longitudinal slot 2632, the firing bar 2660 moves the sled 2658 (FIGS. 37-38B), 2758 (FIGS. 39-39B), or 2858 (FIG. 40) through the cartridge body 2624.

Figure 38:
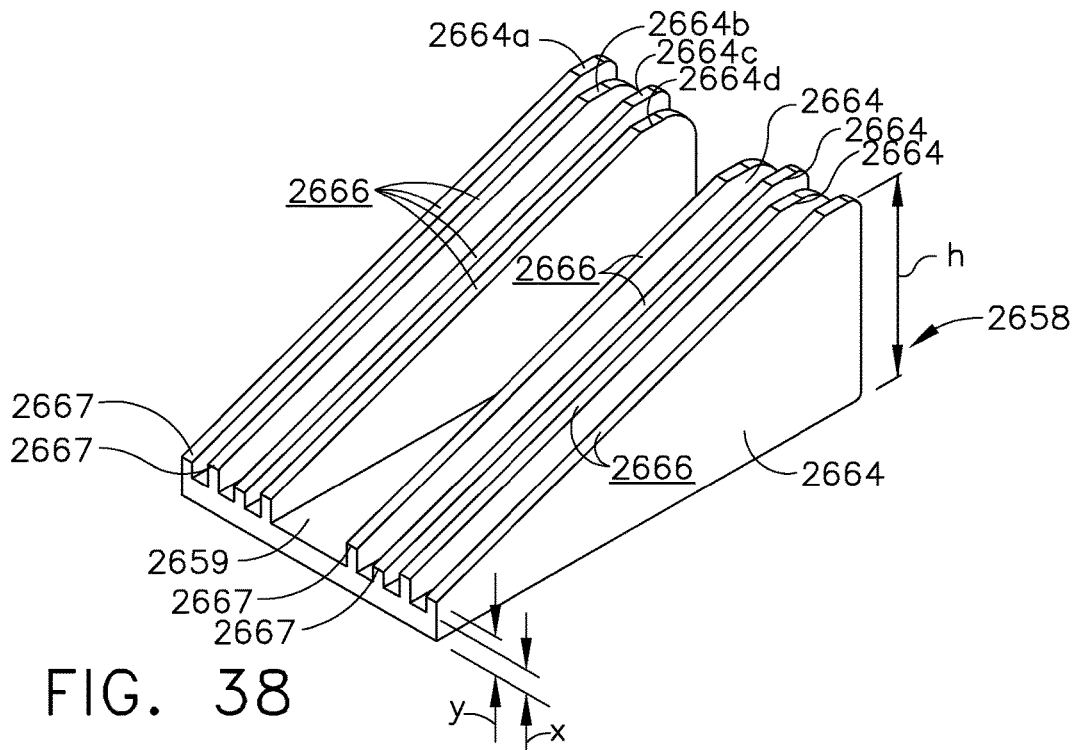
FIG. 38 is a perspective view of the sled of FIG. 37.

The sled 2658 is disclosed in FIGS. 37-38B. The sled 2658 is dimensioned and positioned to directly engage the staples 2612 positioned in the driverless cartridge 2620 (FIG. 37). The depicted sled 2658 includes a central portion 2659 and driving wedges or driving rails 2664. The driving wedges 2664 include a staple-engagement or staple-contacting surface 2666, which are inclined and/or ramped surfaces extending from a distal end to a proximal end of the sled 2658. As depicted in FIGS. 37-38B, the inclined surfaces 2666 of the wedges 2664 have equal, or substantially equal, incline degrees or angles.

Each staple-contacting surface 2666 shown in FIGS. 37-38B is positioned to directly contact the staples 2612 (FIGS. 38A and 38B) positioned in the staple cartridge 2620. More particularly, the staple-contacting surfaces 2666 of the driving wedges 2664 are configured to contact the base 2614 (FIG. 38B) of each staple 2612, and to lift the base 2614 of the staple 2612 upward to eject the staple 2612 from the staple cavity 2628. For example, to lift the staples 2612 from lowered and/or unfired positions to lifted and/or fired positions, the distal end 2667 of each inclined surface 2666 engages the base 2614 of the staple 2612, and the inclined surface 2666 moves distally across the base 2614 of the staple 2612.

In the depicted arrangement, the firing bar 2660 and the cutting edge 2661 thereof are configured to slide and/or translate within the longitudinal slot 2632. Additionally, the driving wedges 2664 depicted in FIGS. 37-38B, which are shown laterally outboard of the firing bar 2660 and the cutting edge 2661, and configured to contact the staples 2612 (FIGS. 38A and 38B) positioned in the staple cavities 2628 (FIG. 37). Multiple driving wedges 2664 are positioned on either side of the central portion 2659 of the wedge sled 2658. For example, in the depicted sled 2658, four driving wedges 2664a, 2664b, 2664c, 2664d are positioned on each side of the central portion 2659.

Moreover, in the arrangement disclosed in FIGS. 37-38B, multiple driving wedges 2664a, 2664b, 2664c, 2664d are configured to engage a single angled staple 2612. For example, the first and second wedges 2664a, 2664b are configured to engage staples 6212 positioned in the first outer row 2633 of staple cavities 2628, the second and third wedges 2664b, 2664c are configured to engage staples 2612 positioned in the first intermediate row 2637, and the third and fourth wedges 2664c, 2664d are configured to engage staples 2612 positioned in the first outer row 2635.

In various circumstances, it is desirable to support and drive staples 2612 in the staple cartridge 2620 disclosed in FIG. 37 from multiple positions along the base 2614 (FIG. 38B) of the staple 2612. For example, staples 2612 that are longitudinally aligned with a firing path of a driving wedge 2664 are supported along the entire length of the base 2614 of the staple 2612. For example, when staples 2612 are angled relative to the firing paths of the sled 2658, as depicted in FIGS. 37-38B, the staples 2612 can be supported at multiple locations along the base by utilizing multiple driving wedges 2664. Because the angled staples 2612 are drivingly supported at multiple locations along the base 2614 thereof, the staples 2612 can be balanced and/or stabilized such that rotation and/or torqueing of the staples 2612 during deployment may be prevented, reduced, and/or controlled. Direct drive staples that are mass balanced relative to multiple sled-engagement surfaces, like the staples 2612, for example, could be incorporated into other embodiments disclosed herein.

The inclined surfaces 2666 disclosed in FIGS. 37-38B are staggered. For example, the depicted inclined surfaces 2666 are longitudinally staggered such that at least one inclined surface 2666 longitudinally leads at least one other inclined surface 2666. The inclined surfaces 2666 of the second and fourth driving wedges 2664b, 2664d longitudinally lead the inclined surfaces 2666 of the first and third driving wedges 2664a, 2664c. The inclined surfaces 2666 of the second and fourth driving wedges 2664b, 2664d are taller than the inclined surfaces 2666 of the first and third driving edges 2664a, 2664c at the aligned distal ends 2667. For example, as shown in FIGS. 38 and 38B, the first and third driving wedges 2664a, 2664c have a distal height y and the second and fourth driving wedges 2664b, 2664d have a distal height x, which is less than the height y.

The longitudinally staggered inclined surfaces 2666 are configured to move into engagement with the angled staples 2612 simultaneously. For example, the staple-engagement surfaces 2666 of the first and second wedges 2664a, 2664b are configured to simultaneously engage angled staples 2612 in the first outer row 2633 (FIG. 37) of staple cavities 2628. Additionally, the staple-engagement surfaces 2666 of the second and third wedges 2664b, 2664c are configured to simultaneously engage angled staples 2612 in the first intermediate row 2637 (FIG. 37). Moreover, the staple-engagement surfaces 2666 of the third and fourth wedges 2664c, 2664d are configured to simultaneously engage staples 2612 positioned in the first outer row 2635 (FIG. 37).

The deployment or firing of a staple 2612 is depicted in FIGS. 38A and 38B, in which the third and fourth wedges 2664c, 2664d of the driver 2658 are in driving engagement with the staple 2612. The third wedge 2664c can initially contact the staple 2612 at point A and the fourth wedge 2664d can initially contact the staple 2612 at point B. The third and fourth wedges 2664c, 2664d are configured to engage the staple 2612 simultaneously such that the staple 2612 contacts points A and B concurrently or nearly concurrently. Because of the height difference between the staple-engagement surfaces 2666 of the third and fourth wedges 2664c, 2664d, points A and B can be longitudinally offset such that points A and B are at the same, or essentially the same, elevation.

Referring still to FIGS. 38A and 38B, as the driver 2658 continues to move distally in the staple cartridge 2620, the staple 2612 can slide up the staple-engagement surfaces 2666 of the third and fourth wedges 2664c, 2664d to points A' and B' on the third and fourth wedges 2664c, 2664d, respectively. As shown in FIG. 38B, the staple 2612 maintains a vertically upright orientation during deployment. Thereafter, the staple 2612 can continue to slide up the staple-engagement surfaces 2666 of the third and fourth wedges 2664c, 2664d to points A" and B" on the third and fourth wedges 2664c, 2664d, respectively. As shown in FIG. 38B, the staple 2612 continues to maintain a vertically upright orientation. In other words, the pair of staple-engagement surfaces 2666 stabilize and/or balance the staple 2612 during deployment, such that rotation or torqueing of the staples 2612 may be prevented, minimized and/or controlled.

In other instances, the driving wedges or rails of a wedge sled can all decline to a height of zero, or essentially zero. For example, referring now to FIGS. 39-39B, the wedge sled 2758 is depicted. The wedge sled 2758 can be employed in the staple cartridge 2620 and the end effector 2600 (FIG. 37) to fire staples 2612 from the staple cartridge 2620 (FIG. 39A).

Figure 39:
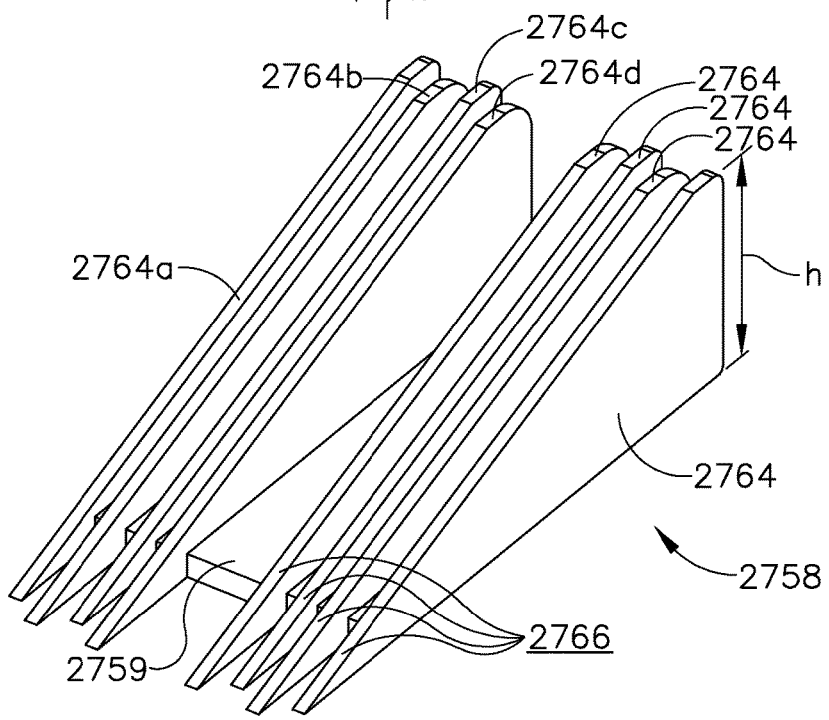
FIG. 39 is a perspective view of a sled for the driverless staple cartridge depicted in FIG. 37, according to various embodiments of the present disclosure.

Similar to the sled 2658, the wedge sled 2758 disclosed in FIGS. 39-39B includes four driving wedges 2764 on either side of a central portion 2759. Each driving wedge 2764 includes an inclined, staple-engagement surface 2766, which is configured to directly engage and drive the staples 2612 from the staple cavities 2628. Also similar to the sled 2658, the staple-engagement surfaces 2766 of the driving wedges 2764 depicted in FIGS. 39-39B are longitudinally staggered, such that the first and third driving wedges 2764a, 2764c longitudinally trail the second and fourth driving wedges 2764b, 2764d.

The longitudinally staggered inclined surfaces 2766 of the driving wedges 2764a, 2764b, 2764c, 2764d disclosed in FIGS. 39-39B are configured to move into engagement with angled staples 2612 simultaneously. For example, the staple-engagement surfaces 2766 of the first and second wedges 2764a, 2764b are configured to simultaneously engage angled staples 2612 positioned in the first outer row 2635 (FIG. 37). Additionally, the staple-engagement surfaces 2766 of the second and third wedges 2764b, 2764c are configured to simultaneously engage angled staples 2612 positioned in the first intermediate row 2637 (FIG. 37). Moreover, the staple-engagement surfaces 2766 of the third and fourth wedges 2764c, 2764d are configured to simultaneously engage angled staples 2612 positioned in the first inner row 2633 (FIG. 37).

Additionally, the longitudinally staggered inclined surfaces 2666 of the driving wedges 2764a, 2764b, 2764c, 2764d disclosed in FIGS. 39-39B are configured to drive the angled staples 2612 simultaneously. For example, the staple-engagement surfaces 2766 of the first and second wedges 2764a, 2764b are configured to simultaneously drive angled staples 2612 in the first outer row 2635 of staple cavities 2628 (FIG. 37). Additionally, the staple-engagement surfaces 2766 of the second and third wedges 2764b, 2764c are configured to simultaneously drive angled staples 2612 positioned in the first intermediate row 2637 (FIG. 37). Moreover, the staple-engagement surfaces 2766 of the third and fourth wedges 2764c, 2764d are configured to simultaneously drive angled staples 2612 positioned in the first inner row 2633 (FIG. 37).

Referring primarily to FIG. 39A, the second wedge 2764b and the third wedge 2764c on the first side 2627 of the cartridge body 2624 are configured to move into engagement with the second staple 2612b, which is the proximal most staple and is aligned with the firing paths of the second wedge 2764b and the third wedge 2764c. Additionally, the second wedge 2764b and the third wedge 2764c can be equidistant from the center of mass (COM) of the second staple 2612b. As the sled 2758 continues to translate distally, the second wedge 2764b and the third wedge 2764c are configured to drivingly engage the second staple 2612b to lift and fire the staple 2612b.

In the arrangement disclosed in FIG. 39A, as the second wedge 2764b and the third wedge 2764c lift the second staple 2612b, the first wedge 2764a and the second wedge 2764b on the first side 2627 of the cartridge body 2624 are configured to move into engagement with the first staple 2612a and the third wedge 2764c and the fourth wedge 2764d on the first side 2627 are configured to move into engagement with the third staple 2612c. Additionally, as depicted in FIG. 39A, the first wedge 2764a and the second wedge 2764b are equidistant from the center of mass (COM) of the first staple 2612a, and the third wedge 2764c and the fourth wedge 2764d are equidistant from the center of mass (COM) of the third staple 2612c. As the sled 2758 continues to translate distally, the first wedge 2764a and the second wedge 2764b drivingly engage the first staple 2612a to lift and fire the staple 2612b, and the third wedge 2764c and the fourth wedge 2764d drivingly engage the third staple 2612c to lift and fire the staple 2612c.

The paired driving wedge arrangement described above and depicted in FIG. 39A is configured to continue simultaneously engaging and lifting the staples 2612 in the staple cartridge 2620 as the sled 2758 continues to translate distally. Because the sled 2758 supports each staple 2612 at multiple locations along the base thereof, the staples 2612 are stabilized and/or balanced during deployment. Additionally, because the staple-engagement surfaces 2766 of the sled 2758 are equidistant from the center of mass (COM) of each contacted staple 2612, rotation and/or torqueing of the staples 2612 may be further prevented, minimized, or controlled. Moreover, because the driving wedges 2764a, 2764b, 2764c, 2764 are longitudinally staggered, the engagement of the multiple driving wedges 2764a, 2764b, 2764c, 2764 with each staple 2612 is timed and/or synchronized to balance the driving forces exerted on each staple 2612 throughout its deployment.

The driving sled 2858 is depicted in FIG. 40. The wedge sled 2758 can be employed in the staple cartridge 2620 and the end effector 2600 (FIG. 37) to fire staples 2612 from the staple cavities 2620 (FIG. 39A). Similar to the sleds 2658 and 2758, the driving sled 2858 includes multiple driving wedges 2864 on either side of a central portion 2859. Each driving wedge 2864 includes an inclined, staple-engagement surface 2866, which is configured to directly engage and drive the staples 2612 from the staple cavities 2628. Moreover, the inclined, staple-engagement surfaces 2866 are angled or sloped laterally. Because the staple-engagement surfaces 2866 are laterally and longitudinally sloped, each surface 2866 includes longitudinally offset support portions, which drivingly engage the angled staples 2612 throughout the deployment and firing thereof.

For example, the sloped staple-engagement surfaces 2866 disclosed in FIG. 40 are configured to drivingly engage the staples 2612 along a portion of the base of each staple 2612. In the arrangement depicted in FIG. 40, the driving force exerted on the staple 2612 is distributed over a larger surface area. For example, a staple-engagement surface 2866 can contact at least 50% of the length of the base of the staple 2612. In other instances, the staple engagement-surface can contact at least 75% of the length of the base of the staple 2612. In still other instances, the staple engagement-surface can contact less than 50% or more than 75% the length of the base of the staple 2612. Moreover, the driving force from the sled 2858 is balanced relative to center of mass of each staple 2612 to further stabilize and balance the staple 2612 during deployment. As a result, rotation and/or torqueing of the staple 2612 may be prevented, minimized, or controlled.

As described herein, a staple array that includes staples angularly-oriented relative to the longitudinal axis of the staple cartridge and/or the firing path of the firing member provides various benefits. For example, such a staple array can provide improved flexibility and/or stretchability within stapled tissue. As a result, incidences of tissue tearing can be reduced. In certain instances, a staple array can also include staples with different length bases. The variable length bases within a staple array can promote increased flexibility and/or stretchability in stapled tissue. Additionally, in certain arrangements, staples having shorter bases can nest within the staple array. For example, the staples having shorter bases can be positioned in narrower spaces between staples having longer bases. Such an arrangement can densify the staple line, which can improve control of bleeding and/or fluid flow in the stapled tissue.

Figure 41:
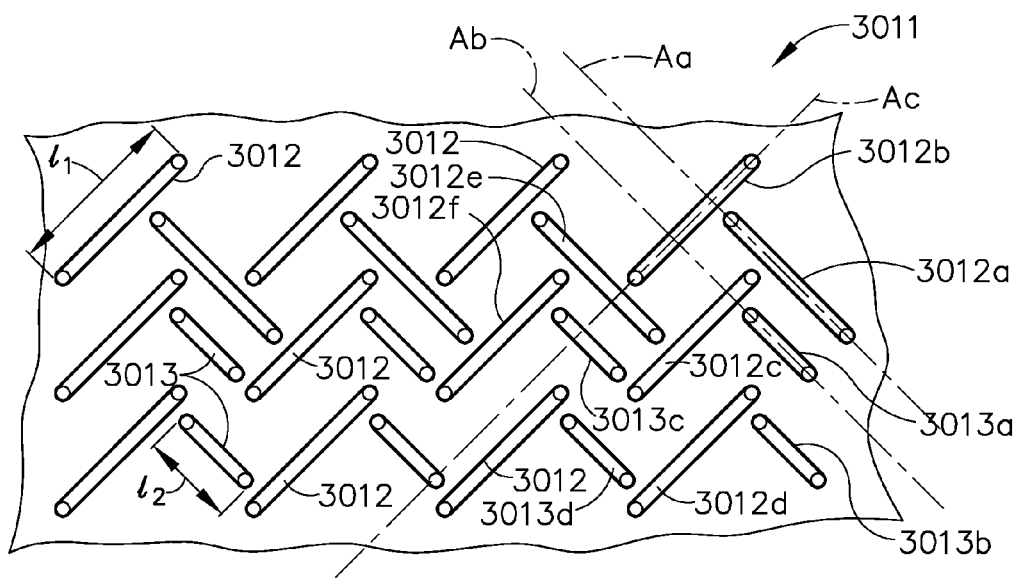
FIG. 41 is a plan view of an array of staples, according to various embodiments of the present disclosure.

A staple array 3011 is depicted in FIG. 41. The array 3011 includes long staples 3012 and short staples 3013. As shown in FIG. 41, the long staples 3012 have a base length of $l_1$, and the short staples 3013 have a base length of $l_2$, which is less than $l_1$. In the depicted array 3011, a first long staple 3012a is aligned with an axis $A_a$, and a first short staple 3013 is aligned with an axis $A_b$, which is parallel to the axis $A_a$. Additional long and short staples 3012, 3013, such as staples 3012e, 3013b, 3013c, and 3013d, for example, are parallel to the axes $A_a$ and $A_b$. As further disclosed in the array 3011 shown in FIG. 41, a second long staple 3012 is aligned with an axis $A_c$, which traverses the axes $A_a$ and $A_b$. Additional long staples 3012, such as staples 3012c, 3012d, and 3012f, for example, are parallel to the axis $A_c$.

In other arrangements, additional short staples 3012 can also be parallel to the axis $A_c$. In some instances, various staples can be arranged along axes that are non-parallel to axes $A_a$, $A_b$ and $A_c$. For example, the staple array 3011 can include staples that are oriented parallel to the longitudinal axis of the staple cartridge and/or to the firing path of a driving sled. Additionally, in various instances, the staple array 3011 can include staples having base lengths that are different than $l_2$ and $l_1$. In some instances, the staple array 3011 can include additional and/or fewer longitudinal rows of staples 3012, 3013. For example, the row of long staples 3012 aligned with the first long staple 3012a can be removed, and/or the row of long staples 3012 aligned with the second long staple 3012b can be removed, and/or the row of short staples aligned with first short staple 3013a can be removed, and/or the row of long staples 3012 aligned with the third long staple 3012c can be removed, and/or the row of short staples 3013 aligned with the second short staple 3013b can be removed, and/or the row of long staples 3013 aligned with the fourth long staple 3012d can be removed.

Referring again to FIG. 41, a short staple 3013 is embedded in the staple array 3011 intermediate two long staples 3012. For example, two long staples 3012 in the array 3011, such as the third long staple 3012c and the sixth long staple 3012f shown in FIG. 41, are parallel and laterally aligned. In such an arrangement, a space is defined between the third and sixth long staples 3012c and 3012f, and the space is configured to accommodate the third short staple 3013c. Accordingly, the third short staple 3013c in the depicted array 3011 is nestled between the third long staple 3012c and the sixth long staple 3012f. In such an arrangement, the third short staple 3013c, and similarly placed shorts staples 3013 in the array 3011, can densify the staple line by filling the spaces between the long staples 3012. In various instances, bleeding and/or fluid flow control is improved because the staple line is densified in the array 3011. Densified staple lines, like the staple array 3011, for example, could be incorporated into other embodiments disclosed herein.

In other instances, the long staples 3012 defining a space therebetween for accommodating a short staple can be non-parallel to each other. For example, the third and sixth long staples 3012c, 3012f can be skewed and/or otherwise non-parallel to each other. Additionally or alternatively, the long staples 3012 defining the space therebetween for accommodating a short staple 3013 can only partially laterally overlap. For example, in certain instances, the third long staple 3012c can be laterally outboard or laterally inboard relative to the sixth long staple 3012f, such that only a portion of the third and sixth staples 3012c, 3012f are laterally aligned.

An array of staples, such as the array 3011, for example, can be positioned in a driverless staple cartridge, such as the driverless staple cartridge 2620 (FIG. 37), for example, and can be directly engaged and driven from the staple cartridge by a driving sled. In such instances, the staples 3012, 3013 in the array 3011 can be mass balanced relative to the driving wedges of a sled that contacts and drives the staples 3012, 3013. For example, the driving wedges can apply the firing force at the ends of the staple bases equidistant from the center of mass of each staple 3012, 3013. In other instances, the firing force can be applied at various spaced locations along the base of a staple 3012, 3013, and the cumulative firing force can be balanced relative to the staple 3012, 3013. In instances where a staple does not overlie a firing path and/or is not balanced relative to the firing path, a staple driver may be employed. For example, a multi-staple driver, as further described herein, can simultaneously lift multiple staples from a staple cartridge.

Figure 42:
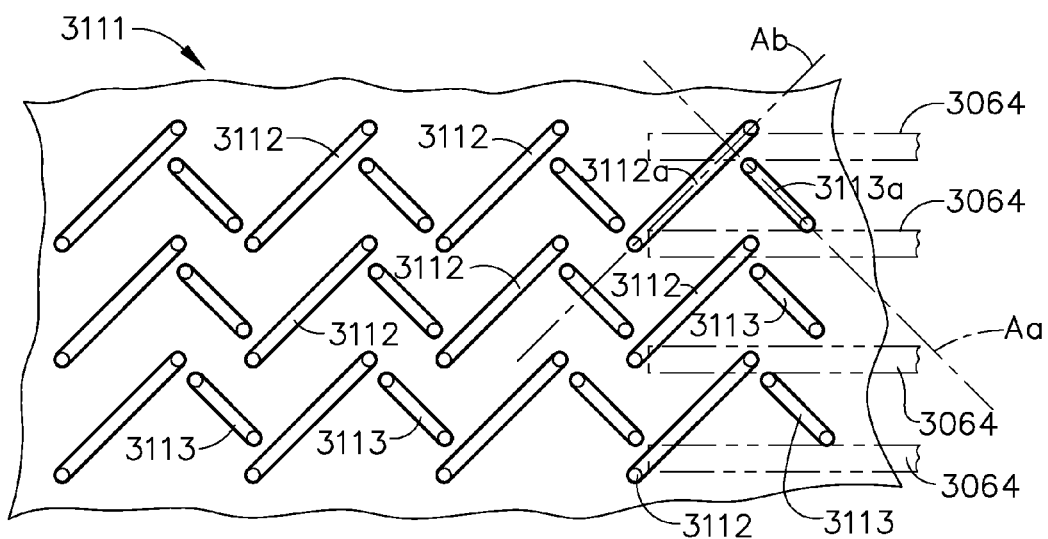
FIG. 42 is a plan view of an array of staples and driving wedges, according to various embodiments of the present disclosure.

A staple array 3111 is depicted in FIG. 42. The array 3111 includes long staples 3112 and short staples 3113. As shown in FIG. 42, the long staples 3112 have a base length of $l_1$, and the short staples 3113 have a base length of $l_2$, which is less than $l_1$. In the depicted array 3111, a first short staple 3113a is aligned with an axis $A_a$, and a first long staple 3112a is aligned with an axis $A_b$, which traverses the axis $A_a$. Additional short staples 3113 are oriented parallel to the axis $A_a$ and additional long staples 3112 are parallel to the axis $A_b$.

In other arrangements, at least one short staple 3113 can be oriented parallel to the axis $A_b$ and/or at least one long staple 3112 can be oriented parallel to the axis $A_a$. In some instances, various staples 3112, 3113 can be arranged along axes that are non-parallel to axes $A_a$ and $A_b$. For example, the staple array 3111 may include staples that are oriented parallel to the longitudinal axis of the staple cartridge and/or to the firing path of the driving wedges 3064, which are also depicted in FIG. 42. Additionally, in various instances, the staple array 3111 can include staples having base lengths that are different than $l_2$ and $l_1$, and/or the staple array 3111 can include additional and/or fewer longitudinal rows of staples 3112, 3113.

Referring still to FIG. 42, a short staple 3113 can be embedded in the staple array 3111 intermediate at least two laterally overlapping long staples 3112. In such an arrangement, the nested short staple 3113 in the array 3111 can densify the staple line by filling the spaces between the adjacent long staples 3112. Because the staple line is densified in the array 3111, bleeding and/or fluid flow control can be improved. Densified staple lines, like the staple array 3111, for example, could be incorporated into other embodiments disclosed herein.

In other instances, the long staples 3112 defining a space therebetween for accommodating a short staple can be non-parallel to each other. Additionally or alternatively, the long staples 3112 defining the space therebetween for accommodating a short staple 3113 may only partially overlap.

An array of staples, such as the array 3111, for example, can be positioned in a driverless staple cartridge, such as the driverless staple cartridge 2620 (FIG. 37), for example, and can be directly engaged and driven from the staple cartridge by a driving sled, such as the sled 2058 (FIG. 37). In such instances, the staples 3112, 3113 in the array 3111 can be mass balanced relative to the driving wedges 3064 of the sled that contact and drive the staples 3112, 3113. For example, the driving wedges 3064 can apply the firing force at the ends of the staple bases equidistant from the center of mass of the staples 3112, 3113.

In other instances, the firing force can be applied at various spaced locations along the base of the staples 3112, 3113, and the cumulative firing force can be balanced relative to the staples 3112, 3113. In instances where a staple 3112, 3113 does not overlie a firing path and/or is not balanced relative to the firing path, a staple driver can be employed. For example, a multi-staple driver, as further described herein, can simultaneously lift multiple staples from a staple cartridge.

In various instances, where a sled is configured to directly drive a staple, the staple can include a sled-engagement surface and the sled can include a staple-engagement surface. The staples can be generally "V-shaped" staples having a base and non-parallelly extending legs. For example, referring again to the staple 2612 depicted in FIGS. 39B and 40, for example, the staple 2612 includes a base 2614, a first leg 2616 extending from a first end of the base 2614, and a second leg 2618 extending from a second end of the base 2614. The staple 2612 can be formed from a wire, such as a wire having a circular cross-section, and thus, the outer perimeter of the staple 2612 can consist of rounded surfaces. As a result, the sled-engagement surface of the staple 2612 can include a rounded and/or contoured surface.

In other instances, the staple 2612 can be formed from a wire having a polygonal cross-section, and thus, the outer perimeter of the staple 2612 can include edges and flat or planar surfaces. In such an embodiment, the sled-engagement surface of the staple 2612 can include at least one flat and/or planar surfaces, for example. In still other instances, the outer perimeter of the staple 2612 can include both contoured and planar surfaces. For example, the staple 2612 can be formed from a wire having a circular cross-section, which can be flattened and/or otherwise deformed to form a flat sled-engagement surface.

In certain instances, a staple can be formed from a piece of material. For example, a staple can be stamped, cut, and/or molded from a sheet of material. Various stamped staples are described in U.S. patent application Ser. No. 14/138,481, entitled SURGICAL STAPLES AND METHODS FOR MAKING THE SAME, filed Dec. 23, 2013, which is hereby incorporated by reference herein in its entirety. In various instances, a staple can be stamped or otherwise formed from a single piece of material, for example, and can remain a single and/or unitary piece of material, for example. In various instances, the sled-engagement surface of a staple, such as a stamped staple, can include a flat or planar surface of the stamped or otherwise formed piece. Additionally, in certain instances, the sled-engagement surface can include a groove and/or cutout, which can be configured to receive a driving wedge of a wedge sled. When a staple is angularly-oriented relative to the firing path of the driving wedge, the groove can traverse the base of the staple at an angle.

Figure 26:
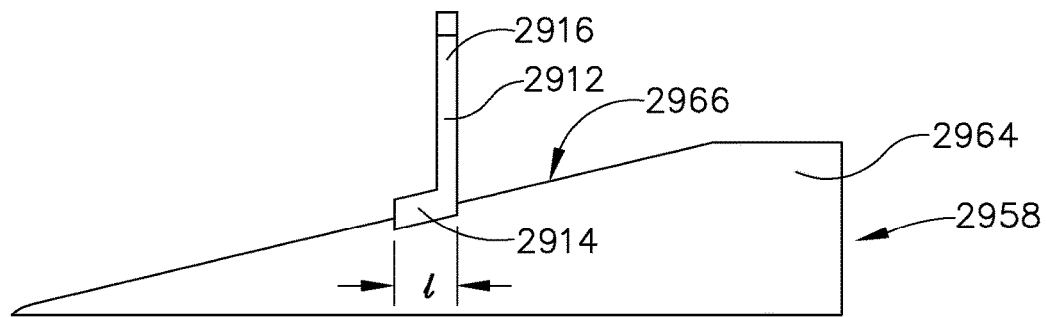
FIG. 26 is an elevation view of a driving wedge and a staple, according to various embodiments of the present disclosure.
Figure 27:
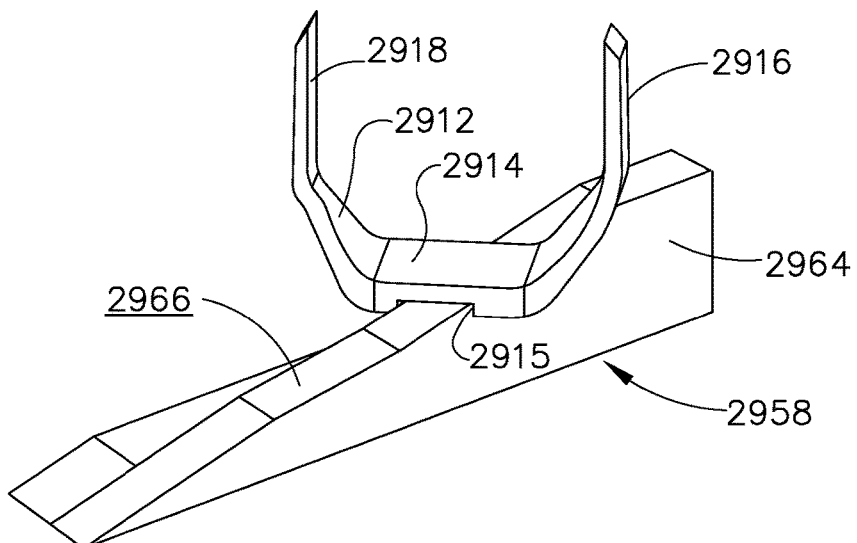
FIG. 27 is a perspective view of the driving wedge and the staple of FIG. 26.
Figure 28:
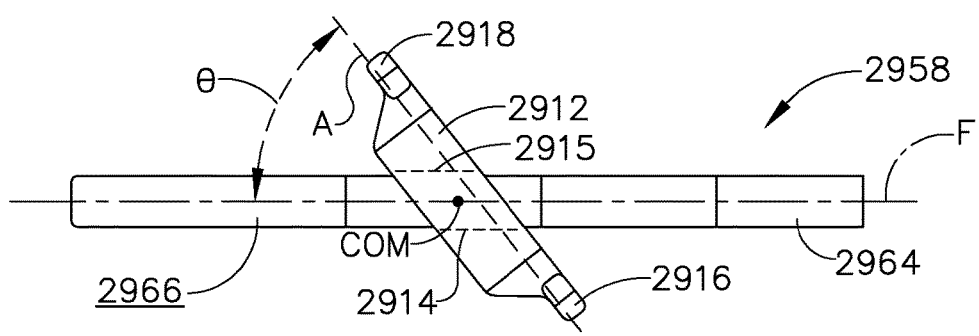
FIG. 28 is a plan view of the driving wedge and the staple of FIG. 26.

A stamped staple 2912 is depicted in FIGS. 26-28. The staple 2912 includes a base 2914, a first leg 2916, and a second leg 2918. As shown in FIGS. 26-28, the outer perimeter of the staple 2912 includes flat and contoured surfaces. Moreover, the staple 2912 includes a groove or track 2915 (FIGS. 27 and 28), which has been cut into the base 2914. The groove 2915 is configured to receive a driving wedge 2964 of a drive sled 2958.

In various instances, the width of the groove 2915 can be slightly larger than the width of the driving wedge 2964 received therein. For example, the width of the groove 2915 can be dimensioned to receive the driving wedge 2964 and prevent lateral shifting of the staple 2915 relative to the wedge 2964.

The staple 2912 depicted in FIGS. 26-28 is angularly-oriented relative to the firing path F (FIG. 28) of the driving wedge 2964. For example, the staple 2912 extends along an axis A (FIG. 27), which traverses the firing path F. As a result, the depicted groove 2915 is angularly-oriented across the base 2914 of the staple 2912. For example, the axis A can be oriented at an angle θ relative to the firing path F. The angle θ depicted in FIG. 28 is 45°.

The base 2914 has an extended length l. For example, the length l of the base 2914 is greater than the length of the staple legs 2916, 2918. Because the base 2914 is elongated, the groove 2915 includes an elongated guide surface or track for the driving wedge 2964, which promotes stability of the staple 2912 during deployment. Staples having an elongated guide or track for receiving a driving wedge, like the staples 2912, for example, could be incorporated into other embodiments disclosed herein.

Referring primarily to FIG. 28, the staple 2912 has a center of mass (COM), which coincides with the firing path F. For example, the firing path F extends through the center of mass (COM) of the staple 2912, such that the staple 2912 is balanced relative to the driving wedge 2964. As a result, the driving force exerted on the staple 2912 can lift the staple legs 2916, 2918 simultaneously and torqueing or rotation of the staple 2912 can be prevented, minimized, and/or controlled.

In various instances, a groove or track similar to the groove 2915 can be defined into an unstamped staple. For example, a wire staple can be cut, stamped, and/or ground to create a track for slidably receiving a driving wedge. In such instances, the staple base may have the same length as the staple legs or, in other instances, the staple base can be flattened to increase or elongate the length thereof. Additionally, in certain instances, as further described herein, multiple driving wedges can drivingly engage a staple. In such instances, the staple can include multiple grooves or tracks, which can each be configured to receive a driving wedge. Moreover, in certain instances, a staple having a guide track, similar to the groove 2915, for example, can be oriented parallel to the longitudinal axis of a staple cartridge. For example, a parallel staple can be longitudinally aligned with a firing path of a driving wedge. In such instances, the guide track defined into the base of the staple can extend along the base of the staple parallel thereto.

As described herein, angularly-oriented staples can provided increased flexibility and/or stretchability to stapled tissue. For example, the angled staples in an array of fired staples can pivot and/or rotate toward alignment with the cut line and/or the longitudinal axis of the staple line to facilitate lengthening and/or longitudinal deformation of the stapled tissue. Because the angled staples can pivot and/or rotate in the array of stapled tissue, tearing and/or stretching of the tissue can be reduced and/or prevented. Moreover, stresses in the tissue and/or trauma to the stapled tissue can be minimized In addition to the longitudinal flexibility afforded by a longitudinally stretchable array of fired staples, it can be desirable to provide lateral customizations to the tissue treated by the array of staples. For example, the compressive force exerted on the tissue can be optimized and/or tailored based on the relative lateral position of the tissue relative to the staple line. In certain instances, it can be desirable to customize the compressive force on the tissue prior to stapling and/or during stapling. In other instances, it can be desirable to customize the compressive force on the stapled tissue. Moreover, in still other instances, it can be desirable to customize the compressive force on tissue prior to staling, during stapling, and after stapling, for example.

The combination of lateral tissue compression customization and longitudinal tissue flexibility can provide synergistic tissue effects. For example, when compressive forces exerted on the tissue during and/or after stapling generate less stress in the compressed tissue and/or affect reduced tissue trauma, the compressed tissue may accommodate increased elastic deformation. In other words, as optimally compressed tissue is stretched and/or elongated, the optimally compressed tissue may better accommodate the rotating and/or pivoting of staples therein. Moreover, when stapled tissue readily accommodates staple pivoting and/or shifting, stresses in the stapled tissue may be reduced and trauma to the stapled tissue may be minimized. Accordingly, as staples pivot and/or shift to accommodate for tissue elongation or longitudinal stretch, stress and/or trauma to the optimally compressed tissue can be further minimized.

Figure 43:
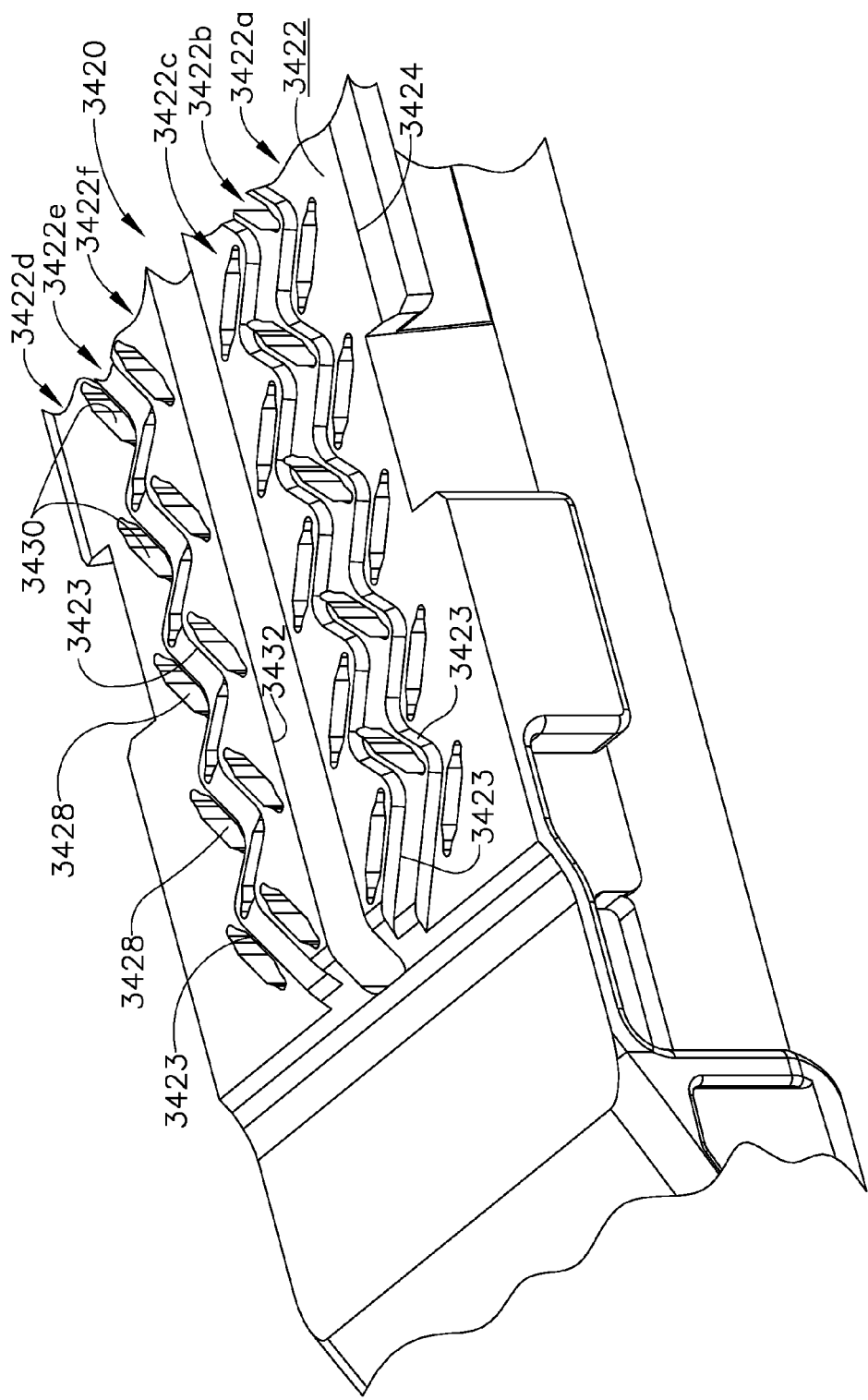
FIG. 43 is a partial perspective view of a staple cartridge having an arrangement of angled staple cavities therein, according to various embodiments of the present disclosure.
Figure 44:
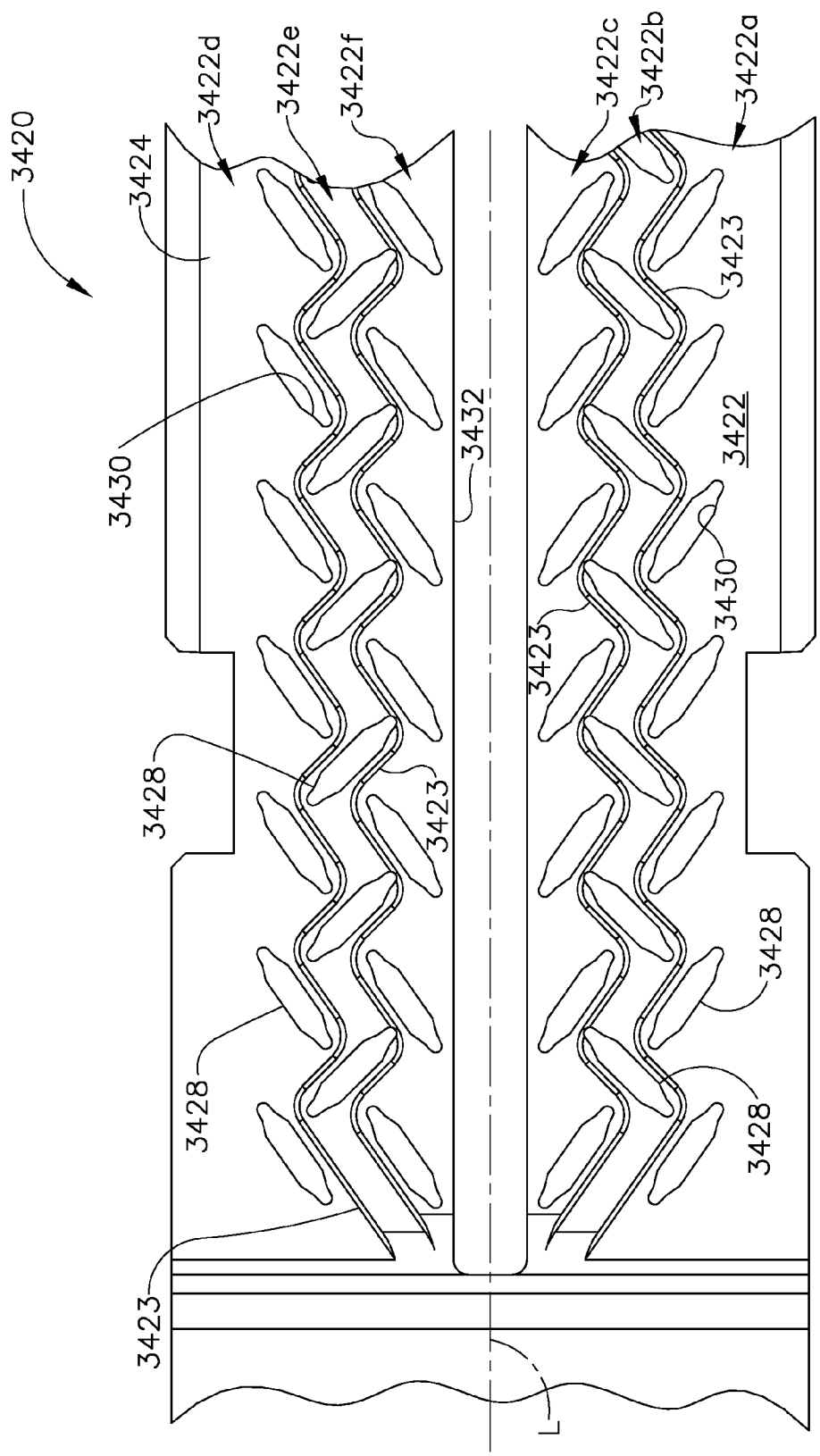
FIG. 44 is a partial plan view of the staple cartridge of FIG. 43.
Figure 45:
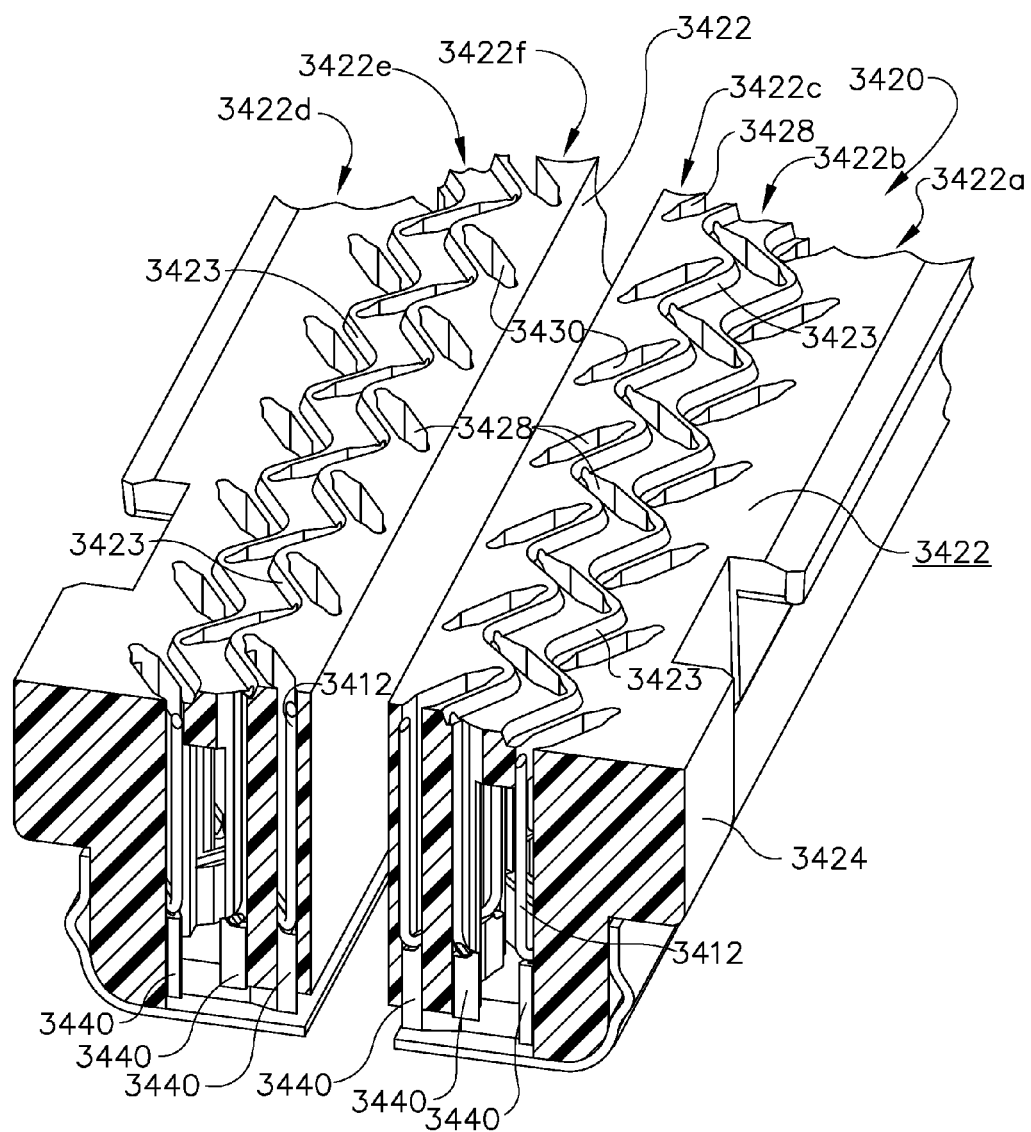
FIG. 45 is a perspective cross-sectional partial view of the staple cartridge of FIG. 43, depicting staples and drivers positioned within the staple cartridge.

A staple cartridge 3420 is depicted in FIGS. 43-45. The depicted staple cartridge 3420 includes a cartridge body 3424 and a deck 3422. Multiple staple cavities 3428 are defined into the body 3424 of the depicted staple cartridge 3420, and each staple cavity 3428 forms an opening 3430 in the deck 3422. Additionally, the staple cavities 3428 shown in FIGS. 43-45 are angularly-oriented relative to the longitudinal axis L (FIG. 44) of the staple cartridge 3420. In the depicted staple cartridge 3420, a longitudinal slot 3432 is defined partially through the cartridge body 3424, and three rows of staple cavities 3428 are positioned on either side of the longitudinal slot 3432. The arrangement of staple cavities 3428 shown in FIGS. 43-45 is configured to receive an array of angled staples. For example, multiple staples, such as the staples 3412 (FIG. 45) are removably positioned in the staple cavities 3428.

In the depicted staple cartridge 3420, the staple cavities 3428 in an outside row on a first side of the longitudinal slot 3432 are oriented at a first angle relative to the longitudinal axis L (FIG. 44), the staple cavities 3428 in an intermediate row on the first side of the longitudinal slot 3432 are oriented at a second angle relative to the longitudinal axis L, and the staple cavities 3428 in an inner row on the first side of the longitudinal slot 3432 are oriented at a third angle relative to the longitudinal axis L. In the depicted staple cartridge 3420, the third angle is the same, or generally the same, as the first angle, and the second angle is 90 degrees, or approximately 90 degrees, offset from the first angle and from the third angle.

As further depicted in FIGS. 43-45, the staple cavities 3428 in an outside row on a second side of the longitudinal slot 3432 are oriented at a fourth angle relative to the longitudinal axis L (FIG. 44), the staple cavities 3428 in an intermediate row on the second side of the longitudinal slot 3432 are oriented at a fifth angle relative to the longitudinal axis L, and the staple cavities 3428 in an inside row on the second side of the longitudinal slot 3432 are oriented at a sixth angle relative to the longitudinal axis L. In the depicted staple cartridge 3420, the sixth angle is the same, or generally the same, as the fourth angle, and the fifth angle is 90 degrees, or approximately 90 degrees, offset from the fourth angle and from the sixth angle. Additionally, in the arrangement depicted in FIGS. 43-45, the second angle is the same, or generally the same, as the fourth angle and the sixth angle, and the first angle is the same, or generally the same, as the third angle and the fifth angle.

In other instances, the staple cartridge 3420 may include additional and/or fewer rows of staple cavities. Additionally or alternatively, the angular orientation of the staples 3412 in each row may be adjusted and/or modified to accommodate a different array. For example, in certain instances, at least one staple cavity can be parallel to the longitudinal axis L.

In various instances, the staple cartridge 3420 depicted in FIGS. 43-45 can be used with the end effector 2000 depicted in FIG. 7. For example, the staple cartridge 3420 can be loaded into the elongate channel of the second jaw 2004. Additionally, in certain instances, the staple cartridge 3420 can be fired with single-staple drivers, multi-staple drivers, and/or a combination thereof. For example, a single-staple driver 3440 (FIG. 45) can be positioned in each staple cavity 3428, and can drivingly engage the staple 3412 supported thereon. The drivers 3440 shown in FIG. 45 can be positioned within the cartridge body 3424 such that the cradle of each driver 3440 is aligned with one of the staples 3412 positioned in one of the staple cavities 3428.

In certain instances, the staple cartridge 3420 can include multi-staple drivers. For example, a multi-staple driver can be configured to fire the staples 3412 (FIG. 45) from a first group of staple cavities 3428, and another multi-staple driver can be configured to fire staples 3412 from a second group of staple cavities 3428. In other instances, the staple cartridge 3420 may not include drivers. For example, a firing member and/or sled, such as the firing member 2660 and the sled 2658 (FIG. 37), for example, can be configured to directly contact, engage, and/or drive the staples 3412. In various instances, the drivers 3440 and/or the staples 3412 can be mass balanced relative to the firing path(s) of a sled, such as the sled 2058 (FIG. 7) and/or sled 2658 (FIG. 37), for example, during deployment.

The deck 3422 depicted in FIGS. 43-45 includes multiple longitudinally extending portions. For example, the deck 3422 includes a first longitudinal portion 3422a, a second longitudinal portion 3422b, and a third longitudinal portion 3422c on one side of the longitudinal slot 3432, and a fourth longitudinal portion 3422d, a fifth longitudinal portion 3422e, and a sixth longitudinal portion 3422f on the other side of the longitudinal slot 3432. As shown in FIGS. 43-45, a longitudinal row of staple cavities 3428 is aligned with each longitudinally extending portion 3422a, 3422b, 3422c, 3422d, 3422e, 3422f. For example, the outside row of staple cavities 3428 on the first side of the longitudinal slot 3432 is aligned with the first longitudinal portion 3422a, the intermediate row of staple cavities 3428 on the first side of the longitudinal slot 3432 is aligned with the second longitudinal portion 3422b, and the inside row of staple cavities 3428 on the first side of the longitudinal slot 3432 is aligned with the third longitudinal portion 3422c. Additionally, the outside row of staple cavities 3428 on the second side of the longitudinal slot 3432 is aligned with the fourth longitudinal portion 3422d, the intermediate row of staple cavities 3428 on the second side of the longitudinal slot 3432 is aligned with the fifth longitudinal portion 3422e, and the inside row of staple cavities 3428 on the second side of the longitudinal slot 3432 is aligned with the sixth longitudinal portion 3422f.

In other instances, the staple cartridge 3420 may include additional and/or fewer longitudinally extending portions. For example, the longitudinal portions can be adjusted and/or modified to correspond to a different arrangement of staple cavities and staples. In certain embodiments, more than one longitudinal row of staple cavities can coincide with at least one longitudinal portion. Additionally or alternatively, at least one longitudinal portion may not include a staple cavity and/or a row of staples, for example.

In the depicted staple cartridge 3420, the adjacent longitudinal portions 3422a, 3422b, 3422c, 3422d, 3422e, and 3422f are vertically offset from each other by a ridge 3423. For example, a ridge 3423 extends between the first portion 3422a and the second portion 3422b, and another ridge 3423 extends between the second portion 3422b and the third portion 3422c. Additionally, in the depicted arrangement, a ridge 3423 extends between the fourth portion 3422d and the fifth portion 3422e, and another ridge 3423 extends between the fifth portion 3422e and the sixth portion 3422f. As shown in FIGS. 43-45, the longitudinal slot 3432 extends between the third portion 3422c and the fourth portion 3422d.

The ridges 3423 disclosed in FIGS. 43-45 define an elevation change in the deck 3422. For example, the ridge 3423 between the first portion 3422a and the second portion 3422b defines a step upward, such that the second portion 3422b has a higher elevation than the first portion 3422. In various instances, the ridges 3423 adjust the height of the deck 3422 laterally. For example, the ridges 3423 increase the height of the deck 3422 inwardly and decrease the height of the deck 3422 outwardly, such that the largest height is adjacent to the longitudinal slot 3432 and the laterally flanking portions have the shortest height.

The gap between the deck 3422 and the staple forming surface of the anvil controls the degree of tissue compression when the jaws of an end effector, such as the first jaw 2002 and the second jaw 2004 of the end effector 2000 (FIG. 7) are clamped. Accordingly, the height of the deck 3422 can affect the degree of tissue compression between the clamped jaws. For example, in regions where the deck 3422 is taller, the adjacent tissue can be relatively more compressed between the clamped jaws, and in regions where the deck 3422 is shorter, the adjacent tissue can be relatively less compressed between the clamped jaws. Accordingly, the ridges 3423 disclosed in FIGS. 43-45 can affect a lateral variation in tissue compression. As further described herein, the degrees of tissue compression can be selected and/or optimized to reduce stress and/or trauma to the compressed tissue. Moreover, because the staple cartridge 3420 is configured to fire a longitudinally flexible array of staples 3412, the integrity of the stapled tissue can be further preserved.

The ridges 3423 disclosed in FIGS. 43-45 affect abrupt and/or steep steps between the adjacent longitudinal portions 3422a, 3422b, 3422c, 3422d, 3422e, and 3422f. FIGS. 43-45 further disclose that the ridges 3423 curve around the staple cavities 3428 in the adjacent rows of staple cavities 3428. For example, the ridges 3423 generally extend along a path that corresponds to and/or matches the angular orientation of the staple cavity or cavities 3428 adjacent thereto. As a result, the ridges 3423 include multiple contours and/or bends. Additionally, the ridges 3423 include multiple straight, or generally straight portions, intermediate the contours.

In other instances, a ridge 3423 may define a less steep elevation change. For example, at least one ridge 3423 and/or a portion thereof can gradually slope and/or incrementally step to a different elevation. Additionally, in certain instances, the height of a longitudinal portion 3422a, 3422b, 3422c, 3422d, 3422e, 3422f can vary. For example, the height of each longitudinal portion 3422a, 3422b, 3422c, 3422d, 3422e, 3422f can vary laterally and/or longitudinally. In such instances, the deck may define sloped and/or angled surfaces intermediate the ridges 3423, for example.

Figure 46:
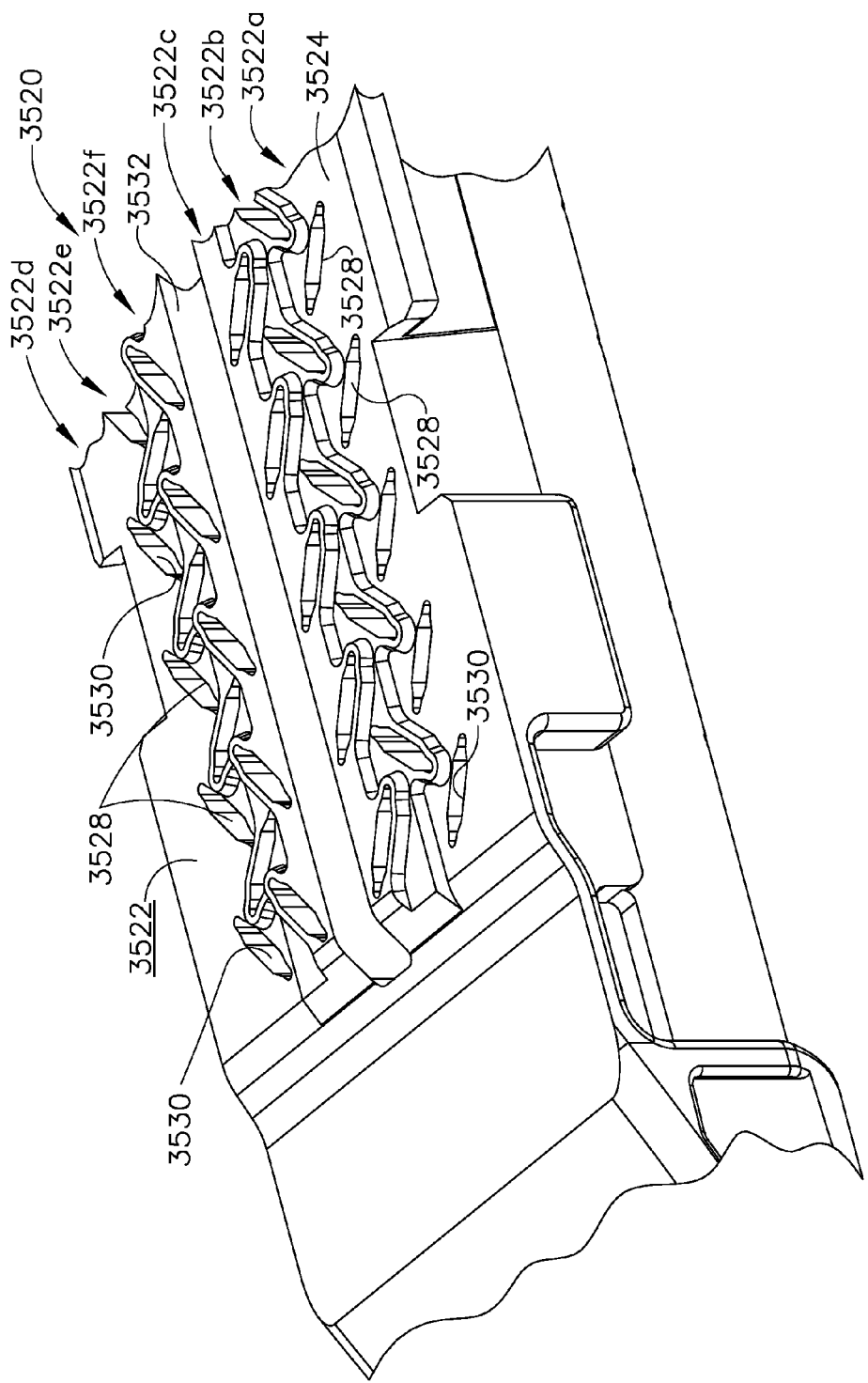
FIG. 46 is a partial, perspective view of a staple cartridge having an arrangement of angled staple cavities therein, according to various embodiments of the present disclosure.
Figure 47:
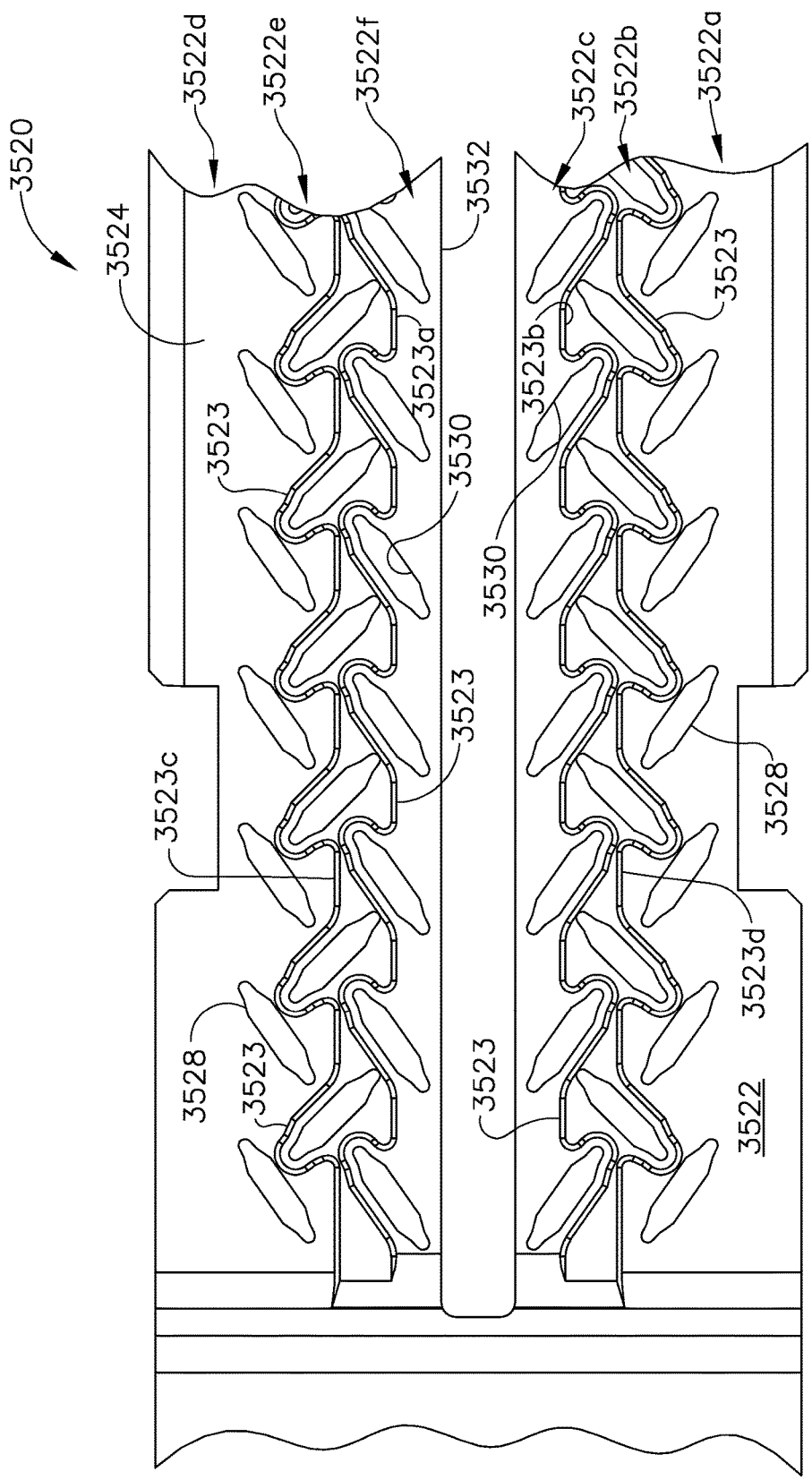
FIG. 47 is a partial, plan view of the staple cartridge of FIG. 46.
Figure 48:
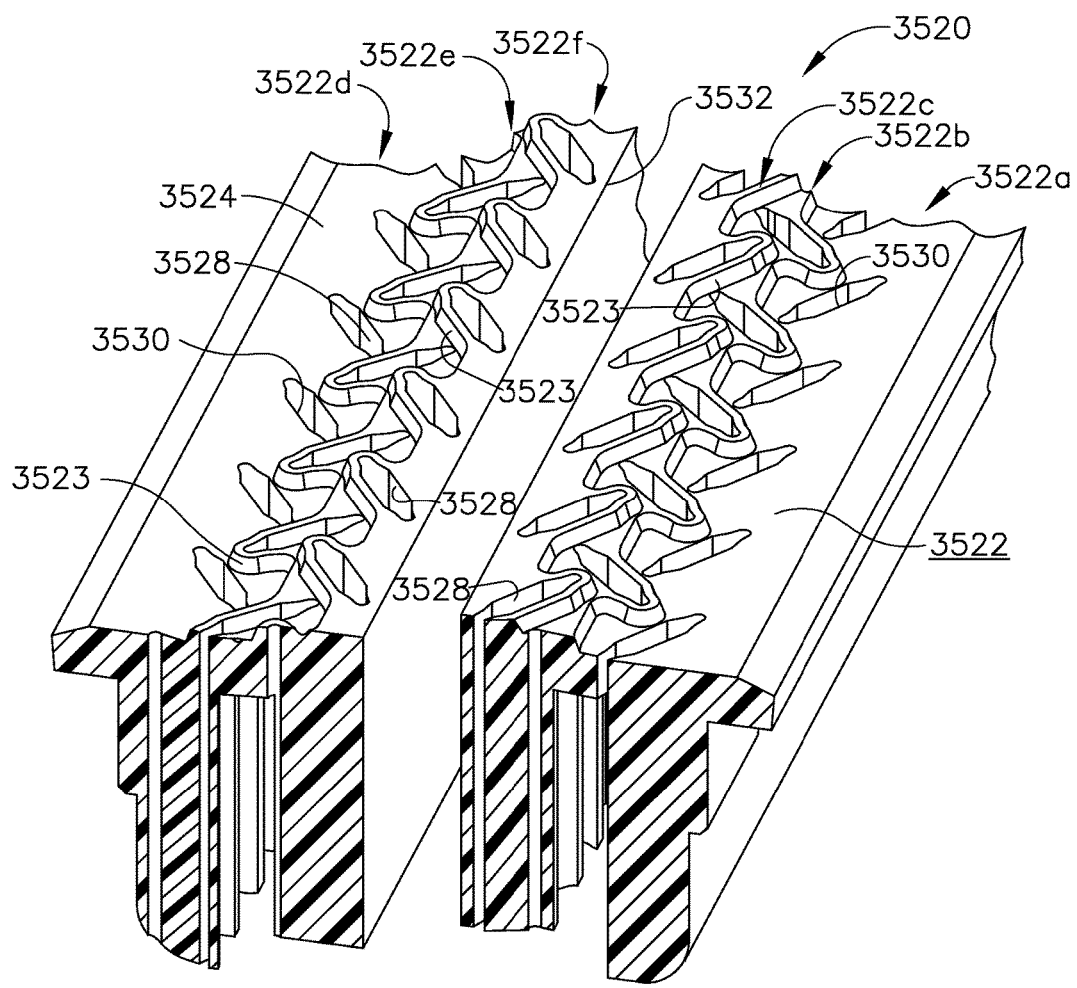
FIG. 48 is a partial, perspective cross-sectional view of the staple cartridge of FIG. 46.

In other staple cartridges, ridges can extend along a different path between the rows of staples and staple cavities. For example, the staple cartridge 3520, which is shown in FIGS. 46-48, is similar to the staple cartridge 3420 (FIGS. 43-45) and like reference characters refer to similar elements. For example, the staple cartridge 3520 includes a cartridge body 3524 and a deck 3522. Multiple staple cavities 3528 are defined into the body 3524 of the depicted staple cartridge 3520, and each staple cavity 3528 forms an opening 3530 in the deck 3422. Additionally, the staple cavities 3528 shown in FIGS. 46-48 match the array of staple cavities 3428 depicted in FIGS. 43-45. For example, in the depicted staple cartridge 3520, a longitudinal slot 3532 is defined partially through the cartridge body 3524, and three rows of staple cavities 3528 are positioned on either side of the longitudinal slot 3532. The arrangement of staple cavities 3528 shown in FIGS. 46-48 is configured to receive an array of angled staples. For example, multiple staples, such as the staples 3412 (FIG. 45) can be removably positioned in the staple cavities 3528.

The deck 3522 disclosed in FIGS. 46-48 includes multiple longitudinally extending portions. For example, the depicted deck 3522 includes a first longitudinal portion 3522a, a second longitudinal portion 3522b, and a third longitudinal portion 3522c on one side of the longitudinal slot 3532, and a fourth longitudinal portion 3522d, a fifth longitudinal portion 3522e, and a sixth longitudinal portion 3522f on the other side of the longitudinal slot 3432. As shown in FIGS. 46-48, a longitudinal row of staple cavities 3528 is aligned with each longitudinally extending portion 3522a, 3522b, 3522c, 3522d, 3522e, 3522f. Additionally, in the depicted staple cartridge 3520, the adjacent longitudinal portions 3522a, 3522b, 3522c, 3522d, 3522e, and 3522f are vertically offset from each other by a ridge 3523.

The ridges 3523 disclosed in FIGS. 46-48 extend along different paths than the ridges 3423 of the deck 3422 (FIGS. 43-45). For example, the ridges 3423 include multiple cut-ins, such as cut-ins 3523a, 3523b, 3523c, and 3523d (FIG. 47), for example, where the ridges 3523 do not extend along and/or adjacent to a staple cavity 3528. The geometry of the cut-ins 3523a, 3523b, 3523c, and 3523d can be selected to adjust the tissue compression. For example, a cut-in can enlarge a region of reduced pressure and reduce an adjacent region of increased pressure. In various instances, it may be desirable to provide the cut-ins 3523a, 3523b, 3523c, and 3523d towards the knife slot 3532 to provide regions of reduced tissue compression, for example.

As further described herein, the ridges 3523 disclosed in FIGS. 46-48 can affect a lateral variation in tissue compression. For example, the degrees of tissue compression can be selected and/or optimized to reduce stress and/or trauma to the compressed tissue. Moreover, because the staple cartridge 3520 is configured to fire a longitudinally flexible array of staples 3512, the integrity of the stapled tissue can be further preserved.

Figure 49:
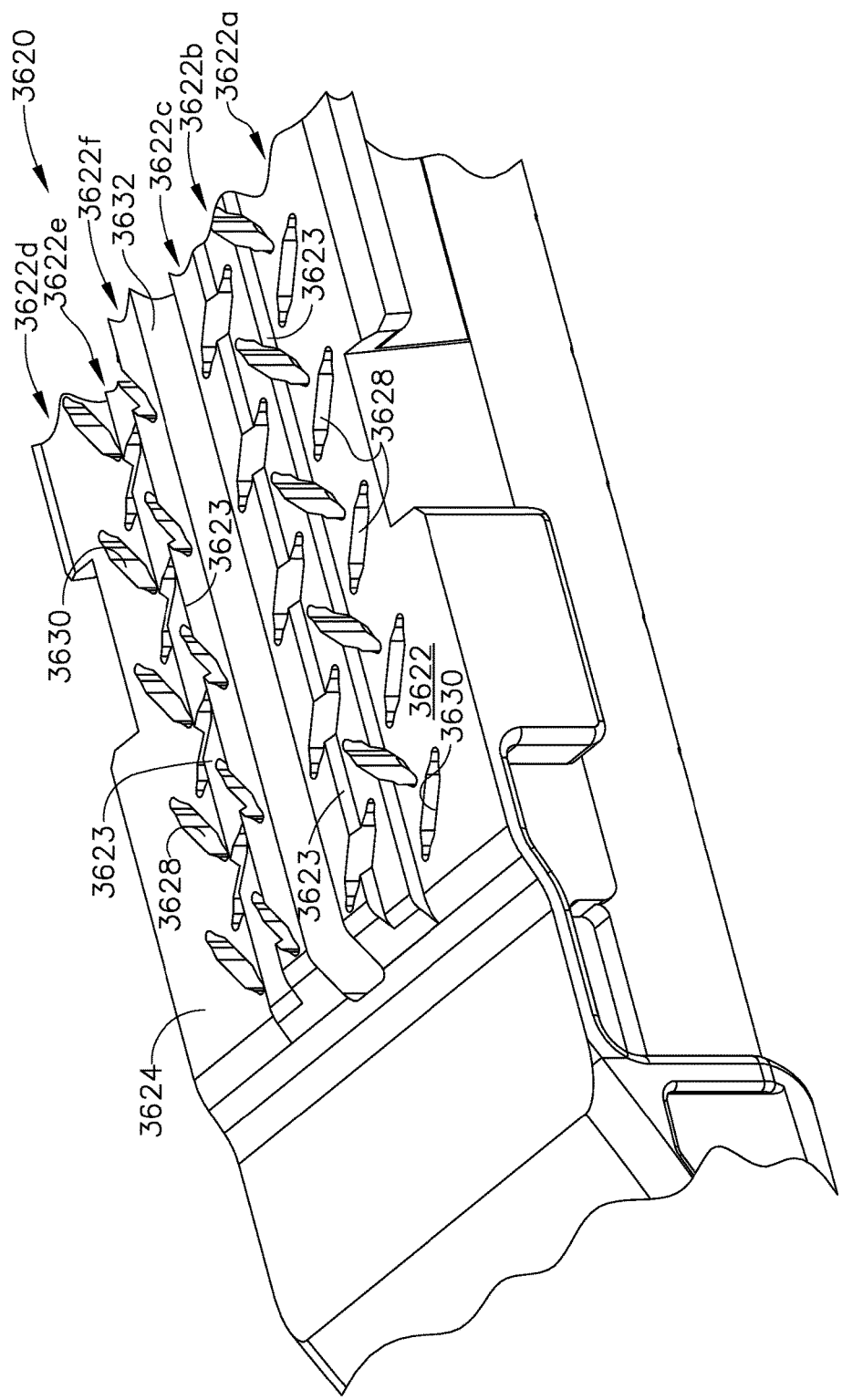
FIG. 49 is a partial, perspective view of a staple cartridge having an arrangement of angled staple cavities therein, according to various embodiments of the present disclosure.
Figure 50:
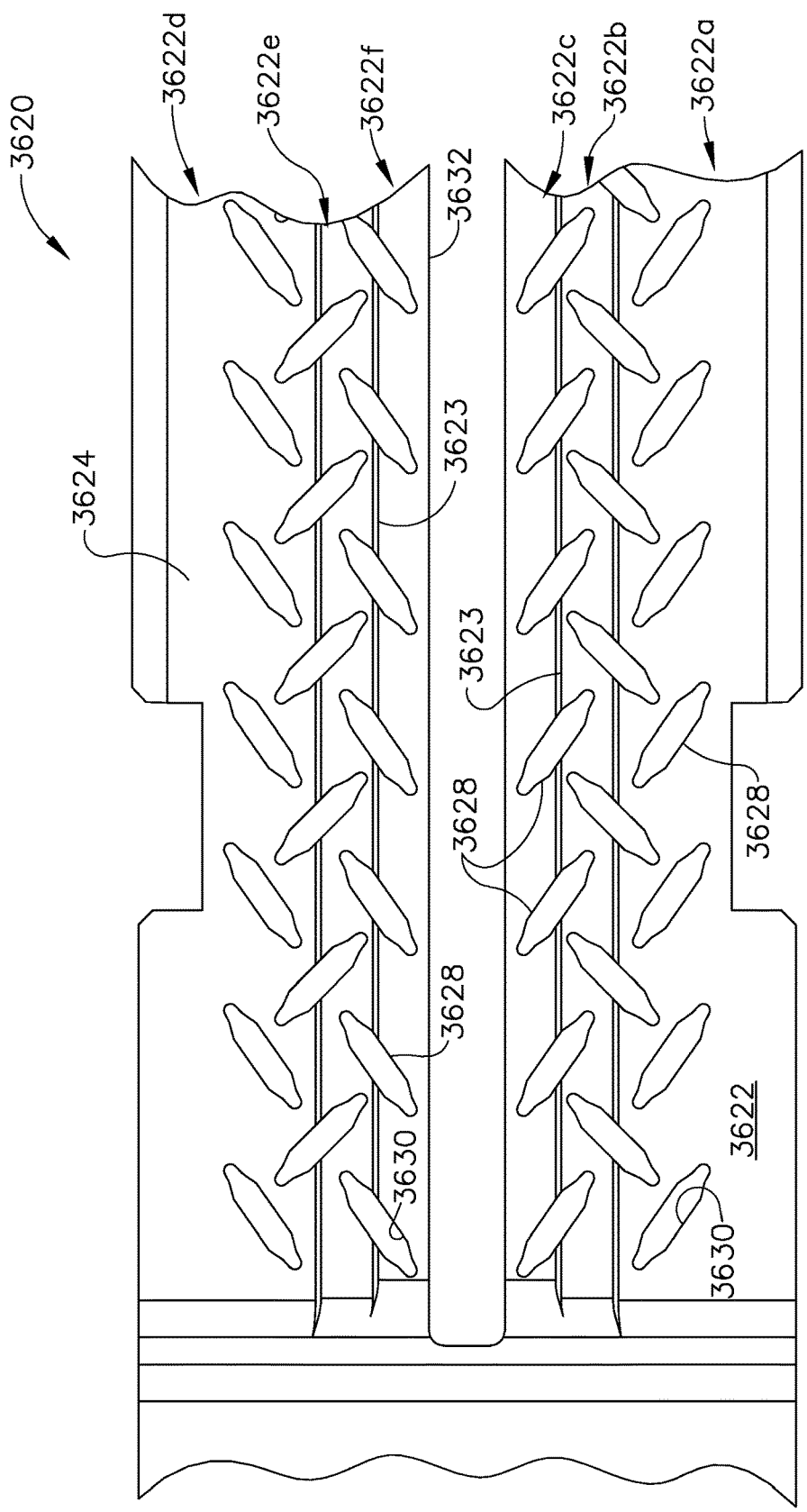
FIG. 50 is a partial, plan view of the staple cartridge of FIG. 49.
Figure 51:
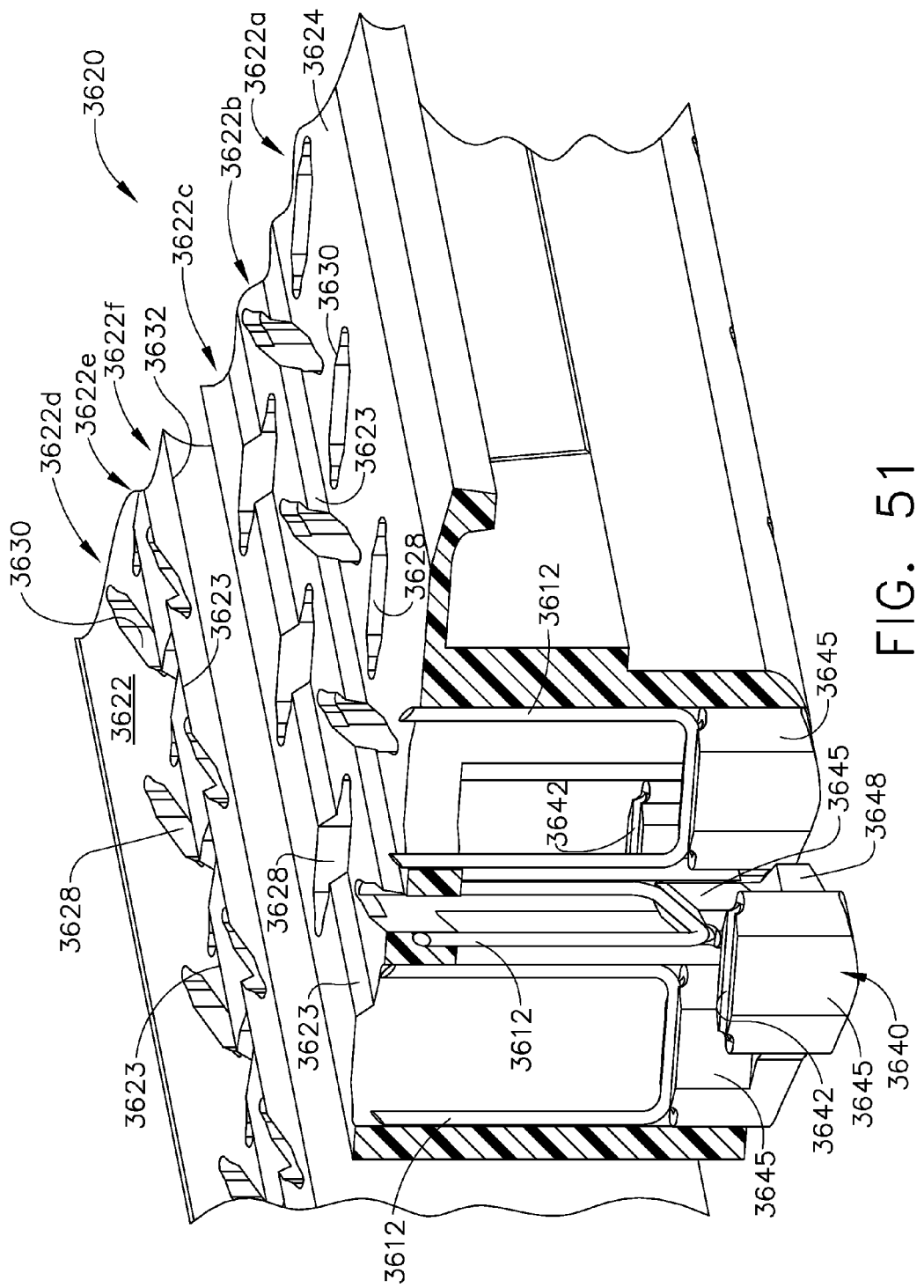
FIG. 51 is a partial, perspective cross-sectional view of the staple cartridge of FIG. 49, depicting staples and multi-staple drivers positioned within the staple cartridge.

In other instances, the ridges on a cartridge deck can be straight or generally straight. For example, the staple cartridge 3620, which is shown in FIGS. 49-51, is similar to the staple cartridge 3420 (FIGS. 43-45) and like reference characters refer to similar elements. For example, the staple cartridge 3620 includes a cartridge body 3624 and a deck 3622. Multiple staple cavities 3628 are defined into the body 3624 of the depicted staple cartridge 3620, and each staple cavity 3628 forms an opening 3630 in the deck 3622. Additionally, the staple cavities 3628 shown in FIGS. 49-51 match the arrangement of staple cavities 3528 depicted in FIGS. 46-48. For example, in the depicted staple cartridge 3620, a longitudinal slot 3632 is defined partially through the cartridge body 3624, and three rows of staple cavities 3628 are positioned on either side of the longitudinal slot 3632. The arrangement of staple cavities 3628 shown in FIGS. 46-48 is configured to receive an array of angled staples. For example, multiple staples, such as staples 3612 (FIG. 51) are removably positioned in the staple cavities 3628.

The deck 3622 disclosed in FIGS. 49-51 includes multiple longitudinally extending portions. For example, the depicted deck 3622 includes a first longitudinal portion 3622a, a second longitudinal portion 3622b, and a third longitudinal portion 3622c on one side of the longitudinal slot 3632, and a fourth longitudinal portion 3622d, a fifth longitudinal portion 3622e, and a sixth longitudinal portion 3622f on the other side of the longitudinal slot 3632. As shown in FIGS. 49-51, a longitudinal row of staple cavities 3628 is aligned with each longitudinally extending portion 3622a, 3622b, 3622c, 3622d, 3622e, 3622f. Additionally, in the depicted staple cartridge 3620, the adjacent longitudinal portions 3622a, 3622b, 3622c, 3622d, 3622e, and 3622f are vertically offset from each other by a ridge 3623.

The ridges 3623 disclosed in FIGS. 49-51 extend along different paths than the ridges 3423 of the deck 3422 (FIGS. 43-45) and the ridges 3523 of the deck 3522 (FIGS. 46-48). For example, the ridges 3623 extend along straight paths, which extend parallel to the longitudinal slot 3632. Moreover, a portion of the longitudinal ridges 3523 extend through staple cavities 3628 in the staple cartridge 3620. As a result, one end or side of a staple cavity 3628 is positioned in one of the longitudinal deck portions 3622a, 3622b, 3622c, 3622d, 3622e, or 3622f, and the other end or side of the same staple cavity 3628 is positioned in another of the longitudinal deck portions 3622a, 3622b, 3622c, 3622d, 3622e, or 3622f.

As further described herein, the ridges 3623 disclosed in FIGS. 49-51 can affect a lateral variation in tissue compression. For example, the degrees of tissue compression can be selected and/or optimized to reduce stress and/or trauma to the compressed tissue. Moreover, because the staple cartridge 3620 is configured to fire a longitudinally flexible array of staples 3612, the integrity of the stapled tissue can be further preserved.

In certain instances, the staple cartridge 3620 includes multi-staple drivers, such as the multi-staple drivers 3640 disclosed in FIG. 51. Each multi-staple driver 3640 is configured to fire the staples 3612 from a group of staple cavities 3628. For example, similar to the multi-staple drivers 2040a, 2040b (FIGS. 7-9), the multi-staple drivers 3640 include three steps 3645, and a trough or cradle 3642 is defined into each step 3645. Additionally, the steps 3645 of the multi-staple drivers 3640 are connected by a connecting flange 3648. Each multi-staple driver 3640 shown in FIG. 51 supports staples 3612 across multiple rows of staple cavities 3628, and is configured to fire staples 3612 from staples cavities 3628 in multiple rows. In FIG. 51, the height of each step 3645 and the depth of each cradle 3642 defined therein is the same, such that the staples 3612 formed between the steps 3645 and a staple forming surface on the anvil have the same formed height.

As further described herein, it may be desirable to customize and/or optimize the formed staple height to affect varied tissue compression within formed staples. Accordingly, at least one of the multi-staple drivers 3640 can be modified to form staples 3612 of different formed heights. For example, the steps 3645 and/or the cradles 3642 of a staple multi-staple driver 3640 can be modified to have different dimensions, such that at least two of the staples 3612 formed by the modified multi-staple driver 3640 have different formed heights. In other instances, the steps 3645 and/or the cradles 3642 of different staple drivers 3640 can be modified, such that a first driver 3640 is configured to form staples 3612 having a first formed height and a second driver 3640 is configured to form staples having a second, different formed height 3612.

In still other instances, the staple cartridge 3620 may include single-staple drivers. Alternatively, the staple cartridge 3620 may not include drivers. For example, a firing member and/or sled, such as the firing member 2660 and/or the sled 2658 (FIG. 37), for example, can be configured to directly contact, engage, and/or drive the staples 3612. In various instances, the drivers 3640 and/or the staples 3612 can be mass balanced relative to the firing path(s) of a sled, such as sled 2058 (FIG. 7) and/or sled 2658 (FIG. 37), for example.

As described herein, to customize and/or optimize the tissue compression within a formed staple, staples in a staple array can be formed to different formed heights. For example, in various instances, it is desirable to vary tissue compression, and thus the formed staple dimensions, laterally. In such circumstances, tissue closer to the cut line can be compressed more than tissue farther from the cut line, for example. Various staple arrays having different unformed heights and/or different formed heights are described in U.S. Pat. No. 7,866,528, entitled STAPLE DRIVE ASSEMBLY, which issued on Jan. 1, 2011; U.S. Pat. No. 7,726,537, entitled SURGICAL STAPLER WITH UNIVERSAL ARTICULATION AND TISSUE PRE-CLAMP, which issued on Jun. 1, 2010; U.S. Pat. No. 7,641,091, entitled STAPLE DRIVE ASSEMBLY, which issued on Jan. 5, 2010; U.S. Pat. No. 7,635,074, entitled STAPLE DRIVE ASSEMBLY, which issued on Dec. 22, 2009; and U.S. Pat. No. 7,997,469, entitled STAPLE DRIVE ASSEMBLY, which issued on Aug. 16, 2011, which are hereby incorporated by reference herein in their respective entireties.

Referring again to FIGS. 49-51, in various instances, the staple cartridge 3620 can be employed with an end effector that is configured to deform the staples 3612 to different formed heights. The angled staple cavities 3628 in the staple cartridge 3620 are arranged in a plurality of rows. For example, angled the staple cavities 3628 are arranged in a first outer row, a first intermediate row, and a first inner row on a first side of the staple cartridge 3620, and the angled staple cavities 3628 are arranged in a second outer row, a second intermediate row, and a second inner row on a second side of the staple cartridge 3620. In various instances, the staples 3612 fired from the staple cavities 3628 in the first outer row can assume a taller formed height than the staples 2612 fired from the staple cavities 3628 in the first intermediate row, and/or the staples 3612 fired from the staple cavities 3628 in the first intermediate row can assume a taller formed height than the staples 2612 fired from the staple cavities 3628 in the first inner row. Additionally or alternatively, the staples 3612 fired from the staple cavities 3628 in the second outer row can assume a taller formed height than the staples 2612 fired from the staple cavities 3628 in the second intermediate row, and/or the staples 3612 fired from the staple cavities 3628 in the second intermediate row can assume a taller formed height than the staples 2612 fired from the staple cavities 3628 in the second inner row.

In certain instances, the staples 3612 fired from the staple cartridge 3620 can have different unformed heights. For example, the staples 3612 fired from the staple cavities 3628 in the first outer row can have a greater unformed height than the staples 2612 fired from the staple cavities 3628 in the first intermediate row, and/or the staples 3612 fired from the staple cavities 3628 in the first intermediate row can have a greater unformed height than the staples 2612 fired from the staple cavities 3628 in the first inner row. Additionally or alternatively, the staples 3612 fired from the staple cavities 3628 in the second outer row can have a greater unformed height than the staples 2612 fired from the staple cavities 3628 in the second intermediate row, and/or the staples 3612 fired from the staple cavities 3628 in the second intermediate row can have a greater unformed height than the staples 2612 fired from the staple cavities 3628 in the second inner row.

In various instances, staple arrays having different unformed heights and/or different formed heights can be incorporated into various staple cartridges described herein. For example, the staple cartridge 3420 (FIGS. 43-45) and/or the staple cartridge 3520 (46-48) can include staples having different unformed heights and/or can be configured to fire staples to different formed heights. In such instances, the stepped cartridge decks 3422 (FIGS. 43-45), 3522 (FIGS. 46-48), and 3622 (FIGS. 49-51) can affect variable pre-firing tissue compression, for example, and the different formed staple heights can affect variable post-firing tissue compression, for example.

As described herein, angled staple arrays provide improved flexibility to the stapled tissue. A staple that is angled relative to the cut line and/or the longitudinal axis of staple cartridge can have one staple leg closer to the cut line than another staple leg. In such an arrangement, to customize and/or optimize the tissue compression laterally, the staple can be formed to different formed heights. For example, one end of a staple can be formed to a first height, and the other end of the staple can be formed to a second, different height. In such instances, tissue treated by the same row of staples could be subjected to different compressive forces.

Figure 79:
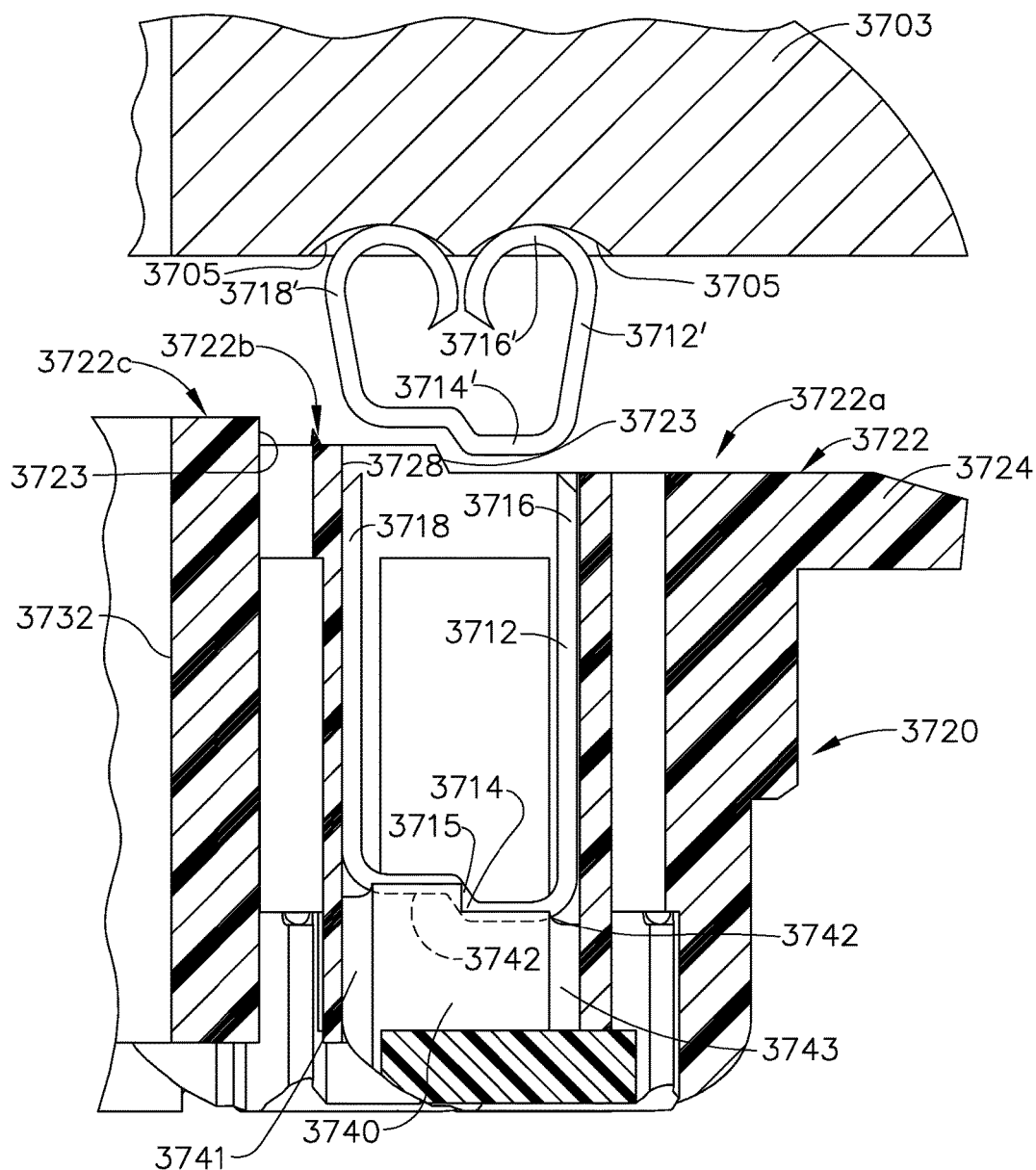
FIG. 79 is a partial, cross-sectional elevation view of a staple cartridge and an anvil, according to various embodiments of the present disclosure.

A staple cartridge 3720 and an anvil 3703 are depicted in FIG. 79. The staple cartridge 3720 is similar to the staple cartridge 3620 (FIGS. 49-51) and like reference characters refer to similar elements. For example, the staple cartridge 3720 includes a cartridge body 3724 and a deck 3722. The deck 3722 includes multiple longitudinally extending portions 3722a, 3722b, 3722c, and adjacent longitudinal portions 3722a, 3722b, 3722c are separated by a ridge 3723. The ridges 3723 extend longitudinally along at least a portion of the length of the cartridge body 3722. An angled staple cavity 3728 is defined into the cartridge body 3724, and a ridge 3723 extends through the staple cavity 3728. As a result, the first end of the depicted staple cavity 3728 is positioned in the first longitudinal portion 3722a and the second end of the depicted staple cartridge 3728 is positioned in the second longitudinal portion 3722b. Additionally, a longitudinal slot 3732 is defined partially through the depicted cartridge body 3724.

In various instances, the staple cartridge 3720 can include multiple staple cavities 3728, which are configured to receive an array of angled staples 3712. For example, the staple cartridge 3720 can include an arrangement of staple cavities 3728 that corresponds to the arrangement of staple cavities 3628 depicted in FIGS. 49-51. In certain instances, three rows of staple cavities 3728 can be positioned on both sides of the longitudinal slot 3732, for example.

An unformed staple 3712 and a deformed staple 3712' are depicted in FIG. 79. The staple 3712 includes a base 3714, a first leg 3716 extending from the base 3714, and a second leg 3718 extending from the base 3714. A driver 3740 is also depicted in FIG. 79. The driver 3740 includes a trough or cradle 3742, which is configured to support the base 3714 of the staple 3712. The driver 3740 and the cradle 3742 defined therein have a variable height between a first end 3741 and a second end 3743 of the driver 3740. For example, the first end 3741 of the driver 3740 defines a first height and the second end 3743 of the driver 3740 defines a second height, which is less than the first height.

As the driver 3740 is fired and lifted within the staple cavity 3728, the staple 3712 rides upward on the lifting driver 3740 and is deformed by the staple forming pockets 3705 of the anvil 3703. The formed staple 3712' is also depicted in FIG. 79. The formed height of the staple 3712' is a function of the distance or gap between the lifted driver 3740 and the staple forming pockets 3705 of the anvil 3703. Because the distance between the staple-supporting surface 3742 of the lifted driver 3740 and the staple forming pockets 3705 varies in the staple cartridge 3720 disclosed in FIG. 79, the formed staple 3712' has a variable height. For example, the height of formed staple 3712' is greater between the first leg 3716' and the base 3714' than between the second leg 3718' and the base 3714'. In various instances, the angular orientation of the staple 3712' can place the first leg 3716' farther from the longitudinal slot 3732 than the second leg 3718'. In such instances, the first leg 3716' can be an outer leg of the staple 3712' and the second leg 3718' can be an inner leg of the staple 3712'. In such an arrangement, the tissue compression can be greater between the inner leg 3718' and the base 3714' than between the outer leg 3716' and the base 3714'.

Staple cartridge and anvil arrangements that are configured to deform angled staples to different formed heights, like the staple cartridge 3720 and the anvil 3705, for example, could be incorporated into other embodiments disclosed herein. For example, drivers having a variable height staple-supporting cradle, like the drivers 2740, for example, could be incorporated into other staple cartridge and/or end effector assemblies disclosed herein.

The unformed staple 3712 depicted in FIG. 79 also has a variable height. For example, the staple 3712 defines a first height at the first leg 3716 and a second height at the second leg 3718, which is less than the first height. Additionally, the base 3714 of the staple 3712 defines a bend or step 3715, which lifts the second leg 3718 relative to the first leg 3716.

In other instances, the unformed staple 3712 may have a uniform height. Additionally or alternatively, the base 3714 of the unformed staple 3712 may be straight, or generally straight, between the first leg 3716 and the second leg 3718. In such instances, the staple 3712 may still assume a variable formed height when the distance between the staple-supporting surface 3742 of the lifted driver 3740 and the staple forming pockets 3705 is variable. For example, one of the staple legs 3716, 3718 can be more deformed and/or compacted than the other staple leg 3716, 3718 to accommodate for the additional leg length. Additionally, because the distance between the staple-supporting surface 3742 and the staple forming pockets 3705 varies, the base 3714 can be bent and/or otherwise deformed during firing to accommodate for the height difference.

Figure 80:
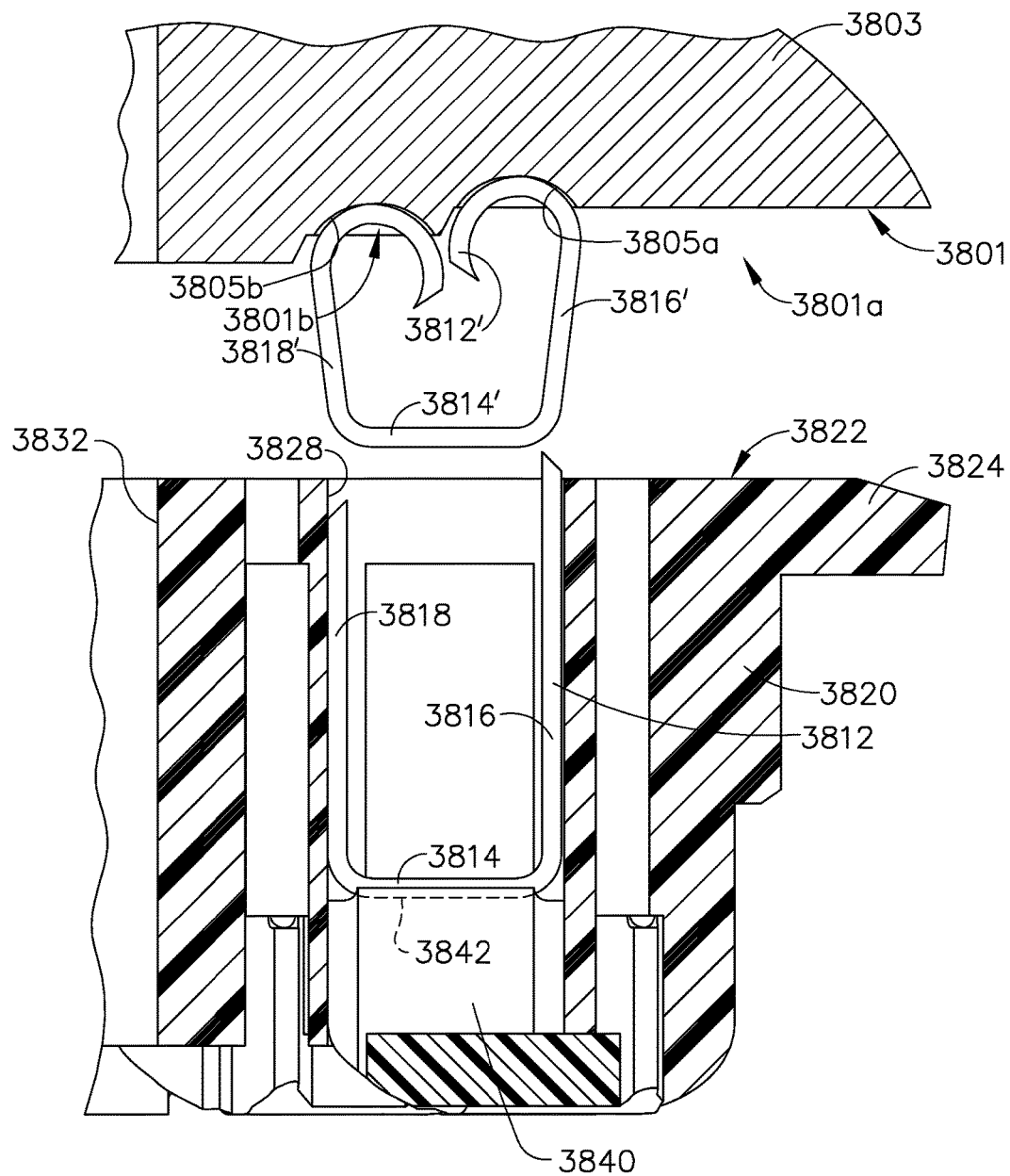
FIG. 80 is a partial, cross-sectional elevation view of a staple cartridge and an anvil, according to various embodiments of the present disclosure.

A staple cartridge 3820 and an anvil 3803 are depicted in FIG. 80. The staple cartridge 3820 is similar to the staple cartridge 3620 (FIGS. 49-51) and like reference characters refer to similar elements. For example, the staple cartridge 3820 includes a cartridge body 3824 and a deck 3822. Unlike the deck 3622 (FIGS. 49-51), the deck 3822 has a flat, or generally flat, unstepped surface. An angled staple cavity 3828 is defined into the cartridge body 3824. Additionally, a longitudinal slot 3832 is defined partially through the depicted cartridge body 3824.

In various instances, the staple cartridge 3820 can include multiple staple cavities 3828, which are configured to receive an array of angled staples. For example, the staple cartridge 3820 can include an arrangement of staple cavities that corresponds to the arrangement of staple cavities 3628 depicted in FIGS. 49-51. In certain instances, three rows of staple cavities 3828 can be positioned on either side of the longitudinal slot 3832, for example.

An unformed staple 3812 is depicted in FIG. 80. The staple 3812 includes a base 3814, a first leg 3816 extending from the base 3814, and a second leg 3818 extending from the base 3814. A driver 3840 is also depicted in FIG. 80. The driver 3840 includes a trough or cradle 3842, which is configured to support the base 3814 of the staple 3812.

The anvil 3803 includes a laterally stepped, cartridge-facing surface 3801. A first staple forming pocket 3805a and a second staple forming pocket 3805b are defined into the stepped surface 3801. As depicted in FIG. 80, the first staple forming pocket 3805a is in a first step 3801a of the stepped surface 3801 and the second staple forming pocket 3805b is in a second step 3801b of the stepped surface 3801.

As the driver 3840 is fired and lifted within the staple cavity 3828, the staple 3812 rides upward on the lifting driver 3840 and is deformed by the staple forming pockets 3805a, 3805b of the anvil 3803. The formed staple 3812' is also depicted in FIG. 80. The formed height of the staple 3812' is a function of the distance or gap between the lifted driver 3840 and the staple forming pockets 3805a, 3805b of the anvil 3803. Because the distance between the staple-supporting surface 3842 of the lifted driver 3840 and each staple forming pockets 3805a, 3805b is different in the staple cartridge 3720 depicted in FIG. 79, the formed staple 3812' assumes a variable height. For example, the height of formed staple 3812' is greater between the first leg 3816' and the base 3814' than between the second leg 3818' and the base 3814'. In various instances, the angular orientation of the staple 3812' can place the first leg 3816' farther from the longitudinal slot 3832 than the second leg 3818'. In such instances, the first leg 3816' can be an outer leg of the staple 3812' and the second leg 3818' can be an inner leg of the staple 3812'. In such an arrangement, the tissue compression can be greater between the inner leg 3818' and the base 3814' than between the outer leg 3816' and the base 3814'.

In other instances, the staple 3812' can be deformed to a smaller height at the outer leg 3816'. As a result, the tissue compression could be greater between the outer leg 3816' and the base 3814' than between the inner leg 3818' and the base 3814'.

Staple cartridge and anvil arrangements that are configured to deform angled staples to different formed heights, like the staple cartridge 3820 and the anvil 3805a, 3805b, for example, could be incorporated into other embodiments disclosed herein. For example, variable depth pockets, like pockets 3805a, 3805b, for example, could be incorporated into other embodiments disclosed herein.

The unformed staple 3812 depicted in FIG. 80 has a variable height. For example, the staple 3812 defines a first height at the first leg 3816 and a second height at the second leg 3818, which is less than the first height.

In other instances, the unformed staple 3812 may have a uniform height. In such instances, the staple 3812 may still assume a variable formed height when the distance between the staple-supporting surface 3842 of the lifted driver 3840 and the staple forming pockets 3805 is variable. For example, one of the staple legs 3816, 3818 can be more deformed and/or compacted than the other staple leg 3816, 3818 to accommodate for the additional length.

In certain types of surgical procedures, the use of surgical staples or surgical fasteners has become the preferred method of joining tissue, and, specially configured surgical staplers or circular surgical fastening devices have been developed for these applications. For example, intra-luminal or circular staplers have been developed for use in surgical procedures used to form an "anastomosis". Circular staplers useful to perform an anastomosis are disclosed, for example, in U.S. Pat. No. 5,104,025, entitled INTRALUMINAL ANASTOMOTIC SURGICAL STAPLER WITH DETACHED ANVIL, U.S. Pat. No. 5,309,927, entitled CIRCULAR STAPLER TISSUE RETENTION SPRING METHOD, U.S. Pat. No. 7,665,647, entitled SURGICAL CUTTING AND STAPLING DEVICE WITH CLOSURE APPARATUS FOR LIMITING MAXIMUM TISSUE COMPRESSION FORCE, U.S. Pat. No. 8,668,130, entitled SURGICAL STAPLING SYSTEMS AND STAPLE CARTRIDGES FOR DEPLOYING SURGICAL STAPLES WITH TISSUE COMPRESSION FEATURES, the entire disclosures of each being hereby incorporated by reference herein.

One form of an "anastomosis" comprises a surgical procedure wherein sections of intestine are joined together after a connecting section (usually a diseased section) has been excised. The procedure requires joining the ends of two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular fastening devices has greatly simplified the anastomosis procedure and has also decreased the time required to perform an anastomosis.

In general, a conventional circular stapler or fastening device consists of an elongated shaft that includes a proximal actuating mechanism and a distal stapling mechanism that is mounted to the shaft. The distal stapling mechanism typically consists of a fixed stapling cartridge that contains a plurality of staples that are arranged in a concentric circular array. A round cutting knife is also concentrically mounted in the cartridge such that it is interior to the staples. The knife is axially moveable in a distal direction. Extending axially from the center of the cartridge is a trocar shaft. The trocar shaft is also axially moveable within the elongated shaft. The trocar shaft is configured to be removably attached to an anvil member. The anvil member includes a staple-forming undersurface that is arranged to confront the staple cartridge for forming the ends of the staples as they are advanced into contact with it. The distance between the distal face of the staple cartridge and the staple forming undersurface of the anvil is controlled by an adjustment mechanism that is mounted to the proximal end of the stapler shaft. Tissue that is contained between the staple cartridge and the staple anvil is simultaneously stapled and cut when the actuating mechanism is actuated by the surgeon.

When performing an anastomosis using a circular stapler, the intestine is typically initially stapled using a conventional surgical stapler with double rows of staples being emplaced on either side of a target section (i.e., the diseased section or specimen) of intestine. The target section is typically simultaneously cut as the section is stapled. Next, after removing the specimen, the surgeon typically inserts the anvil into the proximal end of the lumen (i.e., intestine), proximal of the staple line. This is done by inserting the anvil head into an entry port cut into the proximal lumen (intestine) by the surgeon. On occasion, the anvil can be placed transanally, by placing the anvil head on the distal end of the stapler and inserting the instrument through the rectum. The proximal end of the intestine is then sutured to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge by drawing the anvil towards the staple cartridge. As the anvil moves toward the cartridge, the proximal and distal ends of the intestine are clamped therebetween. The stapler is then actuated causing the rows of staples to be driven through both ends of the intestine into forming contact with the anvil. Simultaneously, as the staples are driven and formed, the circular blade is driven through the intestinal tissue ends, cutting the ends adjacent to the inner row of staples. The surgeon then withdraws the stapler from the intestine and the anastomosis is complete.

The effective healing of a colorectal anastomosis can be challenged by several factors and conditions. For example, healing can be effected by the presence of bacterial contaminates in the area of the anastomosis. In general practice, the success rate of the anastomosis tends to improve with the patient's return to mobility. It is desirable for the patient to return to contents passing as soon as possible. One inhibitor to contents passing is the risk of "stricture". If the colon contents are unable to pass the staple line or if they dramatically stress the staple line, a tear, rupture or leak can occur. A linear expandable line of staples was developed for highly expanding organs like the lungs. However, such staple configurations do not lend themselves to use in connection with a circular stapler.

Figure 29:
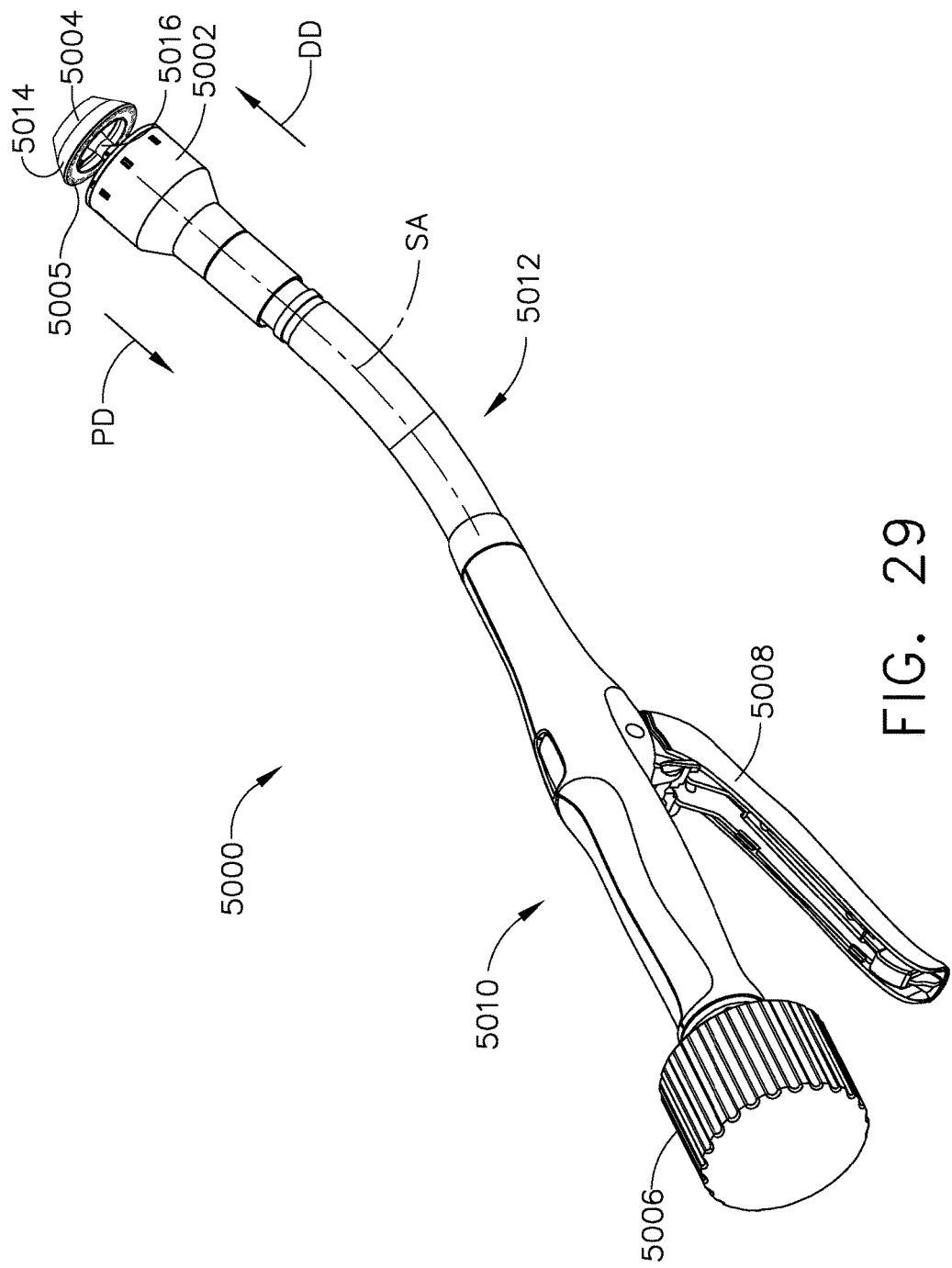
FIG. 29 is a perspective view of a circular stapling device.

FIG. 29 illustrates one form of circular stapler or stapling device generally designated as 5000. A variety of circular stapling devices are well known and employed for installing surgical staples or fasteners. Thus, various details concerning the construction and operation of circular stapling devices will not be discussed in detail herein beyond what may be necessary to understand the innovations and arrangements disclosed herein and depicted in the appended Figures. More details regarding circular fastener and stapling devices may be found in U.S. Pat. No. 7,665,647, entitled SURGICAL CUTTING AND STAPLING DEVICE WITH CLOSURE APPARATUS FOR LIMITING MAXIMUM TISSUE COMPRESSION FORCE, which has been incorporated herein in its entirety as well as other U.S. patents incorporated by reference herein. In general, the circular stapling device 5000 shown in FIG. 29 includes a head 5002, an anvil 5004, an adjustment knob assembly 5006 and a handle 5010 that supports a trigger 5008 thereon. The handle assembly 5010 is coupled to the head 5002 by an arcuate shaft assembly 5012. In the illustrated arrangement, the trigger 5008 is pivotally supported by handle assembly 5010 and is used to operate the stapler 5000 when a safety mechanism (not illustrated) is released. When trigger 5008 is activated, a firing mechanism is movably advanced within the shaft assembly 5012 so that staples or fasteners are expelled, or deployed, from the head 5002 into forming contact with an anvil forming undersurface 5005 of the anvil 5004. Simultaneously, a circular knife (not viewable in FIG. 29) that is operably supported within head 5002 is advanced distally toward the anvil 5004 and serves to cut the tissue that has been clamped between the head 5002 and anvil 5004 in a known manner. Stapling device 5000 is then removed from the surgical site leaving the stapled tissue in place.

As can also be seen in FIG. 29, the anvil 5004 includes circular body portion 5014 that has an anvil shaft 5016 protruding therefrom. The anvil shaft 5016 is configured to be removably attached to a trocar shaft 5050 operably supported within the shaft assembly 5012. See FIG. 29A. As is known, the trocar shaft 5050 is movably supported with the shaft assembly 5012 and operably interfaces with the adjustment knob assembly 5006 that is rotatably supported on the handle assembly 5010. The anvil shaft 5016 may be removably attached to the trocar shaft 5050 by retention clips 5052 or other releasable fastening arrangements may also be employed to removably affix the anvil shaft 5016 to the trocar shaft 5050. Once the anvil shaft 5016 has been attached to the trocar shaft 5050, the clinician can move the anvil 5004 toward and away form the head 5002 by rotating the adjustment knob 5006 in the appropriate rotary direction.

Figure 29A:
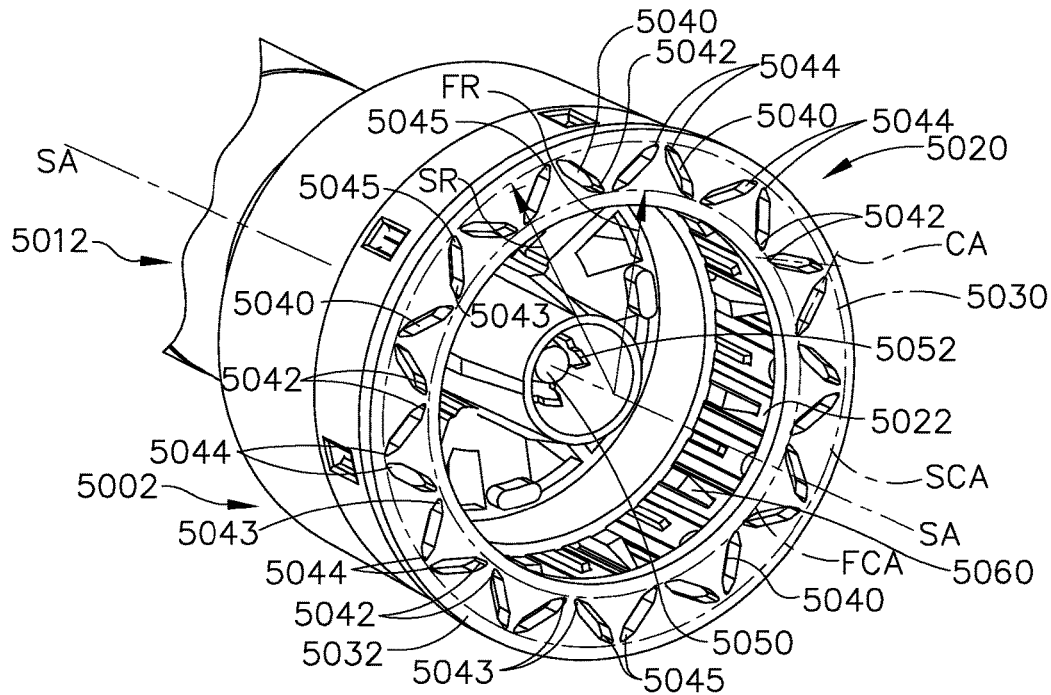
FIG. 29A is perspective view of a portion of a stapling head of a circular stapling device and a fastener cartridge assembly.

FIG. 29A illustrates a head 5002 that has a unique and novel fastener cartridge assembly 5020 operably mounted therein. As can be seen in that Figure, the fastener cartridge assembly 5020 includes a cartridge body 5022 that includes a circular deck 5030. The circular deck 5030 may form a planar surface 5032 that is arranged to confront the staple forming undersurface 5005 of the anvil 5004 when the anvil shaft 5016 is attached to the trocar shaft 5050. A plurality of fastener cavities 5040 are provided in the circular deck 5030 and are configured to receive at least one surgical staple or surgical fastener therein (not shown) that is operably supported on a driver assembly 5060 movably supported in the body 5022 of the fastener cartridge assembly 5020. The driver assembly 5060 is operably coupled to a corresponding movable portion of the shaft assembly 5012 that operably interfaces with the trigger 5008. Activation of the trigger 5008, for example, will result in the axial movement of the driver assembly 5060 in the distal direction "DD". Movement of the driver assembly 5060 in the distal direction "DD" will result in the movement or expulsion of the surgical staple(s) or fastener(s) supported in each fastener cavity 5040 into forming contact with the staple forming undersurface 5005 on the anvil 5004.

Still referring to FIG. 29A, for example, each fastener cavity 5040 includes two cavity ends 5042, 5044. In the illustrated arrangement, each cavity end 5042, which may also be referred to herein as a "first cavity end" is positioned on a first circular axis "FCA" that has a first radius "FR". The first radius "FR" may be measured from the instrument shaft axis "SA". Also in the illustrated arrangement, each cavity end 5044, which may also be referred to herein as a "second cavity end" is positioned on a second circular axis "SCA" that has a second radius "SR" that is different from the first radius "FR". In the illustrated example, the second radius "SR", which is also measured from the shaft axis "SA", is greater than the first radius "FR". Also in the illustrated embodiment, each fastener cavity 5040 includes a cavity axis "CA". In the illustrated embodiment, each fastener cavity 5040 is arranged in the circular deck 5030 relative to the first circular axis "FCA" and the second circular axis "SCA" such that each the cavity axis "CA" forms an acute angle with the first circular axis "FCA" and the second circular axis "SCA". Stated another way, the cavity ends 5042 of adjacent fastener cavities 5040 are adjacent to each other and the ends 5044 of the same fastener cavities 5040 are spaced form each other. Such arrangement may be referred to herein as a "zigzag" orientation. In other arrangements, however, the cavity axis "CA" may be perpendicular to the first and second circular axes "FCA" and "SCA".

In the arrangement illustrated in FIG. 29A, each cavity end 5042, 5044 may be V-shaped such that they generally terminate in a point. For example, each cavity end 5042 may generally terminate in a point 5043 and each end 5044 may terminate in a point 5045. Points 5043 may be positioned on or intersect with the first circular axis "FCA" and points 5045 may be positioned on or intersect with the second circular axis "SCA". Such cavity arrangements result in the application of the surgical staples or fasteners in a similar pattern with the tissue. In the illustrated arrangement, the fastener cavities 5040 each support one surgical staple or surgical fastener therein. In other arrangements, however, more than one staple or fastener may be supported in each cavity. The fastener cartridge assembly 5020 employs like-sized staples in each fastener cavity 5040. In other arrangements, different sizes of surgical staples or fasteners may be employed in the fastener cartridge assembly. The surgical staples that may be employed, for example, include two staple legs that extend from a central body portion or crown. The legs maybe received in the V-shaped ends 5042, 5044 of the fastener cavity 5040 such that when they are ejected out of the cavity 5040, the legs extend through the first or second circular axes, which ever the case may be. These staple orientations may address some of the concerns associated with staple stricture discussed above. In particular, the staple configuration formed when employing the fastener cartridge assembly 5020 may allow the staple line to expand and flex more like the original colon than a common staple line. For example, the staples or fasteners may twist as they are pulled radially allowing them to minimize the stress on the healing zones and maximize the flexibility and strength.

Figure 30:
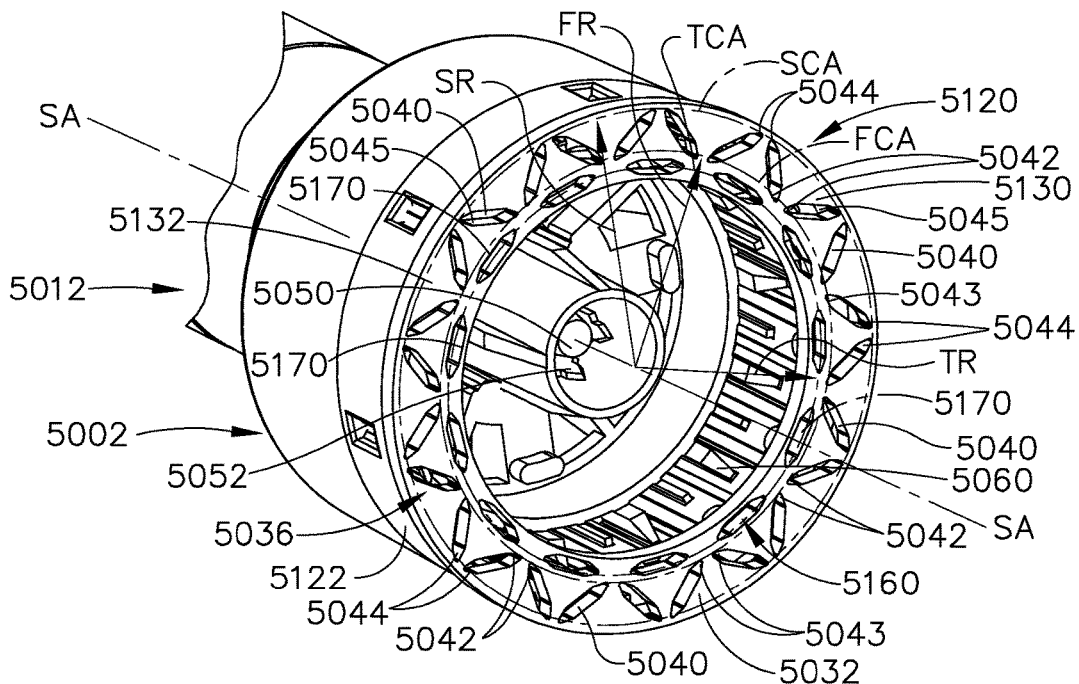
FIG. 30 is a perspective view of portion of a stapling head of a circular stapling device and another fastener cartridge assembly.

Another area of concern associated with colorectal anastomosis procedures relates to radial leakage through the attachment areas. The above-described fastener cartridge assembly 5020 may also address this area of concern. Another fastener cartridge assembly 5120 is shown in FIG. 30 and may also address the various problems and concerns described above. As can be seen in that Figure, the fastener cavities are arrangement in an "asymmetric pattern" wherein the staples applied through the inner ring or inner circular array of cavities function differently from those staples or fasteners applied through the outer ring or outer circular array of cavities.

More specifically and with reference to FIG. 30, the fastener cartridge assembly 5120 includes a cartridge body 5122 that includes a circular deck 5130. The circular deck 5130 may form a planar surface 5132 that is arranged to confront the staple forming undersurface 5005 of the anvil 5004 when the anvil shaft 5016 is attached to the trocar shaft 5050. A first ring 5036 of first cavities 5040 are provided in the circular deck 5130 and a second ring 5160 of second cavities 5170 are provided through the cartridge deck 5130 as shown. Each of the first and second cavities 5040, 5170 are configured to receive at least one surgical staple or surgical fastener therein (not shown) that is operably supported on a driver assembly 5060 movably supported in the body 5122 of the fastener cartridge assembly 5120.

Each fastener cavity 5040 includes two cavity ends 5042, 5044. Each cavity end 5042 is positioned on a first circular axis "FCA" that has a first radius "FR". The first radius "FR" may be measured from the instrument shaft axis "SA". Each cavity end 5044 is positioned on a second circular axis "SCA" that has a second radius "SR" that is different from the first radius "FR". In the illustrated example, the second radius "SR", which is also measured from the shaft axis "SA", is greater than the first radius "FR". Each fastener cavity 5040 includes a cavity axis "CA". In the illustrated embodiment, each fastener cavity 5040 is arranged in the circular deck 5130 relative to the first circular axis "FCA" and the second circular axis "SCA" such that each the cavity axis "CA" forms an acute angle with the first circular axis "FCA" and the second circular axis "SCA". Stated another way, the cavity ends 5042 of adjacent fastener cavities 5040 are adjacent to each other and the ends 5044 of the same fastener cavities 5040 are spaced form each other. Such arrangement may be referred to herein as a "zigzag" orientation. In other arrangements, however, the cavity axis "CA" may be perpendicular to the first and second circular axes "FCA", "SCA".

Also in the arrangement illustrated in FIG. 30, each cavity end 5042, 5044 may be V-shaped such that they generally terminate in a point. For example, each cavity end 5042 may generally terminate in a point 5043 and each end 5044 may generally terminate in a point 5045. Points 5043 may be positioned on or intersect with the first circular axis "FCA" and points 5045 may be positioned on or intersect with the second circular axis "SCA". Such cavity arrangements result in the application of the surgical staples or fasteners in a similar pattern with the tissue. Also in the illustrated arrangement, the second ring 5160 includes a plurality of second fastener cavities 5170 that are aligned on a third circular axis "TCA" that is arranged at a third radius "TR" from the shaft axis "SA". In the illustrated arrangement, the third radius "TR" is less that the first and second radiuses. In other arrangements, however, the third radius "TR" is greater than the first radius. In further arrangements, however, the third radius "TR" is greater than the first and second radiuses.

The unique and novel fastener cartridge assembly 5120 serves to orient the staples or fasteners in the tissue such that they would be "tunable" relative to the amount of expansion applied to the staple line. The surgical staples that may be employed, for example, include two staple legs that extend from a central body portion or crown. The legs maybe received in the V-shaped ends of the fastener cavity such that when they are ejected out of the cavity, the legs extend through the first circular axis "FCA", the second circular axis "SCA" or the third circular axis "TCA", whichever the case may be. These staple orientations may result in an improvement to the issues associated with staple stricture discussed above. For example, one ring of staples or fasteners (e.g., the second ring 5160) provides the standard sealing features and the first ring 5036 may be more aligned to the radial and flexibility aspects of the staple line. Such arrangement therefore, may also provide the same or similar advantages discussed above with respect to fastener cartridge assembly 5020.

Figure 31:
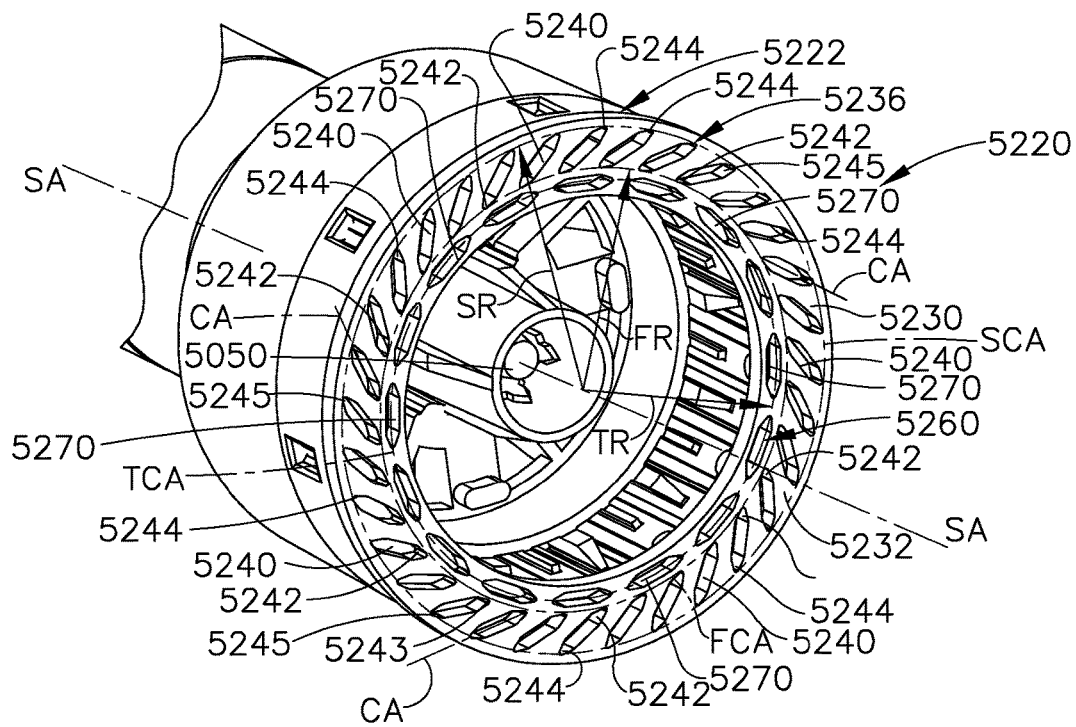
FIG. 31 is a perspective view of portion of a stapling head of a circular stapling device and another fastener cartridge assembly.

FIG. 31 depicts another unique and novel fastener cartridge assembly 5220 that may also address the various problems and concerns described above. As can be seen in that Figure, the fastener cavities are arrangement in an "asymmetric pattern" wherein the staples applied through the inner ring of cavities function differently from those staples or fasteners applied through the outer ring of cavities.

More specifically and with reference to FIG. 31, the fastener cartridge assembly 5220 includes a cartridge body 5222 that includes a circular deck 5230. The circular deck 5230 may form a planar surface 5232 that is arranged to confront the staple forming undersurface 5005 of the anvil 5004 when the anvil shaft 5016 is attached to the trocar shaft 5050. A first ring 5236 of first cavities 5240 are provided in the circular deck 5230 and a second ring 5260 of second cavities 5270 are provided through the cartridge deck 5230 as shown. Each of the first and second cavities 5240, 5270 are configured to receive at least one surgical staple or surgical fastener therein (not shown) that is operably supported on a driver assembly 5060 that is movably supported in the body 5222 of the fastener cartridge assembly 5220.

Each fastener cavity 5240 includes two cavity ends 5242, 5244. Each cavity end 5242 is positioned on a first circular axis "FCA" that has a first radius "FR". The first radius "FR" may be measured from the instrument shaft axis "SA". Each cavity end 5244 is positioned on a second circular axis "SCA" that has a second radius "SR" that is different from the first radius "FR". In the illustrated example, the second radius "SR", which is also measured from the shaft axis "SA", is greater than the first radius "FR". Each fastener cavity 5240 includes a cavity axis "CA". In the illustrated embodiment, each fastener cavity 5240 is arranged in the circular deck 5230 relative to the first circular axis "FCA" and the second circular axis "SCA" such that each the cavity axis "CA" forms an acute angle with the first circular axis "FCA" and the second circular axis "SCA".

Also in the arrangement illustrated in FIG. 31, each cavity end 5242, 5244 may be V-shaped such that they generally terminate in a point. For example, each cavity end 5242 may generally terminate in a point 5243 and each end 5244 may generally terminate in a point 5245. Points 5243 may be positioned on or intersect with the first circular axis "FCA" and points 5245 may be positioned on or intersect with the second circular axis "SCA". Such cavity arrangements result in the application of the surgical staples or fasteners in a similar pattern with the tissue. Also in the illustrated arrangement, the second ring 5260 includes a plurality of second fastener cavities 5270 that are aligned on a third circular axis "TCA" that is arranged at a third radius "TR" from the shaft axis "SA". In the illustrated arrangement, the third radius "TR" is less that the first and second radiuses. In other arrangements, however, the third radius "TR" is greater than the first radius. In further arrangements, however, the third radius "TR" is greater than the first and second radiuses. These staple orientations may result in an improvement to the issues associated with staple structure discussed above. In particular, the staple configuration formed when employing the fastener cartridge assembly 5220 may allow the staple line to expand and flex more like the original colon than a common staple line. For example, the staples or fasteners may twist as they are pulled radially allowing them to minimize the stress on the healing zones and maximize the flexibility and strength.

Figure 58:
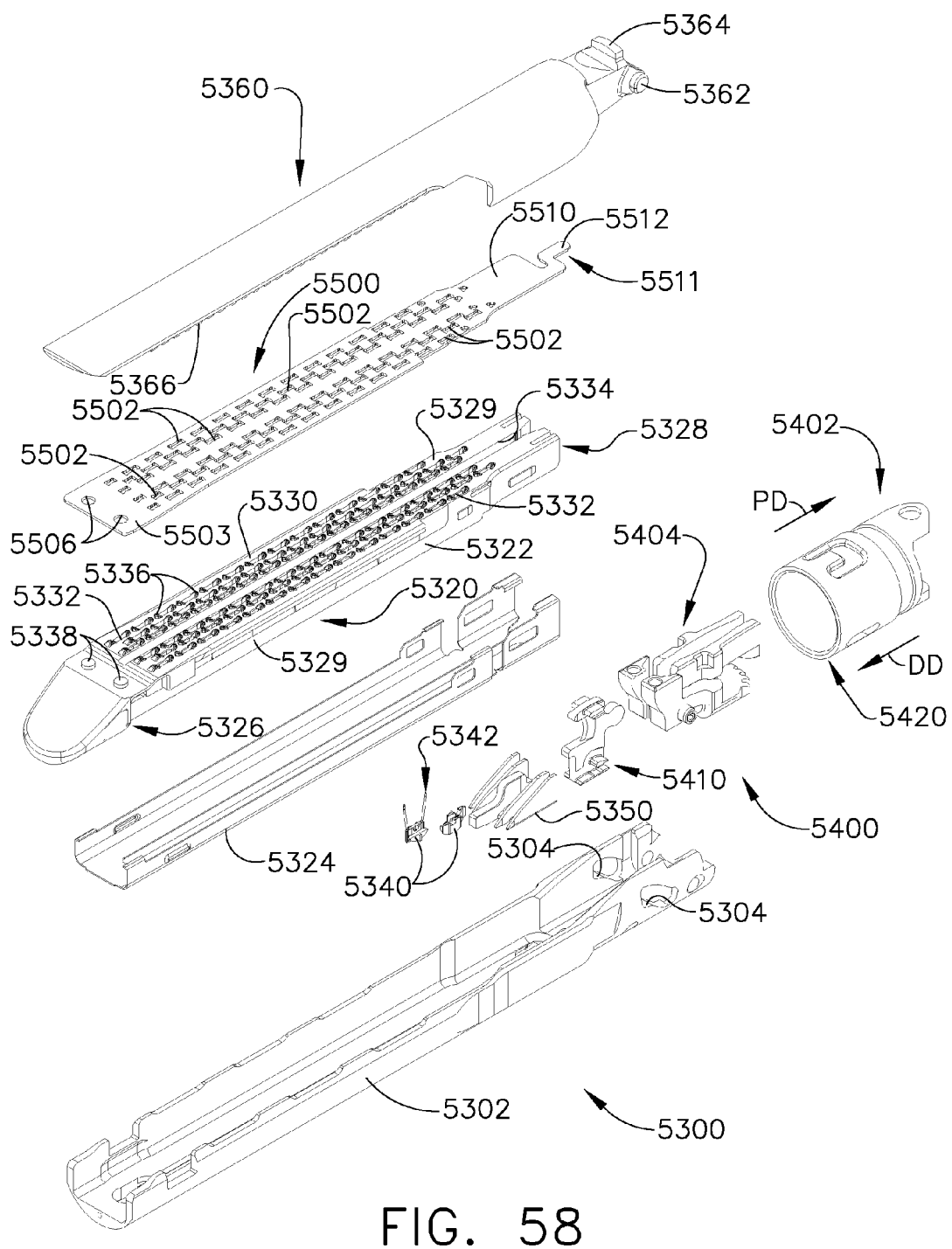
FIG. 58 is an exploded perspective view of an end effector and a portion of a surgical stapling instrument.

Adjunct films/buttress materials have been shown to improve hemostasis and pneumostasis by sealing around the staple tips. In many applications, buttress material is employed to stiffen and/or strengthen soft tissue. A variety of buttress material arrangements have been developed and configured for arrangement on the surgical staple cartridge or the anvil of the surgical stapling device. Attaching the buttress member to the cartridge or anvil and then releasing the buttress material therefrom can be challenging. FIG. 58 illustrates a surgical end effector 5300 and portions of a surgical cutting and fastening instrument 5400. The end effector 5300 employs a unique and novel arrangement for attaching a buttress member 5500 to the surgical staple cartridge 5320 and releasing it therefrom. Examples of surgical cutting and fastening instruments of the type depicted in FIG. 58 are disclosed in U.S. patent application Ser. No. 14/318,991, entitled SURGICAL FASTENER CARTRIDGES WITH DRIVER STABILIZING ARRANGEMENTS, filed on Jun. 30, 2014, the entire disclosure of which is hereby incorporated by reference herein. Further details beyond those which are required to understand the construction and use of the end effector 5300 may be gleaned from reference to that document as well as the numerous other documents incorporated by reference therein.

As can be seen in FIG. 58, the end effector 5300 depicted therein includes an elongate staple channel 5302 that is configured to operably support a staple cartridge 5320 therein. The elongate staple channel 5302 is coupled to a spine portion 5404 that is operably supported within an elongate shaft assembly 5402 of the surgical stapling instrument 5400. The staple cartridge 5320 includes a cartridge body 5322 that may be fabricated from a polymer material. In the illustrated embodiment, a metal bottom tray 5324 is attached to the cartridge body 5322. The cartridge body 5322 includes a deck 5330 that has a plurality of staple cavities 5332 defined therein. Each staple cavity 5332 is configured to removably store a staple therein. The cartridge body 5322 further includes a longitudinal slot that is configured to removably receive a firing member 5410 therein. The cartridge body 5320 can further comprise a distal end 5326, a proximal end 5328, and opposing longitudinal sides 5329 extending between the distal end 5326 and the proximal end 5328. In various instances, each longitudinal side 5329 can comprise a contiguous or continuous edge without interruptions defined therein.

Located within each staple cavity 5332 is a staple 5342 that is supported on a corresponding staple driver 5340 that is movably supported within the cartridge body 5322. The staple drivers 5340 are lifted upwardly when the firing member 5410 is driven distally through the staple cartridge 5320. As discussed in further detail in U.S. patent application Ser. No. 14/318,991, the firing member 5410 is configured to advance a staple sled 5350 distally to lift the staple drivers 5340 and the staples 5342 upward and out of the staple cavity 5332. The end effector 5300 further includes an anvil 5360 that is mounted to the elongate staple channel 5302. In the illustrated embodiment, the anvil 5360 includes a pair of trunnions 5362 that are movably received in trunnion slots 5304 in the elongate staple channel 5302. As can be further seen in FIG. 58, the anvil 5360 includes an anvil tab 5364 that interacts with a closure tube segment 5420. Movement of the closure tube segment 5420 in the distal direction "DD" can move the anvil 5360 in a direction toward the staple cartridge 5320. Movement of the closure tube 5420 in the proximal direction "PD" causes the anvil to move away from the staple cartridge 5320. Other embodiments may employ a cartridge and anvil arrangement wherein the anvil is stationary (e.g., non-movably affixed to the elongate shaft of the surgical device) and the elongate channel and/or the staple cartridge are movable toward and away from the anvil.

Figure 59:
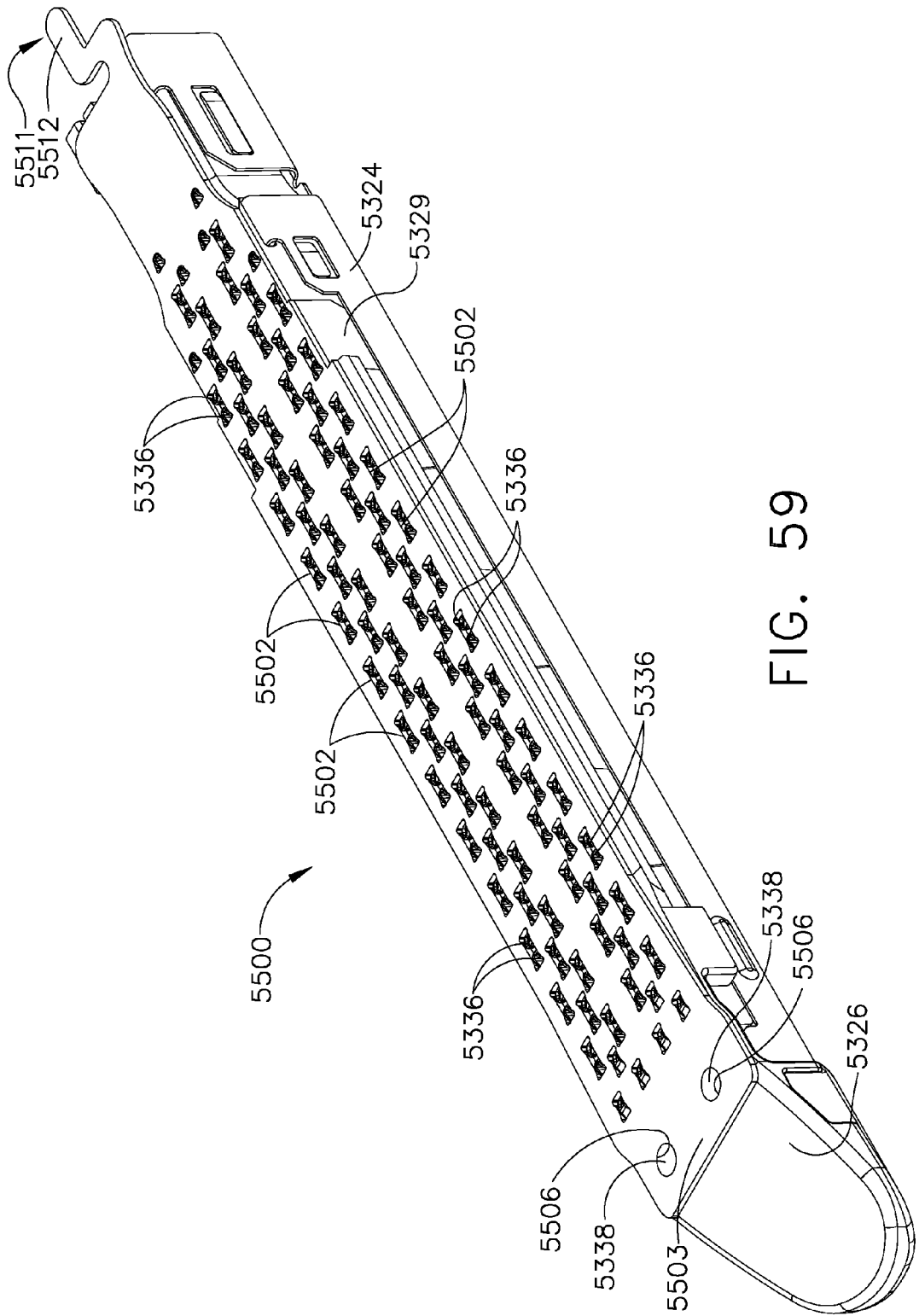
FIG. 59 is a perspective view of a surgical staple cartridge with a buttress member supported on the deck of the staple cartridge in a position wherein the buttress may be removed from the cartridge.

As can be seen in FIGS. 58 and 59, a buttress member 5500 is configured to be received between the surgical staple cartridge 5320 and the anvil 5360. Stated more precisely, the buttress member 5500 is configured to be received between the staple-forming undersurface 5366 of the anvil 5360 and the deck 5330 of the staple cartridge 5320. In the illustrated embodiment, the buttress member 5500 is configured to be mounted in tension on the deck 5330 of the staple cartridge 5320. The buttress material comprising the buttress member 5500 may comprise Gore SeamGuard material, Synovis Peri-Strips material, and/or polyurethane, for example. Other suitable buttress or adjunct materials are disclosed in U.S. patent application Ser. No. 14/318,991, entitled SURGICAL FASTENER CARTRIDGES WITH DRIVER STABILIZING ARRANGEMENTS, filed on Jun. 30, 2014, the entire disclosure of which was previously incorporated by reference herein. Various other suitable buttress and adjunct materials are also disclosed in U.S. patent application Ser. No. 13/763,095, entitled LAYER ARRANGEMENTS FOR SURGICAL STAPLE CARTRIDGES, filed on Feb. 28, 2013, the entire disclosure of which is hereby incorporated by reference herein. The entire disclosures of U.S. patent application Ser. No. 13/531,619, entitled TISSUE STAPLER HAVING A THICKNESS COMPENSATOR COMPRISING INCORPORATING A HEMOSTATIC AGENT, filed on Jun. 25, 2012, U.S. patent application Ser. No. 13/531,623, entitled TISSUE STAPLER HAVING A THICKNESS COMPENSATOR INCORPORATING AN OXYGEN GENERATING AGENT, filed on Jun. 25, 2012, U.S. patent application Ser. No. 13/531,627, entitled TISSUE STAPLER HAVING A THICKNESS COMPENSATOR INCORPORATING AN ANTI-MICROBIAL AGENT, filed on Jun. 25, 2012, and U.S. patent application Ser. No. 13/531,630, entitled TISSUE STAPLER HAVING A THICKNESS COMPENSATOR INCORPORATING AN ANTI-INFLAMMATORY AGENT, filed on Jun. 25, 2012, are also incorporated by reference herein.

In the illustrated embodiment, the staple cartridge 5320 includes projections 5336 that extend upward from the deck 5330 adjacent each staple cavity 5332 in the various manners and arrangements that are described in detail in U.S. patent application Ser. No. 14/318,991. In other embodiments, the staple cartridge does not have such projections. In the illustrated embodiment, the buttress member 5500 includes holes 5502 therein that correspond to the projections 5336. See, e.g., FIGS. 61 and 62. As can be seen in those Figures, however, the holes 5502 only accommodate the projections 5336 such that the buttress material spans the areas that correspond to at least portions of the crowns of the staples supported in the cavities. Those portions of buttress material that correspond to the staple crown portions are generally identified as 5504 in FIGS. 61 and 62.

The buttress member 5500 includes means for releasably affixing the buttress member 5500 to the cartridge body 5322 such that the buttress member 5500 is retained thereon in tension prior to the actuation of the surgical instrument and then is released from the cartridge body 5322 when the surgical instrument is actuated or "fired". For example, as can be seen in FIG. 58, the buttress member 5500 includes a distal end 5503 that has at least one distal retention feature 5506 therein. In the illustrated arrangement, two distal holes 5506 are provided in the distal end 5503 and are configured to receive corresponding retention members 5338 protruding from the distal end 5326 of the cartridge body 5322. As shown in FIGS. 59 and 60, the retention members 5338 are configured to be received within the distal holes 5506 in the distal end portion 5503 of the buttress member 5500 to releasably retain the distal end of the buttress member 5500 on the distal end portion 5326 of the cartridge 5320. Other forms of releasable retention members (shapes, numbers, sizes, configurations) and arrangements may also be employed to releasably retain the buttress member 5500 on the staple cartridge 5320 when a tension force is applied to the buttress member 5500 in the proximal and/or distal directions.

Figure 63:
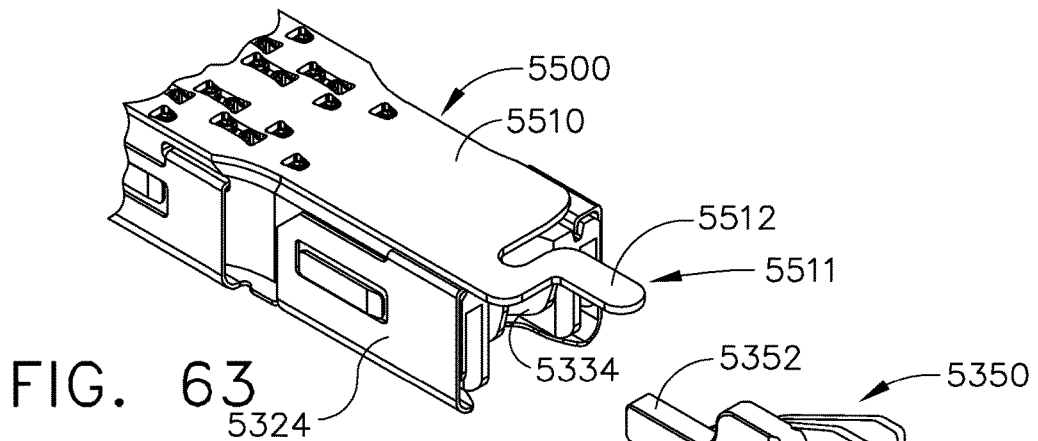
FIG. 63 is a perspective view of a proximal end of the surgical staple cartridge and buttress member of FIGS. 59-62.
Figure 64:
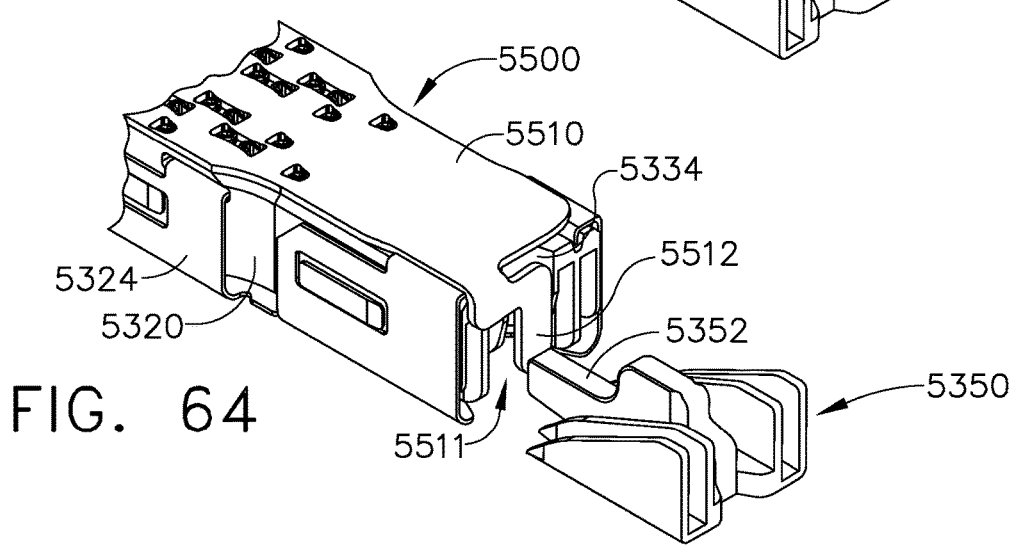
FIG. 64 is another perspective view of the proximal end of the surgical staple cartridge and buttress member of FIGS. 59-63 with the retaining tab folded over for insertion into the longitudinal slot in the cartridge.
Figure 65:
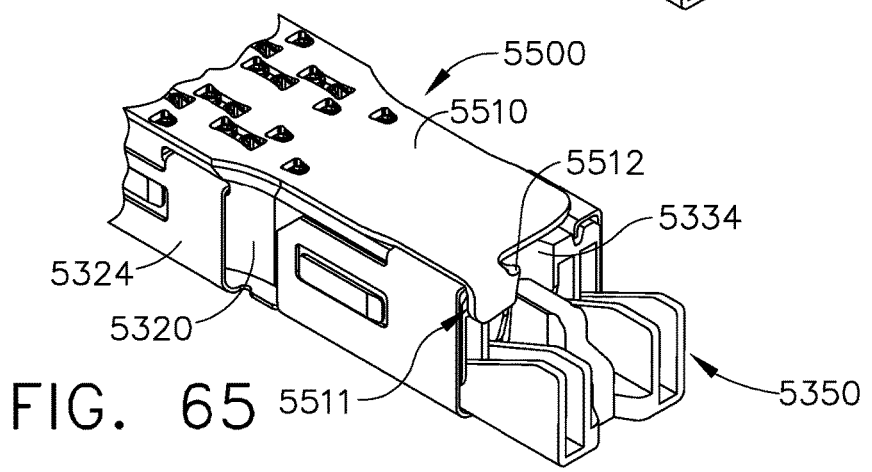
FIG. 65 is another perspective view of the proximal end of the surgical staple cartridge and buttress member of FIGS. 59-64 with the retaining tab inserted into the longitudinal slot and retained therein by the staple sled.

Turning to FIGS. 63-65, the buttress member 5500 includes a proximal end portion 5510 that has a proximal retention feature 5511 thereon. In the illustrated embodiment, the proximal retention feature 5511 comprises at least one retaining tab 5512 that protrudes proximally therefrom. The retaining tab 5512 is located such that when the holes 5506 are inserted over the retention members 5338 on the cartridge body 5322 and the buttress member 5500 is received on the cartridge deck 5330, the retaining tab 5512 is aligned with the elongate slot 5334 in the cartridge body 5322. See FIG. 64. The retaining tab 5512 is folded over the proximal end of the cartridge body and retained within the elongate slot 5334 by the staple sled 5350 when the staple sled 5350 is in its proximal starting position within the cartridge 5320. The staple sled 5350 may be of the type and construction disclosed in U.S. patent Ser. No. 14/318,991 which includes a stabilizing member 5352 that extends distally to stabilize the sled 5350 and prevent and/or inhibit the rocking or rotation of the staple sled 5350. As can be seen in FIG. 65, the retaining tab 5512 is held within the elongate slot 5334 by the stabilizing member 5352 and/or other portions of the staple sled 5350. Such arrangement serves to retain the buttress member 5500 in tension on the staple deck 5330. Stated another way, the buttress member 5500 may be stretched between the retention members 5338 and the proximal end 5328 of the staple cartridge 5320. When the clinician actuates the surgical instrument to commence the firing process, the firing member 5410 is advanced distally in the distal direction "DD". The firing member 5410 interfaces with the staple sled 5350 and, as discussed in U.S. patent application Ser. No. 14/318,991, the firing member 5410 moves the staple sled 5350 distally through the staple cartridge 5320 to drive the staple drivers 5340 upward such that the staples 5342 supported thereon are driven into forming contact with the underside 5366 of the anvil 5360 and the tissue clamped between the anvil 5360 and the staple cartridge 5320 is severed by the cutting member 5410. Once the staple sled 5350 has moved out of retaining engagement with the retention tab 5512, the retention tab 5512 is released enabling the buttress material 5500 to be removed from the staple cartridge 5320 with the stapled tissue. Such arrangement serves to release the tension in the buttress material 5500 at the beginning of the firing process. In addition, such buttress arrangement requires no additional releasing parts or configurations.

Existing stapling technology is not particularly well-suited for use on tissues that experience stretching during the healing process. For example, in thoracic parenchymal stapling, the staple lines are fired on lungs in a collapsed configuration. After the procedure is complete, the lung is inflated which often results in the doubling of the surface area of the lung. Existing stapling technology generally does not have the capacity to stretch to the same extent as the lung tissue. This may result in a dramatic strain gradient in the immediate vicinity of the staple line which can lead to high stresses within the staple line, particularly in the row of staples furthest from the cut edge. Thus, there is a need for technologies that allow the staple line to stretch and/or increase in length in an effort to relieve the strain gradient and the associated stress to eliminate or at least reduce the potential source of air leaks.

Figure 66:
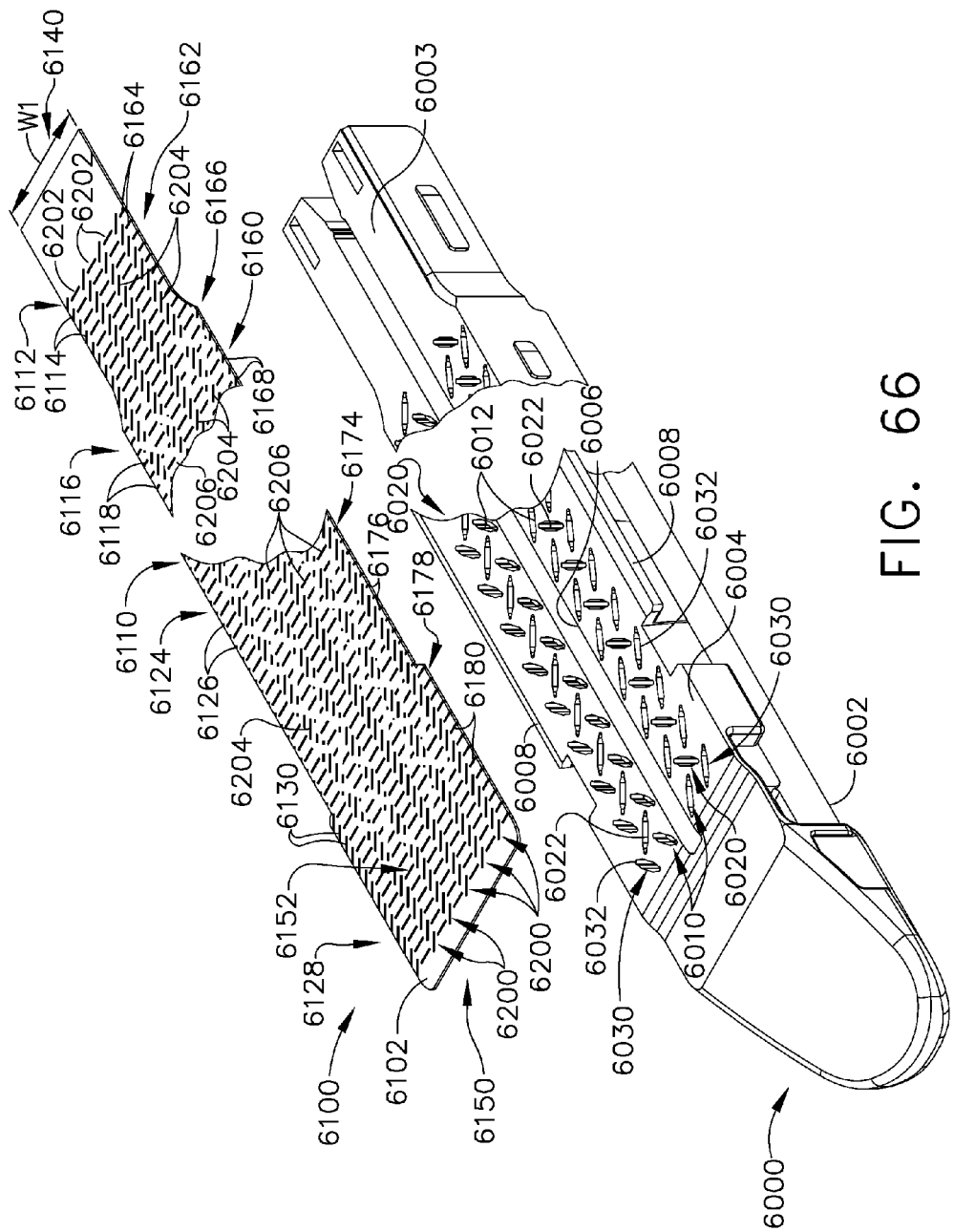
FIG. 66 is an exploded assembly view of another surgical staple cartridge and another buttress member.
Figure 67:
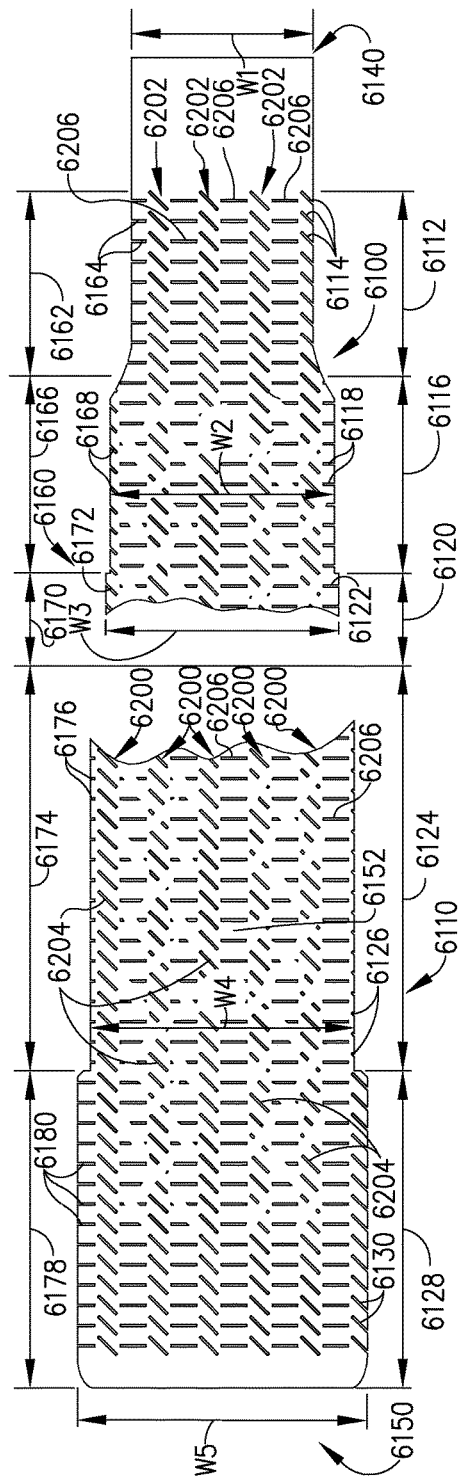
FIG. 67 is a bottom view of the buttress member of FIG. 66.
Figure 68:
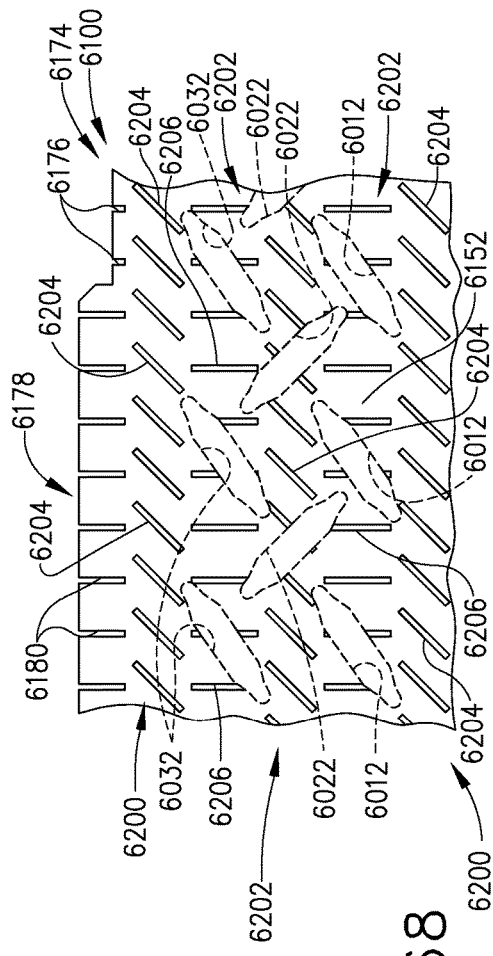
FIG. 68 is an enlarged view of a portion of the buttress member of FIG. 67, with positions of the underlying staple cavities in the staple cartridge shown in broken lines.

Adjunct films/buttress materials have been shown to improve hemostasis and pneumostasis by sealing around the staple tips. In many applications, buttress material is employed to stiffen and/or strengthen soft tissue. However, existing buttress materials may not be sufficiently elastic so as not to impede the compliance of the elastic staple line. FIGS. 66-68 illustrate one form of buttress material 6100 that may address such issues. As can be seen in those Figures, the buttress material 6100 includes a buttress body 6102 that is sized to be operably received on a deck 6004 of a surgical staple cartridge 6000. In the illustrated example, the surgical staple cartridge 6000 includes a cartridge body 6002 that defines the deck 6004. The cartridge body 6002 includes a centrally disposed, elongate slot 6006 that is configured to receive a tissue cutting member (not shown) therethrough. A plurality of staple pockets or staple cavities is provided in the deck 6004 on each side of the elongate slot 6006. As shown, first rows 6010 of first cavities 6012 are provided on each side of the elongate slot 6006. The first cavities 6012 in each first row 6010 are parallel to each other. Each of the first cavities 6012 is arranged at an angle relative to the elongate slot 6006 and is adjacent thereto. The illustrated cartridge body 6002 further includes two rows 6020 of second staple cavities 6022 that are arranged at angles relative to the first staple cavities 6012. Two rows 6030 of third staple cavities 6032 are also provided in the cartridge body 6002 as shown. In at least one form, the third staple cavities 6032 are parallel with corresponding first staple cavities 6012. Other staple or fastener cavity arrangements could be employed, however. In addition, the staple cartridge body 6002 may have lateral ledges 6008 protruding laterally therefrom. As can also be seen in FIG. 66, the proximal end 6003 of the cartridge body 6002 is narrower than the remaining portion of the cartridge body 6002.

In the illustrated embodiment, the buttress body 6102 includes four edges 6110, 6140, 6150, 6160 and a central portion 6152. At least two of the edges 6110, 6140, 6150, 6160 include various edge notch configurations. In the illustrated embodiment, edges 6110, 6160 include edge notches therein. More specifically as can be seen in FIG. 67, a first plurality of first edge notches 6114 are formed in a first portion 6112 of the first edge 6110. In the illustrated embodiment, the first edge notches 6114 extend inward from the first edge portion 6112 at a first acute angle 6115 ("notch angle") and are parallel to each other. As can be further seen in FIGS. 66 and 67, second edge notches 6118 extend inward from a second portion 6116 of the first edge portion 6112. In one arrangement, for example, the second edge notches 6118 extend perpendicularly inward ("notch angle") from the second portion 6116. As can be further seen in FIGS. 66 and 67, third edge notches 6122 extend inward from a third portion 6120 of the first edge portion 6110. In one arrangement, for example, the third edge notches 6122 extend perpendicularly inward ("notch angle") from the third portion 6120. As can be further seen in FIGS. 66 and 67, fourth edge notches 6126 extend inward from a fourth portion 6124 of the first edge portion 6110. In one arrangement, for example, the fourth edge notches 6126 extend inward at an acute angle ("notch angle") from the fourth portion 6124. As can be further seen in FIGS. 66 and 67, fifth edge notches 6130 extend inward from a fifth portion 6128 of the first edge portion 6110. In one arrangement, for example, the fifth edge notches 6130 extend inward at an acute angle ("notch angle") from the fifth portion 6128.

Still referring to FIGS. 66 and 67, a series of primary edge notches 6164 extend inward from a primary portion 6162 of the second edge portion 6160. In the illustrated arrangement, the primary edge notches 6164 extend perpendicularly inward ("notch angle") from primary edge portion 6162. As can be further seen in FIGS. 66 and 67, secondary edge notches 6168 extend inward from a secondary portion 6166 of the second edge 6160. In one arrangement, for example, the secondary edge notches 6168 extend inward at an acute angle ("notch angle") from the secondary edge portion 6166. As can be further seen in FIGS. 66 and 67, tertiary edge notches 6172 extend inward from a tertiary portion 6170 of the second edge 6160. In one arrangement, for example, the tertiary edge notches 6172 extend inward at an acute angle ("notch angle") from the tertiary portion 6170. As can be further seen in FIGS. 66 and 67, quaternary edge notches 6176 extend inward from a quaternary portion 6174 of the second edge 6160. In one arrangement, for example, the quaternary edge notches 6176 extend perpendicularly inward ("notch angle") from the quaternary portion 6174. As can be further seen in FIGS. 66 and 67, quinary edge notches 6180 extend inward from a quinary portion 6178 of the second edge portion 6160. In one arrangement, for example, the quinary edge notches 6180 extend perpendicularly inward ("notch angle") from the quinary portion 6178.

The buttress material 6100 illustrated in FIGS. 66 and 67 also has five different widths, W1, W2, W3, W4, W5 along the total length of the buttress 6100. W1 corresponds to edge portions 6112, 6162. W2 corresponds to edge portions 6116, 6166. W3 corresponds to edge portions 6120, 6170. W4 corresponds to edge portions 6124, 6174. W5 corresponds to edge portions 6128, 6178. Other buttress material embodiments may have a constant width or different numbers of widths that facilitate operational support on the staple cartridge and/or anvil of the surgical stapling instrument. In addition, the numbers, shapes, sizes and arrangements of edge notches may vary depending upon the embodiment.

In the embodiment shown in FIGS. 66 and 67, the buttress material 6100 includes a plurality of cutout openings therein. As can be seen in those Figures, the cutouts are arranged in parallel rows. In particular, the cutouts 6204 in rows 6200 comprise slits that are arranged at an angle relative to the edge portions such that the cutouts 6204 in each row 6200 are parallel to each other. The cutouts 6204 may or may not extend completely through the buttress material 6100. Similarly, the cutouts 6206 in rows 6202 comprise slits that are perpendicularly transverse to the edge portions of the buttress material 6100. The cutouts 6206 may or may not extend completely through the buttress material 6100. In other embodiments, the number, shape, size, orientation, spacing, depth and location of such cutouts may vary.

Figure 69:
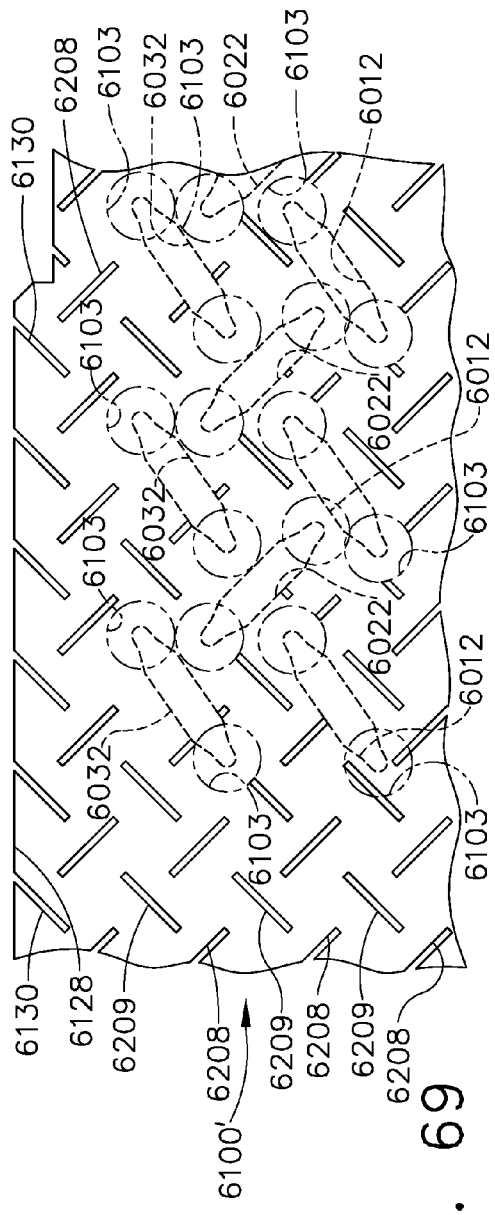
FIG. 69 is an enlarged view of a portion of another buttress member, with positions of the underlying staple cavities in the staple cartridge shown in broken lines.

FIG. 68 illustrates one cutout arrangement wherein the staple cavity positions 6012, 6022, and 6032 are shown in broken lines. As can be seen in that Figure, no portion of any cutouts 6204, 6206 is positioned over any one of the staple cavities, 6012, 6022, 6032 when the buttress material 6100 is positioned in registration on the deck 6004 of the surgical staple cartridge 6000. FIG. 69 illustrates a similar buttress material arrangement wherein the staple cavities 6012, 6022, and 6032 are shown in broken lines. The portions 6103 of the buttress material 6100' wherein the staple/fastener legs will ultimately penetrate through are also shown in broken lines. Portions 6103 may also be referred to herein as "staple penetration zones". As can be seen in that Figure, no portion of any of the cutouts 6208, 6209 is located over any or the staple penetration zones 6103. The cutouts 6208 and 6209 are arranged in longitudinal rows in the buttress material 6100'. The cutouts 6208 in each row are approximately parallel to each other and are arranged at an acute angle relative to the edges of the buttress material 6100'. Similarly, the cutouts 6209 in each row are approximately parallel to each other and are arranged such that they are perpendicular to the cutouts 6208 in adjacent rows. The cutouts 6208 may or may not extend completely through the buttress material 6100'. As can also be seen in FIG. 69 one entire row of cutouts 6208 is located between the locations of fastener cavities 6032 and the edge of the buttress material 6100' to facilitate further flexibility of the buttress material 6100'. As with the other embodiments, the number, shape, size, orientation, spacing, depth and location of such cutouts may vary.

Figure 70:
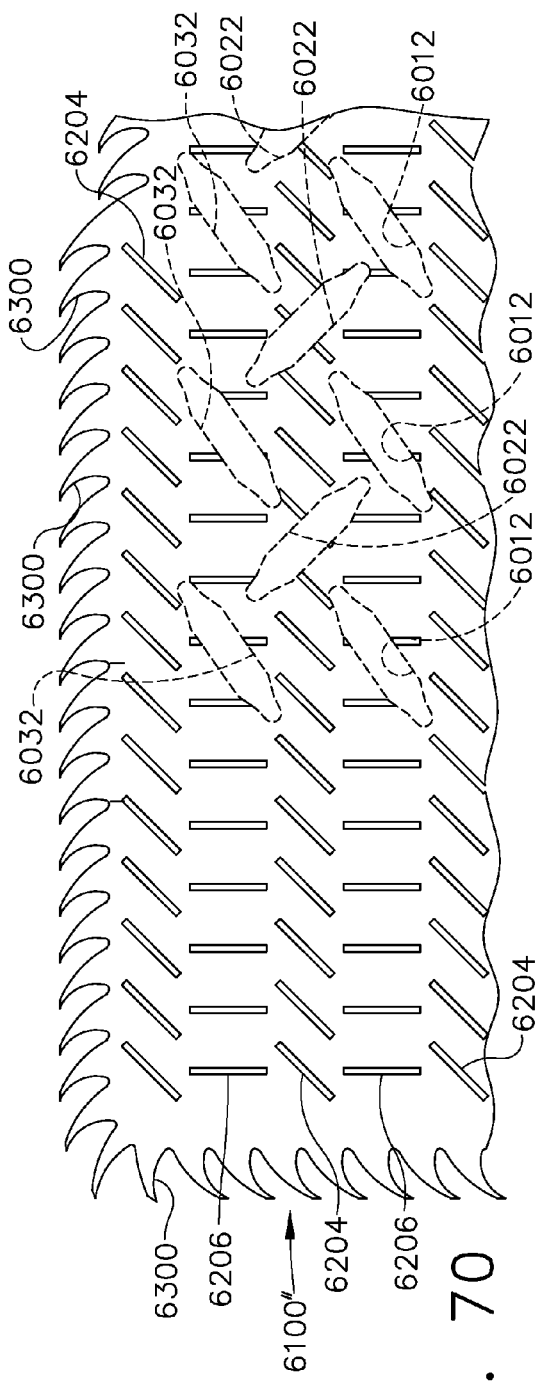
FIG. 70 is a top view of a portion of another buttress member, with positions of the underlying staple cavities in the staple cartridge shown in broken lines.

FIG. 70 illustrates another buttress member embodiment 6100". In this embodiment, the buttress material includes a plurality of edge notches 6300 that comprise undulating wave-like curves which form serpentine edges. Such edge notches/serpentine edges allow for rotation of staples while reducing material stress during expansion.

FIGS. 71 and 72 illustrates another buttress member 6400 that is fabricated out of a woven material that may be bioabsorbable or may not be bioabsorbable. Further, the buttress material may comprise any of the buttress materials described herein and include the unique and novel attributes described below. For example, the buttress member 6400 may include a hole or opening 6402 therethrough for cooperating with a correspondingly-shaped portion of the surgical staple cartridge or anvil (e.g., a post, protrusion, etc.) to support the buttress member 6400 in a desired orientation/registration relative to the staples/fasteners in the staple cartridge. In the illustrated arrangement, the buttress member 6400 includes a plurality of staple zones 6404, 6406, 6408 that are located therein for registration with corresponding 6012, 6022, 6032 fastener cavities in the surgical staple cartridge when the buttress member 6400 is supported on the cartridge deck. The staple zones may be formed by compressing the material and applying heat thereto to cause the material to permanently assume the compressed state. As can be seen in FIG. 72, the compressed staple areas (generally represented as 6410) have a smaller cross-sectional thickness than the adjacent non-compressed portions (generally represented as 6412) of the buttress member 6400. In addition, the buttress member 6400 may have linear edges 6420, 6422, 6424 and/or serpentine edge(s) 6426. The buttress member may have a shape that corresponds to the shape of the surgical staple cartridge and/or anvil of the surgical instrument.

All of the foregoing buttress member embodiments may be employed on the deck of the surgical staple cartridge or used in connection with an anvil of a surgical stapling device. All of the buttress members may have a shape that corresponds to the shape of the surgical staple cartridge and/or anvil and may have straight or linear edges or edge portions and/or wavy, jagged and or serpentine edges or a combination of such edge configurations. The buttress members may have a constant width or they may have a plurality of widths. The cutouts through the buttress material remove excess material to facilitate or allow for more deformation of the buttress, twisting, etc. with less stress throughout the buttress material during longitudinal expansion. Stated another way, the cutouts enable the buttress to "accordion" in the same manner as the staples themselves are moving. Serpentine or irregular edges allow for rotation of staples while reducing material stress during expansion. The buttress configurations described above comprise "softened structures" that allow for increased extensibility, while still sealing relevant regions. In addition, the buttress members described above not only don't inhibit staple twisting, but also allow the staples and adjunct (buttress) to move in the same manner when stretched. Such buttress member arrangements comprise buttress members that essentially comprise regions of various mechanical behaviors which allow for optimal performance of the staple lines.

FIGS. 73-78 illustrate another staple cartridge 6500 that is similar in construction to staple cartridge 6000 discussed above, except that staple cartridge 6500 additional includes a plurality of projections. In the illustrated example, the surgical staple cartridge 6500 includes a cartridge body 6502 that defines the deck 6504. The cartridge body 6502 is mounted within a bottom tray 6524 and includes a centrally disposed elongate slot 6506 that is configured to receive a tissue cutting member (not shown) therethrough. A plurality of staple pockets or staple cavities is provided in the deck 6504 on each side of the elongate slot 6506. As shown, first rows 6510 of first cavities 6512 are provided on each side of the elongate slot 6506. The first cavities 6512 in each first row 6510 are parallel to each other. Each of the first cavities 6512 is arranged at an angle relative to the elongate slot 6506 and is adjacent thereto. The illustrated cartridge body 6502 further includes two rows 6520 of second staple cavities 6522 that are arranged at angles relative to the first staple cavities 6512. Two rows 6530 of third staple cavities 6532 are also provided in the cartridge body as shown. In at least one form, the third staple cavities 6532 are parallel with corresponding first staple cavities 6512. The cartridge body 6502 further has two longitudinal sides 6508.

The cartridge body 6502 can further comprise a plurality of projections 6550 that extend from the deck surface 6504. Projections 6550 can be configured to engage tissue positioned intermediate the anvil 5360 and the cartridge 6500 and control the movement of the tissue relative to the cartridge 6500. Tissue can move relative to the cartridge 6500 in various instances. In at least one instance, tissue can flow relative to the cartridge 6500 when the anvil is moved between an open position and a closed position in which the tissue is squeezed between the anvil and the cartridge 6500. In such instances, the tissue may flow laterally toward the longitudinal sides 6508, distally toward the distal end 6503, and/or proximally toward the proximal end 6505. In at least one other instance, tissue can flow relative to the cartridge 6500 when the cutting member is advanced distally through the tissue captured between the anvil and the cartridge 6500. In such instances, tissue may flow laterally, distally, and/or proximally, but it primarily flows distally due to the distal movement of the cutting edge. In various instances, projections 6550 can be configured to limit or prevent the flow of the tissue relative to the staple cartridge. Projections 6550 can be positioned at the proximal end and/or the distal end of the staple cavities 6512, 6522, 6532. In various instances, each projection 6550 can comprise a cuff extending around an end of a corresponding staple cavity 6512, 6522 and 6532. In certain instances, each projection 6550 can comprise an arcuate ridge that extends around an end of a corresponding staple cavity 6512, 6522 and 6532.

Figure 73:
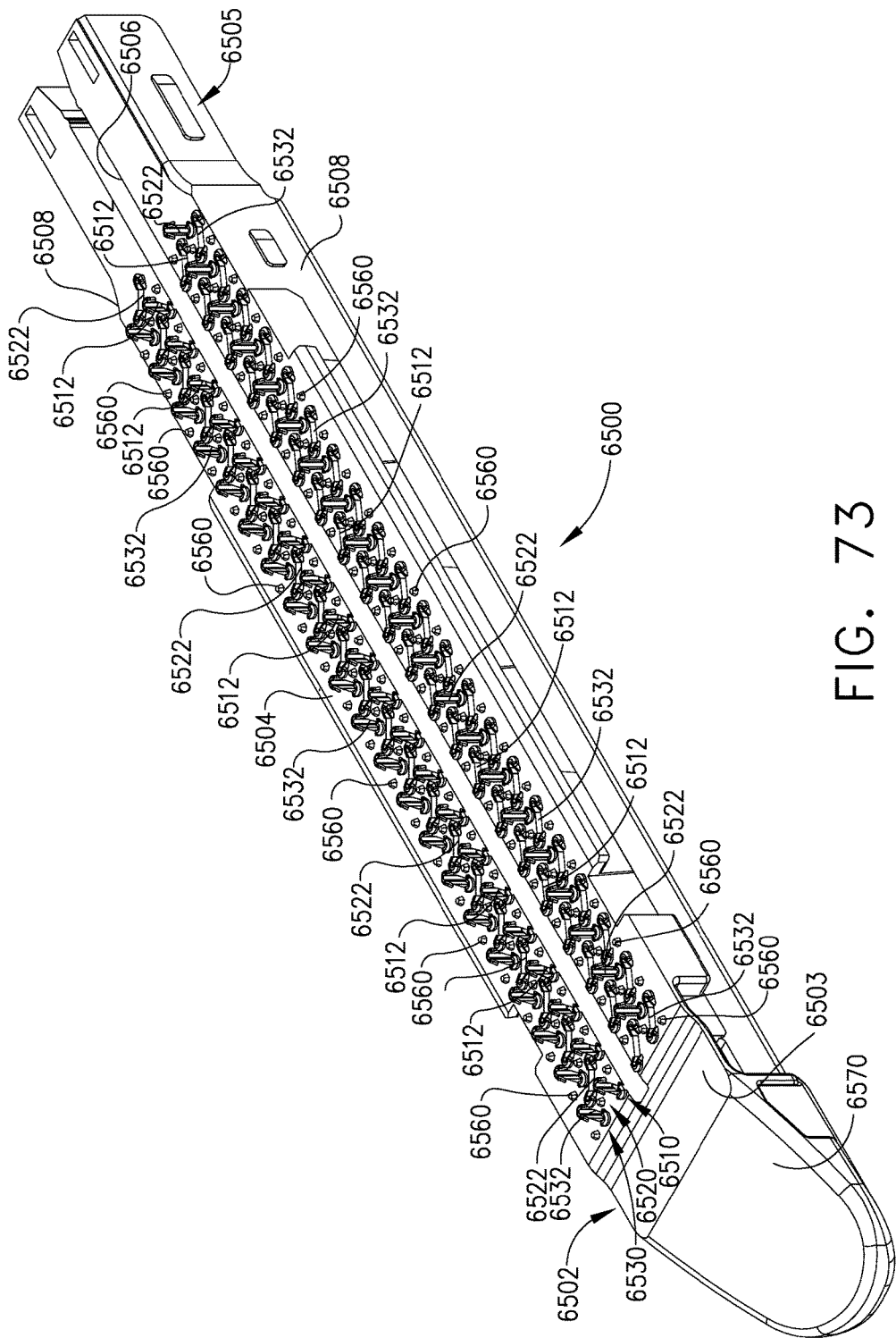
FIG. 73 is a perspective view of another surgical staple cartridge.
Figure 76:
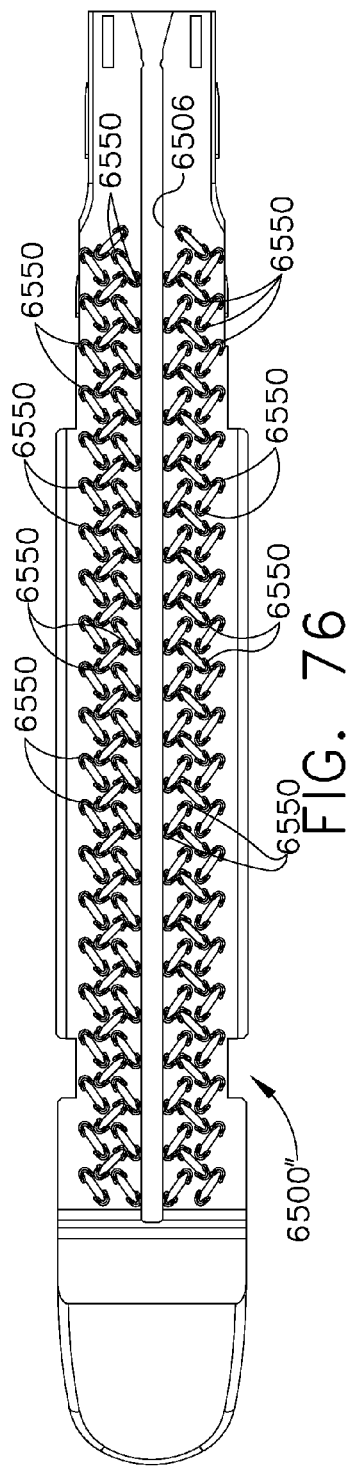
FIG. 76 is a top view of another surgical staple cartridge.
Figure 77:
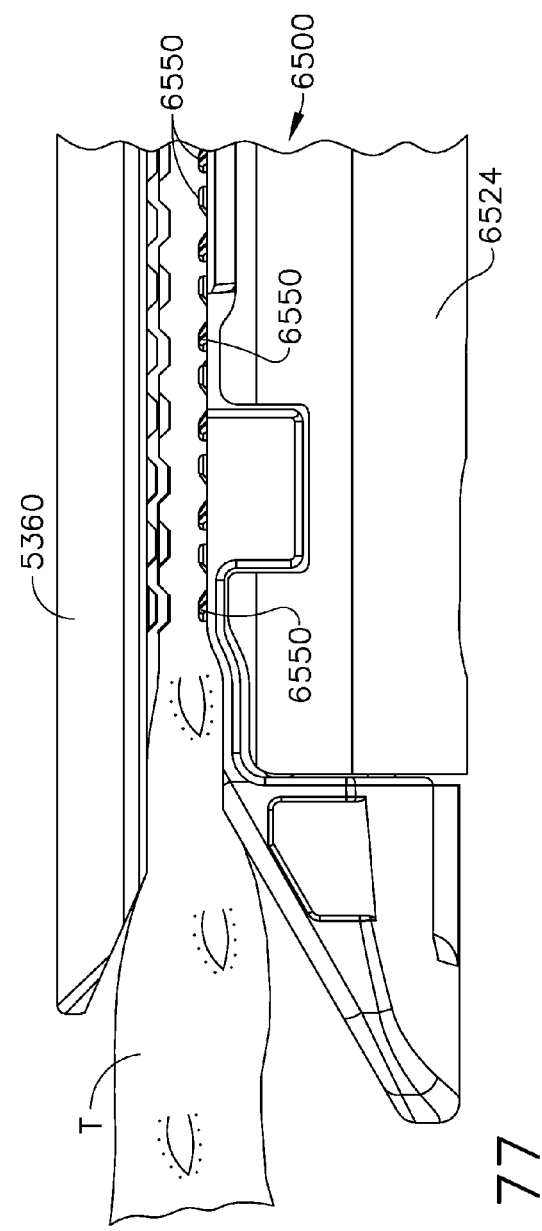
FIG. 77 is a side elevational view of a portion of a surgical stapling device with tissue "T" clamped between the surgical staple cartridge of FIG. 76 and the anvil of the device.
Figure 78:
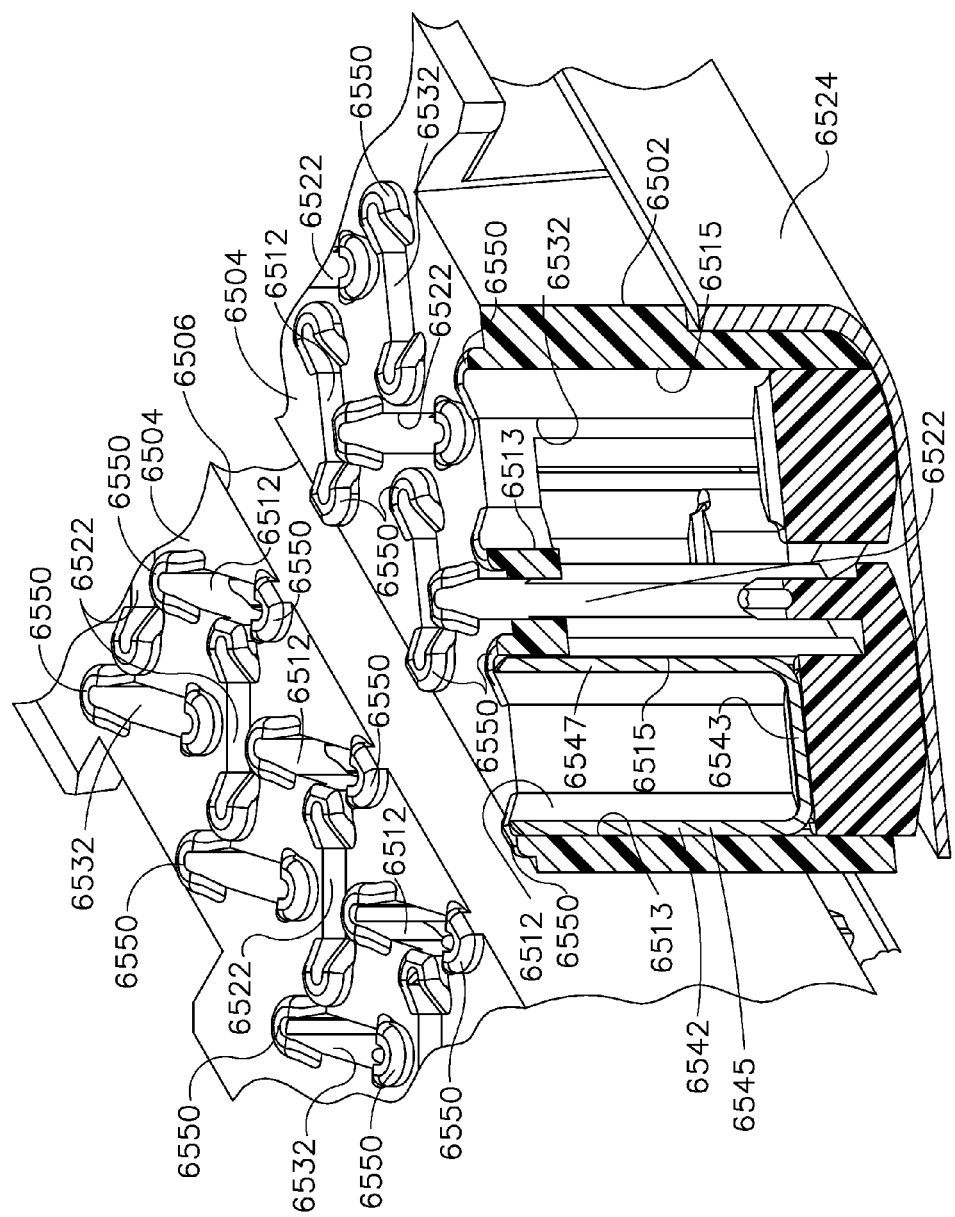
FIG. 78 is an enlarged view of a portion of the surgical staple cartridge of FIGS. 76 and 77 with a portion thereof shown in cross-section.

FIGS. 76-78 illustrate a cartridge arrangement that includes projections 6550. The cartridge arrangement depicted in FIGS. 73-75 is similar to the cartridge of FIGS. 76-78, but also includes rows of projection posts 6560 that are formed on the deck surface 6504. In the arrangement of FIGS. 73-75, for example, a projection post 6560 is provided between each staple cavity 6512, 6522 and 6532 in each row of staple cavities. The projection posts 6560 serve to further control the flow of tissue during the clamping and firing process.

Referring primarily to FIG. 73, the cartridge body 6502 includes a sloped transition 6570 extending between the distal tip of the cartridge body 6502 and the deck surface 6504. The sloped transition 6570 facilitates the movement of the cartridge 6500 relative to the tissue when positioning the cartridge 6500 and the anvil within a surgical site. In such instances, the tissue can slide over the sloped surface 6570. In other arrangements, the sloped surface 6570 comprises a radiused surface. In the illustrated arrangement, the sloped surface 6570 comprises an angled surface. In still other arrangements, the sloped surface 6570 comprises a concave surface and/or a convex surface.

The staple cavities 6512, 6522, and 6532 defined in the cartridge body 6502 are arranged in longitudinal rows on each side of the longitudinal slot 6506. Each projection 6550 can be configured to support at least a portion of a staple 6542 removably stored in a staple cavity 6512, 6522 and 6532. In various instances, each projection 6550 can extend an endwall 6513, 6515 of the staple cavity 6512, 6522, and 6532 above the deck 6504. In certain instances, referring generally to FIG. 78, a staple 6542 positioned within the staple cavity 6512, 6522, 6532 includes a base 6543, a first leg 6545 extending from the base 6543 at a first angle, and a second leg 6547 extending from the base 6543 at a second angle. The first leg 6545 can be in contact with a first endwall 6513 of a staple cavity 6532 and the second leg 6547 can be in contact with a second endwall 6515 of the staple cavity 6512, 6522, 6532. In certain instances, the distance, or spread, between the first leg 6545 and the second leg 6547 of the staple 6542 can be wider than the distance between the endwalls 6513, 6515 such that, when the staple 6542 is positioned within the staple cavity 6512, 6522, 6532, the legs 6545, 6547 are biased inwardly by the endwalls 6513, 6515. When the staple 6542 is stored within the staple cavity 6512, 6522, 6532 in its unfired, or unlifted, position, the tips of the staple legs 6545, 6547 may be positioned within the projections 6550. In such instances, the projections 6550 can support and protect the tips of the staple legs 6545, 6547 above the deck 6504. In some instances, the tips of the staple legs 6545, 6547 may be positioned below the projections 6550 when the staple 6542 is in its unfired position and, thus, the projections 6550 may not support the staple legs 6545, 6547 when the staple 6542 is in its unfired position. When such a staple 6542 is fired, or lifted out of the staple cavity 6512, 6522, 6532, the staple legs 6545, 6547 may then come into contact with and be supported by the projections 6550. In any event, the projections 6550 can continue to support the staple legs 6545, 6547 as the staple 6542 is deployed until the staple 6542 has been sufficiently fired and/or lifted out of the staple cavity 6512, 6522, 6532 such that the staple legs 6545, 6547 are no longer in contact with the projections 6550.

A layer, such as buttress material, for example, may be made from any biocompatible material. Buttress material may be formed from a natural material and/or a synthetic material. Buttress material may be bioabsorbable and/or non-bioabsorbable. It should be understood that any combination of natural, synthetic, bioabsorbable and non-bioabsorbable materials may be used to form buttress material. Some non-limiting examples of materials from which the buttress material may be made include, but are not limited to, poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and/or combinations thereof, for example.

Natural biological polymers can be used in forming the buttress material. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and/or combinations thereof, for example. Natural biological polymers may be combined with any of the other polymeric materials described herein to produce the buttress material. Collagen of human and/or animal origin, e.g., type I porcine or bovine collagen, type I human collagen or type III human collagen may be used to form the buttress material. The buttress material may be made from denatured collagen or collagen which has at least partially lost its helical structure through heating or any other method, consisting mainly of non-hydrated α chains, of molecular weight close to 100 kDa, for example. The term "denatured collagen" means collagen which has lost its helical structure. The collagen used for the porous layer as described herein may be native collagen or atellocollagen, notably as obtained through pepsin digestion and/or after moderate heating as defined previously, for example. The collagen may have been previously chemically modified by oxidation, methylation, succinylation, ethylation and/or any other known process.

Where the buttress material is fibrous, the fibers may be filaments or threads suitable for knitting or weaving or may be staple fibers, such as those frequently used for preparing non-woven materials. The fibers may be made from any biocompatible material. The fibers may be formed from a natural material or a synthetic material. The material from which the fibers are formed may be bioabsorbable or non-bioabsorbable. It should be understood that any combination of natural, synthetic, bioabsorbable and non-bioabsorbable materials may be used to form the fibers. Some non-limiting examples of materials from which the fibers may be made include, but are not limited to, poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and/or combinations thereof. Where the buttress material is fibrous, the buttress material may be formed using any method suitable to forming fibrous structures including, but not limited to, knitting, weaving, non-woven techniques and the like, for example. Where the buttress material is a foam, the porous layer may be formed using any method suitable to forming a foam or sponge including, but not limited to the lyophilization or freeze-drying of a composition, for example.

The buttress material may possesses haemostatic properties. Illustrative examples of materials which may be used in providing the buttress material with the capacity to assist in stopping bleeding or hemorrhage include, but are not limited to, poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, epsilon amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and/or combinations thereof, for example. The use of natural biological polymers, and in particular proteins, may be useful in forming buttress material having haemostatic properties. Suitable natural biological polymers include, but are not limited to, collagen, gelatin, fibrin, fibrinogen, elastin, keratin, albumin and/or combinations thereof, for example. Natural biological polymers may be combined with any other haemostatic agent to produce the porous layer of the buttress. The entire disclosure of U.S. Pat. No. 8,496,683, entitled BUTTRESS AND SURGICAL STA- PLING APPARATUS, which issued on Jul. 30, 2013, is incorporated by reference herein.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012; now U.S. Patent Application Publication No. 2013/0334278;

U.S. patent application Ser. No. 13/800,025, entitled STAPLE CARTRIDGE TISSUE THICKNESS SENSOR SYSTEM, filed on Mar. 13, 2013;

U.S. patent application Ser. No. 13/800,067, entitled STAPLE CARTRIDGE TISSUE THICKNESS SENSOR SYSTEM, filed on Mar. 13, 2013;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A fastener cartridge assembly for use with a circular surgical fastening device comprising a circular knife and an anvil, wherein the fastener cartridge assembly comprises:
a cartridge body comprising a circular deck, wherein said circular deck comprises an inner edge, wherein said inner edge comprises an inner circular axis having an inner radius, and wherein said circular knife is configured to cut tissue clamped between said circular deck and the anvil along a circular knife path having a knife radius that is less than said inner radius;
a plurality of transverse fastener cavities opening through the circular deck in a transverse cavity zone, wherein each said transverse fastener cavity comprises two cavity ends, wherein one said cavity end of each of the transverse fastener cavities is positioned on a first circular axis having a first radius, and wherein the other said cavity end of each said transverse fastener cavity is positioned on a second circular axis that has a second radius that differs from the first radius;
a plurality of circumferential fastener cavities opening through the circular deck, wherein each of the circumferential fastener cavities are aligned on a third circular axis that comprises a third radius that differs from the first and second radiuses, and wherein the circumferential fastener cavities are not positioned in said transverse cavity zone; and
a plurality of fasteners removably positioned within said fastener cavities, wherein said plurality of fasteners are configured to be ejected from said fastener cavities simultaneously, and wherein said plurality of fasteners comprises:
a plurality of first fasteners comprising a first formed height; and
a plurality of second fasteners comprising a second formed height, wherein said first formed height and said second formed height are different,
wherein said third radius is greater than said inner radius, and
wherein said first radius and said second radius are greater than said third radius.

2. The fastener cartridge assembly of claim 1, wherein said transverse fastener cavities are arranged in a circular array, and wherein said circular array includes at least one line of said transverse fastener cavities that are arranged in a zigzagged orientation.

3. The fastener cartridge assembly of claim 1, wherein each said cavity end is V-shaped and terminates in a point, and wherein the points of the cavity ends are positioned on one of the first circular axis and the second circular axis.

4. The fastener cartridge assembly of claim 1, wherein each of the circumferential fastener cavities includes a size that differs from a size of the transverse fastener cavities.

5. The fastener cartridge assembly of claim 1, wherein said first fasteners comprise a first size and said second fasteners comprise a second size, and wherein said first size and said second size are different.

6. The fastener cartridge assembly of claim 5, wherein said first fasteners comprise a first unfired height and said second fasteners comprise a second unfired height, and wherein said first unfired height and said second unfired height are different.

7. A fastener cartridge assembly for use with a circular surgical instrument comprising a circular knife and an anvil, wherein the fastener cartridge assembly comprises:
a cartridge body comprising a circular deck, wherein said circular deck comprises an inner edge, wherein said inner edge comprises an inner circular axis having an inner radius, and wherein said circular knife is configured to cut tissue clamped between said circular deck and the anvil along a circular knife path having a knife radius that is less than said inner radius;
a plurality of transverse fastener cavities opening through the circular deck in a transverse cavity zone, wherein the plurality of transverse fastener cavities are arranged in a circular array, wherein said circular array includes at least one line of the transverse fastener cavities arranged in a zigzagged orientation, and wherein said transverse cavities are aligned along a transverse cavity axis comprising a first radius;
a plurality of circumferential fastener cavities opening through the circular deck, wherein each of the circumferential fastener cavities are aligned on a circular axis not positioned in said transverse cavity zone, and wherein said circular axis comprises a second radius that is greater than said inner radius; and
a plurality of fasteners removably positioned within said fastener cavities, wherein said plurality of fasteners are configured to be ejected from said fastener cavities simultaneously and formed against an anvil surface of the circular surgical instrument, and wherein said plurality of fasteners comprises:
a plurality of first fasteners configured to be deformed against the anvil into a first formed height; and
a plurality of second fasteners configured to be deformed against the anvil into a second formed height, wherein said first formed height and said second formed height are different,
wherein said first radius is greater than said second radius.

8. The fastener cartridge assembly of claim 7, wherein said first fasteners comprise a first size and said second fasteners comprise a second size, and wherein said first size and said second size are different.

9. The fastener cartridge assembly of claim 8, wherein said first fasteners comprise a first unfired height and said second fasteners comprise a second unfired height, and wherein said first unfired height and said second unfired height are different.

* * * * *